US006986890B1

(12) United States Patent
Shitara et al.

(10) Patent No.: US 6,986,890 B1
(45) Date of Patent: Jan. 17, 2006

(54) ANTI-HUMAN VEGF RECEPTOR FLT-1 MONOCLONAL ANTIBODY

(75) Inventors: Kenya Shitara, Fujisawa (JP); Mikito Ito, Machida (JP); Nobuo Hanai, Sagamihara (JP); Yoko Kawada, Abiko (JP); Kazuyasu Nakamura, Machida (JP); Masabumi Shibuya, Kawaguchi (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/453,718

(22) Filed: Dec. 3, 1999

Related U.S. Application Data

(63) Continuation-in-part of application No. 09/315,051, filed on May 20, 1999, now abandoned, which is a continuation-in-part of application No. 09/119,014, filed on Jul. 20, 1998, now Pat. No. 6,617,160, which is a continuation-in-part of application No. PCT/JP97/04259, filed on Nov. 21, 1997.

(30) Foreign Application Priority Data

| Nov. 21, 1996 | (JP) | 8-311109 |
| Nov. 21, 1997 | (WO) | PCT/JP97/04259 |
| May 20, 1998 | (JP) | 10-139000 |
| May 20, 1999 | (WO) | PCT/JP99/02661 |

(51) Int. Cl.
*A61K 39/395* (2006.01)
(52) U.S. Cl. .............................. 424/141.1; 424/142.1; 424/143.1; 424/152.1
(58) Field of Classification Search ............. 424/141.1, 424/130.1, 142.1, 143.1
See application file for complete search history.

(56) References Cited

U.S. PATENT DOCUMENTS

| 5,750,078 | A | 5/1998 | Shitara et al. |
| 5,807,548 | A | 9/1998 | Shitara et al. |
| 5,830,470 | A | 11/1998 | Nakamura et al. |
| 5,840,301 | A | 11/1998 | Rockwell et al. |
| 5,866,692 | A | 2/1999 | Shitara et al. |
| 5,874,255 | A | 2/1999 | Nakamura et al. |
| 5,874,542 | A | 2/1999 | Rockwell et al. |
| 6,018,032 | A | 1/2000 | Koike et al. |
| 6,365,157 | B2 | 4/2002 | Rockwell |

FOREIGN PATENT DOCUMENTS

| EP | 0 882 799 A1 | 12/1998 |
| WO | WO 95 21868 A | 8/1995 |

OTHER PUBLICATIONS

Chen et al. EMBO J 14(12): 2784-2794, 1995.*
Davis-Smyth et al. *EMBO J.*, vol. 15, pp. 4919-4927, 1996.*
NCBI g125361 VGR1$_{13}$ Human (Shibuya et al, Oncogene 5(4), 519-524 (1990)).
Bird et al., "Single-Chain Antigen-Binding Proteins", Science, vol. 242, Oct. 1988, pp. 423-426.
Mitola et al., "Tat-Human Immunodeficiency Virus-1 Induces Human Monocyte Chemotaxis by Activation of Vascular Endothelial Growth Factor Receptor-1", Blood, vol. 90, No. 4, (Aug. 15, 1997, pp. 1365-1372.
Webber et al., "Preparation and Characterization of a Disulfide-Stabilized Fv Fragment of the Anti-TAC Antibody: Comparison with its Single-Chain Analog", Molecular Immunology, vol. 32, No. 4, pp. 249-258, 1995.
Shibuya et al., "Nucleotide Sequence and Expression of a Novel Human Receptor-Type Tyrosin Kinase Gene (flt) Closely Related to the fms Family", Oncogene (1990), 5, 519-524.
Tanaka, et al., Characterization of the Extracellular Domain in Vascular Endothelial Growth Factor Receptor-1 (Flt-1 Tyrosine Kinase), Jpn. J. Cancer Res., 88, 867-876, 1997.
Wiesmann, et al., Crystal Structure at 1.7 Å Resolution of VEGF in Complex with Domain 2 of the Flt-1 Receptor, Cell, vol. 91, 695-704, 1997.
Shibuya et al., "Nucleotide sequence and expression of a novel human receptor", Oncogene (1990), 5, 519-524.
Seetharam et al., "A Unique signal transduction from FLT tyrosine kinase, a receptor for vascular endothelial growth factor VEGF", Oncogene (1995) 10. 135-147.
Kim et al., "Inhibition of vascular endothelial growth factor-induced angiogenesis suppresses tumour growth in vivo", NATURE, vol. 362, Apr. 29, 1993, pp. 841-844.
De Vries et al., "The fms-Like Tyrosine Kinase, a Receptor for Vascular Endothelial Growth Factor", Reports, Feb. 21, 1992, pp. 989-991.
Melnyk et al., "Vascular Endothelial Growth Factor Promotes Tumor Dissemination by a Mechanism Distinct from Its Effect on Primary Tumor Growth", Cancer Research 56, pp. 921-924, Feb. 15, 1996.
Folkman et al., "Minireview: Angiogenesis", The Journal of Biological Chemistry, vol. 267, No. 16, Issue of Jun. 5, pp. 10931-10934, 1992.
Masabumi Shibuya, "Role Of VEGF-FLT Receptor System In Normal And Tumor Angiogenesis", Institute of Medical Science, University of Tokyo, Tokyo 108, Japan, pp. 281-317.

(Continued)

*Primary Examiner*—Janet Andres
*Assistant Examiner*—Stephen Gucker
(74) *Attorney, Agent, or Firm*—Nixon & Vanderhye P.C.

(57) ABSTRACT

The present invention provides an antibody or peptide which immunologically reacts with human VEGF receptor Flt-1 and cells in which human VEGF receptor Flt-1 is expressed on the cell surface and an antibody or peptide which inhibits binding of human VEGF to human VEGF receptor Flt-1. It also provides a means for the diagnosis or treatment of diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

6 Claims, 48 Drawing Sheets

OTHER PUBLICATIONS

Senger et al., "Tumor Cells Secrete a Vascular Permeability Factor That Promotes Accumulation of Ascites Fluid", Science, vol. 219, Feb. 25, 1983, pp. 983-985.

Ferrara et al., "Pituitary Follicular Cells Secrete A Novel Heparin-Binding Gworth Factor Specific For Vascular Endothelial Cells", Biochemical and Biophysical Research Communications, vol. 161, No. 2, Jun. 15, 1989, pp. 851-858.

Leung et al., "Vascular Endothelial Growth Factor is a Secreted Angiogenic Mitogen", Science, pp. 1306-1309, Dec. 8, 1989.

Koch et al., "Vascular Endothelial Growth Factor A Cytokine Modulating Endothelial Function in Rheumatoid Arthritis", Journal of Immunology, 1994, 152: 4149-4156.

Unemori et al., "Vascular Endothelial Growth Factor Induces Intersitial Collagenase Expression in Human Endothelial Cells", Journal of Cellular Physiology 153: 557-562 (1992).

Pepper et al., "Vascular Endothelial Growth Factor (VEGF) Induces Plasminogen Activators and Plasminogen Activator Inhibitor-1 in Microvascular Endothelial Cells", Biochemical and Biophysical Research Communications, vol. 181, No. 2, Dec. 16, 1991, pp. 902-906.

Asahara et al., "Synergistic Effect of Vascular Endothelial Growth Factor and Basic Fibroblast Growth Factor on Angiogeneis In Vivo", Basic Research, Supplement II, Circulation, vol. 92, No. 9, Nov. 1, 1995, pp. 365-371.

Houck et al., "Dual Regulation of Vascular Endothelial Growth Factor Bioavailability by Genetic and Proteolytic Mechanisms", The Journal of Biological Chemistry, vol. 267, No. 36, Dec. 25, 1992, pp. 26031-26037.

Takahashi et al., "Markedly Increased Amounts of Messenger RNAs for Vascular Endothelial Growth Factor and Placenta Growth Factor in Renal Cell Carcinoma Associated with Angiogenesis", Cancer Research 54, 4233-4237, Aug. 1, 1994.

Berkman et al., "Expression of the Vascular Permeability Factor/Vascular Endothelial Growth Factor Gene in Central Nervous System Neoplasms", The Journal of Clinical Investigation, Inc., vol. 91, Jan. 1993, pp. 153-159.

Brown et al., "Expression of Vascular Permeability Factor (Vascular Endothelial Growth Factor) and Its Receptors in Adenocarcinomas of the Gastrointestinal Tract", Cancer Research 53, 4727-4735, Oct. 1, 1993.

Olson et al., "Vascular Permeability Factor Gene Expression in Normal and Neoplastic Human Ovaries", Cancer Research 54, 276-280, Jan. 1, 1994.

Toi et al., "Association of Vascular Endothelial Growth Factor Expression with Tumor Angiogenesis and with Early Relapse Breast Cancer", Jpn. J. Cancer Res., 85, 1045-1049, Oct. 1994.

Kondo et al., "Vascular Endothelial Growth Factor/Vascular Permeability Factor is Detectable in the Sera of Tumor-Bearing Mice and Cancer Patients", Biochimica et Biophysica Acta 1221 (1994) pp. 211-214.

Aiello et al., "Vascular Endothelial Growth Factor in Ocular Fluid of Patients with Diabetic Retinopathy and Other Retinal Disorders", The New England Journal of Medicine, vol. 331, No. 22, pp. 1480-1487, Dec. 1, 1994.

Fava et al., "Vascular Permeability Factor/Endothelial Growth Factor (VPE/VEGF): Accumulation and Expression in Human Synovial Fluids and Rheumatoid Synovial Tissue", J. Exp. Med., vol. 180, Jul. 1994, pp. 341-346.

Matthews et al., "A Receptor Tyrosine Kinase cDNA Isolated from a Population of Enriched Primitive Hematopoietic Cells and Exhibiting Close Genetic Linkage to c-kit", Proc. Natl. Acad. Sci. USA, vol. 88, pp. 9026-9030, Oct. 1991 Biochemistry.

Terman et al., "Identification of the KDR Tyrosine Kinase as a Receptor for Vascular Endothelial Cell Growth Factor", Biochemical and Biophysical Research Communications, vol. 187, No. 3, 1992, pp. 1579-1586, Sep. 30, 1992.

Quinn et al., "Fetal Liver Kinase 1 is a Receptor for Vascular Endothelial Growth Factor and is Selectively Expressed in Vascular Endothelium", Proc. Natl. Acad. Sci. USA. vol. 90, pp. 7533-7537, Aug. 1993 Cell Biology.

Peters et al., "Vascular Endothelial Growth Factor Receptor Expression During Embryogenesis and Tissue Repair Suggests a Role in Endothelial Differentiation and Blood Vessel Growth", Proc. Natl. Acad. Sci. USA, vol. 90, pp. 8915-8919, Oct. 1993 Developmental Biology.

Plate et al., "Vascular Endothelial Growth Factor is a Potential Tumour Angiogenesis Factor in Human Gliomas In Vivo", Nature, vol. 359, Oct. 29, 1992, pp. 845-848.

Fong et al., "Role of the Flt-1 Receptor Tyrosine Kinase in Regulating the Assembly of Vascular Endothelium", Nature, vol. 376, Jul. 6, 1995, pp. 66-70.

Sawano et al., "Flt-1 But Not KDR/Flk-1 Tyrosin Kinase Is a Receptor for Placenta Growth Factor, Which is Related to Vascular Endothelial Growth Factor", Cell Growth & Differentiation, vol. 7, pp. 213-221, Feb. 1996.

Hanai et al., "Detailed Characterization of Reactivities of Anti-Gastric Cancer Monoclonal Antibodies to Carbohydrate Antigen", Anticancer Research 10: 1579-1586.

Hanai et al., "Generation of Monoclonal Antibodies Against Human Lung Squamous Cell Carcinoma and Adenocarcinoma Using Mice Rendered Tolerant to Normal Human Lung", Cancer Research 46, 4438-4443, Sep. 1986.

Shitara et al., "Application of Anti Lung Adenocarcinoma Monoclonal Antibody Recognizing Cytokeratin-Like Cytoplasmic Antigen for Tumor Diagnosis", Anticancer Research 12: 1121-1130 (1992).

Davis-Smith et al, EMBO Journal, vol. 15, No. 18, 1996, pp. 4919-4927.

Kanno S, Oda N, Abe M, Terai Y, Ito M, Shitara K, Tabayashi K, Shibuya M, Sato Y; Oncogene Apr. 20, 2000; 19(17):2138-46 (Abstract).

* cited by examiner

Lane 1: Low molecular weight marker
Lane 2: KM2532 (Reducing conditions)
Lane 3: KM2550 (Reducing conditions)
Lane 4: High molecular Weight maker
Lane 5: KM2532 (Non-reducing conditions)
Lane 6: KM2550 (Non-reducing conditions)

Fig. 24
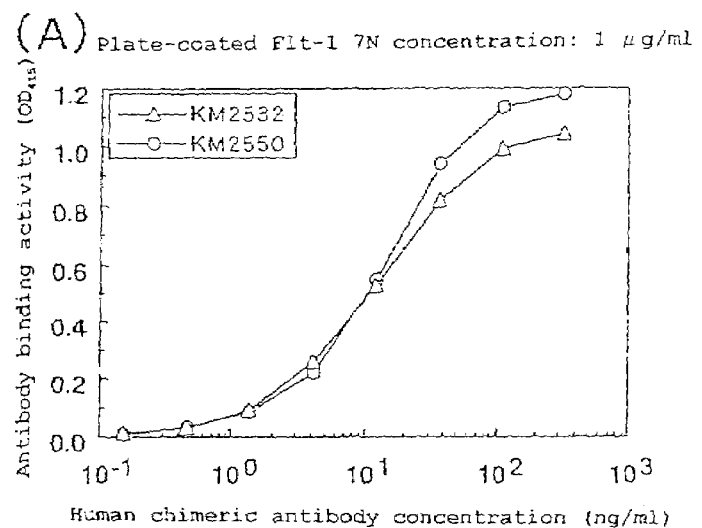
(A) Plate-coated Flt-1 7N concentration: 1 μg/ml
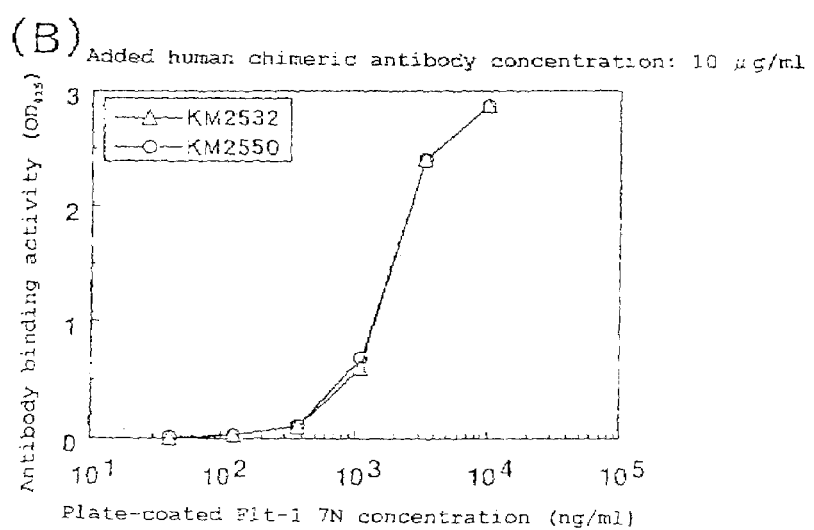
(B) Added human chimeric antibody concentration: 10 μg/ml Fig. 33
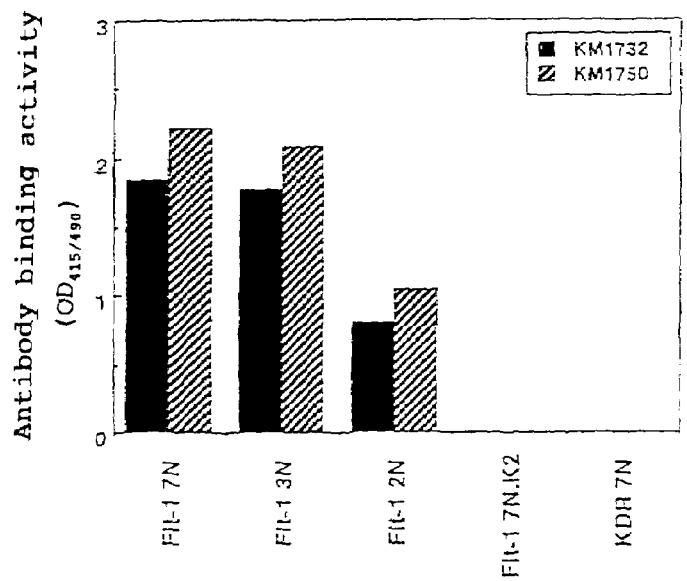
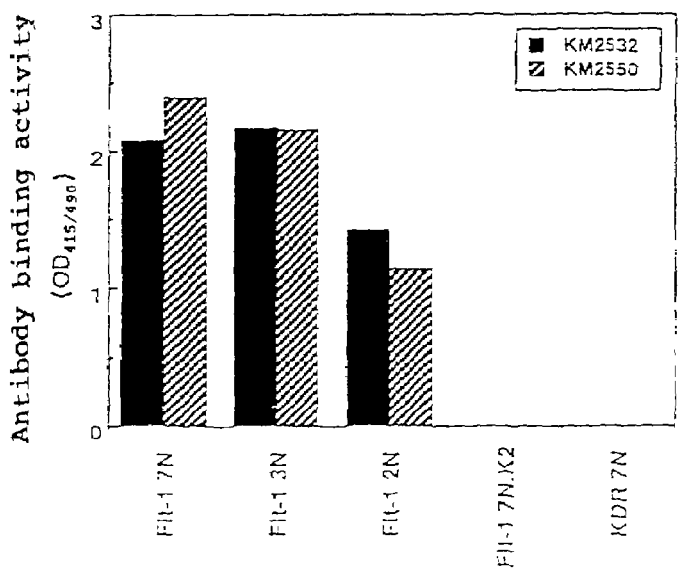

Fig. 48

H chain

```
                FR1                                          CDR1     FR2                 CDR2
KM1750 mouse  1 QAFLQQSGAELVRPGASVKMSCKASGYTFI NYNMH WVKQTPRQGLEWIG AIFPGNGFTSY  60
KM1750 HV0    1 QVQLVQSGAEVKKPGASVKVSCKASGYTFI NYNMH WVRQAPGQGLEWMG AIFPGNGFTSY  60
KM1750 HV3    1 QVQLVQSGAEVKKPGASVKVSCKASGYTFI NYNMH WVRQAPGQGLEWMG AIFPGNGFTSY  60

FR3                                     CDR3        FR4
          61 NQKFKG KATLTVDKSSSTVYMQLRSLTSEDSAVYFCAR DGDYYFDY WGQGTTLTVSS  117
          61 NQKFKG RVTITVDKSTSTAYMELSSLRSEDTAVYYCAR DGDYYFDY WGQGTLVTVSS  117
          61 NQKFKG RVTITVDKSTSTAYMQLRSLRSEDTAVYFCAR DGDYYFDY WGQGTLVTVSS  117
                        8284                        95
```

Fig. 49

```
L chain
                     FR1                                                          CDR1              FR2                          CDR2       FR3
KM1750 mouse    1    QIVLTQSPAIMSASLGEEITLTC    SASSSVSYMH    WYQQKSGTSPKLLIY    RTSNLAS    GVPFR    60
KM1750 LV0(I)   1    DIQMTQSPSSLSASVGDRVTITC    SASSSVSYMH    WYQQKPGKAPKLLIY    RTSNLAS    GVPSR    60
KM1750 LV4      1    DIQMTQSPSSLSASVGEEVTITC    SASSSVSYMH    WYQQKPGKAPKLLIY    RTSNLAS    GVPSR    60
                                                  1718
                                                                  CDR3                FR4
                61   FSGSGSGTFYSLTISSVEAEDAADYYC    HQWSMYT    FGGGTKLEIKR    105
                61   FSGSGSGTDFTLTISSLQPEDFATYYC    HQWSMYT    FGQGTKVEIKR    105
                61   FSGSGSGTFYTLTISSLQPEDFATYYC    HQWSMYT    FGQGTKVEIKR    105
                                     6970

FR1                                                          CDR1              FR2                          CDR2       FR3
KM1750 mouse    1    QIVLTQSPAIMSASLGEEITLTC    SASSSVSYMH    WYQQKSGTSPKLLIY    RTSNLAS    GVPFR    60
KM1750 LV0(IV)  1    DIVMTQSPDSLAVSLGERATINC    SASSSVSYMH    WYQQKPGQPPKLLIY    RTSNLAS    GVPDR    60
                                                                  CDR3                FR4
                61   FSGSGSGTFYSLTISSVEAEDAADYYC    HQWSMYT    FGGGTKLEIKR    105
                61   FSGSGSGTDFTLTISSLQAEDVAVYYC    HQWSMYT    FGQGTKVEIKR    105
```

ANTI-HUMAN VEGF RECEPTOR FLT-1 MONOCLONAL ANTIBODY

CROSS-REFERENCE TO RELATED APPLICATION

This is a continuation-in-part of U.S. Ser. No. 09/315,051 filed on May 20, 1999, now abandoned, which is a continuation-in-part of U.S. Ser. No. 09/119,014 U.S. Pat. No. 6,617,160 filed on Jul. 20, 1998, which is a continuation-in-part of PCT/JP97/04259 filed on Nov. 21, 1997.

BACKGROUND OF THE INVENTION

1. Field of the Invention

This invention relates to an antibody or a peptide capable of specifically binding to human VEGF receptor Flt-1 which is useful for the diagnosis or treatment of diseases in which their morbid states progress by abnormal angiogenesis, such as proliferation or metastasis of solid tumors, arthritis in rheumatoid arthritis, diabetic retinopathy, retinopathy of prematurity and psoriasis; a hybridoma capable of producing the antibody; a method for immunologically detecting human VEGF receptor Flt-1 using the antibody or the peptide; and a diagnostic method and a therapeutic method for diseases, such as solid tumor, rheumatoid arthritis, diabetic retinopathy, retinopathy of prematurity, psoriasis and the like, using the antibody or the peptide.

2. Brief Description of the Background Art

Angiogenesis plays an important role in the individual development and construction of tissues in vertebrates, is directly involved in the formation of the corpus luteum during the sexual cycle, transient proliferation of the uterine endometrium and formation of the placenta in mature individuals (females). With regard to pathological states, angiogenesis is involved in the proliferation or metastasis of solid tumors and formation or acceleration of morbidity in diabetic retinopathy and rheumatoid arthritis [*J. Biol. Chem.,* 267: 10931 (1992)]. Angiogenesis occurs by the secretion of an angiogenesis factor and involves the process of a tube formation and producing a new blood vessel. During this process, the basement membrane and interstitum are destroyed by a protease secreted from endothelial cells of an existing blood vessel around the secreted angiogenesis factor, followed by subsequent migration and proliferation of vascular endothelial cells [*J. Biol. Chem.,* 267: 10931 (1992)]. Factors which induce angiogenesis include vascular permeability factor (hereinafter "VPF") and vascular endothelial growth factor (hereinafter "VEGF") (hereinafter "VPF/VEGF"). These factors are considered the most important factors in pathological and non-pathological angiogenesis [*Advances in Cancer Research,* 67: 281 (1995)]. VPF/VEGF is a protein having a molecular weight of about 40,000 constituted by homodimers, which had been reported to be independent molecules as vascular permeability factor (VPF) in 1983 [*Science,* 219: 983 (1983)] and as vascular endothelial growth factor (VEGF) in 1989 [*Biochem. Biophys. Res. Comm.,* 161: 851 (1989)], but it has been revealed as the results of cDNA cloning that they are the same substance [*Science,* 246: 1306 (1989); *Science,* 246: 1309 (1989)] (hereinafter, the term "VPF/VEGF" is recited as "VEGF"). Beyond the activity of VEGF upon vascular endothelial cells described above, VEGF has also been shown to have a growth enhancing activity [*Biochem. Biophys. Res. Comm.,* 161: 851 (1989)], a migration enhancing activity [*J. Immunology,* 152: 4149 (1994)], a metalloprotease secretion enhancing activity [*J. Cell Physiol.,* 153: 557 (1992)], a urokinase and tPA secretion enhancing activity [*Biochem. Biophys. Res. Comm.,* 181: 902 (1991)], and the like. Furthermore, VEGF has been shown to have an angiogenesis enhancing activity [*Circulation,* 92 suppl II: 365 (1995)], a vascular permeability enhancing activity [*Science,* 219: 983 (1983)], and the like as its in vivo activities. It has been reported that VEGF is a growth factor having extremely high specificity for vascular endothelial cells [*Biochem. Biophys. Res. Comm.,* 161: 851 (1989)] and that four proteins having different molecular weight are present due to alternative splicing of mRNA [*J. Biol. Chem.,* 267: 26031 (1991)].

Among diseases accompanied by angiogenesis, it has been reported that VEGF plays an important role in the proliferation or metastasis of solid tumors and formation of morbid states of diabetic retinopathy and rheumatoid arthritis. With regard to solid tumors, production of VEGF in a number of human tumor tissues has been reported, such as in renal carcinoma [*Cancer Research,* 54: 4233 (1994)], breast cancer [*Human Pathology,* 26: 86 (1995)], brain tumor [*J. Clinical Investigation,* 91: 153 (1993)], gastrointestinal cancer [*Cancer Research,* 53: 4727 (1993)], ovarian cancer [*Cancer Research,* 54: 276 (1994)], and the like. Also, results of a study on the correlation between VEGF expression quantity in tumors and survival ratio of patients in patients with breast cancer have revealed that tumor angiogenesis is more active in tumors expressing high levels of VEGF than low VEGF expression tumors and that the survival ratio is lower in breast cancer patients having high VEGF expression tumors than breast cancer patients having low VEGF expression tumors [*Japanese J. Cancer Research,* 85: 1045 (1994)]. It has been reported also that an anti-VEGF monoclonal antibody inhibited tumor growth in a xenograft model test system in which a human tumor was transferred into nude mice by subcutaneous transplantation [*Nature,* 362: 841 (1993)]. Also, it has been reported that, in a metastatic cancer model of a human tumor in nude mice, an anti-VEGF monoclonal antibody inhibited metastasis of the tumor [*Cancer Research,* 56: 921 (1996)]. Additionally, since a high concentration of VEGF was detected in human carcinomatous pleural perfusions and ascites, the possibility that VEGF is a major factor involved in the retention of pleural perfusions and ascites has been suggested [*Biochimica Biophysica Acta,* 1221: 211 (1994)].

In diabetic retinopathy, abnormal angiogenesis causes retinal detachment and hemorrhage of the vitreous body, resulting in blindness, and it has been reported that angiogenesis in diabetic retinopathy and the expression level of VEGF in the patient's eye balls are positively correlative [*New England J. Medicine,* 331: 1480 (1994)]. Also, it has been reported that angiogenesis in a monkey retinopathy model is inhibited when the VEGF activity is inhibited by the intraocular administration of an anti-VEGF neutralizing monoclonal antibody [*Arch. Ophthalmol.,* 114: 66 (1996)].

Progress in the morbid states of rheumatoid arthritis (destruction of bone and cartilage) is accompanied by angiogenesis, and it has been reported that a high concentration of VEGF is contained in the synovial fluid of patients with rheumatoid arthritis and that macrophages in joints of patients with rheumatoid produce VEGF rheumatoid arthritis [*Journal of Immunology,* 152: 4149 (1994); *J. Experimental Medicine,* 180: 341 (1994)].

VEGF receptors have been reported. These include fms-like tyrosine kinase (referred to as "Flt-1" hereinafter) [*Oncogene,* 5: 519 (1990); *Science,* 255: 989 (1992)] and kinase insert domain-containing receptor (referred to as "KDR" hereinafter) [WO 92/14748; *Proc. Natl. Acad. Sci.*

USA, 88: 9026 (1991)]; *Biochem. Biophys. Res. Comm.,* 187: 1579 (1992); WO 94/11499), which belong to the receptor type tyrosine kinase family. Each of Flt-1 and KDR is a membrane protein of 180 to 200 kilodalton in molecular weight which has an extracellular domain consisting of 7 immunoglobulin-like regions and an intracellular domain consisting of a tyrosine kinase region. It has been reported that VEGF specifically binds to Flt-1 and KDR at Kd values of 20 pM and 75 pM and that Flt-1 and KDR are expressed in vascular endothelial cells in a specific manner [*Proc. Natl. Acad. Sci. USA,* 90: 7533 (1993); *Proc. Natl. Acad. Sci. USA,* 90: 8915 (1993)]. With regard to Flt-1 in various diseases, it has been reported that, in comparison with vascular endothelial cells in normal tissues, expression of Flt-1 mRNA increases in tumor vascular endothelial cells of human glioblastoma tissues [*Nature,* 359: 845 (1992)] and tumor vascular endothelial cells of human digestive organ cancer tissues [*Cancer Research,* 53: 4727 (1993)]. Additionally, it has been reported that expression of Flt-1 mRNA is observed by in situ hybridization in vascular endothelial cells of joints of patients with rheumatoid arthritis [*J. Experimental Medicine,* 180: 341 (1994)]. These results strongly suggest that a VEGF/VEGF receptor Flt-1 system plays an important role in tumor angiogenesis. Although it has been reported that VEGF binds to Flt-1 and the intracellular domain is auto-phosphorylated [*Science,* 255: 989 (1992)], the detailed function of the receptor mechanism is still unclear. However, it has been discovered that knock out mice in which the Flt-1 gene was destroyed die after a fetal age of 8.5 to 9.5 days due to abnormal blood vessel construction caused by abnormal morphology of vascular endothelial cells during blood island formation in the early stage of development and subsequent angiogenesis. This had led to an assumption that Flt-1 has a function essential for the tube formation of vascular endothelial cells in angiogenesis [*Nature,* 376: 66 (1995)].

In view of the above, it is expected that an antibody which can inhibit biological activities of VEGF through its binding to VEGF receptor Flt-1 will be useful for the diagnosis or treatment of diseases in which their morbid states progress by abnormal angiogenesis, such as proliferation or metastasis of solid tumors, arthritis in rheumatoid arthritis, diabetic retinopathy, retinopathy of prematurity and psoriasis. However, an anti-VEGF receptor Flt-1 monoclonal antibody which can detect cells in which VEGF receptor Flt-1 is expressed and anti-VEGF receptor Flt-1 monoclonal antibody which can inhibit biological activities of VEGF has not been described in the art.

Generally, when a monoclonal antibody derived from non-human animal is administered to human, the monoclonal antibody is recognized as a foreign material so that an antibody against the monoclonal antibody derived from non-human animal is produced in the body. As a result, the antibody is allowed to react with the monoclonal antibody derived from non-human animal, and it is known that side effects are caused [*J. Clin. Oncol.,* 2: 881 (1984); *Blood,* 65: 1349 (1985); *J. Natl. Cancer Inst.,* 80: 932 (1988); *Proc. Natl. Acad. Sci. USA,* 82: 1242 (1985)], the monoclonal antibody is shortly cleared [*J. Nucl. Med.,* 26: 1011 (1985); *Blood,* 65: 1349 (1985); *J. Natl. Cancer Inst.,* 80: 937 (1988)], and that the treating effect of the antibody is decreased [*J. Immunol.,* 135: 1530 (1985); *Cancer Res.,* 46: 6489 (1986)].

In order to solve the above problems, it has been attempted that a monoclonal antibody derived from non-human animal is modified to a humanized antibody, such as a human chimeric antibody or a human CDR-grafted antibody (reconstructed human antibody), using gene engineering technique. The human chimeric antibody is an antibody in which an antibody variable region (V region) is derived from a non-human animal antibody and an antibody constant region (C region) is derived from a human antibody [*Proc. Natl. Acad. Sci. USA,* 81: 6851 (1984)]. It is reported that when the human chimeric antibody is administered to human, antibodies against the monoclonal antibody derived from non-human animal are not almost induced and the half-life in blood is prolonged six times [*Proc. Natl. Acad. Sci. USA,* 86: 4220 (1989)]. The human CDR-grafted antibody is an antibody in which the complementarity-determining region (CDR) of a human antibody is replaced with the CDR of an antibody derived from non-human animal [*Nature,* 321: 522 (1986)]. It is reported that in the experiment using a monkey, immunogenicity is lowered by the human CDR-grafted antibody as compared with a mouse antibody, and the half-life in blood is prolonged four to five times [*J. Immunol.,* 147: 1352 (1991)].

Accordingly, when the chimeric antibody and the humanized antibody which specifically react with human VEGF receptor Flt-1, side effects are decreased and the half-life in blood is prolonged because no antibody against a monoclonal antibody derived from non-human animal is produced. Therefore, it is expected that these antibodies can treat diseases in which their morbid states progress by abnormal angiogenesis, such as proliferation or metastasis of solid tumors, arthritis in rheumatoid arthritis, diabetic retinopathy, retinopathy of prematurity and psoriasis, and the like.

In addition, with the recent progress of protein engineering and gene engineering, the production of smaller antibody molecules, such as a single chain antibody [*Science,* 242: 423 (1988)] and a disulfide stabilized antibody [*Molecular Immunology,* 32: 249 (1995)], have been tried. Since the single chain antibody and the disulfide stabilized antibody have a molecular weight lower than a monoclonal antibody or a humanized antibody, they are excellent in tissue transition property and clearance from blood and are applied to imaging and the like, a composite thereof with a toxin was prepared, and therefore, the treatment effect can be expected [*Cancer Research,* 55: 318 (1995)]. Therefore, it is expected that these antibodies can treat diseases in which their morbid states progress by abnormal angiogenesis, such as proliferation or metastasis of solid tumors, arthritis in rheumatoid arthritis, diabetic retinopathy, retinopathy of prematurity and psoriasis, and the like.

SUMMARY OF THE INVENTION

Concern has been directed toward the development of a method which is useful for the diagnosis or treatment of diseases in which their morbid states progress by abnormal angiogenesis, such as proliferation or metastasis of solid tumors, arthritis in rheumatoid arthritis, diabetic retinopathy, retinopathy of prematurity and psoriasis. Although nothing has been reported on the anti-human VEGF receptor Flt-1 monoclonal antibody, it is considered that detection of the regions of angiogenesis and inhibition of angiogenesis by the use of an anti-human VEGF receptor Flt-1 monoclonal antibody will be useful for the diagnosis and treatment of these diseases.

The above and other objects of the present invention may be accomplished by a monoclonal antibody, that is, an antibody produced by a hybridoma, a humanized antibody, such as a human chimeric antibody and a human CDR-grafted antibody, and an antibody fragment, such as Fab, Fab', F(ab')$_2$, single chain Fv, a disulfide stabilized antibody, and a peptide comprising CDR, which each specifically reacts with human VEGF receptor Flt-1, preferably which each recognizes an epitope present in a region of the 1st to 750th, more preferably 1st to 338th, and most preferably 100th to 204th, positions from the N-terminal amino acid including a signal sequence of human VEGF receptor Flt-1 signal and receptor protein.

BRIEF DESCRIPTION OF THE DRAWINGS

FIG. 24 is a graph showing the activity of purified anti-human VEGF receptor Flt-1 human chimeric antibodies KM2532 and KM2550 to bind to soluble human VEGF receptor Flt-1 7N. The upper drawing (A) shows the results when concentration of soluble human VEGF receptor Flt-1 7N to be adsorbed on the plate is fixed (1 μg/ml) and concentration of each human chimeric antibody to be added is varied. The binding activity with soluble human VEGF receptor Flt-1 7N is plotted as ordinate and the concentration of each human chimeric antibody as abscissa. The symbol Δ indicates binding activity of KM2532 and ○ indicates that of KM2550. The lower drawing (B) shows the results when binding activity of each human chimeric antibody at a fixed concentration (10 μg/ml) was measured by varying concentration of soluble human VEGF receptor Flt-1 7N to be adsorbed on the plate. The binding activity with soluble human VEGF receptor Flt-1 7N is plotted as ordinate, and the concentration of soluble human VEGF receptor Flt-1 7N adsorbed on the plate as abscissa. The symbol Δ indicates binding activity of KM2532 and ○ indicates that of KM2550.

FIG. 33 is a graph showing results of the enzyme immunoassay evaluation of the binding reactivity of anti-human VEGF receptor Flt-1 monoclonal antibodies KM1732 and KM1750 and anti-human VEGF receptor Flt-1 human chimeric antibodies KM2532 and KM2550.

FIG. 48 is a graph showing amino acid sequences of the H chain of anti-human VEGF receptor Flt-1 human chimeric antibody and CDR-grafted antibody. In the drawing, KM1750 mouse shows H chain V region amino acid sequence of KM1750 (SEQ ID NO:99); KM1750HV0 (SEQ ID NO:102) shows an amino acid sequence constituted by inserting CDR of H chain V region of KM1750 into a human framework; and KM1750HV3 (SEQ ID NO:106) shows an amino acid sequence in which some of the amino acid sequence of the framework of KM 1750HV0 are substituted with the amino acids of KM1750 mouse.

FIG. 49 is a graph showing amino acid sequences of L chain of anti-human VEGF receptor Flt-1 human chimeric antibody and CDR-grafted antibody. In the drawing, KM1750 mouse shows an amino acid sequence of L chain V region of KM1750 (SEQ ID NO:108); KM1750LV0 (I) (SEQ ID NO:109) and KM1750LV0 (IV) (SEQ ID NO:110) each shows an amino acid sequence constituted by inserting CDR of L chain V region of KM1750 into a human framework; and KM1750LV4 (SEQ ID NO:110) shows an amino acid sequence in which some of the amino acid sequence of the framework of KM1750LV0 (I) are substituted with the amino acids of KM1750 mouse.

DETAILED DESCRIPTION OF THE INVENTION

Figure 1:
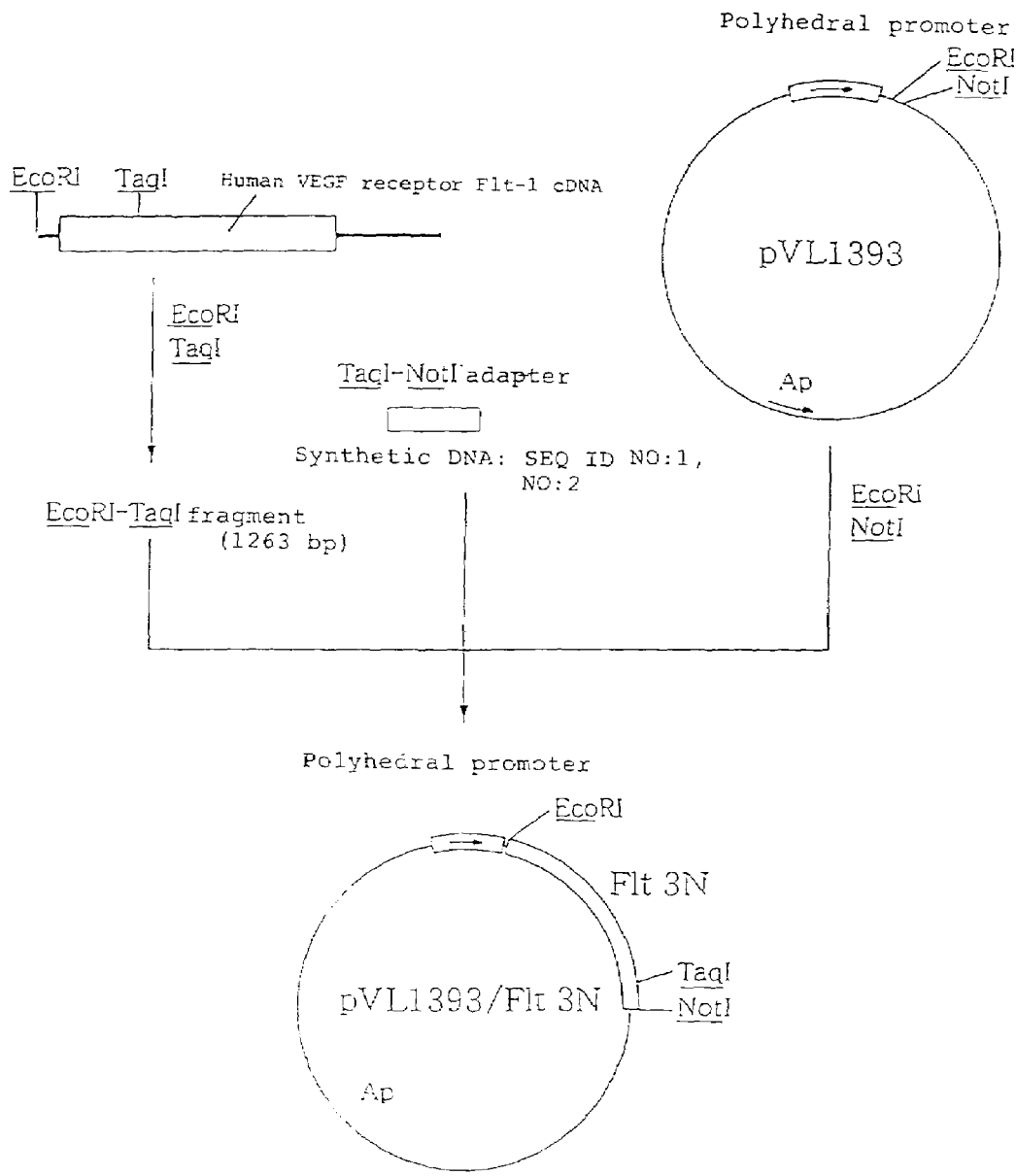
FIG. 1 is a graph showing construction steps of plasmid pVL1393/Flt 3N.

The present invention relates to a monoclonal antibody which specifically reacts with human VEGF receptor Flt-1; a monoclonal antibody which recognizes an epitope present in a region of amino acids 1 to 750, preferably 1 to 338, and more preferably 100 to 204, of the N-terminal sequence of human VEGF receptor Flt-1 including a signal sequence; a monoclonal antibody which specifically reacts with human VEGF receptor Flt-1 by immunocyte staining; a monoclonal antibody which inhibits binding of human VEGF to human VEGF receptor Flt-1 and inhibits biological activities of human VEGF; and a monoclonal antibody which inhibits migration of vascular endothelial cells.

Furthermore, the present invention relates to monoclonal antibody KM1730 belonging to mouse IgG1 subclass produced by hybridoma KM1730 (FERM BP-5697); monoclonal antibody KM1731 belonging to mouse IgG2a subclass produced by hybridoma KM1731 (FERM BP-5718); monoclonal antibody KM1732 belonging to mouse IgG1 subclass produced by hybridoma KM1732 (FERM BP-5698); monoclonal antibody KM1748 belonging to mouse IgG2b subclass produced by hybridoma KM1748 (FERM BP-5699); and monoclonal antibody M1750 belonging to mouse IgG2b subclass produced by hybridoma KM1750 (FERM BP-5700).

Moreover, the present invention relates to hybridoma KM1730 (FERM BP-5697) which produces monoclonal antibody KM1730; hybridoma KM1731 (FERM BP-5718) which produces monoclonal antibody KM1731; hybridoma KM1732 (FERM BP-5698) which produces monoclonal antibody KM1732; hybridoma KM1748 (FERM BP-5699) which produces monoclonal antibody of KM1748; and hybridoma KM1750 (FERM BP-5700) which produces monoclonal antibody KM1750.

Also, the present invention relates to a treating or diagnostic agent of diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

The inventors of the present invention have found that anti-human VEGF receptor Flt-1 monoclonal antibody capable of recognizing an epitope present in a region of the 1st to 750th positions from the N-terminal amino acid of human VEGF receptor Flt-1 can specifically react with the human VEGF receptor Flt-1 by immunocyte staining, and that biological activities of human VEGF can be inhibited by the inhibition of binding of VEGF to VEGF receptor Flt-1. Diagnosis and treatment of the above-described diseases in which their morbid states progress by abnormal angiogenesis, such as proliferation or metastasis of solid tumors, arthritis in rheumatoid arthritis, diabetic retinopathy, prematurity retinopathy and psoriasis, can be carried out by using these monoclonal antibodies.

Consequently, the present invention provides antibodies which specifically react with human VEGF receptor Flt-1. With regard to the monoclonal antibody of the present invention, a monoclonal antibody is provided that recognizes an epitope which is present in a region of the 1st to 750th, preferably 1st to 338th, and more preferably 100th to 204th, positions from the N-terminal amino acid including a signal sequence of human VEGF receptor Flt-1, and also specifically reacts with human VEGF receptor Flt-1 by immunocyte staining. Also, the present invention provides a monoclonal antibody which inhibits binding of human VEGF to human VEGF receptor Flt-1 and also inhibits biological activities of the human VEGF. Examples of the monoclonal antibody which recognizes the epitope and also specifically reacts with human VEGF receptor Flt-1 by immunocyte staining include monoclonal antibody KM1730 produced by the hybridoma KM1730 (FERM BP-5697), monoclonal antibody KM1731 produced by the hybridoma KM1731 (FERM BP-5718), monoclonal antibody KM1732 produced by the hybridoma KM1732 (FERM BP-5698), monoclonal antibody KM1748 produced by the hybridoma M1748 (FERM BP-5699), and monoclonal antibody KM1750 produced by the hybridoma M1750 (FERM BP-5700). Examples of the monoclonal antibody which inhibits binding of human VEGF to human VEGF receptor Flt-1 and also inhibits biological activities of human VEGF include monoclonal antibody KM1732 produced by the hybridoma KM1732 (FERM BP-5698), monoclonal antibody KM1748 produced by the hybridoma KM1748 (FERM BP-5699), and monoclonal antibody KM1750 produced by the hybridoma KM1750 (FERM BP-5700).

The monoclonal antibody of the present invention may be any antibody, so long as it specifically reacts with human VEGF receptor Flt-1. Examples of the monoclonal antibody include an antibody produced by a hybridoma and a recombinant antibody produced by a transformant transformed with an expression vector containing the antibody gene. For example, those which are established by the following production method can be cited as preferred examples. That is, anti-human VEGF receptor Flt-1 monoclonal antibody can be obtained by preparing human VEGF receptor Flt-1 protein as an antigen, immunizing an animal capable of providing a hybridoma with the antigen, such as mouse, rat, hamster, rabbit or the like, thereby inducing plasma cells having the antigen specificity, preparing a hybridoma capable of producing the monoclonal antibody through fusion of the cells with a myeloma cell line and subsequently culturing the hybridoma.

The monoclonal antibody which specifically reacts with human VEGF receptor Flt-1 of the present invention may be a recombinant antibody. Examples of the recombinant antibody includes a humanized antibody and an antibody fragment.

The recombinant antibody of the present invention can be obtained by modifying the above-described monoclonal antibody of the present invention using gene recombination technique. The recombinant antibody includes antibodies produced by gene recombination, such as a humanized antibody and an antibody fragment (e.g., single chain antibody, disulfide stabilized antibody). Among these, antibodies which have the characteristics of monoclonal antibodies, show low antigenicity and have prolonged half-life in blood are preferred as therapeutic agents.

The humanized antibody of the present invention includes a human chimeric antibody and a human CDR (complementarity-determining region; hereinafter referred to as "CDR")-grafted antibody.

The antibody fragment of the present invention includes a fragment of antigen binding (hereinafter referred to as "Fab"), Fab', F(ab')$_2$, a single chain antibody (single chain Fv; hereinafter referred to as "scFv"), and a disulfide stabilized antibody (disulfide stabilized Fv; hereinafter referred to as "dsFv"), which specifically react with human VEGF receptor Flt-1. Hereinafter, the antibody which specifically reacts with human VEGF receptor Flt-1 is referred to as an "anti-human VEGF receptor Flt-1 antibody". Futhermore, the antibody fragments of the present invention are included within the scope of the antibodies of the present invention.

The antibody which reacts with human VEGF receptor Flt-1 of the present invention may be a humanized antibody which is selected from a human chimeric antibody and a human CDR-grafted antibody.

The humanized antibody of the present invention may comprise CDR of an antibody heavy chain (H chain) variable region (V region) comprising amino acid sequences of from 31 to 35, from 50 to 66, and from 99 to 108 positions (SEQ ID NOS:9, 10 and 11, respectively) described in SEQ ID NO:86 (corresponding to nulceic acid sequence of SEQ ID NO:5) or amino acid sequences of from 31 to 35, from 50 to 66, and from 99 to 106 positions (SEQ ID NOS:15, 16 and 17, respectively) described in SEQ ID NO:88 (corresponding to nucleic acid sequence of SEQ ID NO:7). Also, the humanized antibody may comprise CDR of an antibody light chain (L chain) variable region (V region) comprising amino acid sequences of from 24 to 34, from 49 to 55, and from 88 to 96 positions (SEQ ID NO:12, 13 and 14, respectively) described in SEQ ID NO:87 (corresponding to nucleic acid sequence of SEQ ID NO:6) or amino acid sequences of from 24 to 33, from 49 to 55, and from 88 to 94 positions (SEQ ID NOS:15, 16 and 17, respectively) described in SEQ ID NO:89 (corresponding to nucleic acid sequence of SEQ ID NO:8).

The human chimeric antibody of the present invention may comprise an antibody H chain V region and an antibody L chain V region of a monoclonal antibody which specifically reacts with human VEGF receptor Flt-1, and H chain constant region (C region) and L chain C region of a human antibody.

Specifically, the human chimeric antibody means an antibody which comprises V region H chain (hereinafter referred to as "VH") and V region L chain (hereinafter referred to as "VL") of an antibody of a non-human animal, C region H chain (hereinafter referred to as "CH") of a human antibody, and C region L chain (hereinafter referred to as "CL") of a human antibody.

The human chimeric antibody of the present invention can be produced by preparing cDNAs encoding VH and VL from a hybridoma capable of producing a monoclonal antibody which specifically reacts with human VEGF receptor Flt-1, inserting them into an expression vector for animal cells having genes encoding human antibody CH and human antibody CL to construct a human chimeric antibody expression vector, and then introducing the vector into cells of an animal to express the antibody of interest.

The structure of the human chimeric antibody of the present invention may belong to any immunoglobulin (Ig)

class, but preferably contains the C region of IgG type immunoglobulin, particularly of IgG subclasses, such as IgG1, IgG2, IgG3, and IgG4.

The H chain V region and the L chain V region of the human chimeric antibody of the present invention may comprise an amino acid sequence of H chain V region and L chain V region, respectively, of a monoclonal antibody selected from the group consisting of monoclonal antibody KM1732 (FERM BP-5698) and monoclonal antibody KM1750 (FERM BP-5700). Also, in the human chimeric antibody of the present invention, the amino acid sequence of H chain V region may be an amino acid sequence of SEQ ID NO:86 or 88, and the amino acid sequence of L chain V region may be an amino acid sequence of SEQ ID NO:87 or 89.

An example of the human chimeric antibody of the present invention wherein the amino acid sequence of H chain V region is an amino acid sequence of SEQ ID NO:86, and the amino acid sequence of L chain V region is an amino acid sequence of SEQ ID NO:87 includes KM2532. Also, an example of the human chimeric antibody of the present invention wherein the amino acid sequence of H chain V region is an amino acid sequence of SEQ ID NO:88, and the amino acid sequence of L chain V region is an amino acid sequence of SEQ ID NO:89 includes KM2550.

In addition, the present invention includes a DNA which encodes any one of the above human chimeric antibodies which specifically react with human VEGF receptor Flt-1.

According to the present invention, a recombinant vector comprising the above DNA and tandem cassette vector pKANTEX93 can be provided; a transformant can be obtained by introducing the recombinant vector into a host cell; and the human chimeric antibody can be provided culturing the transformant in a medium to produce and accumulate a human chimeric antibody in a culture, and recovering the antibody from the resulting culture.

The anti-human VEGF receptor Flt-1 antibody may be a humanized antibody which is a human CDR-grafted antibody.

The human CDR-grafted antibody of the present invention means an antibody in which the CDRs of VH and VL of a human antibody are replaced with respective CDRs of an antibody of a non-human animal.

The human CDR-grafted antibody of the present invention can be produced by constructing V region-encoding cDNAs in which CDRs of VH and VL of a human antibody are replaced with CDRs of VH and VL of an antibody of a non-human animal, which specifically reacts with human VEGF receptor Flt-1, inserting them into an expression vector for animal cells having genes encoding human antibody CH and human antibody CL to construct a human CDR-grafted antibody expression vector, and then introducing the vector into cells of an animal to express the antibody of interest.

The structure of the C region of the human CDR-grafted antibody of the present invention may belong to any immunoglobulin (Ig) class, but preferably contains the C region of IgG type immunoglobulin, particularly of IgG subclasses such as IgG1, IgG2, IgG3 and IgG4.

The human CDR-grafted antibody of the present invention may comprise V region complementarity-determining regions (CDRs) of H chain and L chain of a monoclonal antibody capable of specifically reacting with human VEGF receptor Flt-1, and C region and V region framework regions of H chain and L chain of a human antibody.

In the human CDR-grafted antibody of the present invention, the CDR of H chain V region of the human CDR-grafted antibody may comprise amino acid sequences of SEQ ID NOS:9, 10 and 11 or amino acid sequences of SEQ ID NOS:15, 16 and 17; and the CDR of L chain V region of the human CDR-grafted antibody may comprise amino acid sequences of SEQ ID NOS:12, 13 and 14 or amino acid sequences of SEQ ID NOS:18, 19 and 20.

Also, examples of the human CDR-grafted antibody of the present invention include a human CDR-grafted antibody wherein the CDR of H chain V region of the human CDR-grafted antibody comprises amino acid sequences of SEQ ID NOS:9, 10 and 11, and the CDR of L chain V region of the human CDR-grafted antibody comprises amino acid sequences of SEQ ID NOS:12, 13 and 14; and a human CDR-grafted antibody wherein the CDR of H chain V region of the human CDR-grafted antibody comprises amino acid sequences of SEQ ID NOS:15, 16 and 17, and the CDR of L chain V region of the human CDR-grafted antibody comprises amino acid sequences of SEQ ID NOS:18, 19 and 20.

Further examples of the human CDR-grafted antibody of the present invention include a human CDR-grafted antibody wherein the H chain V region of the human CDR-grafted antibody comprises an amino acid sequence of SEQ ID NO:90, and the L chain V region of the human CDR-grafted antibody comprises an amino acid sequence of SEQ ID NO:92; and a human CDR-grafted antibody wherein the H chain V region of the human CDR-grafted antibody comprises an amino acid sequence of SEQ ID NO:91 or 95, and the L chain V region of the human CDR-grafted antibody comprises an amino acid sequence of SEQ ID NO:93, 94 or 96.

Specific examples of the human CDR-grafted antibody of the present invention include human CDR-grafted antibody KM8550, human CDR-grafted antibody KM8551, human CDR-grafted antibody KM8552, human CDR-grafted antibody KM8553, human CDR-grafted antibody KM8554, and human CDR-grafted antibody KM8555.

In addition, the present invention includes a DNA which encodes any one of the human CDR-grafted antibodies.

According to the present invention, a recombinant vector comprising the above DNA and tandem cassette vector pKANTEX93 can be provided; a transformant can be obtained by introducing the recombinant vector into a host cell; and the human CDR-grafted antibody can be prepared by culturing the transformant in a medium to produce and accumulate a CDR-grafted antibody in a culture, and recovering the antibody from the resulting culture.

The anti-human VEGF receptor Flt-1 antibody of the present invention may be an antibody fragment selected from the group consisting of Fab, Fab', F(ab')$_2$, scFv, and dsFv.

The Fab is a fragment having a molecular weight of about 50,000 and antigen-binding activity which comprises about half of the N-terminal side of H chain and a full portion of L chain obtained by digesting, with papain, the peptide moiety of the upper side of two disulfide bonds that crosslink two H chains at the hinge region of IgG.

The Fab of the present invention can be obtained by treating an anti-human VEGF receptor Flt-1 antibody with papain. Alternatively, the Fab can be produced by inserting a DNA fragment which encodes the Fab fragment of the antibody into an expression vector for animal cells, and introducing the vector into cells of an animal to express the antibody of interest.

The Fab' is a fragment of about 50,000 in molecular weight having antigen-binding ability which is obtained by hydrolyzing the disulfide bond between hinges of the above-described F(ab')$_2$.

The Fab' of the present invention can be obtained by treating an anti-human VEGF receptor Flt-1 antibody with a reducing agent such as dithiothreitol. Alternatively, the Fab' can be produced by inserting a DNA fragment which encodes the Fab' fragment of the antibody into an expression vector for animal cells, and introducing the vector into cells of an animal to express the antibody of interest.

The F(ab')$_2$ of the present invention is a fragment having a molecular weight of about 100,000 and antigen-binding ability, comprising two Fab regions bonded at the hinge part, which is obtained by hydrolyzing, with trypsin, the lower side of two disulfide bonds at the hinge region of IgG.

The F(ab')$_2$ of the present invention can be obtained by treating an anti-human VEGF receptor Flt-1 antibody with trypsin. Alternatively, F(ab')$_2$ can be produced by inserting a DNA fragment which encodes the F(ab')$_2$ fragment of the antibody into an expression vector for animal cells, and introducing the vector into cells of an animal to express the antibody of interest.

The anti-human VEGF receptor Flt-1 antibody of the present invention may be scFv comprising H chain V region and L chain V region of an antibody.

The scFv of the present invention means a VH—P—VL or VL—P—VH polypeptide obtained by linking a VH chain with a VL chain using an appropriate peptide linker (hereinafter referred to as "P"). The VH and VL of the scFv of the present invention may be any of the monoclonal antibody and human CDR-grafted antibody of the present invention.

The scFv of the present invention can be prepared by preparing cDNAs encoding VH and VL from a hybridoma capable of producing an anti-human VEGF receptor Flt-1 antibody to construct an scFv expression vector, inserting the cDNAs into the scFv expression vector, and introducing the expression vector into cells of *Escherichia coli*, a yeast or an animal to express the antibody of interest.

In the scFv of the present invention, the H chain V region and the L chain V region of the scFv may comprise an amino acid sequence which is the same as an amino acid sequence of H chain V region and L chain V region, respectively, of a monoclonal antibody which specifically reacts with human VEGF receptor Flt-1; or the H chain V region and the L chain V region of the scFv may comprise CDR comprising an amino acid sequence which is the same as an amino acid sequence of CDR of H chain V region and L chain V region, respectively, of a monoclonal antibody which specifically reacts with human VEGF receptor Flt-1.

Also, in the scFv of the present invention, the H chain V region and the L chain V region of the scFv may comprise an amino acid sequences of SEQ ID NOS:86 and 87, respectively; or the H chain V region and the L chain V region of the scFv may comprise an amino acid sequence of SEQ ID NOS:88 and 89, respectively.

Examples of the scFv of the present invention include scFv wherein the CDR of the H chain V region of the scFv comprises amino acid sequences of SEQ ID NOS:9, 10 and 11, and the CDR of the L chain V region of the scFv comprises amino acid sequences of SEQ ID NOS:12, 13 and 14; and scFv wherein the CDR of the H chain V region of the scFv comprises amino acid sequences of SEQ ID NOS: 15, 16 and 17, and the CDR of the L chain V region of the scFv comprises amino acid sequences of SEQ ID NOS:18, 19 and 20.

Further examples of the scFv of the present invention include scFv wherein the H chain V region of the scFv comprises an amino acid sequence of SEQ ID NO:90, and the L chain V region of the scFv comprises an amino acid sequence of SEQ ID NO:92; and scFv wherein the H chain V region of the scFv comprises an amino acid sequence of SEQ ID NO:91 or 95, and the L chain V region of the scFv comprises an amino acid sequence of SEQ ID NO:93, 94 or 96.

The anti-human VEGF receptor Flt-1 antibody may be dsFv comprising H chain V region and L chain V region of an antibody.

The dsFv means an antibody obtained by bonding, via a disulfide bond, polypeptides in which one amino acid residue in each of VH and VL is replaced with a cysteine residue. The amino acid residue to be replaced with a cysteine residue can be selected based on the three-dimensional structure estimation of antibodies in accordance with the method reported by Reiter et al. [*Protein Engineering*, 7: 697 (1994)]. The VH or VL contained in the dsFv of the present invention may be any of the monoclonal antibody and human CDR-grafted antibody of the present invention.

The dsFv of the present invention can be prepared by preparing cDNAs encoding VH and VL from a hybridoma capable of producing an anti-human VEGF receptor Flt-1 antibody, inserting the cDNAs into an appropriate expression vector, introducing the expression vector into cells of *Escherichia coli*, a yeast, an animal or the like to express the antibody of interest.

In the dsFv of the present invention, the H chain V region and the L chain V region of the dsFv may comprise an amino acid sequence which is the same as an amino acid sequence of H chain V region and L chain V region, respectively, of a monoclonal antibody which specifically reacts with human VEGF receptor Flt-1; or the H chain V region and the L chain V region of the sdFv may comprise CDR comprising an amino acid sequence which is the same as an amino acid sequence of CDR of H chain V region and L chain V region, respectively, of a monoclonal antibody which specifically reacts with human VEGF receptor Flt-1.

Also, in the dsFv of the present invention, the H chain V region and the L chain V region of the dsFv may comprise an amino acid sequence of SEQ ID NOS:86 and 87, respectively; or the H chain V region and the L chain V region of the dsFv may comprise an amino acid sequence which is the same as an amino acid sequence of SEQ ID NOS:88 and 89, respectively.

Examples of the dsFv of the present invention include dsFv wherein the CDR of the H chain V region of the dsFv comprises amino acid sequences of SEQ ID NOS:9, 10 and 11, and the CDR of the L chain V region of the dsFv comprises amino acid sequences of SEQ ID NOS:12, 13 and 14; and dsFv wherein the CDR of the H chain V region of the dsFv comprises amino acid sequences of SEQ ID NOS:15, 16 and 17, and the CDR of the L chain V region of the dsFv comprises amino acid sequences of SEQ ID NOS:18, 19 and 20.

Further examples of the dsFv of the present invention include dsFv wherein the H chain V region of the dsFv comprises an amino acid sequence of SEQ ID NO:90, and the L chain V region of the dsFv comprises an amino acid sequence of SEQ ID NO:92; and dsFv wherein the H chain V region of the dsFv comprises an amino acid sequence of SEQ ID NO:91 or 95, and the L chain V region of the dsFv comprises an amino acid sequence of SEQ ID NO:93, 94 or 96.

Still furthermore, the present invention relates to a peptide comprising amino acids selected from CDRs of H chain and L chain of an antibody, which specifically reacts with human VEGF receptor Flt-1, such as a peptide comprising an amino acid sequence selected from amino acid sequences of SEQ ID NOS:9, 10, 11, 12, 13 and 14, and a peptide comprising an amino acid sequence selected from amino acid sequences of SEQ ID NOS:15, 16, 17, 18, 19 and 20.

Still moreover, the present invention relates to a fusion antibody or a fusion peptide which is an antibody or a peptide chemically or gene-engineeringly linked with a radioisotope, a protein or a low molecular agent.

The fusion antibody and the fusion peptide of the present invention can be produced by chemically linking a radioactive isotope, a protein or a low molecular agent with the antibody or peptide which specifically reacts with human VEGF receptor Flt-1 of the present invention. In the case of a fusion antibody or a fusion peptide with a protein, it can be produced by connecting an antibody- or a peptide-encoding cDNA to a protein-encoding cDNA, inserting the thus ligated cDNA into an appropriate expression vector, and expressing the expression vector in cells of *Escherichia coli*, a yeast, an animal or the like.

In addition, the present invention relates to the following methods:

- a method for immunologically detecting human VEGF receptor Flt-1, comprising reacting human VEGF receptor Flt-1 with the antibody or peptide of the present invention;
- a method for immunologically detecting cells in which human VEGF receptor Flt-1 is expressed on the surface thereof, comprising reacting human VEGF receptor Flt-1 with the antibody or peptide of the present invention;
- a method for inhibiting binding of human VEGF to human VEGF receptor Flt-1, comprising reacting human VEGF receptor Flt-1 with the antibody or peptide of the present invention;
- a method for inhibiting biological activities of human VEGF, comprising reacting human VEGF receptor Flt-1 with the antibody or peptide of the present invention;
- a method for detecting a disease in which the morbid states progress by abnormal angiogenesis, comprising reacting a sample with the antibody or peptide of the present invention; and
- a method for preventing or treating a disease, comprising the step of administering to human or animal in need of such prevention or treatment an effective amount of the antibody or peptide of the present invention.

In the above method for immunologically detecting human VEGF receptor Flt-1, the human VEGF receptor Flt-1 may be soluble.

In the above method for inhibiting biological activities of human VEGF, for example, the activity of human VEGF receptor Flt-1 is inhibited.

In the above method for detecting a disease, for example, the method may comprise (a) separating human cell or a crushing solution thereof, tissue or a crushing solution thereof, serum, pleural fluid, ascites fluid, or ocular fluid to prepare a sample, (b) reacting the separated sample prepared in the step (a) with the monoclonal antibody or peptide of the present invention, (c) further reacting the reacted sample prepared in the step (b) with a labeled anti-mouse IgG antibody or binding fragment, and (d) measuring or observing the labeled sample prepared in the step (c).

In the above method for preventing or treating a disease, examples of the disease include diseases in which the morbid states progress by abnormal angiogenesis.

Examples of the diseases in which their morbid states progress by abnormal angiogenesis include proliferation or metastasis of solid tumor, arthritis in chronic rheumatoid arthritis, diabetic retinopathy, retinopathy of prematurity, and psoriasis. Examples of the solid tumor include breast cancer, prostatic cancer, large bowel cancer, gastric cancer and lung cancer.

Besides, the present invention relates to a composition comprising the antibody or peptide of the present invention and a diagnostic or pharmaceutical acceptable carrier.

The present invention is discussed below in more detail.

The production method of the anti-human VEGF receptor Flt-1 antibody of the present invention is described below.

1. Production Method of Anti-Human VEGF Receptor Flt-1 Monoclonal Antibody (1) Preparation of Antigen Examples of the substance useful as the antigen for the preparation of the anti-human VEGF receptor Flt-1 monoclonal antibody include cells in which human VEGF receptor Flt-1 is expressed on the cell surface or a cell membrane fraction thereof, soluble human VEGF receptor Flt-1 protein having an extracellular region of different length and a fusion protein of the protein with Fc region of the antibody. As the cells capable of expressing human VEGF receptor Flt-1 on the cell surface, NIH3T3-Flt-1 cells [*Oncogene*, 10: 135 (1995)] can be exemplified. In a method for expressing the antigen as soluble human VEGF receptor Flt-1 protein having an extracellular region of different length or a fusion protein of the protein with Fc region of the antibody, the whole length or a partial fragment of cDNA which encodes human VEGF receptor Flt-1 [*Oncogene*, 5: 519 (1990); *Abstract of Papers, the 18th Annual meeting of Japan Molecular Biology Society*, 2P-227 (December, 1995)] is inserted into a downstream site of the promoter of an appropriate vector, the thus constructed recombinant vector is inserted into host cells and the thus obtained human VEGF receptor Flt-1 expression cells are cultured in an appropriate medium, thereby producing the whole length of a partial fragment of human VEGF receptor Flt-1 in the cells or culture supernatant as such or as a fusion protein.

As the host cells, any one of bacteria, yeast, animal cells, insect cells and the like can be used so long as they can express the gene of interest. Examples of the bacteria include the genus *Escherichia*, the genus *Bacillus* and the like, such as *Escherichia coli*, *Bacillus subtilis* and the like. Examples of the yeast include *Saccharomyces cerevisiae*, *Schizosaccharomyces pompe* and the like. Examples of the animal cells include namalwa cells which are human cells, COS cells which are monkey cells and CHO cells which are Chinese hamster cells. Examples of the insect cells include Sf9 and Sf21 (manufactured by Pharmingen), High Five (manufactured by Invitrogen) and the like.

When a bacterium such as *Escherichia coli* is used as the host, the expression vector may be preferably constructed with a promoter, a ribosome binding sequence, the DNA of the present invention, a transcription termination sequence and, as occasion demands, a promoter controlling sequence. Examples include commercially available pGEX (manufactured by Pharmacia), pET System (manufactured by Novagen) and the like.

With regard to the method for introducing the recombinant vector into a bacterium, any one of the known methods for introducing DNA into bacteria, such as a method in which calcium ion is used [*Proc. Natl. Acad. Sci. USA,* 69: 2110–2114 (1972)], a protoplast method (Japanese Published Unexamined Patent Application No. 2483942/91), and the like can be used.

When yeast is used as the host, YEp13 (ATCC 37115), YEp24 (ATCC 37051), YCp50 (ATCC 37419), or the like is used as the expression vector.

With regard to the method for introducing the recombinant vector into yeast, any one of the known methods for introducing DNA into yeast, such as an electroporation method [*Methods. Enzymol.,* 194: 182–187 (1990)], a spheroplast method [*Proc. Natl. Acad. Sci. USA,* 84: 1929–1933 (1978)], a lithium acetate method [*J. Bacteriol.,* 153: 163–168 (1983)], and the like can be used.

When animal cells are used as the host, pAGE107 [Japanese Published Unexamined Patent Application No. 22979/88; *Cytotechnology,* 3: 133 (1990)], pAGE103 [*J. Biochem.,* 101: 1307 (1987)], and the like can be exemplified as the useful expression vector.

Any promoter capable of carrying out the expression in animal cells can be used. Examples include the promoter of IE (immediate early) gene of cytomegalovirus (CMV), the SV40 promoter, the metallothionein promoter and the like. Furthermore, the enhancer of the IE gene of human CMV may be used together with the promoter.

With regard to the method for the introduction of the recombinant vector into animal cells, any one of the known methods for introducing DNA into animal cells, such as an electroporation method [*Cytotechnology,* 3: 133 (1990)], a calcium phosphate method (Japanese Published Unexamined Patent Application No. 227075/90), a lipofection method [*Proc. Natl. Acad. Sci. USA,* 84: 7413 (1987)] and the like can be used.

When insect cells are used as the host, the protein can be expressed by the known method described in, for example, *Current Protocols in Molecular Biology,* Supplement 1–34 and Baculovirus expression vectors, A laboratory manual. That is, the recombinant gene introducing vector and baculovirus described in the following are simultaneously introduced into insect cells to obtain a recombinant virus in the insect cell culture supernatant and then the insect cells are infected with the thus obtained recombinant virus to obtain protein-expressing insect cells.

Examples of the gene introducing vector include pVL1392, pVL1393, pBlueBacIII (all manufactured by Invitrogen), and the like.

Examples of the baculovirus include Autograph californica nuclear polyhedrosis virus with which insects of the family Barathra are infected.

With regard to the method for the simultaneous introduction of the above-described recombinant gene introducing vector and the above-described baculovirus into insect cells for the preparation of the recombinant virus, calcium phosphate method (Japanese Published Unexamined Patent Application No. 227075/90), lipofection method [*Proc. Natl. Acad. Sci. USA,* 84: 7413 (1987)] and the like can be exemplified.

Alternatively, the protein of interest can be produced by preparing a recombinant baculovirus making use, for example, of BaculoGold Starter Kit manufactured by Pharmigen and then infecting the above-described insect cells, such as Sf9, Sf21, High Five, or the like, with the recombinant virus [*Bio/Technology,* 6: 47 (1988)].

With regard to the gene expression method, techniques, such as secretion production, fusion protein expression and the like have been developed, and each of these every methods can be used. For example, gene expression can be produced in accordance with the method described in *Molecular Cloning* 2nd edition, Cold Spring Harbor Lab. Press, New York (1989), or by direct expression.

The whole length or a partial fragment of a human VEGF receptor Flt-1 can be produced as such or as a fusion protein thereof by culturing a transformant obtained in the above-described manner in a culture medium to form and accumulate the protein of the present invention in the resulting culture mixture, and then collecting the protein from the culture mixture.

Culturing of the transformant of the present invention in a culture medium is carried out in accordance with a usual method which is used in the culturing of respective host cells.

With regard to the medium for use in the culturing of the transformant obtained using a microorganism, such as *Escherichia coli*, yeast, or the like, as the host, either a natural medium or a synthetic medium may be used, so long as it contains materials which can be assimilated by the microorganism, such as carbon sources, nitrogen sources, inorganic salts, and the like, and can perform culturing of the transformant efficiently [*Molecular Cloning 2nd edition*, Cold Spring Harbor Lab. Press, New York (1989)]. The culturing is carried out generally under aerobic conditions, such as a shaking culture, submerged agitation aeration culture, or the like, at 15 to 40° C. for 16 to 96 hours. During the culturing, the pH is controlled to 3.0 to 9.0. Adjustment of the pH is carried out using an inorganic or organic acid, an alkali solution, urea, calcium carbonate, ammonia, and the like. As occasion demands, antibiotics, such as ampicillin, tetracycline, and the like may be added to the medium during the culturing.

With regard to the medium for use in the culturing of a transformant obtained using animal cells as the host, RPMI 1640 medium, Eagle's MEM medium or any one of these media further supplemented with fetal calf serum may be used. The culturing is carried out generally at 35 to 37° C. for 3 to 7 days in the presence of 5% $CO_2$. As occasion demands, antibiotics, such as kanamycin, penicillin, and the like may be added to the medium during the culturing.

With regard to the medium for use in the culturing of a transformant obtained using insect cells as the host, TNM-FH medium (manufactured by Pharmingen), Sf900IISFM (manufactured by Life Technologies), ExCell400 or ExCell405 (both manufactured by JRH Biosciences), or the like may be used. The culturing is carried out generally at 25 to 30° C. for 1 to 4 days, and gentamicin and the like antibiotics may be added to the medium during the culturing as occasion demands.

Although media for the culturing of animal cells and insect cells contain serum, it is desirable to use a serum-free medium in order to efficiently purify the whole length or a partial fragment of human VEGF receptor Flt-1 as such or as a fusion protein.

When the whole length or a partial fragment of human VEGF receptor Flt-1 is accumulated inside the host cells as such or as a fusion protein, the cells after completion of the culturing are collected by centrifugation, suspended in an aqueous buffer and then disrupted using ultrasonic oscillator, French press, or the like, and subsequently collecting the protein from a supernatant fluid prepared by centrifuging the thus disrupted cells.

Also, when an insoluble body is formed inside the cells, the insoluble body is solubilized using a protein denaturing agent and then higher-order structure of the protein is formed by diluting or dialyzing the thus solubilized protein in or against a solution which does not contain the protein denaturing agent or contains the agent but in such a low concentration that the protein is not denatured.

When the whole length or a partial fragment of human VEGF receptor Flt-1 is secreted outside the cells as such or as a fusion protein, the expressed protein can be collected from the culture supernatant. The isolation and purification can be carried out by employing separation means, such as solvent extraction, fractional precipitation with organic solvents, salting out, dialysis, centrifugation, ultracentrifugation, ion exchange chromatography, gel filtration chromatography, hydrophobic chromatography, affinity chromatography, reverse phase chromatography, crystallization, electrophoresis, and the like, alone or in combination.

(2) Immunization of Animals and Preparation of Antibody Producing Cells

Although any one of animals, such as mice, rats, hamsters, rabbits, and the like, can be used in the immunization, so long as a hybridoma can be prepared, an example in which mice and rats are used is described in this invention. A mouse or rat of 3 to 20 weeks of age is immunized with the protein obtained in the above step 1-(1) as the antigen, and antibody producing cells are collected from the spleen, lymph node or peripheral blood of the animal. The immunization is carried out by administering the antigen several times through subcutaneous, intravenous or intraperitoneal injection together with an appropriate adjuvant. As the adjuvant, a complete Freund's adjuvant or a combination of aluminum hydroxide gel with pertussis vaccine can be exemplified. A blood sample is collected from the fundus of the eye or caudal vein of the animal 3 to 7 days after each administration, the sample is tested, for example, by enzyme immunoassay [Enzyme-linked Immunosorbent Assay (ELISA), published by Igaku Shoin, (1976)] as to whether it is reactive with the antigen used, namely soluble human VEGF receptor Flt-1 or NIH3T3 cells in which human VEGF receptor Flt-1 is expressed on the cell surface, and then a mouse or rat showing sufficient antibody titer in their sera is submitted for use as the supply source of antibody producing cells. On the 3rd to 7th day after final administration of the antigen, the spleen is excised from the immunized mouse or rat to carry out fusion of the spleen cells with myeloma cells in accordance with the known method [*Antibodies—A Laboratory Manual*, Cold Spring Harbor Laboratory, (1988); referred to as "*Antibodies—A Laboratory Manual*" hereinafter).

(3) Preparation of Myeloma Cells

As the myeloma cells, any myeloma cells capable of growing in vitro may be used, which include established cells obtained from mouse, such as 8-azaguanine-resistant mouse (BALB/c) myeloma cell line P3-X63Ag8-U1 (P3-U1) [G. Kohler et al., *Europ. J. Immunol*, 6: 511 (1976)], SP2/O—Ag14 (SP-2) [M. Shulman et al., *Nature*, 276: 269 (1978)], P3-X63-Ag8653 (653) [J. F. Kearney et al., *J. Immunol.*, 123: 1548 (1979)], P3-X63-Ag8 (X63) [G. Kohler et al., *Nature*, 256: 495 (1975)], and the like. These cell lines are cultured and subcultured in accordance with the known method (*Antibodies—A Laboratory Manual*) and $2 \times 10^7$ or more of the cells are secured until cell fusion.

(4) Cell Fusion

The antibody producing cells obtained in the above step (2) and the myeloma cells obtained in the above step (3) are washed, mixed with cell aggregating medium, polyethylene glycol-1000 (PEG-1000) or the like, to carry out cell fusion and then suspended in a culture medium. For the washing of the cells, MEM medium or PBS (1.83 g of disodium hydrogen phosphate, 0.21 g of potassium dihydrogen phosphate, 7.65 g of sodium chloride, 1 liter of distilled water, pH 7.2) is used. In order to obtain the fused cells of interest selectively, HAT medium {normal medium [a medium prepared by adding glutamine (1.5 mM), 2-mercaptoethanol ($5 \times 10^{-5}$ M), gentamicin (10 µg/ml) and fetal calf serum (FCS) (10%, produced by CSL) to RPMI-1640 medium] further supplemented with hypoxanthine ($10^{-4}$ M), thymidine ($1.5 \times 10^{-5}$ M) and aminopterin ($4 \times 10^{-7}$ M)} is used as the medium for suspending the fused cells.

After the culturing, a portion of the culture supernatant is sampled and tested, for example, by an enzyme immunoassay method which will be described in the following step (5) to select wells which can specifically react with human VEGF receptor Flt-1 or a recombinant protein such as a fusion protein with human VEGF receptor Flt-1 described in the above step (1). Thereafter, cloning is carried out twice by limiting dilution analysis [using HT medium (a medium prepared by eliminating aminopterin from the HAT medium) for the first analysis and the normal medium for the second analysis], and a hybridoma which shows stable and high antibody titer is selected as the hybridoma capable of producing the anti-human VEGF receptor Flt-1 monoclonal antibody.

(5) Selection of Anti-Human VEGF Receptor Flt-1 Monoclonal Antibody

Selection of a hybridoma capable of producing the anti-human VEGF receptor Flt-1 monoclonal antibody is carried out by the enzyme immunoassay method described below.

Enzyme Immunoassay

Human VEGF receptor Flt-1 or a recombinant protein such as a fusion protein with the human VEGF receptor Flt-1 described in the above step 1-(1) is coated on an appropriate plate and allowed to react with a first antibody, namely a hybridoma culture supernatant or a purified antibody obtained in the following step 1-(6), and then with a second antibody, namely an anti-mouse immunoglobulin antibody or anti-rat immunoglobulin antibody labeled with biotin, an enzyme, a chemiluminescent substance, a radioactive compound or the like, and then a reaction suitable for the label used is carried out in order to select a sample which specifically reacts with human VEGF receptor Flt-1 as a hybridoma capable of producing anti-human VEGF receptor Flt-1 monoclonal antibody. Examples of the hybridoma include hybridomas KM1730, KM1731, KM1732, KM1748 and KM1750. The hybridomas KM1730, KM1732, KM1748 and KM1750, on Oct. 8, 1996, and the hybridoma KM1731, on Oct. 22, 1996, were deposited with National Institute of Bioscience and Human Technology, Agency of Industrial Science and Technology (Higashi 1-1-3, Tsukuba-shi, Ibaraki, Japan), and were assigned the designations as FERM BP-5697, FERM BP-5698, FERM BP-5699, FERM BP-5700 and FERM BP-5718, respectively.

(6) Preparation of Monoclonal Antibody

The anti-human VEGF receptor Flt-1 monoclonal antibody-producing hybridoma cells obtained in the above-described step 1-(3) are administered by intraperitoneal injection into 8- to 10-week-old mice or nude mice treated with pristane [by intraperitoneal administration of 0.5 ml of 2,6,10,14-tetramethylpentadecane (pristane) followed by 2 weeks of feeding] at a dose of $2 \times 10^7$ to $5 \times 10^6$ cells/animal. The hybridoma causes ascites tumor in 10 to 21 days. The ascitic fluid is collected from the mice or nude mice, centrifuged, subjected to salting out with 40 to 50% saturated ammonium sulfate or to caprylic acid precipitation and then passed through a DEAE-Sepharose column, protein A column or Cellulofine GSL 2000 (manufactured by Seikagaku Kogyo) to collect an IgG or IgM fraction to give a purified monoclonal antibody.

The subclass of the purified monoclonal antibody can be determined using a mouse monoclonal antibody typing kit or a rat monoclonal antibody typing kit. The amount of protein can be determined by the Lowry method or by calculation based on the optical density at 280 nm.

The term "subclass of antibody" as used herein means isotypes within the class, such as IgG1, IgG2a, IgG2b and IgG3 in the case of mouse, and IgG1, IgG2, IgG3 and IgG4 in the case of human. The mouse IgG1 and IgG2a and human IgG1 types have complement-dependent cytotoxicity (hereinafter referred to as "CDC") and antibody-dependent cellular cytotoxicity (hereinafter referred to as "ADCC"), so that they are useful in applying to medical treatments.

2. Production of Recombinant Antibody (I)—Anti-Human VEGF Receptor Flt-1 Humanized Antibody (1) Construction of Humanized Antibody Expression Vector In order to produce a humanized antibody from a non-human animal antibody, a humanized antibody expression vector is prepared. The humanized antibody expression vector is a vector for expression in animal cells into which a gene encoding CH and CL, C regions of a human antibody, have been inserted. Such an expression vector is constructed by inserting two genes, one encoding CH of a human antibody and the other encoding CL of a human antibody, into an expression vector for animal cells.

Any C regions of a human antibody such as Cγ1 and Cγ4 of a human antibody H chain, Cκ of a human antibody L chain and the like can be used. A chromosomal DNA consisting of an exon(s) and an intron(s) or cDNA can be used as a gene encoding a C region of a human antibody. Any expression vectors can be used as expression vectors for animal cells, provided that they can incorporate and express a gene encoding a C region of a human antibody.

Examples include pAGE107 [*Cytotechnology*, 3: 133 (1990)], pAGE103 [*J. Biochem.*, 101: 1307 (1987)], pHSG274 [*Gene*, 27: 223 (1984)], pKCR [*Proc. Natl. Acad. Sci. USA*, 78: 1527 (1981)] and pSGI βd2-4 [*Cytotechnology*, 4: 173 (1990)]. A promoter and an enhancer to be used in preparation of an expression vector for animal cells are exemplified by an SV40 early promoter and enhancer [*J. Biochem.*, 101: 1307 (1987)], a Moloney mouse leukemia virus LTR promoter and enhancer [*Biochem. Biophys. Res. Comun.*, 149: 960 (1987)], an immunoglobulin H chain promoter [*Cell*, 41: 479 (1985)] and enhancer [*Cell*, 33: 717 (1983)], and the like.

The humanized antibody expression vector may be either of a type in which a gene encoding an antibody H chain and a gene encoding an antibody L chain exist on separate vectors or of a type in which both genes exist on the same vector (tandem type). In terms of ease of construction of a humanized antibody expression vector, easiness of introduction into animal cells, balance between the expression amounts of antibody H and L chains in the animal cells and for other reasons, a tandem type of humanized antibody expression vector is more preferred [*J. Immunol. Methods*, 167: 271 (1994)].

(2) Preparation of cDNA Encoding VH and VL of Non-Human Animal Antibody cDNA encoding VH and VL of a non-human animal antibody such as a mouse anti-human VEGF receptor Flt-1 monoclonal antibody is obtained, for example, as follows:

mRNA is extracted from an anti-human VEGF receptor Flt-1 monoclonal antibody-producing cell such as a mouse anti-human VEGF receptor Flt-1 antibody-producing hybridoma and used to synthesize cDNA. The synthesized cDNA is inserted into a vector such as a phage or a plasmid to prepare a cDNA library. From the library, with a portion in a V or C region of a non-human animal antibody such as a mouse antibody being used as a probe, a recombinant phage or plasmid which contains cDNA encoding VH and a recombinant phage or plasmid which contains cDNA encoding VL are isolated separately. The full nucleotide sequences of VH and VL of an antibody of interest which exist on the recombinant phage or plasmid are determined and the full amino acid sequences of the VH and VL are deduced from the nucleotide sequences.

(3) Construction of Human Chimeric Antibody Expression Vector

A human chimeric antibody expression vector can be constructed by inserting cDNA encoding VH and VL of a non-human animal antibody in a region upstream of the gene encoding CH and CL of the human antibody on the humanized antibody expression vector which has been constructed in 2(1). For example, a restriction enzyme recognition site for cloning of cDNA encoding VH and VL of a non-human animal antibody is created preliminarily in a region upstream of a gene encoding CH and CL of the human antibody on a chimeric antibody expression vector. At the cloning site, cDNA encoding a V region of a non-human animal antibody is inserted through a synthetic DNA (see below) to prepare a human chimeric antibody expression vector. The synthetic DNA consists of a nucleotide sequence at the 3' end of a V region of the non-human animal and a nucleotide sequence at the 5' end of a C region of the human antibody and are prepared by a DNA synthesizer such that it has appropriate restriction enzyme sites at both ends.

(4) Identification of CDR Sequences of Non-Human Animal Antibody

VH and VL which form an antigen-binding site of an antibody consist of 4 framework regions (hereinafter referred to as "FR regions") having relatively conserved sequences and 3 complementarity-determining regions (CDRs) having a wide variety of sequences which link the FR regions [*Sequences of Proteins of Immunological Interest*, US Dept. Health and Human Services (1991) (hereinafter referred to as "*Sequences of Proteins of Immunological Interest*"]. The amino acid sequence of the respective CDR (CDR sequence) can be identified by comparison with the amino acid sequences of V regions of known antibodies (Sequences of Proteins of Immunological Interest).

(5) Construction of cDNA Encoding V Region of Human CDR-Grafted Antibody cDNA encoding VH and VL of a human CDR-grafted antibody can be obtained as follows:

In the first step, for each of VH and VL, the amino acid sequence of FR in a V region of a human antibody to which CDR in a V region of a non-human animal antibody of interest is to be grafted is selected. Any amino acid sequences of FRs in V regions derived from human antibodies can be used as the amino acid sequences of FRs in V regions of human antibodies.

For example, the amino acid sequences of FRs in V regions of human antibodies recorded in Protein Data Bank and amino acid sequences common to subgroups of FRs in V regions of human antibodies (Sequences of Proteins of Immunological Interest) can be used. In order to produce a human CDR-grafted antibody having an excellent activity, an amino acid sequence having high homology, preferably homology of 65% or more, with the amino acid sequence of a V region of a non-human animal antibody of interest is desired. In the second step, a DNA sequence encoding the selected amino acid sequence of FR in a V region of a human antibody is ligated to a DNA sequence encoding the amino acid sequence of CDR in a V region of a non-human animal antibody and a DNA sequence encoding the amino acid sequences of VH and VL is desired. In order to obtain a DNA sequence designed to construct a CDR-grafted antibody variable region gene, several synthetic DNAs are designed for each chain such that the full DNA sequence is covered. Using the synthetic DNAs, polymerase chain reaction (hereinafter referred to as "PCR") is performed. For each chain, preferably 6 synthetic DNAs are designed in view of the reaction efficiency of PCR and the lengths of DNAs which can be synthesized. After the reaction, amplified fragments are subcloned into appropriate vectors and their nucleotide sequences are determined to obtain a plasmid which contains cDNA encoding the amino acid sequence of a V region of each chain of a human CDR-grafted antibody of interest. Alternatively, cDNA encoding the amino sequence of a V region of each chain of a human CDR-grafted antibody of interest may be constructed by synthesizing the full sequences of sense and antisense strand using synthetic DNAs consisting of about 100 bases and annealing and ligating them.

(6) Modification of the Amino Acid Sequence of V Region of Human CDR-Grafted Antibody It is known that if a human CDR-grafted antibody is prepared by simply grafting only CDR in a V region of a non-human animal antibody of interest between FRs in a V region of a human antibody, its activity is lower than that of the original non-human animal antibody [*BIO/TECHNOLOGY*, 9: 266 (1991)]. Hence, among the amino acid sequences of FR in a V region of a human antibody, an amino acid residue which takes part in direct binding to an antigen, an amino acid residue which interacts with an amino acid residue in CDR, or an amino acid residue which may take part in the maintenance of the steric structure of an antibody is modified to an amino acid residue that is found in the original non-human animal antibody such that the activity of the human CDR-grafted antibody is increased. For efficient identification of the amino acid residue, the steric structure of an antibody is constructed and analyzed by X-ray crystallography, computer-modeling or the like. However, no method for producing a human CDR-grafted antibody which can be applied to any antibodies has yet been established and, therefore, various attempts must currently be made on a case-by-case basis.

The modification of the selected amino acid sequence of FR in a V region of a human antibody can be accomplished using various primers for mutation by PCR described in 2(5). Amplified fragments obtained by the PCR are subcloned into appropriate vectors and their nucleotide sequences are determined to obtain a vector containing cDNA into which a mutation of interest has been introduced (hereinafter referred to as "amino acid sequence-replaced vector").

Alternatively, the modification of an amino acid sequence in a narrow region may be accomplished by a PCR-mutagenesis method using primers for mutation consisting of 20–35 bases. More specifically, a sense mutation primer and an antisense mutation primer which consist of 20 to 35 bases and which contain DNA sequences encoding the amino acid residue to be modified are synthesized and used to perform 2-step PCR using as a plasmid as a template which contains cDNA encoding the amino acid sequence of a V region which is to be modified. The finally amplified fragments are subcloned into appropriate vectors and their nucleotide sequences are determined to obtain an amino acid sequence-modified vector containing cDNA into which a mutation of interest has been introduced.

(7) Construction of Human CDR-Grafted Antibody Expression Vector

A human CDR-grafted antibody expression vector can be constructed by inserting the cDNA encoding VH and VL of the human CDR-grafted antibody obtained in 2(5) and 2(6) in a region upstream of the gene encoding CH and CL of the human antibody in the humanized antibody expression vector described in 2(1). For example, if recognition sites for appropriate enzymes are introduced at the ends of the 5' and 3' terminal synthetic DNAs during PCR for construction of cDNA encoding the amino acid sequences of VH and VL of the human CDR-grafted antibody, the cDNA can be inserted in a region upstream of a gene encoding a C region of a desired human antibody such that it is expressed in an appropriate form.

(8) Transient Expression of Humanized Antibodies and Evaluation of their Activities In order to evaluate the activities of a wide variety of humanized antibodies efficiently, the human chimeric antibody expression vector described in 2(3), and the human CDR-grafted antibody expression vector described in 2(7) or their modified vectors may be transfected into COS-7 cells (ATCC CRL 1651) and humanized antibodies expressed transiently [*Methods in Nucleic Acids Res.*, CRC Press, p. 283, (1991)], followed by determination of their activities.

Examples of the method for transfecting the expression vector into a COS-7 cell include a DEAE-dextran method [*Methods in Nucleic Acids Res.*, CRC Press, p. 283, (1991)], a lipofection method [*Proc. Natl. Acad. Sci. USA*, 84: 7413 (1987)] and the like.

After transfection of the vector, the activities of the humanized antibodies in the culture supernatant can be determined by the enzyme immunoassay (ELISA) described in 1(5) and the like.

(9) Stable Expression of Humanized Antibodies and Evaluation of their Activities Transformants which produce a humanized antibody stably can be obtained by transfecting into appropriate host cells the human chimeric antibody expression vector described in 2(3) and the human CDR-grafted antibody expression vector described in 2(7).

Examples of the method for transfecting the expression vector into host cells include electroporation (Japanese Published Unexamined Patent Application No. 257891/90, *Cytotechnology*, 3: 133 (1990)] and the like.

Any cells can be used as host cells into which the humanized antibody expression vector is to be transfected, provided that they can express a humanized antibody. Examples include mouse SP2/0-Ag14 cell (ATCC CRL1581), mouse P3×63-Ag8.653 cell (ATCC CRL1580), CHO cells which are detective in dihydrofolate reductase gene (hereinafter referred to as "DHFR gene") [*Proc. Natl. Acad. Sci. USA*, 77: 4216 (1980)] and rat YB2/3HL.P2.G11.16Ag.20 cell (ATCC CRL1662, hereinafter referred to as "YB2/0 cell").

After transfection of the vector, transformants which express a humanized antibody stably are selected in accordance with the method disclosed in Japanese Published Unexamined Patent Application No. 257891/90, using an RPMI1640 medium containing G418 and FCS. The humanized antibody can be produced and accumulated in a culture medium by culturing the selected transformants in a medium. The activity of the humanized antibody in the culture medium is determined by the method described in 1(5) or the like. The production of the humanized antibody by the transformants can be increased by the method described in Japanese Published Unexamined Patent Application No. 257891/90, utilizing a DHFR gene-amplification system or the like.

The humanized antibody can be purified from the culture supernatant of the transformants by using a protein A column [*Antibodies, A Laboratory Manual*, Cold Spring harbor, Chapter 8 (1988)]. Any other conventional methods for protein purification can be used. For example, the humanized antibody can be purified by a combination of gel filtration, ion-exchange chromatography, ultrafiltration and the like. The molecular weight of the H chain or L chain of the purified humanized antibody or the antibody molecule as a whole is determined by polyacrylamide gel electrophoresis (SDS-PAGE) [*Nature*, 227: 680, (1970)], Western blotting [*Antibodies, A Laboratory Manual*, Cold Spring Harbor Laboratory, Chapter 12 (1988)] and the like.

The reactivity of the purified humanized antibody and the inhibition activity of the humanized antibody against human VEGF receptor Flt-1 can be determined by the method described in 1(5).

3. Method of Use of Recombinant Antibody (II)

(1) Preparation Method of Antibody Fragments, Fab, Fab' and F(ab')$_2$

Antibody fragments are formed by treating the above antibody with an enzyme. Examples of the enzyme include papain and trypsin.

Alternatively, Fab, Fab' or F(ab')$_2$ can also be produced by inserting a DNA fragment which encodes the Fab, Fab' or F(ab')$_2$ fragment of the anti-human VEGF receptor Flt-1 antibody into an expression vector for animal cells and introducing the vector into cells of an animal to express the fragment of interest.

The thus formed antibody fragments can be purified by carrying out suitable combination of techniques such as gel filtration, ion exchange chromatography, affinity chromatography and ultrafiltration. Molecular weight of the thus purified Fab, Fab' or F(ab')$_2$ fragment is measured by polyacrylamide gel electrophoresis (SDS-PAGE) [*Nature*, 227: 680 (1970)] or [*Antibodies, A Laboratory Manual*, Cold Spring Harbor Laboratory, Chapter 12 (1988)].

Reactivity of the thus purified Fab, Fab' or F(ab')$_2$ and binding activity of Fab, Fab' or F(ab')$_2$ upon VEGF receptor Flt-1 can be measured by the method described in the aforementioned step 1-(5) or the like.

(2) Construction of Anti-Human VEGF Receptor Flt-1 scFv

A vector for expression of scFv of a non-human animal antibody or scFv of a human CDR-grafted antibody can be constructed by inserting into scFv expression vector the cDNAs encoding VH and VL of a non-human animal antibody or a human CDR-grafted antibody which are described in 2(2), 2(5) and 2(6). Any expression vectors can be used as scFv expression vectors, provided that they can incorporate and express the cDNAs encoding VH and VL of a non-human animal antibody or a human CDR-grafted antibody.

Examples include pAGE107 [*Cytotechnology*, 3: 133 (1990)], pAGE103 [*J. Biochem.*, 101: 1307 (1987)], pHSG274 [*Gene*, 27: 223 (1984)], pKCR [*Proc. Natl. Acad. Sci. USA*, 78: 1527 (1981)] and pSGI βd2-4 [*Cytotechnololgy*, 4: 173 (1990)]. A host for expressing scFv can be selected from among *E. coli*, yeast, animal cells, and the like. In this case, an expression vector which is compatible with the specific host should be selected. The scFv can be secreted out of the cell and transported into the periplasm region or retained within the cell by inserting a cDNA encoding an appropriate signal peptide into the expression vector.

An scFv expression vector into which the cDNA encoding scFv of interest has been inserted can be constructed by inserting the cDNA encoding scFv consisting of VH—P—VL or VL—P—VH (where P is a peptide linker) into the selected expression vector in a region downstream of an appropriate promoter and a signal peptide.

The cDNA encoding scFv can be obtained by linking a VH encoding cDNA to a VL encoding cDNA through a synthetic DNA encoding a peptide linker having recognition sites for appropriate restriction enzymes at both the ends. It is important to optimize the linker peptide such that its addition does not interfere with the binding of VH and VL to an antigen. For example, the linker descried by Pantoliano et al. [*Biochemistry*, 30: 10117 (1991)] and its modified versions may be used.

(3) Production of Anti-Human VEGF Receptor Flt-1 dsFv dsFv can be produced by a process comprising the steps of providing cDNAs encoding VH and VL of a non-human animal antibody or cDNAs encoding VH and VL of a human CDR-grafted antibody, modifying the DNA sequence which corresponds to a one-amino acid residue at an appropriate position in the respective cDNA with a DNA sequence corresponding to a cysteine residue, expressing the modified cDNAs and purifying the resultant peptide and then forming a disulfide bond. The modification of an amino acid residue to a cysteine residue can be performed by a mutagenesis method using PCR described in 2(5).

A dsFv H chain expression vector and a dsFv L chain expression vector can be constructed by inserting the resulting cDNAs encoding the modified VH and modified VL into appropriate expression vectors. Any expression vectors can be used as dsFv expression vectors, provided that they can incorporate and express cDNAs encoding a modified VH and a modified VL. For example, pAGE107 [*Cytotechnology*, 3: 133 (1990)], pAGE103 [*J. Biochem.*, 101: 1307 (1987)], pHSG274 (*Gene*, 27: 223 (1984)], pKCR [*Proc. Natl. Acad. Sci. USA*, 78: 1527 (1981)], pSGI βd2-4 [*Cytotechnololgy*, 4: 173 (1990)] and the like can be used. A host used to express a dsFv L chain expression vector and a dsFv H chain expression vector for formation of dsFv can be selected from among *E. coli*, yeast, animal cells, and the like. In this case, an expression vector which is compatible with the specific host should be selected. The dsFv can be secreted out of the cell and transported into the periplasm region or retained within the cell by inserting a cDNA encoding an appropriate signal peptide into the expression vector.

(4) Expression of Various Antibodies and Evaluation of their Activity

A transformant which produces an antibody fragment, scFv, a dsFv H chain or a dsFv L chain of interest can be obtained by transfecting into a host cell the antibody fragment expression vector, the scFv expression vector, the dsFv H chain expression vector or the dsFv L chain expression vector that was constructed in 3(1) to 3(3) by electroporation [Japanese Published Unexamined Patent Application No. 257891/90; *Cytotechnology*, 3: 133 (1990)] or the like. After introduction of the expression vector, the expression of the antibody fragment, scFv, dsFv H chain, or dsFv L chain in the culture supernatant or the like can be confirmed by the method described in 1(5).

The collection and purification of the antibody fragment, scFv, dsFv H chain, or dsFv L chain can be accomplished by combinations of known techniques. For example, if the antibody fragment, scFv, dsFv H chain, or dsFv L chain is secreted in a medium, they can be concentrated by ultrafiltration and their collection and purification can be then performed by various types of chromatography or gel filtration. If the antibody fragment, scFv, dsFv H chain, or dsFv L chains is transported into the periplasm region of the host cell, they can be concentrated by ultrafiltration after the application of an osmotic shock to the cell and their collection and purification can be then performed by various types of chromatography or gel filtration. If the antibody fragment, scFv, dsFv H chain, or dsFv L chain is insoluble and exists as a granule (i.e., inclusion body), their collection and purification can be performed by lysis of the cells, repeated centrifugation and washing for isolation of the granule, solubilization with guanidine-HCl and subsequent performance of various types of chromatography or gel filtration.

The purified scFv can be measured by the method described in the above 1(5) and the like.

The purified dsFv H chain and dsFv L chain are mixed and subjected to a refolding procedure for deriving an active structure [*Molecular Immunology*, 32: 249 (1995)] to form a disulfide bond. Subsequently, the active dsFv can be purified by antigen affinity chromatography or ion-exchange chromatography or gel filtration. The activity of the dsFv can be determined by the method described in 1(5) or the like.

4. Preparation Method of Fusion Antibody and Fusion Peptide

The fusion antibodies prepared by chemically or by gene-engineeringly linking a radioactive isotope, a protein or a low molecular agent with the antibody or antibody fragment of the present invention can also be used as derivatives of the antibody.

A fusion antibody in which an antibody and a toxic protein are chemically linked can be prepared in accordance, for example, with the method described in *Anticancer Research*, 11: 2003 (1991) or *Nature Medicine*, 3: 350 (1996).

A fusion antibody in which an antibody and a toxin or a protein such as cytokine is gene-engineeringly linked can be prepared in accordance, for example, with the method described in *Proc. Natl. Acad. Sci. USA*, 93: 974 (1996) or *Proc. Natl. Acad. Sci. USA*, 93: 7826 (1996).

A fusion antibody in which an antibody and a low molecular weight anticancer agent are chemically linked can be prepared in accordance, for example, with the method described in *Science*, 261: 212 (1993).

A fusion antibody in which an antibody and a radioactive isotope are chemically linked can be prepared in accordance, for example, with the method described in *Antibody Immunoconjugates and Radiopharmaceuticals*, 3: 60 (1990) or *Anticancer Research*, 11: 2003 (1991).

Examples of the low molecular agent include antibacterial agents, such as alkylating agents (e.g., nitrogen mustards, cyclophosphamide), antimetabolites (e.g., 5-fluorouracil, methotrexate), antibiotics (e.g., mitomycin C, daunorubicin), plant alkaloids (e.g., vincristine, vinblastine), and hormone agents (e.g., tamoxifen, dexamethasone) [*Clinic Oncology*, edited by Japan Clinic Oncology Society, published by Cancer and Chemotherapy Corporation (1996)]; and antiinflammatory agents, such as steroid drugs (e.g., hydrocortisone, prednisone), non-steroid drugs (e.g., aspirin, indomethacin), immunomodulators (e.g., cyclophosphamide, azathioprine), and antihistamic agents (e.g., chlorpheniramine maleate, clemastine) [*Inflammation and Anti-Inflammatory Therapy*, published by Ishiyaku Shuppan (1982)].

It is expected that these derivatives can provide more effective and side effect-reduced diagnoses and treatments by accumulating a radioactive isotope, a protein (such as cytokine, a toxin or an enzyme) or a low molecular agent within the peripheral of a target tissue, based on the specificity of antibody molecules.

The fusion peptide of the present invention can be prepared in the same manner as the fusion antibody of the present invention described above.

5. Method of Use of Antibody and Peptide (I)

The antibodies and peptides of the present invention specific for human VEGF receptor Flt-1 can be used as a diagnostic agent or a treating agent of diseases in which the morbid states progress abnormal angiogenesis, which include proliferation or metastasis of solid tumors such as breast cancer, prostatic cancer, large bowel cancer, gastric cancer and lung cancer, arthritis in chronic rheumatoid arthritis, diabetic retinopathy, retinopathy of prematurity and psoriasis.

In addition, since the antibodies and peptides of the present invention can inhibit biological activities of human VEGF, auto-phosphorylation of Flt-1 can be inhibited by inhibiting binding of human VEGF to Flt-1. As a result, they can inhibit VEGF-dependent proliferation of human vascular endothelial cells and therefore can be used as an agent for treating diseases in which their morbid states progress by abnormal angiogenesis, which include proliferation or metastasis of solid tumors such as breast cancer, prostatic cancer, large bowel cancer, gastric cancer and lung cancer, arthritis in chronic rheumatoid arthritis, diabetic retinopathy, retinopathy of prematurity and psoriasis.

The above-described anti-human VEGF receptor Flt-1 antibodies, peptides, and fusion antibodies and fusion peptides thereof fused with other molecules are linked to human VEGF receptor Flt-1 and, via antibody effector activities such as ADCC and CDC, destroy cells in which VEGF receptor Flt-1 is expressed on the cell surface, so that they are useful in treating diseases in which the morbid states progress by abnormal angiogenesis, which include proliferation or metastasis of solid tumors, such as breast cancer, prostatic cancer, large bowel cancer, gastric cancer and lung cancer, arthritis in chronic rheumatoid arthritis, diabetic retinopathy, retinopathy of prematurity and psoriasis.

The pharmaceutical preparation containing the antibody or peptide of the present invention can be administered directly as a treating agent, but it is generally preferred to provide it in the form of a pharmaceutical medicament produced by mixing it with at least one pharmacologically acceptable carrier in accordance with optional methods well known in the technical field of pharmaceutics.

It is preferred to select a route of administration which is the most effective in carrying out the intended treatment, such as oral administration or parenteral administration that includes tracheal administration, rectal administration, subcutaneous injection, intramuscular injection and intravenous injection. Intravenous injection is preferred in the case of an antibody or peptide preparation.

The dosage form includes sprays, capsules, tablets, granules, syrups, emulsions, suppositories, injections, ointments, and tapes.

Examples of the pharmaceutical preparation suitable for oral administration include emulsions, syrups, capsules, tablets, powders, and granules.

Liquid preparations, such as emulsions and syrups, are produced using additives, such as water, saccharides (e.g., sucrose, sorbitol, fructose), glycols (e.g., polyethylene glycol, propylene glycol), oils (e.g., sesame oil, olive oil, soybean oil), antiseptics (e.g., p-hydroxybenzoic acid esters), and flavors (e.g., strawberry flavor, peppermint).

Solid preparations, such as capsules, tablets, powders and granules, can be produced using additives, such as fillers (e.g., lactose, glucose, sucrose, mannitol), disintegrating agents (e.g., starch, sodium alginate), lubricating agents (e.g., magnesium stearate, talc), binders (e.g., polyvinyl alcohol, hydroxypropylcellulose, gelatin), surfactants (e.g., fatty acid esters), and plasticizers (e.g., glycerol).

Preferred examples of pharmaceutical preparations suitable for parenteral administration include injections, suppositories and sprays.

Injections are prepared using a carrier, such as a salt solution, glucose solution or a mixture thereof.

Suppositories are prepared using a carrier such as cacao butter, hydrogenated fat or a carboxylic acid.

Sprays are prepared from the compound itself or using a carrier which does not stimulate oral and airway mucous membranes of patients and can facilitate absorption of the compound by dispersing it as minute particles.

Examples of the carrier include lactose and glycerol. Depending on the properties of the antibody or peptide and the carrier to be used, other preparations, such as aerosols and dry powders, can be produced. The components exemplified as additives of oral preparations can also be added to these parenteral preparations.

The dose and frequency of administration vary depending on the conditions such as intended therapeutic effect, administration method, treating period, age and body weight, but the dose is generally from 10 $\mu$g/kg to 8 mg/kg per day per adult.

The methods for the examination of antitumor effects of the antibody or peptide of the present invention upon various tumor cells include complement-dependent cytotoxicity (CDC) activity assay, and antibody-dependent cellular cytotoxicity (ADCC) activity assay as in vitro tests. An antitumor test in which a tumor system of an experimental animal, such as mouse, is used can be exemplified as in vivo tests.

The CDC activity assay, the ADCC activity assay and the antitumor test can be carried out in accordance, for example, with the methods described in the literature [*Cancer Immunology Immunotherapy*, 36: 373 (1993); *Cancer Research*, 54: 1511 (1994)].

Furthermore, the present invention relates to, using the antibody or peptide of the present invention, a method for immunologically detecting human VEGF receptor Flt-1 or cells in which human VEGF receptor Flt-1 is expressed on the surface thereof, a method for immunologically detecting and determining soluble human VEGF receptor Flt-1, and a method for inhibiting binding of a human VEGF to human VEGF receptor Flt-1 or biological activities of human VEGF.

Moreover, the present invention relates to a diagnostic agent for diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

The methods for detecting and determining human VEGF receptor Flt-1 are described below.

6. Method of Use of Antibody or Peptide (II)

The method for detecting a disease in which the morbid states progress by abnormal angiogenesis includes a fluorescent antibody method, an enzyme-linked immunosorbent assay (ELISA), a radioactive material labeled immunoassay (RIA), an immunocyte staining method, an immunotissue staining method, Western blotting method, an immunoprecipitation method, and the like.

The fluorescent antibody method comprises the steps of: (a) separating human cell or a crushing solution thereof, tissue or a crushing solution thereof, serum, preural fluid, ascites fluid, ocular fluid or the like to prepare a sample; (b) reacting the separated sample prepared in the step (a) with the antibody or peptide of the present invention; (c) further reacting the reacted sample prepared in the step (b) with an anti-mouse IgG antibody or binding fragment labeled with a fluorescence substance, such as fluorescin isothiocyanate (FITC) or the like; and (d) measuring the fluorescence substance with a flow cytometer.

The enzyme-linked immunosorbent assay (ELISA) comprises the steps of: (a) separating human cell or a crushing solution thereof, tissue or a crushing solution thereof, serum, preural fluid, ascites fluid, ocular fluid or the like to prepare a sample; (b) reacting the separated sample prepared in the step (a) with the antibody or peptide of the present invention; (c) further reacting the reacted sample prepared in the step (b) with an anti-mouse IgG antibody or binding fragment labeled with an enzyme, such as peroxydase, biotin or the like; and (d) measuring the resultant developed dye with an absorption measuring apparatus.

The radioactive material labeled immunoassay (RIA) comprises the steps of: (a) separating human cell or a crushing solution thereof, tissue or a crushing solution thereof, serum, preural fluid, ascites fluid, ocular fluid, or the like to prepare a sample; (b) reacting the separated sample prepared in the step (a) with the antibody or peptide of the present invention; (c) further reacting the reacted sample prepared in the step (b) with an anti-mouse IgG antibody or binding fragment labeled with radioactive ray; and (d) measuring the radioactive ray with a scintillation counter or the like.

The immunocyte staining and immunotissue staining methods comprise the steps of: (a) separating human cell, tissue or the like to prepare a sample; (b) reacting the separated sample prepared in the step (a) with the antibody or peptide of the present invention; (c) further reacting the reacted sample prepared in the step (b) with an anti-mouse IgG antibody or binding fragment labeled with a fluorescence substance, such as fluorescin isothiocyanate (FITC) or the like, or an enzyme, such as peroxydase, biotin, or the like; and (d) observing the cell, tissue or the like with a microscope.

Examples of the methods, using the monoclonal antibody of the present invention, for immunologically detecting human VEGF receptor Flt-1 or a cell in which human VEGF receptor Flt-1 is expressed on the surface thereof and for immunologically detecting and determining soluble human VEGF receptor Flt-1 include immunocyte staining, Western blotting, sandwich ELISA, and the like. These methods are described below.

(1) Immunocyte Staining Using Monoclonal Antibody

First, the cells in which human VEGF receptor Flt-1 is expressed on the cell surface are prepared. Suspending cells as such or adherent cells after detachment of the cells using trypsin-EDTA are suspended, for example, in a buffer solution for immunocyte staining use (PBS containing 1% BSA, 0.02% EDTA and 0.05% sodium azide) and dispensed in $1 \times 10^5$ to $2 \times 10^6$ portions. A culture supernatant of the anti-human VEGF receptor Flt-1 monoclonal antibody-producing hybridoma obtained in the above-described step 1-(4), the purified monoclonal antibody obtained in the above-described step 1-(6) or the monoclonal antibody labeled with biotin by a known method [*Enzyme Antibody Method*: published by Gakusai Kikaku (1985)] is diluted with the buffer solution for immunocyte staining use or the buffer solution for immunocyte staining use further supplemented with 10% animal serum to a concentration of 0.1 to 50 μg/ml and dispensed in 20 to 500 μl portions to carry out the reaction under cooling for 30 minutes. When the culture supernatant of the anti-human VEGF receptor Flt-1 monoclonal antibody-producing hybridoma obtained in the above-described step 1-(4) or the purified monoclonal antibody obtained in the above-described step 1-(6) is used in the reaction, the cells are washed with the buffer solution for immunocyte staining use and then an anti-mouse immunoglobulin antibody or anti-rat immunoglobulin labeled with fluorescence dye, such as FITC, phycoerythrin, or the like, which is dissolved in the buffer solution for immunocyte staining use to a concentration of about 0.1 to 50 μg/ml, is dispensed in 50 to 500 μl portions to carry out the reaction under cooling for 30 minutes. When the monoclonal antibody labeled with biotin is used in the reaction, streptoavidin is dispensed in 50 to 500 μl portions and then the reaction is carried out under cooling in the dark for 30 minutes. After completion of the reaction, the cells are thoroughly washed with the buffer solution for immunocyte staining use and analyzed by a cell sorter.

(2) Detection of Human VEGF Receptor Flt-1 by Western Blotting

Cell membrane components are prepared from cells in which human VEGF receptor Flt-1 is expressed, such as human VEGF receptor Flt-1-expressing NIH3T3 cells (referred to as "NIH3T3-Flt-1" hereinafter), and from control cells such as NIH3T3 cells (referred to as "NIH3T3-Neo" hereinafter) [*Oncogene*, 10: 135 (1995)], and the membrane components are electrophoresed by the SDS-PAGE method under reducing conditions in an amount of 0.1 to 30 μl as protein per lane. The thus treated proteins are transferred on a PVDF membrane and allowed to react with PBS containing 1% BSA at room temperature for 30 minutes to carry out blocking. They are allowed to react with the culture supernatant of the anti-human VEGF receptor Flt-1 monoclonal antibody-producing hybridoma obtained in the above-described step 1-(4) or the purified monoclonal antibody obtained in the above-described step 1-(6), washed with PBS containing 0.05% Tween and then allowed to react with peroxidase-labeled goat anti-mouse IgG at room temperature for 2 hours. After washing with PBS containing 0.05% Tween, bands to which the anti-human VEGF receptor Flt-1 monoclonal antibody is linked are detected using ECL™ Western blotting detection reagents (manufactured by Amersham) or the like.

(3) Determination of Soluble VEGF Receptor Flt-1 Using Monoclonal Antibody

As a first antibody, the purified monoclonal antibody obtained in the above-described step 1-(6) is coated on an appropriate plate and allowed to react with 0.056 to 10,000 ng/ml of the purified soluble anti-human VEGF receptor Flt-1 monoclonal antibody-producing hybridoma obtained in the above-described step 1-(1), or with a sample, such as human serum or the like. After through washing of the plate, this is allowed to react with a second antibody, namely a monoclonal antibody labeled with biotin, an enzyme, a chemiluminescence substance, a radioactive compound or the like, which is one of the purified monoclonal antibodies obtained in the above-described step 1-(6) but recognizes different epitope from that of the monoclonal antibody used as the first antibody, under reaction conditions suitable for binding of the labeled antibody to the epitope with which it binds. A calibration curve is prepared based on the reactivity for the purified soluble VEGF receptor Flt-1, and the concentration of the soluble VEGF receptor Flt-1 in the samples is calculated.

The activity of inhibiting binding of human VEGF and human VEGF receptor Flt-1 can be confirmed by carrying out a VEGF—VEGF receptor Flt-1 binding inhibition test using the antibody of the present invention in accordance, for example, with the measuring method of binding between growth factors and receptors described in *New Biochemical Experiment Course*, Vol. 7, Growth and Differentiation Factors and their Receptors, published by Tokyo Kagaku Dojin (1991).

In this method, for example, VEGF labeled with a radioactive material is allowed to react with cells or tissues in which Flt-1 is expressed, and the VEGF linked to the Flt-1 expressing cells or tissues is measured using a scintillation counter. The activity of inhibiting binding of VEGF labeled with a radioactive material or the like to Flt-1 can be measured by reacting the antibody or peptide of the present invention together with the radioactive material-labeled VEGF.

Auto-phosphorylation inhibition activity of VEGF receptor Flt-1 can be confirmed by carrying out a VEGF—VEGF receptor Flt-1 auto-phosphorylation inhibition test using a antibody or a peptide in accordance, for example, with the measuring method of auto-phosphorylation of growth factor receptors described in *Second Series Biochemical Experiment Course*, Signal Transduction and Cellular Response, published by Tokyo Kagaku Dojin (1986).

In this method, VEGF is allowed to react with cells or tissues in which Flt-1 is expressed, and auto-phosphorylation of Flt-1 accelerated by the binding of VEGF is detected by immunoprecipitation or Western blotting. The activity of inhibiting auto-phosphorylation of Flt-1 accelerated by the binding of VEGF can be measured by reacting the antibody or peptide of the present invention together with VEGF.

The activity of inhibiting biological activities of human VEGF can be confirmed by carrying out growth, migration and tube formation tests of VEGF dependent vascular endothelial cells [*New Biochemical Experiment Course*, Vol. 10, Blood Vessels (Endothelium and Smooth Muscle), published by Tokyo Kagaku Dojin (1991)].

The growth test of VEGF dependent vascular endothelial cells is a method in which VEGF is allowed to react with vascular endothelial cells, and the growth enhancing activity of vascular endothelial cells accelerated by the binding of VEGF is measured by counting the number of cells. The activity of inhibiting growth enhancing activity of vascular endothelial cells accelerated by VEGF can be measured by reacting the antibody or peptide of the present invention together with VEGF.

The migration test of VEGF dependent vascular endothelial cells is a method in which VEGF is allowed to react with vascular endothelial cells, and the wondering enhancing activity of vascular endothelial cells accelerated by the binding of VEGF is observed under a microscope. The activity of inhibiting aberrance enhancing activity of vascular endothelial cells accelerated by VEGF can be measured by reacting the antibody or peptide of the present invention together with VEGF.

The tube formation test of VEGF dependent vascular endothelial cells is a method in which VEGF is allowed to react with vascular endothelial cells, and the tube formation enhancing activity of vascular endothelial cells accelerated by the binding of VEGF is observed under a microscope. The activity of inhibiting tube formation enhancing activity of vascular endothelial cells accelerated by VEGF can be measured by reacting the antibody or peptide of the present invention together with VEGF.

The inhibition methods of the bonding of human VEGF to human VEGF receptor Flt-1 and of the biological activities of human VEGF are exemplified.

(4) Inhibition Test of Binding of VEGF to VEGF Receptor Flt-1 Using Monoclonal Antibody Methanol is dispensed in 100 µl portions into wells of a 96 well MultiScreen-IP Plate (manufactured by Millipore) to give hydrophilic nature to the PVDF membrane on the bottom of the plate. After washing with water, human VEGF receptor Flt-1 or a recombinant protein such as a fusion protein with human VEGF receptor Flt-1 is diluted to a concentration of 0.1 to 10 µg/ml, dispensed in 50 µl/well portions and then allowed to stand overnight at 4° C. for its adsorption. After washing, PBS containing 1% bovine serum albumin (BSA) is dispensed in 100 µl/well portions and the reaction is carried out at room temperature for 1 hour to block any remaining active groups. After washing with PBS, the culture supernatant of the anti-human VEGF receptor Flt-1 monoclonal antibody-producing hybridoma obtained in the above-described step 1-(4) or the purified monoclonal antibody obtained in the above-described step 1-(6) is dispensed in 50 µl/well portions and then 0.1 to 10 ng/ml of $^{125}$I-labeled VEGF (manufactured by Amersham) is dispensed in 50 µl/well portions, subsequently carrying out the reaction at room temperature for 1.5 hours. After washing with 0.05% Tween-PBS, the wells are dried at 50° C., and a scintillator is dispensed in 20 to 100 µl/well portions to measure the radioactivity of the $^{125}$I-labeled VEGF linked to each well using Top Count (manufactured by Packard) or the like.

(5) Inhibition Test of Binding of VEGF to VEGF Receptor Flt-1-Expressing Cells Using Monoclonal Antibody PBS containing 1% bovine serum albumin (BSA) is dispensed in 100 µl portions into wells of a 96 well Multi-Screen-HV Plate (manufactured by Millipore), the reaction is carried out at room temperature for 1 hour to block the active groups in wells and then NIH3T3-Flt-1 cells suspended in 1% BSA-PBS containing 0.05% NaN$_3$ is dispensed in 1×10$^4$ to 1×10$^5$/well portions. After washing with 1% BSA-PBS, the culture supernatant of the anti-human VEGF receptor Flt-1 monoclonal antibody-producing hybridoma obtained in the above-described step 1-(4) or the purified monoclonal antibody obtained in the above-described step 1-(6) is dispensed in 50 µl/well portions and then 0.1 to 10 ng/ml of $^{125}$I-labeled VEGF (manufactured by Amersham) is dispensed in 50 µl/well portions, subsequently carrying out the reaction at room temperature for 1.5 hours. After washing with PBS, the wells are dried at 50° C., and a scintillator is dispensed in 20 to 100 µl/well portions to measure the radioactivity of the $^{125}$I-labeled VEGF linked to each well using Top Count (manufactured by Packard) or the like.

The other antibodies and peptides of the present invention can be used in the same manner as the monoclonal antibody of the present invention described above.

The present invention renders possible provision of antibodies and peptides that specifically binds to human VEGF receptor Flt-1 which is considered to be expressed specifically in vascular endothelial cells of human angiogenesis regions. The antibodies and peptides of the present invention are useful for the immunological detection of human angiogenesis regions by immunocyte staining and for the diagnosis or treatment, through the inhibition of the biological activities of human VEGF, of diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

The present invention will be explained by Examples below; however, the invention is not limited thereto.

EXAMPLE 1

1. Preparation of Antigen (1) Construction of Soluble Human VEGF Receptor Flt-1 3N Expression Vector A vector was prepared in the following manner, for use in the expression of a soluble human VEGF receptor Flt-1 fragment (hereinafter referred to as "soluble human VEGF receptor Flt-1 3N") which corresponds to a region of the 1st to 338th positions (including a signal sequence) from the N-terminal amino acid of human VEGF receptor Flt-1. The soluble human VEGF receptor Flt-1 3N corresponds to the N-terminal side three immunoglobulin-like regions of the extracellular domain of the soluble human VEGF receptor Flt-1.

A cDNA clone flt#3-7 [M. Shibuya et al., *Oncogene*, 5: 519 (1990)] which contains whole length cDNA encoding the human VEGF receptor Flt-1 was partially digested with restriction enzymes EcoRI and TaqI to collect a 1,263 bp EcoRI-TaqI DNA fragment from the 5'-end, and the thus collected fragment was inserted into the 5' side EcoRI site and 3' side NotI site downstream of the transcription initiation point of the polyhedrin gene of a baculovirus gene recombinant vector pVL1393 plasmid (manufactured by Invitrogen) using a TaqI-NotI adapter into which a termination codon had been artificially introduced (a synthetic DNA fragment having the nucleotide sequences shown in the SEQ ID NO:1 and NO:2) to obtain soluble human VEGF receptor Flt-1 3N expression vector pVL1393/Flt 3N (FIG. 1).

(2) Construction of Soluble Human VEGF Receptor Flt-1 7N Expression Vector

A vector was prepared in the following manner, for use in the expression of a soluble human VEGF receptor Flt-1 fragment (referred to as "soluble human VEGF receptor Flt-1 7N" hereinafter) which corresponds to a region of the 1st to 750th positions (including a signal sequence) from the N-terminal amino acid of human VEGF receptor Flt-1. The soluble human VEGF receptor. Flt-1 7N corresponds to the seven immunoglobulin-like regions of the extracellular domain of the soluble human VEGF receptor Flt-1.

Figure 2:
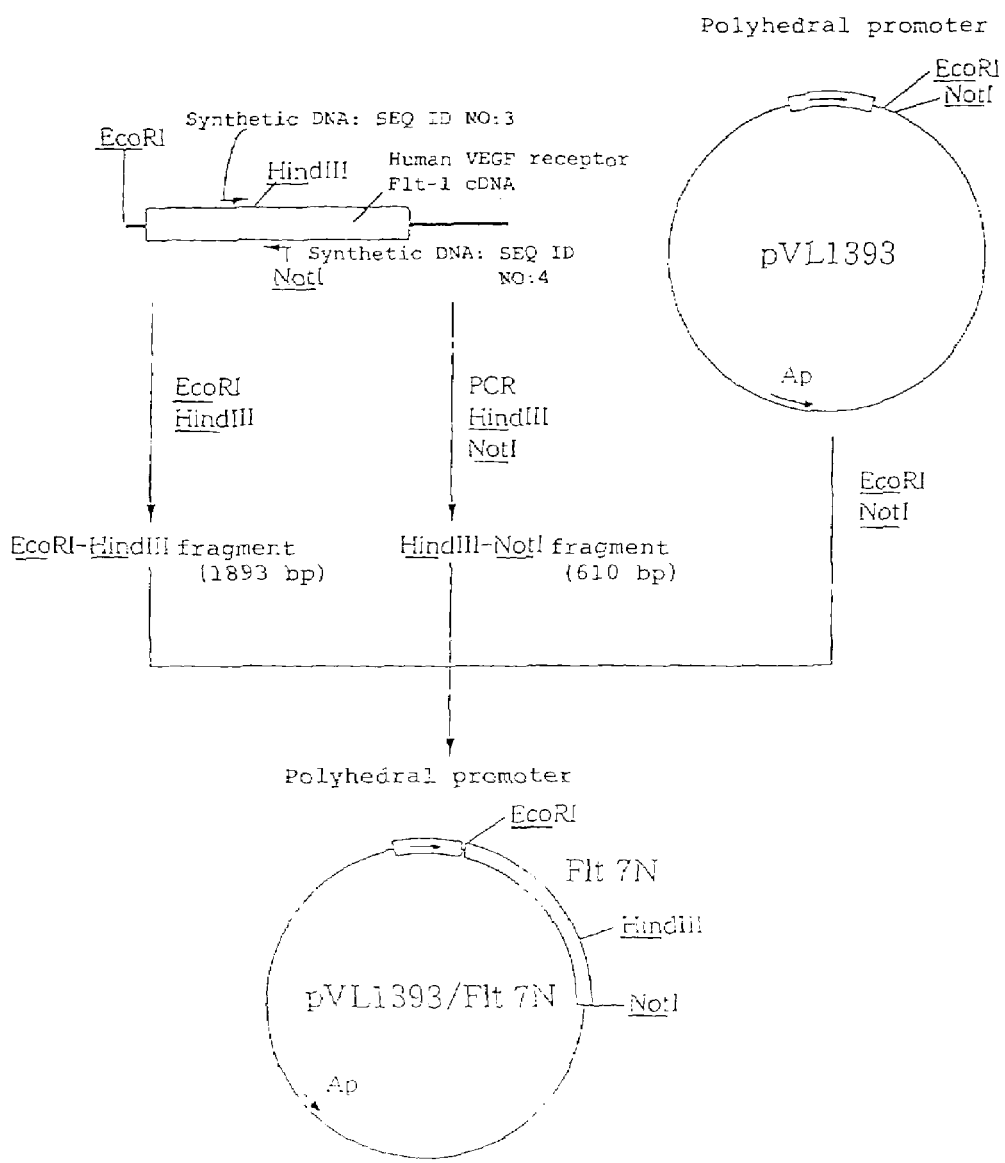
FIG. 2 is a graph showing construction steps of plasmid pVL1393/Flt 7N.

A 2.5 unit portion of Taq polymerase was added to 100 µl of 0.001% (w/v) gelatin solution of 10 mM MgCl$_2$ containing 10 pmol of primers having the nucleotide sequences shown in SEQ ID NO:3 and NO:4, 10 ng of flt#3-7 clone [*Oncogene*, 5: 519, (1990)] DNA and 10 mM deoxynucleotide triphosphates. The polymerase chain reaction (PCR) was repeated 30 times in which one reaction consisted, after pretreatment at 95° C. for 5 minutes, of treatments at 95° C. for 90 seconds, at 50° C. for 90 seconds and finally at 72° C. for 90 seconds, subsequently collecting a DNA fragment. The DNA fragment was digested with HindIII (the 1893 bp position in the flt#3-7 clone) and NotI to obtain a 610 bp HindIII-NotI DNA fragment, namely a DNA fragment containing a 1894–2499 bp fragment of the flt#3-7 clone, termination codon and NotI recognition sequence. Next, the flt#3-7 clone was digested with restriction enzymes EcoRI and HindIII to collect an EcoRI-HindIII fragment of 1893 bp from the 5'-end. The 610 bp HindIII-NotI DNA fragment and the 1893 bp EcoRI-HindIII fragments were then inserted into the 5' side EcoRI site and 3' side NotI site downstream of the transcription initiation point of the polyhedrin gene of a baculovirus gene recombinant vector pVL1393 plasmid, thereby preparing soluble human VEGF receptor Flt-1 7N expression vector pVL1393/Flt 7N (FIG. 2).

(3) Preparation of Recombinant Virus for Use in the Expression of Soluble Human VEGF Receptor Flt-1 in Insect Cells For the production of protein by insect cells, it is necessary to prepare a recombinant virus into which a gene of interest is integrated, and the preparation process consists of a step in which a cDNA molecule encoding a protein of interest is inserted into a special plasmid, which is called a transfer vector, and a subsequent step in which a wild type virus and the transfer vector are co-transfected into insect cells to obtain a recombinant virus by homologous recombination. These steps were carried out in the following manner using BaculoGold Starter Kit manufactured by Pharmigen (product no. PM-21001K) in accordance with the manual.

A recombinant baculovirus was prepared in the following manner by introducing a filamentous baculovirus DNA (BaculoGold baculovirus DNA, produced by Pharmigen) and the thus prepared transfer vector DNA into insect cells Sf9 (manufactured by Pharmigen) which had been cultured using TMN-FH insect medium (manufactured by Pharmigen), using a lipofectin method [*Protein, Nucleic Acid, Enzyme*, 37: 2701 (1992)].

A 1 μg portion of pV-1393/Flt7N prepared in the above step (2) or pVL1393/Flt3N prepared in the above step (1) and 20 ng of filamentous baculovirus DNA were dissolved in 12 μl of distilled water, the solution was mixed with a mixture of 6 μl lipofectin and 6 μl distilled water and then the resulting mixture was allowed to stand at room temperature for 15 minutes. Separately from this, $1 \times 10^6$ of Sf9 cells were suspended in 2 ml of Sf900-II medium (manufactured by Gibco) and put into a cell culture plastic Petri dish of 35 mm in diameter. To this was added whole volume of the just described solution of plasmid DNA, filamentous baculovirus DNA and lipofectin mixture, followed by 3 days of culturing at 27° C. to collect 1 ml of the culture supernatant containing the recombinant virus. A 1 ml portion of Sf900-II medium was added to the resulting Petri dish and 3 days of culturing was carried out at 27° C. to obtain an additional 1.5 ml of the recombinant virus containing culture supernatant.

Next, the thus obtained recombinant virus for use in the protein expression was grown in the following manner.

A $2 \times 10^7$ portion of Sf9 cells were suspended in 10 ml of Sf900-II medium, put into a 175 cm² flask (manufactured by Greiner) and allowed to stand at room temperature for 1 hour to adhere the cells to the flask. The supernatant fluid was subsequently discarded and 15 ml of fresh TMN-FH insect medium and a 1 ml portion of the recombinant virus containing culture supernatant described above were added and cultured for 3 days at 27° C. After the culturing, the supernatant fluid was centrifuged at 1,500×g for 10 minutes to remove the cells to obtain a recombinant virus solution for use in the protein expression.

The titer of virus in the thus obtained recombinant virus solution was calculated by the method described in BaculoGold Starter Kit Manual (Pharmigen).

A $6 \times 10^6$ portion of Sf9 cells were suspended in 4 ml of Sf900-II medium, put into a cell culture plastic Petri dishes of 60 mm in diameter and allowed to stand at room temperature for 1 hour to adhere the cells to the dish. Next, the supernatant fluid was discarded, 400 μl of fresh Sf900-II medium and the above-described recombinant virus solution diluted 10,000 times with Sf900-II medium were added to the dish and allowed to stand at room temperature for 1 hour, the medium was removed and then 5 ml of a medium containing 1% low melting point agarose (Agarplaque Agarose, produced by Pharmigen) (prepared by mixing 1 ml of sterilized 5% Agarplaque plus agarose aqueous solution with 4 ml of TMN-FH insect medium and stored at 42° C.) was poured into the dish. After standing at room temperature for 15 minutes, the dish was tied with a vinyl tape to prevent drying, put into a sealable plastic container and then cultured at 27° C. for 6 days. A 1 ml portion of PBS containing 0.01% of Neutral Red was added to the dish to carry out the additional culturing for 1 day and then the number of the thus formed plaques was counted. By the above procedure, it was found that each of the recombinant virus solutions contained virus particles of about $1 \times 10^7$ plaque forming units (hereinafter referred to as "PFU") per ml.

(4) Expression of Soluble Human VEGF Receptors Flt-1 7N and Flt-1 3N in Insect Cells and Purification Thereof Soluble human VEGF receptors Flt-1 7N and Flt-1 3N were obtained in the following manner. A $4 \times 10^7$ portion of High Five cells were suspended in 30 ml of EX-CELL™ 400 medium (manufactured by JRH Biosciences) contained in a 175 cm² flask (manufactured by Greiner) and allowed to stand at room temperature for 1 hour to adhere the cells to the flask. A 1 ml portion of a solution containing about 1 to $3 \times 10^8$ PFU/ml of recombinant virus particles obtained in the above step (3) from the transfer vectors pVL1393/Flt 7N and pVL1393/Flt 3N was added to the flask to carry out infection at room temperature for 2 hours. The culture supernatant was removed and 30 ml of fresh EX-CELL™ 400 medium was added to carry out 3 to 4 days of culturing at 27° C. After completion of the culturing, the culture supernatant was collected and centrifuged at 1,500×g for 10 minutes to obtain a supernatant fluid.

A column was packed with about 60 ml of heparin-Sepharose CL-6B gel (manufactured by Pharmacia Biotech AB) and washed with 600 ml of 20 mM Tris-HCl (pH 7.5) buffer at a flow rate of 0.5 ml/minute. After the washing, 1,000 ml of the culture medium containing soluble human VEGF receptors Flt-1 7N and Flt-1 3N, which had been prepared in the above-described manner, was passed through the heparin-Sepharose CL-6B column at a flow rate of 0.5 ml/minute. After washing with 600 ml of 20 mM Tris-HCl (pH 7.5) buffer at a flow rate of 0.5 ml/minute, 600 ml of 20 mM Tris-HCl (pH 7.5) buffer having a density gradient of 0 M to 1.1 M NaCl was passed through the column to carry out elution of the proteins adsorbed to the heparin-Sepharose, and the eluate was fractionated in 8 ml portions. Proteins contained in each fraction were analyzed by SDS polyacrylamide gel electrophoresis (SDS-PAGE), and 60 to 80 ml of fractions containing soluble human VEGF receptors Flt-1 7N and Flt-1 3N were collected and concentrated using CentriPrep 10 (manufactured by Amicon). After the concentration, soluble human Flt-1 7N and Flt-1 3N were obtained as solutions of 5 ml and 13 ml, respectively (protein concentrations were 331 µg/ml and 204 µl/ml).

Figure 3:
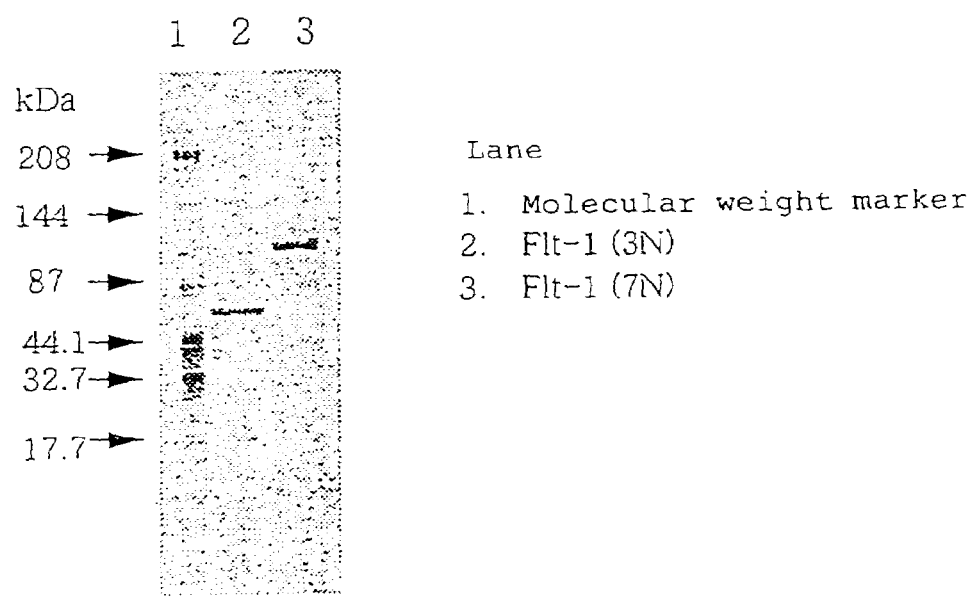
FIG. 3 is a graph showing patterns of SDS polyacrylamide electrophoresis (a 5 to 20% gradient gel was used) of purified Flt-1 7N and Flt-1 3N. Starting from the left side, electrophoresis patterns of molecular weight markers, Flt-1 3N and Flt-1 7N are shown respectively. The electrophoresis was carried out under reducing conditions.

(5) Confirmation of the Purity of Soluble Human VEGF Receptors Flt-1 7N and Flt-1 3N Purity of the thus purified soluble human VEGF receptors Flt-1 7N and Flt-1 3N was confirmed by SDS-PAGE. The SDS-PAGE was carried out in accordance with a known method [*Anticancer Research*, 12: 1121 (1992)]. Using a 5 to 20% gradient gel (manufactured by Atto) as the gel, electrophoresis of Flt-1 7N and Flt-1 3N, each 2 µg as protein per lane, was carried out under reducing conditions, and the resulting gel was stained with Coomassie Brilliant Blue. The results are shown in FIG. 3. Purity of Flt-1 7N and Flt-1 3N was found to be 95% or more.

(6) Purification of Control Antigen Protein of Soluble Human VEGF Receptors Flt-1 7N and Flt-1 3N The control antigen protein (negative control protein) of soluble human VEGF receptors Flt-1 7N and Flt-1 3N was obtained in the following manner. A $4 \times 10^7$ portion of High Five cells were suspended in 30 ml of EX-CELL™ 400 medium (manufactured by JRH Biosciences) contained in a 175 cm² flask (manufactured by Greiner), allowed to stand at room temperature for 1 hour to adhere the cells to the flask and then cultured at 27° C. for 3 to 4 days. After completion of the culturing, the culture supernatant was collected and centrifuged at 1,500×g for 10 minutes to obtain a supernatant fluid.

A column was packed with about 20 ml of heparin-Sepharose CL-6B gel (manufactured by Pharmacia Biotech AB) and washed with 200 ml of 20 mM Tris-HCl (pH 7.5) buffer at a flow rate of 0.5 ml/minute. After the washing, 500 ml of the culture medium of High Five cells was passed through the heparin-Sepharose CL-6B column at a flow rate of 0.5 ml/minute. After washing with 200 ml of 20 mM Tris-HCl (pH 7.5) buffer at a flow rate of 0.5 ml/minute, 200 ml of 20 mM Tris-HCl (pH 7.5) buffer containing 1 M NaCl was passed through the column to carry out elution of the protein adsorbed to the heparin-Sepharose. The 1 M NaCl elution fraction was concentrated using CentriPrep 10 (manufactured by Amicon) to obtain 7 ml of the control antigen protein (867 µg/ml as protein concentration).

(7) Confirmation of Human VEGF Binding Activity of Soluble Human VEGF Receptors Flt-1 7N and Flt-1 3N The human VEGF binding activity of soluble human VEGF receptors Flt-1 7N and Flt-1 3N was confirmed in the following manner.

Methanol was dispensed in 100 µl portions into wells of a 96 well Immobilon™-P Filtration Plate (manufactured by Millipore) to give a hydrophilic nature to the PVDF membrane on the bottom of the plate. After washing with water, the soluble human Flt-1 7N diluted to a concentration of 2 µl/ml was dispensed in 50 µl/well portions and allowed to stand overnight at 4° C. for its adsorption. After washing, PBS containing 1% bovine serum albumin (BSA) was dispensed in 100 µl/well portions and the reaction was carried out at room temperature for 1 hour to block the remained active groups. After washing with PBS, each of the purified soluble human VEGF receptors Flt-1 7N and Flt-1 3N obtained in the above-described step (4) was dispensed in 50 µl/well portions (final concentration, 1 to 1,000 ng/ml) and then $^{125}$I-labeled human VEGF (final concentration, 3 ng/ml: produced by Amersham) was dispensed in 50 µl/well portions, subsequently carrying out the reaction at room temperature for 1.5 hours. After washing with 0.05% Tween-PBS, the wells were dried at 50° C., and Microscinti-0 (manufactured by Packard) was dispensed in 20 µl/well portions to measure the radioactivity of the $^{125}$I-labeled human VEGF linked to each well using Top Count (manufactured by Packard).

Figure 4:
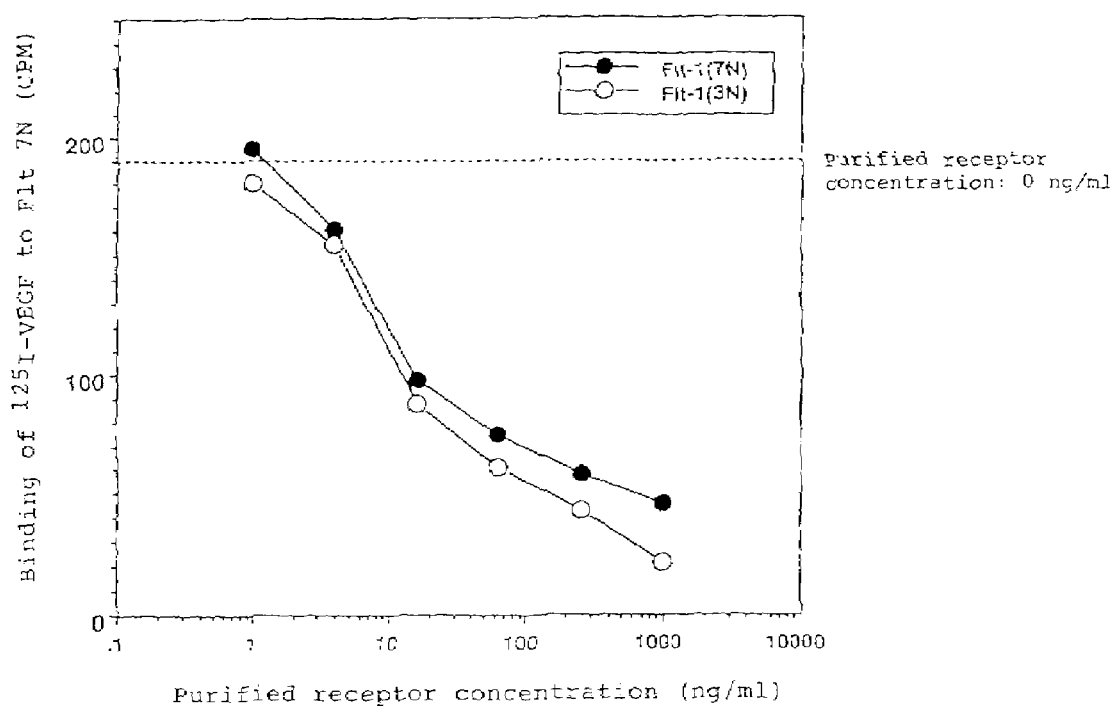
FIG. 4 is a graph showing results of the analysis of the effect of soluble human VEGF receptors Flt-1 7N and Flt-1 3N to inhibit binding of a $^{125}$I-human VEGF to a plate-coated soluble human VEGF receptor Flt-1 7N.

The results are shown in FIG. 4. It was shown that soluble human VEGF receptors Flt-1 7N and Flt-1 3N inhibit binding of $^{125}$I-labeled human VEGF to soluble human VEGF receptor Flt-1 7N in a concentration dependent manner. Since the soluble human VEGF receptors Flt-1 7N and Flt-1 3N showed similar degree of the human VEGF binding activity, it was revealed that the human VEGF binds to the Flt-1 3N moiety (the 1st to 338th positions from the N-terminal amino acid including signal sequence).

(8) Expression of Human VEGF in Insect Cells

The human VEGF was obtained in the following manner. A $4 \times 10^7$ portion of High Five cells were suspended in 30 ml of EX-CELL™ 400 medium (manufactured by JRH Biosciences) contained in a 175 cm² flask (manufactured by Greiner) and allowed to stand at room temperature for 1 hour to adhere the cells to the flask. A 1 ml portion of a solution containing about 1 to $3 \times 10^8$ PFU/ml of human VEGF recombinant baculovirus particles obtained in accordance with the known method [*Cell Growth & Differentiation*, 7: 213 (1996)] was added to the flask to carry out infection at room temperature for 2 hours. The culture supernatant was removed and 30 ml of fresh EX-CELL™ 400 medium was added to carry out 3 to 4 days of culturing at 27° C. After completion of the culturing, the culture supernatant was collected and centrifuged at 1,500×g for 10 minutes to obtain a supernatant fluid.

A column was packed with about 40 ml of heparin-Sepharose CL-6B gel (manufactured by Pharmacia Biotech AB) and washed with 400 ml of 20 mM Tris-HCl (pH 7.5) buffer at a flow rate of 0.5 ml/minute. After washing, 1,500 ml of the culture medium containing human VEGF prepared in the above-described manner was passed through the heparin-Sepharose CL-6B column at a flow rate of 0.5 ml/minute. After washing with 400 ml of 20 mM Tris-HCl (pH 7.5) buffer at a flow rate of 0.5 ml/minute, 120 ml of each of 20 mM Tris-HCl (pH 7.5) buffers containing 0.2 M, 0.5 M and 1 M NaCl was passed through the column in that order to carry out stepwise elution of the proteins adsorbed to the heparin-Sepharose, and the eluate was fractionated in 8 ml portions. Proteins contained in each fraction were analyzed by SDS polyacrylamide gel electrophoresis, and 120 ml of fractions (0.5 to 1 M NaCl fractions) containing human VEGF were collected. After concentration using CentriPrep-10 (manufactured by Amicon), human VEGF was obtained as 4 ml of solution (protein concentration, 1.2 mg/ml).

2. Immunization of Animals and Preparation of Antibody Producing Cells

A 50 µg portion of each of the antigens obtained in the above-described step 1-(4) was administered, together with 2 mg of aluminum hydroxide gel and $1 \times 10^9$ cells of pertussis vaccine (manufactured by Chiba Serum Institute), into 5-week-old female BALB/c mice (SLC Japan), B6C3F1 mice (Charles River Japan) or female SD rats (SLC Japan), and, starting on 2 weeks thereafter, 10 to 50 µg of the protein was administered once a week for a total of four times. Also, 1×10⁷ of NIH3T3-Flt-1 cells were administered 6 times into three, 5 week old female BALB/c (SLC Japan) mice. Blood samples were collected from the fundus of the eye or the caudal vein, their serum antibody titers were examined by the enzyme immunoassay described in the following, and spleens were excised from mice or rats showing sufficient antibody titer 3 days after the final immunization. In this connection, immunization was not induced in the 5-week-old female BALB/c to which NIH3T3-Flt-1 cells were administered, so that the antibody titer upon soluble Flt-1 7N was not increased.

The thus excised spleen was cut to pieces in MEM medium (manufactured by Nissui Pharmaceutical), unbound using a pair of forceps and then centrifuged (1,200 rpm for 5 minutes). The resulting supernatant was discarded, and the thus obtained sediment was treated with Tris-ammonium chloride buffer (pH 7.65) for 1 to 2 minutes to eliminate erythrocytes, washed three times with MEM medium and used in cell fusion.

3. Enzyme Immunoassay

With regard to the measurement of antisera derived from mice or rats immunized with the soluble human Flt-1 7N and Flt-1 3N obtained in the above-described step 1-(4) and culture supernatants of hybridomas, the soluble human VEGF receptors Flt-1 7N and Flt-1 3N obtained from the insect cell culture supernatant of 1-(4) were used as antigens. A 1 to 10 µg/ml PBS-diluted solution of each of the soluble human VEGF receptors Flt-1 7N and Flt-1 3N and the heparin column adsorption fraction of High Five cell culture supernatant obtained in the above-described step 1-(6) as a control antigen was dispensed in 50 µl/well portions into a 96 well plate for EIA (manufactured by Greiner) and allowed to stand overnight at 4° C. for coating. After washing, PBS containing 1% bovine serum albumin (BSA) was dispensed in 100 µl/well portions and the reaction was carried out at room temperature for 1 hour to block the remained active groups. After discarding 1% BSA-PBS, antiserum of immunized mouse or immunized rat and culture supernatant of a hybridoma were dispensed in 50 µl/well portions to carry out the reaction for 2 hours. After washing with 0.05% Tween-PBS, peroxidase-labeled rabbit anti-mouse immunoglobulin or peroxidase-labeled rabbit anti-rat immunoglobulin (both manufactured by DAKO) was dispensed in 50 µl/well portions and the reaction was carried out at room temperature for 1 hour, the plate was washed with 0.05% Tween-PBS and then color development was caused using ABTS substrate solution (2,2-azinobis(3-ethylbenzothiazole-6-sulfonic acid) ammonium salt) to measure maximum absorbance at OD415 nm using E max (manufactured by Molecular Devices).

4. Preparation of Mouse Myeloma Cells

8-Azaguanine-resistant mouse myeloma cell line P3U1 was cultured using normal medium to secure 2×10⁷ or more of the cells for use in cell fusion as the parent cell line.

5. Preparation of Hybridoma

The mouse spleen cells or rat spleen cells obtained in the above-described section 2 and the myeloma cells obtained in the above section 4 were mixed to a ratio of 10:1 and centrifuged (1,200 rpm for 5 minutes), the supernatant was discarded, the precipitated cells were thoroughly loosened to which, while stirring at 37° C., were subsequently added a mixed solution of 2 g polyethylene glycol-1000 (PEG-1000), 2 ml MEM medium and 0.7 ml DMSO in an amount of 0.2 to 1 ml/10⁸ mouse myeloma cells and then 1 to 2 ml of MEM medium several times at 1 to 2 minute intervals, and then the total volume was adjusted to 50 ml by adding MEM medium. After centrifugation (900 rpm for 5 minutes), the supernatant was discarded and the thus obtained cells were gently loosened and then gently suspended in 100 ml of HAT medium by repeated drawing up into and discharging from a graduated pipette.

The suspension was dispensed in 100 µl portions into wells of a 96 well culture plate and cultured at 37° C. for 10 to 14 days in an atmosphere of 5% $CO_2$ in a 5% $CO_2$ incubator. The resulting culture supernatant was examined by the enzyme immunoassay method described in Example 1-3 to select wells which reacted specifically with the soluble human VEGF receptor Flt-1 7N or Flt-1 3N obtained in the above-described step 1-(4) but did not react with the control antigen obtained in the step 1-(6), and then cloning was repeated twice by changing the medium to HT medium and normal medium to establish hybridomas capable of producing anti-human VEGF receptor Flt-1 monoclonal antibodies. The results are shown in the following table.

TABLE 1

| Animal | Head | Immunogen | Screening source | Wells screened | The number of hybridomas established |
|---|---|---|---|---|---|
| Balb/c mouse | 3 | NIH3T3-Flt-1 | Flt 7N | — | — |
| SD rat | 1 | Flt 7N | Flt 7N | 1008 | 3 (KM1733, 1735, 1736) |
| Balb/c mouse | 1 | Flt 7N | Flt 7N | 672 | 5 (KM1737, 1739, 1740, 1742, 1743) |
| SD rat | 1 | Flt 7N | Flt 7N | 1176 | 3 (KM1745, 1746, 1747) |
| B3C3F1 mouse | 1 | Flt 7N | Flt 3N | 672 | 3 (KM1748, 1749, 1750) |
| Balb/c mouse | 1 | Flt 7N | Flt 3N | 420 | 3 (KM1730, 1731, 1732) |

When hybridomas obtained from one Balb/c mouse and two SD rats immunized with the soluble human VEGF receptor Flt-1 7N prepared in the above-described step 1-(4) were screened for about 672 wells and about 2,184 wells, respectively, using the soluble human VEGF receptor Flt-1 7N, respective 5 clones and 6 clones of anti-human VEGF receptor Flt-1 monoclonal antibodies were obtained, and they were named KM1737, KM1739, KM1740, KM1742 and M1743 and KM1733, KM1735, KM1736, KM1745, KM1746 and KM1747, respectively. None of these clones showed the action to inhibit binding of human VEGF to Flt-1 as shown in the following section 8. Additionally, KM1735, KM1736, KM1742, M1743 and KM1745 reacted with human VEGF receptor Flt-1 expression cells by the immunocyte staining method described in the following section 10, but the reaction was extremely weak in comparison with KM1730, KM1731 and KM1732.

On the other hand, when hybridomas obtained from one B3C3F1 mouse and one Balb/c mouse immunized with the soluble human VEGF receptor Flt-1 7N prepared in the above-described step 1-(4) were screened for about 672 wells and about 420 wells, respectively, using the soluble human VEGF receptor Flt-1 3N, 3 clones for each of anti-human VEGF receptor Flt-1 monoclonal antibodies were obtained, and they were named KM1748, KM1749 and KM1750 and KM1730, KM1731 and KM1732, respectively. Of these clones, three clones KM1732, KM1748 and KM1750 showed the action to inhibit binding of human VEGF to Flt-1 as shown in the following section 8. Additionally, three clones KM1730, KM1731 and KM1732 reacted markedly strongly with human VEGF receptor Flt-1 expression cells by the immunocyte staining method described in the following section 10.

The antibody class of these monoclonal antibodies was determined by enzyme immunoassay using Subclass Typing Kit (manufactured by Zymed). The results are shown in the following table.

TABLE 2

| Monoclonal antibody | Antibody subclass |
|---|---|
| KM1733 | mouse IgG2a |
| KM1735 | rat IgG1 |
| KM1736 | rat IgG2a |
| KM1737 | mouse IgG1 |
| KM1739 | mouse IgG1 |
| KM1740 | mouse IgG1 |
| KM1742 | mouse IgG1 |
| KM1743 | mouse IgG1 |
| KM1745 | rat IgG2a |
| KM1746 | rat IgG1 |
| KM1747 | rat IgG1 |
| KM1748 | mouse IgG2b |
| KM1749 | mouse IgG1 |
| KM1750 | mouse IgG2b |
| KM1730 | mouse IgG1 |
| KM1731 | mouse IgG2a |
| KM1732 | mouse IgG1 |

All of the monoclonal antibodies established in the present invention were IgG class.

6. Purification of Monoclonal Antibody

The hybridomas obtained in the above section 5 were respectively administered to pristane-treated female nude mice (Balb/c) of 8 weeks of age by intraperitoneal injection at a dose of 5 to 20×10$^6$ cells per animal. The hybridomas caused ascites tumor formation in 10 to 21 days. The ascitic fluid was collected from each ascitic fluid-carrying mouse (1 to 8 ml per animal), centrifuged (3,000 rpm for 5 minutes) for removing solid matter and then purified by a caprylic acid precipitation method (*Antibodies—A Laboratory Manual*).

7. Confirmation of the Specificity of Monoclonal Antibodies

Specificity of the anti-human VEGF receptor Flt-1 monoclonal antibodies described in the above-described section 5 was confirmed using the enzyme immunoassay method described in the above-described section 3.

Figure 5:
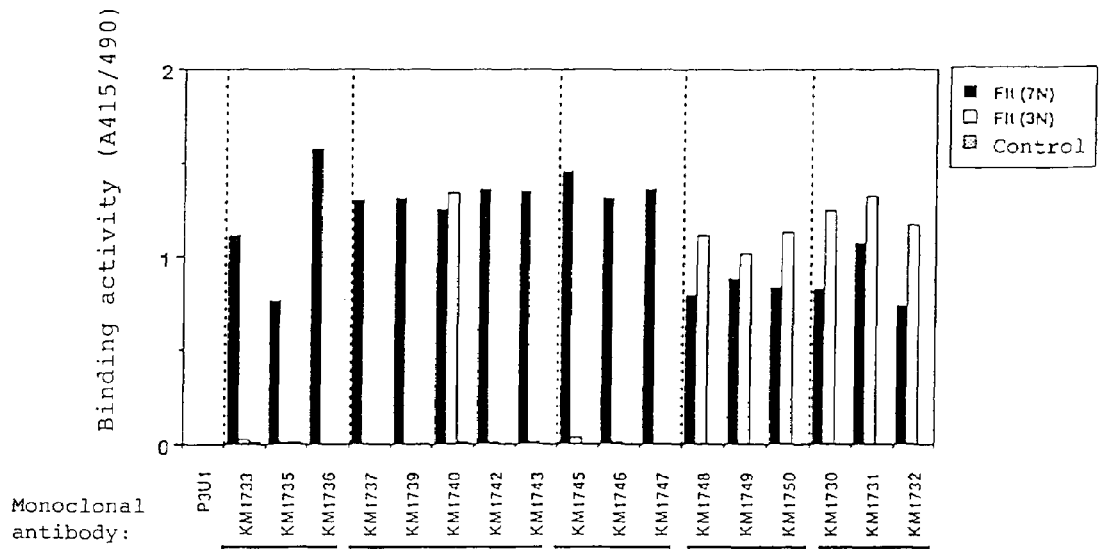
FIG. 5 is a graph showing results of the examination of the binding reactivity of anti-human VEGF receptor Flt-1 monoclonal antibody by enzyme immunoassay.

The results are shown in FIG. 5. Among the monoclonal antibodies obtained by preparing hybridomas from mice and rats immunized with Flt-1 7N and selected using Flt-1 7N (M1733, KM1735, KM1736, KM1737, KM1739, KM1740, KM1742, KM1743, KM1745, KM1746 and KM1747), only KM1740 reacted with Flt-1 7N and Flt-1 3N, revealing that it recognizes an epitope which is present in a region of the 1st to 338th positions from the N-terminal amino acid of Flt-1 (including signal sequence). Since the remaining 10 clones reacted with Flt-1 7N but not with Flt-1 3N, it was revealed that they recognize an epitope which is present in a region of the 339th to 750th positions from the N-terminal amino acid of Flt-1 (including signal sequence). On the other hand, since all of the monoclonal antibodies obtained by preparing hybridomas from mice immunized with Flt-1 7N and selecting using Flt-1 3N (KM1748, KM1749, KM1750, KM1730, KM1731 and KM1732) reacted with Flt-1 7N and Flt-1 3N, it was revealed that they recognize an epitope which is present in a region of the 1st to 338th positions from the N-terminal amino acid of Flt-1 (including signal sequence).

8. Confirmation of the Activity of Anti-Flt-1 Monoclonal Antibodies to Inhibit Binding of a Human VEGF to a Human VEGF Receptor Flt-1

The activity of the anti-human VEGF receptor Flt-1 monoclonal antibodies described in the above-described section 5 to inhibit binding of human VEGF to human VEGF receptor Flt-1 was confirmed in the following manner.

Methanol was dispensed in 100 µl portions into wells of a 96 well MultiScreen-IP Plate (manufactured by Millipore) to give hydrophilic nature to the PVDF membrane on the bottom of the plate. After washing with water, the soluble human VEGF receptor Flt-1 7N diluted with PBS to a concentration of 1.6 µg/ml was dispensed ein 50 µl/well portions and then allowed to stand overnight at 4° C. for its adsorption. After washing, PBS containing 1% bovine serum albumin (BSA) is dispensed in 50 µl/well portions and the reaction was carried out at room temperature for 1 hour to block the remained active groups. After washing with PBS, each hybridoma culture supernatant or a purified monoclonal antibody diluted with 1% BSA-PBS containing 0.5 M NaCl (0.01 to 7.29 µg/ml) was dispensed in 50 µl/well portions and then 3 ng/ml of $^{125}$I-labeled human VEGF (manufactured by Amersham) was dispensed in 50 µl/well portions, subsequently carrying out the reaction at room temperature for 1.5 hours. After washing with 0.05% Tween-PBS, the wells were dried at 50° C., and Microscinti-0 (manufactured by Packard) was dispensed in 30 µl/well portions to measure the radioactivity of the $^{125}$I-labeled human VEGF linked to each well using Top Count (manufactured by Packard).

Figure 6:
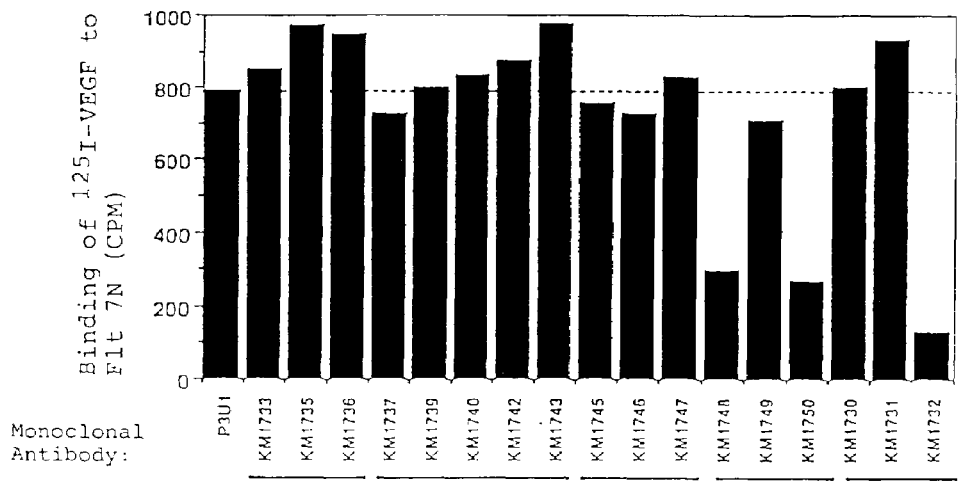
FIG. 6 is a graph showing results of the examination of the activity of anti-human VEGF receptor Flt-1 monoclonal antibody to inhibit binding of VEGF to human VEGF receptor Flt-1.

Results of the examination of activities of hybridoma culture supernatants are shown in FIG. 6. Among 17 established monoclonal antibodies, three monoclonal antibodies, KM1748, KM1750 and KM1732 inhibited binding of human VEGF to human VEGF receptor Flt-1 at inhibition ratios of 62.6%, 66.3% and 83.1%, respectively.

In general, screening of monoclonal antibody producing hybridomas is carried out using the same protein as the antigen used as the immunogen. A total of 11 monoclonal antibodies selected using Flt-1 7N as the immunogen showed no binding inhibition activity, and, among 6 monoclonal antibodies selected using Flt-1 3N (KM1748, KM1749, KM1750, KM1730, KM1731 and KM1732), KM1748, KM1750 and KM1732 showed the binding inhibition activity. It was an unexpected effect that monoclonal antibodies having the binding inhibition activity were obtained by the use of Flt-1 3N in the screening of hybridomas. Thus, it was revealed that Flt-1 3N is markedly important in establishing monoclonal antibodies having the binding inhibition activity.

Figure 7:
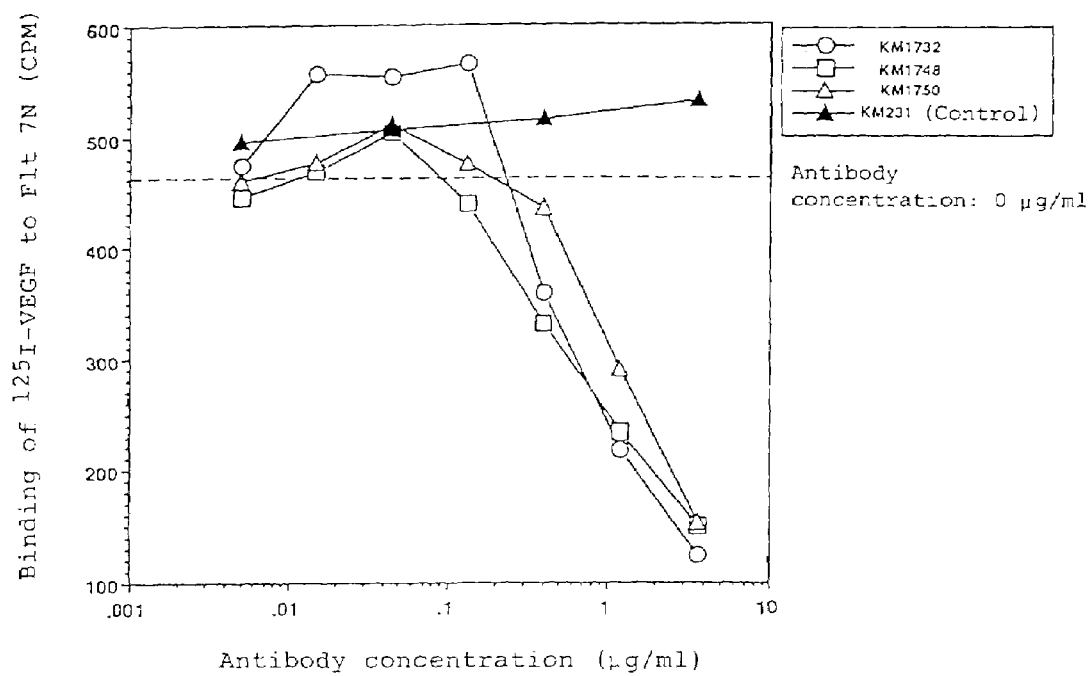
FIG. 7 is a graph showing results of the examination of the activity of anti-human VEGF receptor Flt-1 monoclonal antibodies KM1732, KM1748 and KM1750 to inhibit binding of human VEGF to human VEGF receptor Flt-1.

FIG. 7 shows results of the examination of binding inhibition activity using purified anti-Flt-1 monoclonal antibodies KM1732, KM1748 and KM1750. These antibodies KM1732, KM1748 and KM1750 inhibited binding of human VEGF to human VEGF receptor Flt-1 in a concentration dependent manner. Concentrations of KM1732, KM1748 and KM1750, which indicate 50% inhibition of the binding of human VEGF to human VEGF receptor Flt-1 ($IC_{50}$), were 1.1, 1.3 and 2.0 µg/ml, respectively. On the other hand, an anti-sialyl-Le$^a$ monoclonal antibody a KM231 of a mouse IgG1 class [*Anticancer Research*, 10: 1579 (1990)] used as the control showed no inhibition activity.

9. Confirmation of the Activity of Anti-Flt-1 Monoclonal Antibodies to Inhibit Binding of Human VEGF to Human VEGF Receptor Flt-1 Expression Cells The activity of the anti-human VEGF receptor Flt-1 monoclonal antibodies KM1732, KM1748 and KM1750 to inhibit binding of human VEGF to human VEGF receptor Flt-1 was confirmed in the following manner.

PBS containing 1% bovine serum albumin (BSA) was dispensed in 100 µl portions into wells of a 96 well Multi-Screen-HV Plate (manufactured by Millipore), the reaction was carried out at room temperature for 1 hour to block the active groups in the wells and then NIH3T3-Flt-1 cells suspended in 1% BSA-PBS containing 0.05% $NaN_3$ were dispensed in $5 \times 10^4$ cells/well portions. After washing with 1% BSA-PBS, a purified monoclonal antibody (0.01 to 7.29 µg/ml) was dispensed in 50 µl/well portions and then 3 ng/ml of $^{125}$I-labeled human VEGF (manufactured by Amersham) was dispensed in 50 µl/well portions and the reaction was carried out under cooling for 2 hours. After washing with PBS, the wells were dried at 0.50° C., and Microscinti-0 (manufactured by Packard) was dispensed in 30 µl/well portions to measure the radioactivity of the $^{125}$I-labeled human VEGF linked to each well using Top Count (manufactured by Packard).

Figure 8:
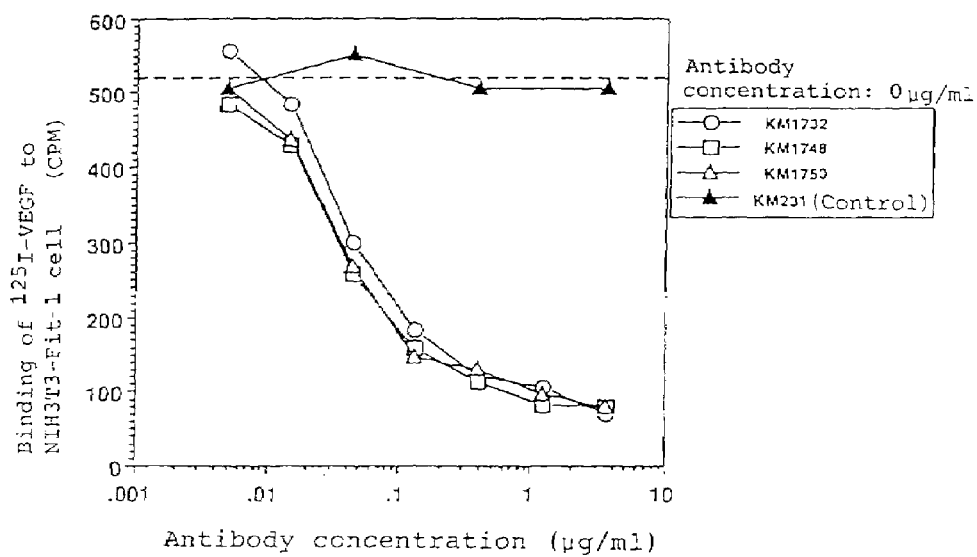
FIG. 8 is a graph showing results of the examination of the activity of anti-human VEGF receptor Flt-1 monoclonal antibodies KM1732, KM1748 and KM1750 to inhibit binding of human VEGF to human VEGF receptor Flt-1-expressing cells.

FIG. 8 shows results of the examination of binding inhibition activity using purified anti-Flt-1 monoclonal antibodies KM1732, KM1748 and KM1750. These antibodies KM1732, KM1748 and KM1750 inhibited binding of human VEGF to NIH3T3-Flt-1 cells in a concentration dependent manner. Concentrations of KM1732, KM1748 and KM1750, which indicate 50% inhibition of the binding of human VEGF to NIH3T3-Flt-1 cells ($IC_{50}$), were 0.050, 0.037 and 0.041 µg/ml, respectively. On the other hand, the anti-sialyl-Le$^a$ monoclonal antibody KM231 of a mouse IgG1 class used as the control showed no inhibition activity.

10. Confirmation of the Reactivity of Monoclonal Antibodies with Human VEGF Receptor Flt-1 Expression Cells Specificity of the anti-human VEGF receptor Flt-1 monoclonal antibodies described in the above-described section 5 was confirmed using immunocyte staining method in accordance the following procedure.

A total of $5 \times 10^5$ cells of each of human VEGF receptor Flt-1 expression NIH3T3 cells (NIH3T3-Flt-1) and control NIH3T3 cells (NIH3T3-Neo) [*Oncogene*, 10: 135 (1995)] were suspended in 100 µl of a buffer solution for immunocyte staining use (PBS containing 1% BSA, 0.02% EDTA and 0.05% sodium azide) and dispensed in a round bottom 96 well plate. After centrifugation at 4° C. and at 350×g for 1 minute, the supernatant fluid was discarded and the resulting cells were mixed with 50 µl of a hybridoma culture supernatant or purified antibody (10 µg/ml) and reaction was carried out at 4° C. for 30 minutes. After the reaction, 200 µl of the buffer solution for immunocyte staining use was added to each well, and the cells were washed by centrifugation at 4° C. and 350×g for 1 minute followed by discarding the resulting supernatant. After repeating this washing step twice, the cells were mixed with 50 µl of the buffer solution for immunocyte staining use containing 1 µg/ml of an FITC-labeled anti-mouse immunoglobulin antibody or FITC-labeled anti-rat immunoglobulin antibody (manufactured by Wako Pure Chemical Industries), and the reaction was carried out at 4° C. for 30 minutes. After this reaction, the above-described washing step was repeated three times and then analysis was carried out using Flow Cytometer (manufactured by Coulter).

Figure 9:
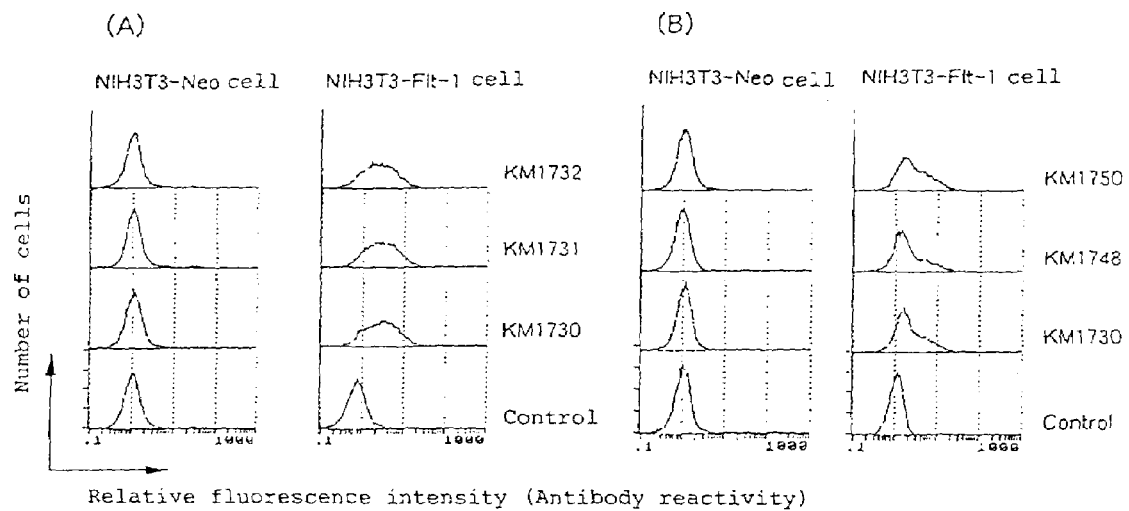
FIG. 9 is a graph showing results of the flow cytometry analysis of the reactivity of anti-human VEGF receptor Flt-1 monoclonal antibodies KM1730, KM1731, KM1732, KM1748 and KM1750 with human VEGF receptor Flt-1-expressing cells NIH3T3-Flt-1 and control cells NIH3T3-Neo cells.

The results are shown in FIG. 9. The anti-human VEGF receptor Flt-1 monoclonal antibodies KM1730, KM1731 and KM1732 did not react with the control cells but specifically reacted in significant amounts with the Flt-1 expression cells. Neither, the anti-human VEGF receptor Flt-1 monoclonal antibody KM1748 (10 µg/ml) nor the hybridoma culture supernatant KM1748 reacted with the control cells. Each specifically reacted in significant amounts with the Flt-1 expression cells (B). As the results, it was discovered that the monoclonal antibodies KM1730, KM1731, KM1732, KM1748 and KM1750 specifically recognize the human VEGF receptor Flt-1 on the cell surface. On the other hand, KM1735, KM1736, KM1742, KM1743 and KM1745 only weakly reacted with the human VEGF receptor Flt-1 expression cells in comparison with KM1730, KM1731, KM1732, KM1748 and KM1750.

11. Detection of Human VEGF Receptor Flt-1 by Western Blotting Using Monoclonal Antibody Cell membrane components were prepared from NIH3T3-Flt-1 cells and control NIH3T3 cells (NIH3T3-Neo) in accordance with a known method [*Cancer Research*, 46: 4438 (1986)] and electrophoresed by the SDS-PAGE method. The SDS-PAGE was carried out in accordance with a known method [*Anticancer Research*, 12: 1121 (1992)] by subjecting 15 µg, as protein per lane, of the cell membrane components to the electrophoresis using a 5 to 20% gradient gel (manufactured by Atto) under reducing conditions. The thus treated proteins were transferred to a PVDF membrane in accordance with a known method [*Anticancer Research*, 12: 1121 (1992)]. Next, the PVDF membrane was allowed to react with PBS containing 1% BSA at room temperature for 30 minutes to carry out blocking and then to react with the culture supernatant of the anti-human VEGF receptor Flt-1 monoclonal antibody KM1737 overnight at 4° C. The thus treated membrane was washed with PBS containing 0.05% Tween and then allowed to react with peroxidase-labeled goat anti-mouse IgG (5,000 times dilution: produced by Chemicon) at room temperature for 2 hours. After washing with 0.05% Tween-containing PBS, bands to which the anti-human VEGF receptor Flt-1 monoclonal antibody KM1737 was linked were detected using ECL™ Western blotting detection reagents (manufactured by Amersham).

Figure 10:
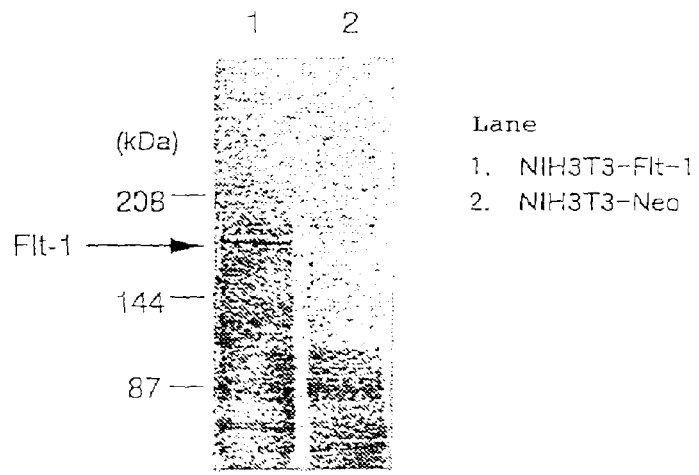
FIG. 10 is a graph showing results of the examination of the reactivity of anti-human VEGF receptor Flt-1 monoclonal antibody KM1737 with human VEGF receptor Flt-1 by Western blotting. Lane 1 shows Western blotting pattern of NIH3T3-Flt-1 cells and lane 2 shows the pattern of NIH3T3-Neo cells.

The results are shown in FIG. 10. It was confirmed that the anti-human VEGF receptor Flt-1 monoclonal antibody KM1737 can detect the human VEGF receptor Flt-1 of 180 kilo dalton in molecular weight expressed in the NIH3T3-Flt-1 cells.

12. Detection of Soluble Human VEGF Receptor Flt-1 Using Monoclonal Antibody

The anti-human VEGF receptor Flt-1 monoclonal antibody KM1732 was diluted with PBS to a concentration of 10 µg/ml and dispensed in 50 µl/well portions into a 96 well plate for EIA (manufactured by Greiner) and allowed to stand overnight at 4° C. for coating. After washing, PBS containing 1% bovine serum albumin (BSA) was dispensed in 100 µl/well portions and the reaction was carried out at room temperature for 1 hour to block the remained active groups. After discarding 1% BSA-PBS, the purified soluble human VEGF receptors Flt-1 7N and Flt-1 3N obtained in the above-described step 1-(4) and diluted with 1% BSA-PBS to a concentration of 1,000 to 0.0056 ng/ml were allowed to react with the antibody overnight at 4° C. After washing with 0.05% Tween-PBS, the anti-human VEGF receptor Flt-1 monoclonal antibody KM1730 labeled with biotin by a known method [*Enzyme Antibody Method*:

published by Gakusai Kikaku (1985)] was diluted with 1% BSA-PBS to a concentration of 0.1 μg/ml and dispensed in 50 μl/well portions to carry out the reaction at room temperature for 2 hours. After washing with 0.05% Tween-PBS, avidin-labeled peroxidase (manufactured by Vector) diluted 4,000 times with 1% BSA-PBS was dispensed in 50 μl/well portions to carry out the reaction at room temperature for 1 hour. After washing with 0.05% Tween-PBS, color development was caused using ABTS substrate solution [2,2-azinobis(3-ethylbenzothiazole-6-sulfonic acid) ammonium salt] to measure absorbance at OD415 nm using E max (manufactured by Molecular Devices).

Figure 11:
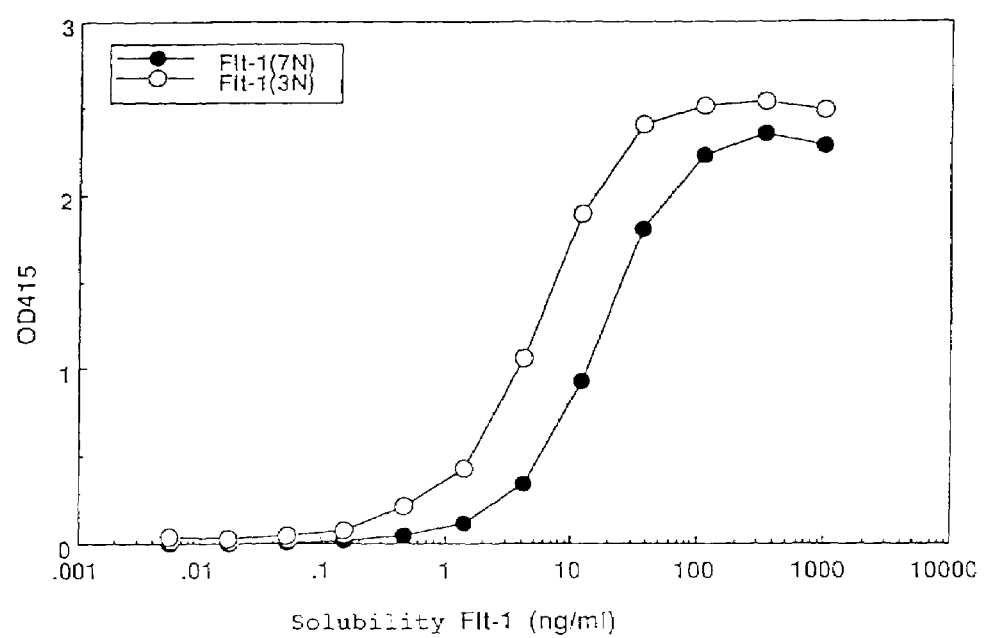
FIG. 11 is a graph showing results of the examination of the determination system of soluble human VEGF receptors Flt-1 3N and Flt-1 7N, carried out using anti-human VEGF receptor. Flt-1 monoclonal antibodies KM1732 and biotinated KM1730.

The results are shown in FIG. 11. As the results, it was found that the soluble human VEGF receptors Flt-1 3N and Flt-1 7N can be measured from minimum concentrations of 0.46 ng/ml and 1.37 ng/ml, respectively, by the use of the anti-human VEGF receptor Flt-1 monoclonal antibody KM1732 and the biotin-labeled anti-human VEGF receptor Flt-1 monoclonal antibody KM1730.

13. Confirmation of the Reactivity of Monoclonal Antibodies with Human Vascular Endothelial Cells HUVEC The reactivity of anti-human VEGF receptor Flt-1 monoclonal antibodies described in the above-described section 5 with human vascular endothelial cells HUVEC was confirmed by immunocyte staining in the following manner.

A total of $2 \times 10^5$ cells of human umbilical vein endothelial cells (HUVEC) were suspended in 100 μl of a buffer solution for immunocyte staining use (PBS containing 1% BSA, 0.02% EDTA and 0.05% sodium azide) and dispensed in a round bottom 96 well plate. After centrifugation at 4° C. and at 350×g for 1 minute, the supernatant fluid was discarded and the resulting cells were mixed with 50 μl (10 μg/ml) of each of biotinated purified antibodies KM1730 and KM1750 and control antibodies thereof, individually, and subsequently incubated at 4° C. for 30 minutes. As the control antibody of KM1730, an anti-MxA monoclonal antibody KM1135 (WO 96/05230) of IgG1 type which is the same subclass of KM1730 was used. As the control antibody of KM1750, an anti-T cell receptor γ chain monoclonal antibody KM365 (Japanese Published Unexamined Patent Application No. 491/90) of IgG2b which is the same subclass as KM1750 was used. Thereafter, 200 μl of the buffer solution for immunocyte staining use was added to each well, and the cells were washed by carrying out centrifugation at 4° C. and at 350×g for 1 minute and then the resulting supernatant was discarded. After again repeating this washing step twice, the cells were mixed with 20 μl of the buffer solution for immunocyte staining use containing 5 μg/ml in concentration of Avidin-PE (Streptoavidin-R-Phycoerythrin) (manufactured by Gibco), and the reaction was carried out at 4° C. for 30 minutes. After the reaction, the above-described washing step was repeated three times and then the analysis was carried out using Flow Cytometer (manufactured by Coulter).

Figure 12:
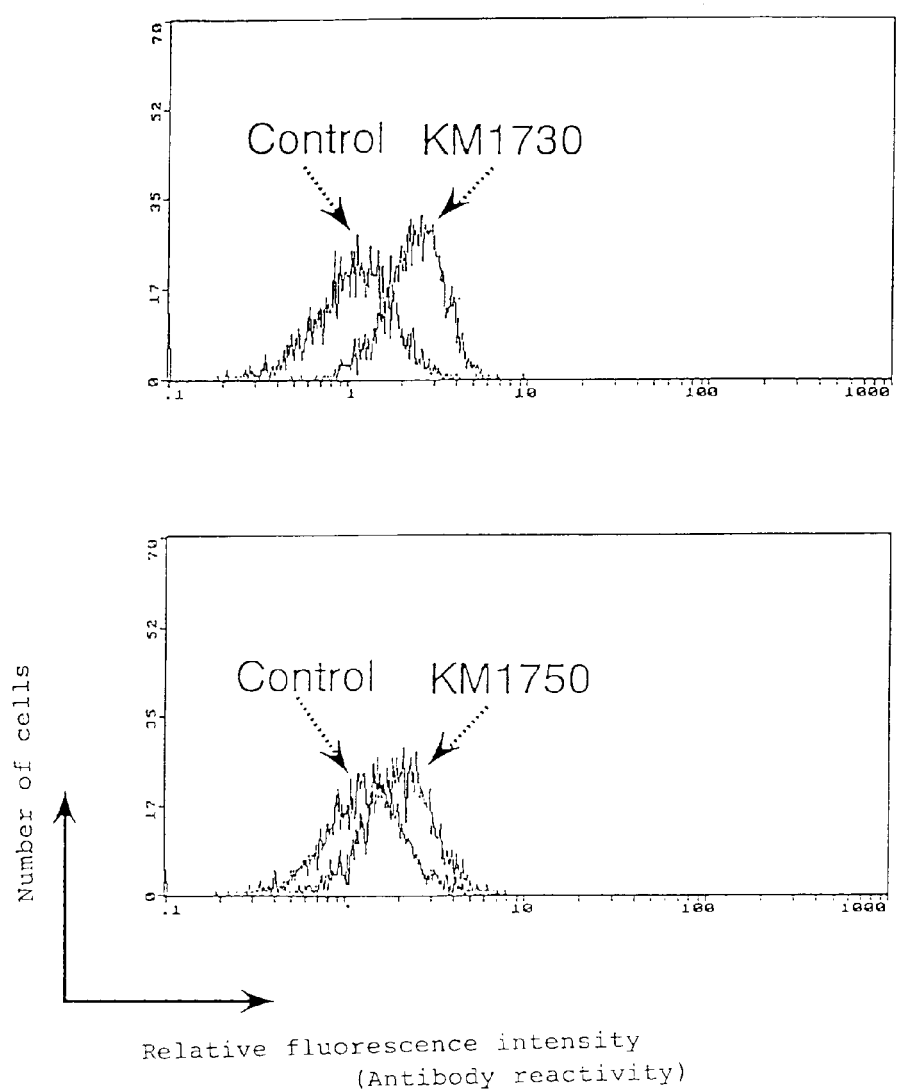
FIG. 12 is a graph showing results of the flow cytometry analysis of the reactivity of anti-human VEGF receptor Flt-1 monoclonal antibody with human vascular endothelial cells HUVEC.

The results are shown in FIG. 12. The anti-human VEGF receptor Flt-1 monoclonal antibodies KH1730 and KM1750 reacted with HUVEC when compared with their control antibodies. These results demonstrate that the monoclonal antibodies KM1730 and KM1750 can detect human VEGF receptor Flt-1 on human vascular endothelial cells.

14. Increase of the Expression Quantity of Flt-1 on HUVEC by VEGF Stimulation

As a model of vascular endothelial cells in an angiogenesis region, changes in the expression of human VEGF receptor Flt-1 before and after stimulation with VEGF were examined using the anti-human VEGF receptor Flt-1 monoclonal antibody KM1730 in accordance with the following procedure.

A total of 4 to $6 \times 10^5$ cells of each of four lots of HUVEC (lot #4031, #4102, #2477 and #4723; purchased from Clonetics) were suspended in 20 ml of a medium (manufactured by KURABO) (control medium) comprising E-BM medium further supplemented with 5% fetal bovine serum (FBS), 10 ng/ml of human recombinant type epidermal growth factor (hEGF), 1 μg/ml of hydrocortisone, 50 μg/ml of gentamicin and 50 ng/ml of amphotericin, and the suspension was further mixed with 1.2 μg/ml of bovine brain extract (BBE) (manufactured by KURABO) as a growth factor and cultured at 37° C. for 2 to 3 days. When the cells were proliferated into 1 to $2 \times 10^6$ cells, the medium was removed and replaced with 20 ml of fresh control medium to carry out a total of 2 days of culturing. After the culturing for 1 day, human VEGF was added to a final concentration of 5 ng/ml, and the cells after the additional culturing for 1 day were used as VEGF-stimulated cells. Cells cultured for 2 days without adding VEGF were used as control cells (VEGF-non-stimulated cells). After the culturing, the cells were collected to examine reactivity of the anti-human VEGF receptor Flt-1 monoclonal antibody KM1730 by the immunocyte staining method in accordance with the procedure described in the above section 13.

Figure 13:
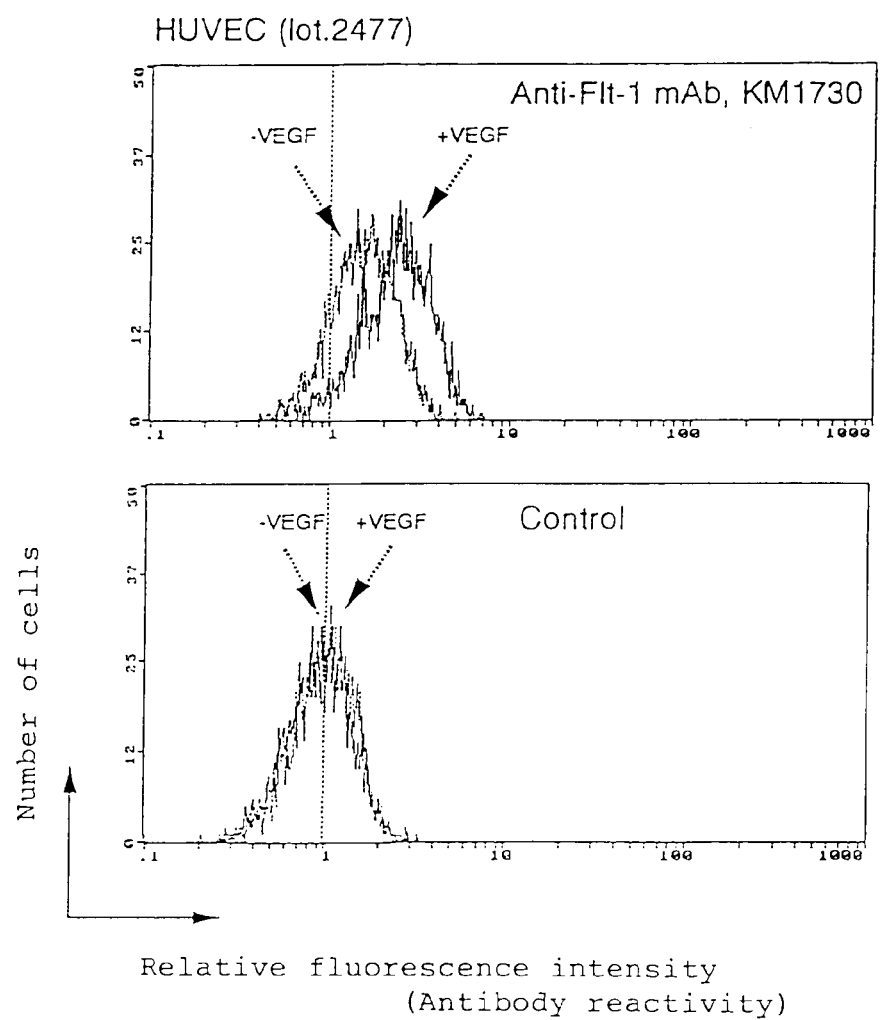
FIG. 13 is a graph showing results of the flow cytometry analysis of the reactivity of anti-human VEGF receptor Flt-1 monoclonal antibody with human vascular endothelial cells HUVEC under a VEGF non-stimulation or stimulation condition.
Figure 14:
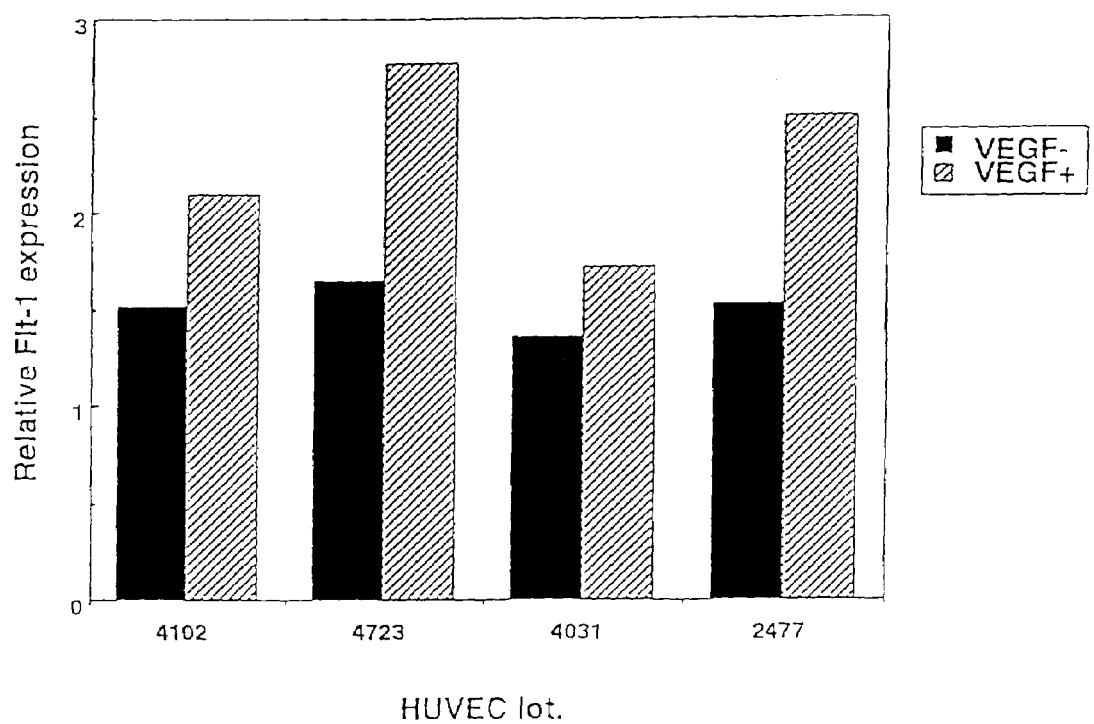
FIG. 14 is a graph showing results of the analysis on the changes in the expression quantity of human VEGF receptor Flt-1 in human vascular endothelial cells HUVEC under a VEGF non-stimulation or stimulation condition. The expression quantity of Flt-1 is shown as a relative reaction value of anti-human VEGF receptor Flt-1 monoclonal antibody KM1730 when the reactivity of a control antibody is defined as 1.

Results of the examination of its reactivity with the lot #2477 HUVEC are shown in FIG. 13. KM1730 reacted with VEGF-non-stimulated HUVEC but more strongly with VEGF-stimulated HUVEC. Reactivity of the control antibody KM1135 did not change independent of the VEGF stimulation or non-stimulation. FIG. 14 shows changes in the Flt-1 expression in four lots of HUVEC (lot #4031, #4102, #2477 and #4723) by VEGF stimulation. The expression quantity of Flt-1 which can express the reactivity of KM1730 as an index is shown as a relative value when reactivity of the control antibody is defined as 1. It was revealed that all of the four lots of HUVEC can express Flt-1 by VEGF non-stimulation, and the expression quantity of Flt-1 increases by the VEGF stimulation.

The increase of the expression quantity of Flt-1 and the reactivity of anti-Flt-1 monoclonal antibody in the VEGF-stimulated human vascular endothelial cells HUVEC as a model of angiogenesis shows that the monoclonal antibody is useful for the diagnosis or treatment of diseases in which their morbid states progress by the acceleration of angiogenesis caused by VEGF, such as tumors, rheumatoid arthritis, diabetic retinopathy, and the like.

EXAMPLE 2

1. Isolation and Analysis of cDNA Encoding Anti-Human VEGF Receptor Flt-1 Mouse Monoclonal Antibody (1) Preparation of mRNA from Hybridoma Capable of Producing Anti-Human VEGF Receptor Flt-1 Mouse Monoclonal Antibody Using a mRNA extraction kit, Fast Track manufactured by Invitrogen, and in accordance with the manual attached to the kit, mRNA was prepared from $1 \times 10^8$ cells of each of hybridomas capable of producing anti-human VEGF receptor Flt-1 mouse monoclonal antibodies KM1732 and KM1750 obtained in Example 1 (FERM BP-5698 and FERM BP-5700, respectively).

(2) Preparation of Heavy Chain and Light Chain cDNA Libraries of Hybridoma Capable of Producing Anti-Human VEGF Receptor Flt-1 Mouse Monoclonal Antibody Using cDNA Synthesis Kit (manufactured by Pharmacia Biotech) and in accordance with the manual attached to the kit, cDNA having EcoRI-NotI adapter on both termini was synthesized from 5 μg of each of KM1732 and KM1750 mRNA samples obtained in 1(1) of Example 2. About 6 μg of each of the thus prepared cDNA samples was dissolved in 10 μl of sterilized water and fractionated by agarose gel electrophoresis to recover about 0.1 μg of a cDNA fragment of about 1.5 kb which corresponds to the heavy chain (hereinafter referred to as "H chain") of the IgG type antibody and similar amount of a cDNA fragment of about 1.0 kb that corresponds to the light chain (hereinafter referred to as "L chain") thereof. Next, 0.1 μg of the cDNA fragment of about 1.5 kb, 0.1 μg of the cDNA fragment of about 1.0 kb and 1 μg of Lambda ZAPII Vector (a preparation obtained by digesting Lambda ZAPII Vector with EcoRI and then treating it with calf intestine alkaline phosphatase: manufactured by Stratagene) were dissolved in 11.5 μl of a T4 ligase buffer solution (manufactured by Takara Shuzo Co., Ltd.), and the thus prepared solution was mixed with 175 units of T4 DNA ligase (manufactured by Takara Shuzo Co., Ltd.) and incubated at 12° C. for 24 hours and then at room temperature for 2 hours. Thereafter, a 4 μl portion of each of the reaction solutions was packaged in lambda phage using Gigapack Gold Packaging Kit (manufactured by Stratagene) in accordance with the conventional method [*Molecular Cloning*, 2.95, Cold Spring Harbor Laboratory (1989)], and *Escherichia coli* XL1-Blue [*Biotechniques*, 5: 376 (1987)] attached to Gigapack Gold Packaging Kit (manufactured by Stratagene) was infected with the resulting phage in accordance with the conventional method [*Molecular Cloning*, 2.95-107, Cold Spring Harbor Laboratory (1989)] to obtain about 4×10³ phage clones as each of the H chain cDNA libraries and L chain cDNA libraries of KM1732 and KM17540.

(3) Cloning of cDNA Encoding H Chain and L Chain of Hybridoma Capable of Producing Anti-Human VEGF Receptor Flt-1 Mouse Monoclonal Antibody Respective phage particles prepared in the step 1-(2) of Example 2 were fixed on nitrocellulose filters in accordance with the conventional method [*Molecular Cloning*, 2.12, Cold Spring Harbor Laboratory (1989)]. Each of the resulting nitrocellulose filters was treated in accordance with the manual attached to ECL direct nucleic acid labelling and detection systems (manufactured by Amersham) to obtain phage clones which strongly bonded to a probe cDNA encoding the constant region (hereinafter referred to as "C region") of mouse immunoglobulin {cDNA encoding H chain is a fragment of mouse Cγ1 cDNA [*Cell*, 18: 559 (1979)] and cDNA encoding L chain is a fragment of mouse CK cDNA [*Cell*, 22: 197 (1980)]}. Thereafter, the phage clones were transformed into plasmid pBluescript SK(−) in accordance with the manual attached to Lambda ZAPII Vector (manufactured by Stratagene), thus finally obtaining a recombinant plasmid KM1732HA2 containing cDNA encoding the H chain of KM1732, a recombinant plasmid KM1732L2-1 containing cDNA encoding L chain of KM1732, a recombinant plasmid KM1750H2-1 containing cDNA encoding the H chain of KM1750 and a recombinant plasmid KM1750L3-1 containing cDNA encoding L chain of KM1750. *Escherichia coli* XL1-Blue MRF'/ KM1732HA2 containing the recombinant plasmid KM1732HA2, *Escherichia coli* XL1-Blue MRF'/ KM1732L2-1 containing the recombinant plasmid KM1732L2-1, *Escherichia coli* XL1-Blue MRF'/ KM1750H2-1 containing the recombinant plasmid KM1750H2-1 and *Escherichia coli* XL1-Blue MRF'/ KM1750L3-1 containing the recombinant plasmid KM1750L3-1 have been deposited on May 14, 1998, in National Institute of Bioscience and Human Technology, Agency of Industrial Science and Technology, and have been assigned the designations as FERM BP-6354, FERM BP-6352, FERM BP-6353 and FERM BP-6355, respectively.

(4) Determination of Variable Region Nucleotide Sequence of cDNA Encoding H Chain and L Chain of Anti-Human VEGF Receptor Flt-1 Mouse Monoclonal Antibody Variable region (hereinafter referred to as "V region") nucleotide sequence of each of the cDNA samples obtained in the step 1-(3) of Example 2 encoding H chain and L chain of anti-human VEGF receptor Flt-1 mouse monoclonal antibody was determined by reacting 0.1 μg of each of the obtained plasmid samples in accordance with the manual attached to BigDye Terminator Cycle Sequencing Ready Reaction Kit (manufactured by Applied Biosystems) and then carrying out electrophoresis using ABI PRISM™ 377 (manufactured by Applied Biosystems). Based on the thus determined nucleotide sequence of each cDNA, amino acid sequences of the V region of H chain (hereinafter referred to as "VH") and the V region of L chain (hereinafter referred to as "VL") of KM1732 and KM1750 were determined. The nucleotide sequence and amino acid sequence of the VH of KM1732 are shown in SEQ ID NOS:5 and 86, respectively, those of the VL of KM1732 are shown in SEQ ID NOS:6 and 87, respectively, those of the VH of KM1750 are shown in SEQ ID NOS:7 and 88, respectively, and those of the VL of KM1750 in SEQ ID NOS:8 and 89, respectively.

(5) Identification of CDR Sequences of H Chain and L Chain of Anti-Human VEGF Receptor Flt-1 Mouse Monoclonal Antibody Based on the amino acid sequences of the VH and VL of anti-human VEGF receptor Flt-1 mouse monoclonal antibody determined in the step 1-(4) of Example 2, CDR sequences of respective VH and VL were identified by comparing them with known antibody V region amino acid sequences (*Sequences of Proteins of Immunological Interest*). The amino acid sequences of CDR 1, 2 and 3 of the VH of KM1732 are shown in SEQ ID NOS:9, 10 and 11, respectively; those of CDR 1, 2 and 3 of the VL of KM1732 are shown in SEQ ID NOS:12, 13 and 14, respectively; those of CDR 1, 2 and 3 of the VH of KM1750 are shown in SEQ ID NOS:15, 16 and 17, respectively; and those of CDR 1, 2 and 3 of the VL of KM1750 are shown in SEQ ID NOS:18, 19 and 20, respectively.

2. Production of Anti-Human VEGF Receptor Flt-1 Human Chimeric Antibodies

Anti-human VEGF receptor Flt-1 human chimeric antibodies KM2532 and KM2550 originated from the anti-human VEGF receptor Flt-1 mouse monoclonal antibodies KM1732 and KM1750 having the activity to inhibit biological activities of human VEGF receptor Flt-1 were produced in the following manner.

(1) Construction of Expression Vector pKANTEX1732 of Anti-Human VEGF Receptor Flt-1 Human Chimeric Antibody The expression vector pKANTEX1732 of anti-human VEGF receptor Flt-1 human chimeric antibody was constructed in the following manner using a tandem cassette vector pKANTEX93 for humanized antibody expression use described in WO 97/10354 and the plasmids KM1732HA2 and KM1732L2-1 obtained in Example 2-1.

A 3 µg portion of plasmid pBluescript SK(−) (manufactured by Stratagene) was added to 10 µl of a buffer solution comprising 10 mM Tris-HCl (pH 7.5), 10 mM magnesium chloride and 1 mM DTT, 10 units of a restriction enzyme ApaI (manufactured by Takara Shuzo Co., Ltd.) were further added thereto, and then the reaction was carried out at 37° C. for 1 hour. The reaction solution was precipitated with ethanol, the thus obtained precipitate was added to 10 µl of a buffer solution comprising 50 mM Tris-HCl (pH 7.5), 100 mM sodium chloride, 10 mM magnesium chloride, 1 mM DTT, 100 µg/ml bovine serum albumin (hereinafter referred to as "BSA") and 0.01% Triton X-100, 10 units of a restriction enzyme NotI (manufactured by Takara Shuzo Co., Ltd.) were further added thereto, and then the reaction was carried out at 37° C. for 1 hour. The reaction solution was fractionated by agarose gel electrophoresis to recover about 2 µg of an ApaI-NotI fragment of about 2.95 kb. Next, 5 µg of the plasmid KM1732HA2 was added to 10 µl of a buffer solution comprising 20 mM Tris-HCl (pH 7.9), 10 mM magnesium acetate, 50 mM potassium acetate, 1 mM DTT and 100 µg/ml BSA, 10 units of a restriction enzyme NlaIV (manufactured by New England Biolabs) were further added thereto, and then the reaction was carried out at 37° C. for 1 hour. The reaction solution was precipitated with ethanol, the thus obtained precipitate was added to 10 µl of a buffer solution comprising 50 mM Tris-HCl (pH 7.5), 100 mM sodium chloride, 10 mM magnesium chloride, 1 mM DTT, 100 µg/ml BSA and 0.01% Triton X-100, 10 units of a restriction enzyme NotI (manufactured by Takara Shuzo Co., Ltd.) were further added thereto, and then the reaction was carried out at 37° C. for 1 hour. The reaction solution was fractionated by agarose gel electrophoresis to recover about 0.5 µg of an NlaIV-NotI fragment of about 0.41 kb. Next, a synthetic DNA having the nucleotide sequence of SEQ ID NO:21 or 22 was synthesized (manufactured by Sawady Technology), and a 0.3 µg portion of each synthetic DNA was added to 15 µl of sterilized water and heated at 65° C. for 5 minutes. The reaction solution was allowed to stand at room temperature for 30 minutes, mixed with 2 µl of a 10-fold buffer solution [500 mM Tris-HCl (pH 7.6), 100 mM magnesium chloride and 50 mM DTT] and 2 µl of 10 mM ATP and then with 10 units of T4 polynucleotide kinase (manufactured by Takara Shuzo Co., Ltd.), and the mixture was allowed to react at 37° C. for 30 minutes to phosphorylating the 5' end.

Figure 15:
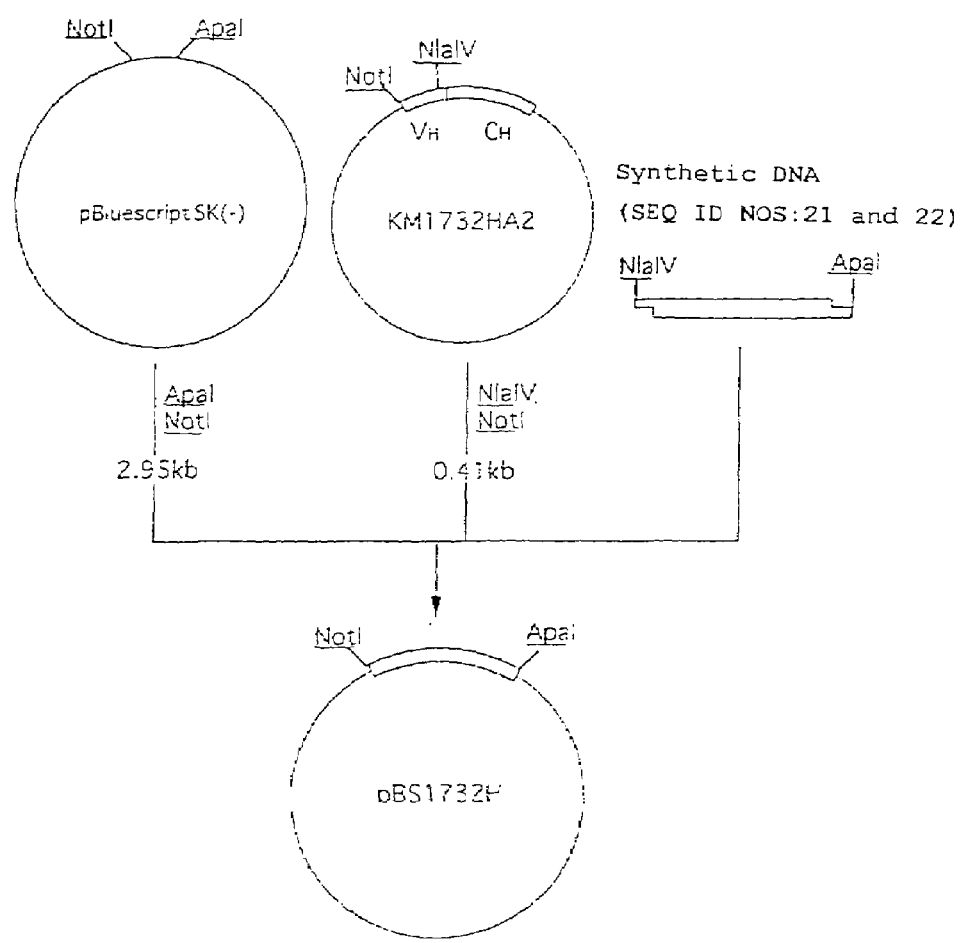
FIG. 15 is a graph showing construction steps of plasmid pBS1732H.

A 0.1 µg portion of the ApaI-NotI fragment derived from plasmid pBluescript SK(−), 0.1 µg of the NlaIV-NotI fragment derived from plasmid KM1732HA2 and 0.05 µg of the phosphorylated synthetic DNA, obtained by the just described procedures, were added to 10 µl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pBS1732H shown in FIG. 15.

Next, 3 µg portion of plasmid phKM1259LV0 described in WO 97/10354 was added to 10 µl of a buffer solution comprising 50 mM Tris-HCl (pH 7.5), 100 mM sodium chloride, 10 mM magnesium chloride, 1 mM DTT and 100 µg/ml BSA, 10 units of a restriction enzyme EcoRI (manufactured by Takara Shuzo Co., Ltd.) and 10 units of a restriction enzyme SplI (manufactured by Takara Shuzo Co., Ltd.) were further added thereto, and then the reaction was carried out at 37° C. for 1 hour. The reaction solution was fractionated by agarose gel electrophoresis to recover about 2 µg of an EcoRI-SplI fragment of about 2.95 kb. Next, 5 µg of the plasmid KM1732L2-1 was added to 10 µl of a buffer solution comprising 10 mM Tris-HCl (pH 7.5), 100 mM magnesium chloride and 1 mM DTT, 10 units of a restriction enzyme MboII (manufactured by TOYOBO CO., LTD.) were further added thereto, and then the reaction was carried out at 37° C. for 1 hour. The reaction solution was precipitated with ethanol, the thus obtained precipitate was added to 10 µl of a buffer solution comprising 50 mM Tris-HCl (pH 7.5), 100 mM sodium chloride, 10 mM magnesium chloride and 1 mM DTT, 10 units of a restriction enzyme EcoRI (manufactured by Takara Shuzo Co., Ltd.) were further added thereto, and then the reaction was carried out at 37° C. for 1 hour. The reaction solution was fractionated by agarose gel electrophoresis to recover about 0.5 µg of a MboII-EcoRI fragment of about 0.38 kb. Next, a synthetic DNA having the nucleotide sequence of SEQ ID NO:23 or 24 was synthesized (manufactured by Sawady Technology), and a 0.3 µg portion of each synthetic DNA was added to 15 µl of sterilized water and heated at 65° C. for 5 minutes. The reaction solution was allowed to stand at room temperature for 30 minutes, mixed with 2 µl of a 10-fold buffer solution [500 mM Tris-HCl (pH 7.6), 100 mM magnesium chloride and 50 mM DTT] and 2 µl of 10 mM ATP and then with 10 units of T4 polynucleotide kinase (manufactured by Takara Shuzo Co., Ltd.), and the mixture was allowed to react at 37° C. for 30 minutes to phosphorylate the 5' end.

Figure 16:
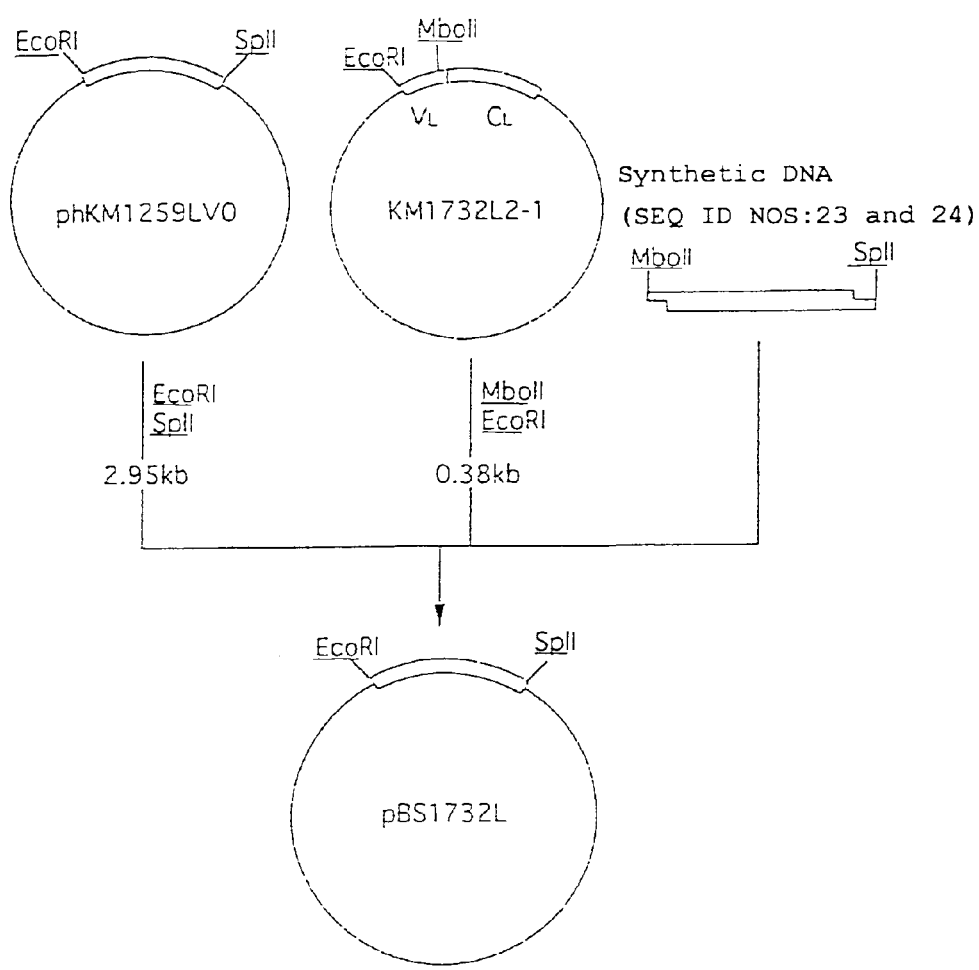
FIG. 16 is a graph showing construction steps of plasmid pBS1732L.

A 0.1 µg portion of the EcoRI-SplI fragment derived from plasmid phKM1259LV0, 0.1 µg of the MboII-EcoRI fragment derived from plasmid KM1732L2-1 and 0.05 µg of the phosphorylated synthetic DNA, obtained by the just described procedures, were added to 10 µl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pBS1732L shown in FIG. 16.

Next, 3 µg of the vector pKANTEX93 for humanized antibody expression was added to 10 µl of a buffer solution comprising 10 mM Tris-HCl (pH 7.5), 10 mM magnesium chloride and 1 mM DTT, 10 units of a restriction enzyme ApaI (manufactured by Takara Shuzo Co., Ltd.) were further added thereto, and then the reaction was carried out at 37° C. for 1 hour. The reaction solution was precipitated with ethanol, the thus obtained precipitate was added to 10 µl of a buffer solution comprising 50 mM Tris-HCl (pH 7.5), 100 mM sodium chloride, 10 mM magnesium chloride, 1 mM DTT, 100 µg/ml BSA and 0.01% Triton X-100, 10 units of a restriction enzyme NotI (manufactured by Takara Shuzo Co., Ltd.) were further added thereto, and then the reaction was carried out at 37° C. for 1 hour. The reaction solution was fractionated by agarose gel electrophoresis to recover about 1 µg of an ApaI-NotI fragment of about 12.75 kb. Next, 5 µg of the plasmid pBS1732H obtained in the foregoing was added to 10 µl of a buffer solution comprising 10 mM Tris-HCl (pH 7.5), 10 mM magnesium chloride and 1 mM DTT, 10 units of a restriction enzyme ApaI (manufactured by Takara Shuzo Co., Ltd.) were further added thereto, and then the reaction was carried out at 37° C. for 1 hour. The reaction solution was precipitated with ethanol, the thus obtained precipitate was added to 10 µl of a buffer solution comprising 50 mM Tris-HCl (pH 7.5), 100 mM sodium chloride, 10 mM magnesium chloride, 1 mM DTT, 100 µg/ml BSA and 0.01% Triton X-100, 10 units of a restriction enzyme NotI (manufactured by Takara Shuzo Co., Ltd.) were further added thereto, and then the reaction was carried out at 37° C. for 1 hour. The reaction solution was fractionated by agarose gel electrophoresis to recover about 0.5 μg of an ApaI-NotI fragment of about 0.46 kb.

Figure 17:
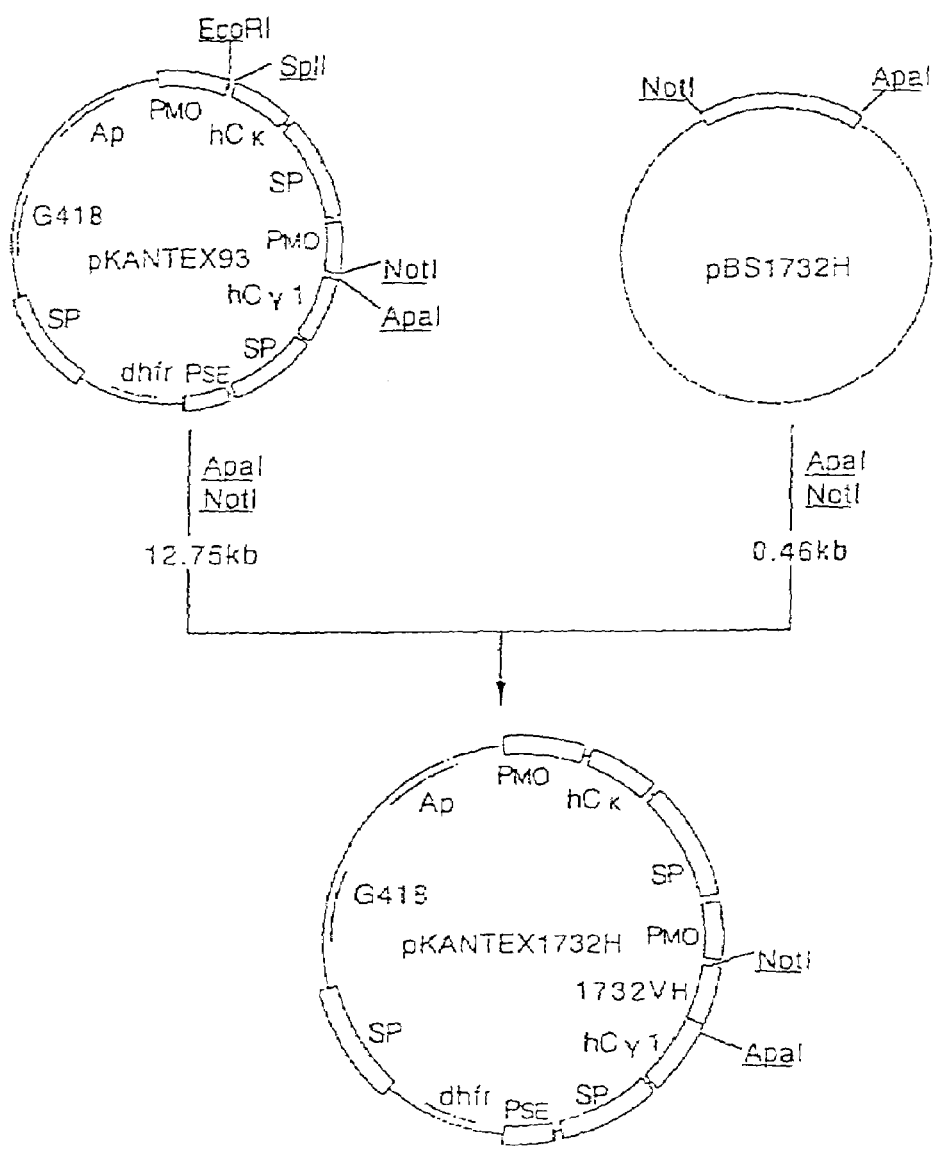
FIG. 17 is a graph showing construction steps of plasmid pKANTEX1732H.

A 0.1 μg portion of the ApaI-NotI fragment derived from the vector pKANTEX93 for humanized antibody expression and 0.1 μg of the ApaI-NotI fragment derived from the plasmid pBS1732H, obtained by the just described procedures, were added to 10 μl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pKANTEX1732H shown in FIG. 17.

Next, 3 μg of the just obtained plasmid pKANTEX1732H was added to 10 μl of a buffer solution comprising 50 mM Tris-HCl (pH 7.5), 100 mM sodium chloride, 10 mM magnesium chloride, 1 mM DTT and 100 μg/ml BSA, 10 units of a restriction enzyme EcoRI (manufactured by Takara Shuzo Co., Ltd.) and 10 units of a restriction enzyme SplI (manufactured by Takara Shuzo Co., Ltd.) which were further added thereto, and then the reaction was carried out at 37° C. for 1 hour. The reaction solution was fractionated by agarose gel electrophoresis to recover about 1 μg of an EcoRI-SplI fragment of about 13.20 kb. Next, 5 μg of the plasmid pBS1732L obtained in the foregoing was added to 10 μl of a buffer solution comprising 50 mM Tris-HCl (pH 7.5), 100 mM sodium chloride, 10 mM magnesium chloride, 1 mM DTT and 100 μg/ml BSA, 10 units of a restriction enzyme EcoRI (manufactured by Takara Shuzo Co., Ltd.) and 10 units of a restriction enzyme SplI (manufactured by Takara Shuzo Co., Ltd.) were further added thereto, and then the reaction was carried out at 37° C. for 1 hour. The reaction solution was fractionated by agarose gel electrophoresis to recover about 0.5 μg of an EcoRI-SplI fragment of about 0.39 kb.

Figure 18:
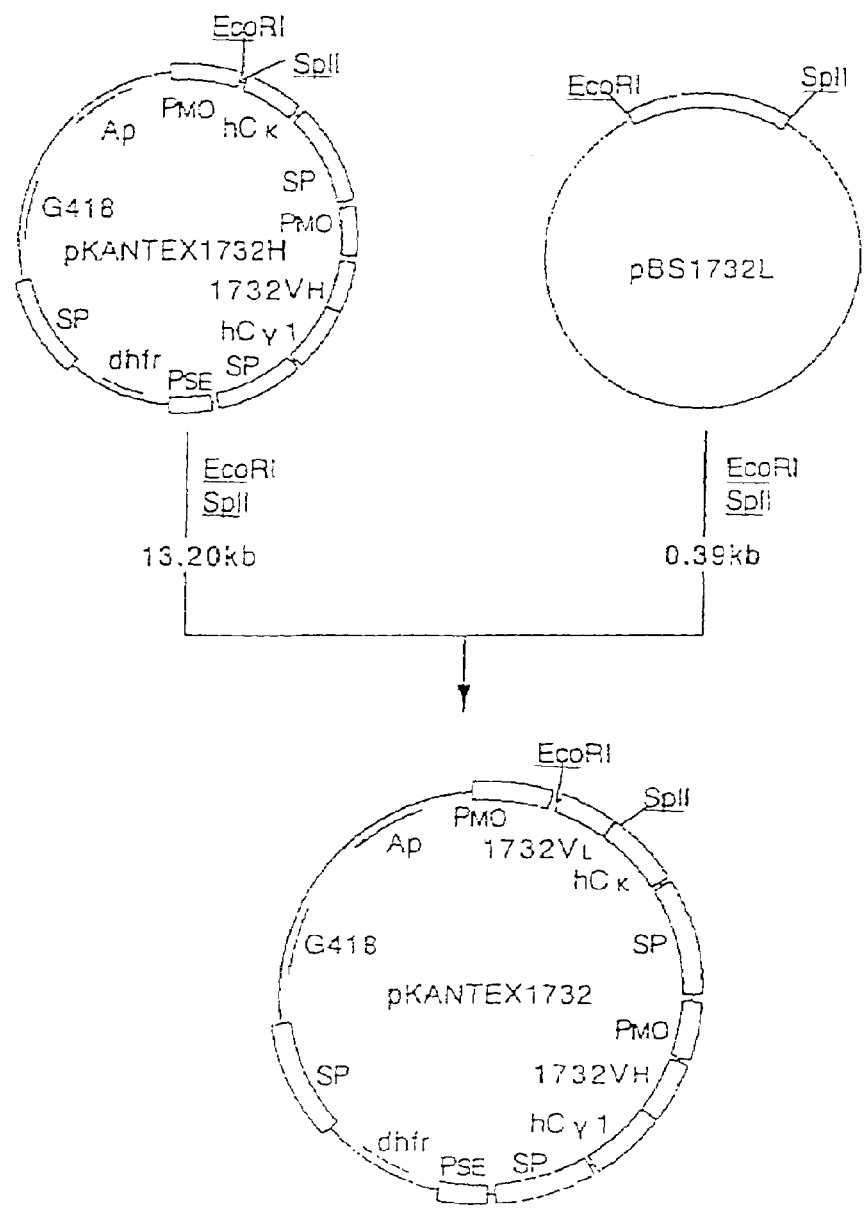
FIG. 18 is a graph showing construction steps of plasmid pKANTEX1732.

A 0.1 μg portion of the EcoRI-SplI fragment derived from the plasmid pKANTEX1732H and 0.1 μg of the EcoRI-SplI fragment derived from the plasmid pBS1732L, obtained by the just described procedures, were added to 10 μl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pKANTEX1732 shown in FIG. 18.

(2) Construction of Expression Vector pKANTEX1750 of Anti-Human VEGF Receptor Flt-1 Human Chimeric Antibody The expression vector pKANTEX1750 of anti-human VEGF receptor Flt-1 human chimeric antibody was constructed in the following manner using a tandem cassette vector pKANTEX93 for humanized antibody expression described in WO 97/10354 and the plasmids KM1750H2-1 and KM1750L3-1 obtained in Example 2-1.

A 5 μg portion of the plasmid KM1750H2-1 was added to 10 μl of a buffer solution comprising 33 mM Tris-HCl (pH 7.9), 10 mM magnesium acetate, 66 mM potassium acetate and 100 μg/ml BSA, 10 units of a restriction enzyme Alw26I (manufactured by New England Biolabs) were further added thereto, and then the reaction was carried out at 37° C. for 1 hour. The reaction solution was precipitated with ethanol, the thus obtained precipitate was added to 10 μl of a buffer solution comprising 50 mM Tris-HCl (pH 7.5), 100 mM sodium chloride, 10 mM magnesium chloride, 1 mM DTT, 100 μg/ml BSA and 0.01% Triton X-100, 10 units of a restriction enzyme NotI (manufactured by Takara Shuzo Co., Ltd.) were further added thereto, and then the reaction was carried out at 37° C. for 1 hour. The reaction solution was fractionated by agarose gel electrophoresis to recover about 0.5 μg of an Alw261I-NotI fragment of about 0.41 kb. Next, a synthetic DNA having the nucleotide sequence of SEQ ID NO:25 or 26 was synthesized (manufactured by Sawady Technology), and a 0.3 μg portion of each synthetic DNA was added to 15 μl of sterilized water and heated at 65° C. for 5 minutes. The reaction solution was allowed to stand at room temperature for 30 minutes, mixed with 2 μl of a 10-fold buffer solution [500 mM Tris-HCl (pH 7.6), 100 mM magnesium chloride and 50 mM DTT] and 2 μl of 10 mM ATP and then with 10 units of T4 polynucleotide kinase (manufactured by Takara Shuzo Co., Ltd.), and the mixture was allowed to react at 37° C. for 30 minutes to phosphorylate the 5' end.

Figure 19:
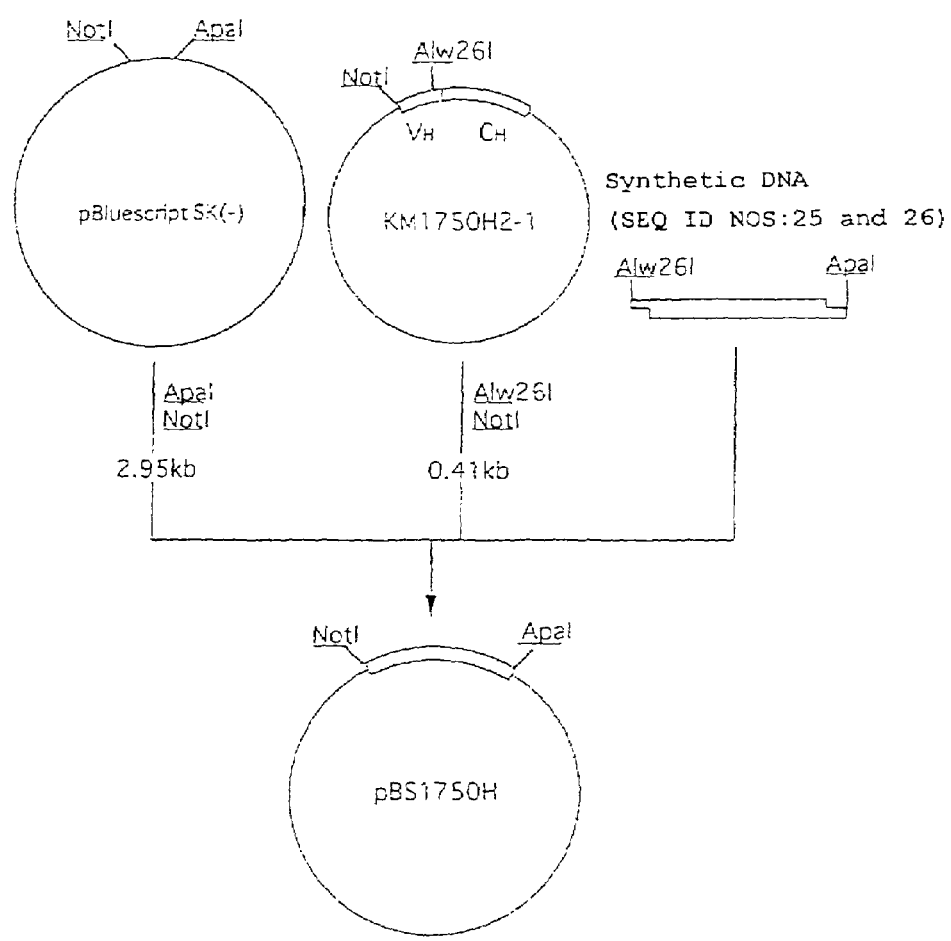
FIG. 19 is a graph showing construction steps of plasmid pBS1750H.

A 0.1 μg portion of the ApaI-NotI fragment derived from plasmid pBluescript SK(−) in the step 2-(1) of Example 2, 0.1 μg of the AlwI-NotI fragment derived from plasmid KM1750H2-1 and 0.05 μg of the phosphorylated synthetic DNA were added to 10 μl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pBS1750H shown in FIG. 19.

Next, 5 μg of the plasmid KM1750L3-1 was added to 10 μl of a buffer solution comprising 100 mM Tris-HCl (pH 8.8), 440 mM sodium chloride, 12 mM magnesium chloride, 14 mM 2-mercaptoethanol and 200 μg/ml BSA, 10 units of a restriction enzyme MaeII (manufactured by Boehringer-Mannheim) were further added thereto, and then the reaction was carried out at 50° C. for 1 hour. The reaction solution was precipitated with ethanol, the thus obtained precipitate was added to 10 μl of a buffer solution comprisng 50 mM Tris-HCl (pH 7.5), 100 mM sodium chloride, 10 mM magnesium chloride and 1 mM DTT, 10 units of a restriction enzyme EcoRI (manufactured by Takara Shuzo Co., Ltd.) were further added thereto, and then the reaction was carried out at 37° C. for 1 hour. The reaction solution was fractionated by agarose gel electrophoresis to recover about 0.5 μg of a MaeII-EcoRI fragment of about 0.38 kb. Next, a synthetic DNA having the nucleotide sequence of SEQ ID NO:27 or 28 was synthesized (manufactured by Sawady Technology), and a 0.3 μg portion of each synthetic DNA was added to 15 μl of sterilized water and heated at 65° C. for 5 minutes. The reaction solution was allowed to stand at room temperature for 30 minutes, mixed with 2 μl of a 10-fold buffer solution [500 mM Tris-HCl (pH 7.6), 100 mM magnesium chloride and 50 mM DTT] and 2 μl of 10 mM ATP and then with 10 units of T4 polynucleotide kinase (manufactured by Takara Shuzo Co., Ltd.), and the mixture was allowed to react at 37° C. for 30 minutes to phosphrylate the 5' end.

Figure 20:
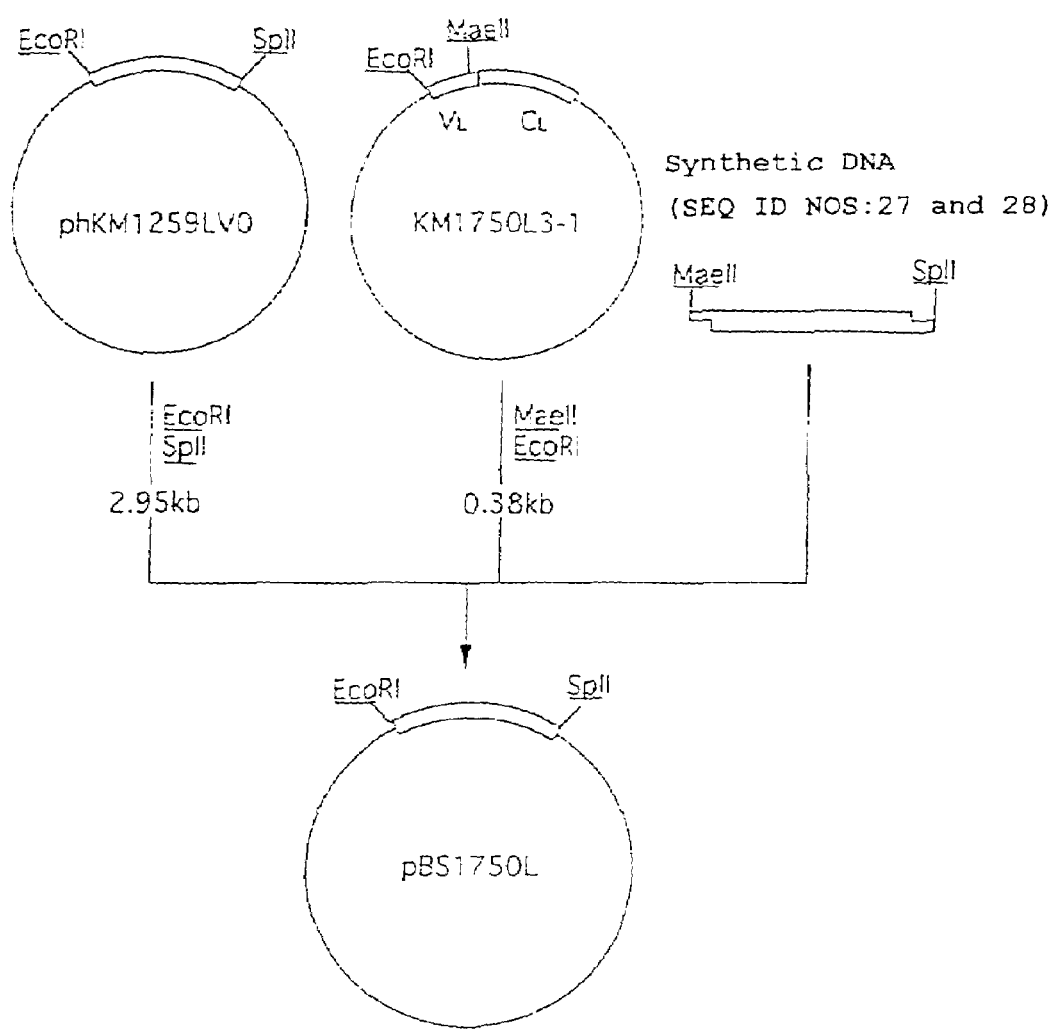
FIG. 20 is a graph showing construction steps of plasmid pBS1750L.

A 0.1 μg portion of the EcoRI-SplI fragment derived from plasmid pphKM1259LV0 in the step 2-(1) of Example 2, 0.1 μg of the MaeII-EcoRI fragment derived from plasmid KM1750L3-1 and 0.05 μg of the phosphorylated synthetic DNA were added to 10 μl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pBS1750L shown in FIG. 20.

Next, 5 μg of the plasmid pBS1750H obtained in the foregoing was added to 10 μl of a buffer solution comprising 10 mM Tris-HCl (pH 7.5), 10 mM magnesium chloride and 1 mM DTT, 10 units of a restriction enzyme ApaI (manufactured by Takara Shuzo Co., Ltd.) were futher added thereto, and then the reaction was carried out at 37° C. for 1 hour. The reaction solution was precipitated with ethanol, the thus obtained precipitate was added to 10 μl of a buffer solution comprising 50 mM Tris-HCl (pH 7.5), 100 mM sodium chloride, 10 mM magnesium chloride, 1 mM DTT, 100 μg/ml BSA and 0.01% Triton X-100, 10 units of a restriction enzyme NotI (manufactured by Takara Shuzo Co., Ltd.) were futher added thereto, and then the reaction was carried out at 37° C. for 1 hour. The reaction solution was fractionated by agarose gel electrophoresis to recover about 0.5 μg of an ApaI-NotI fragment of about 0.46 kb.

Figure 21:
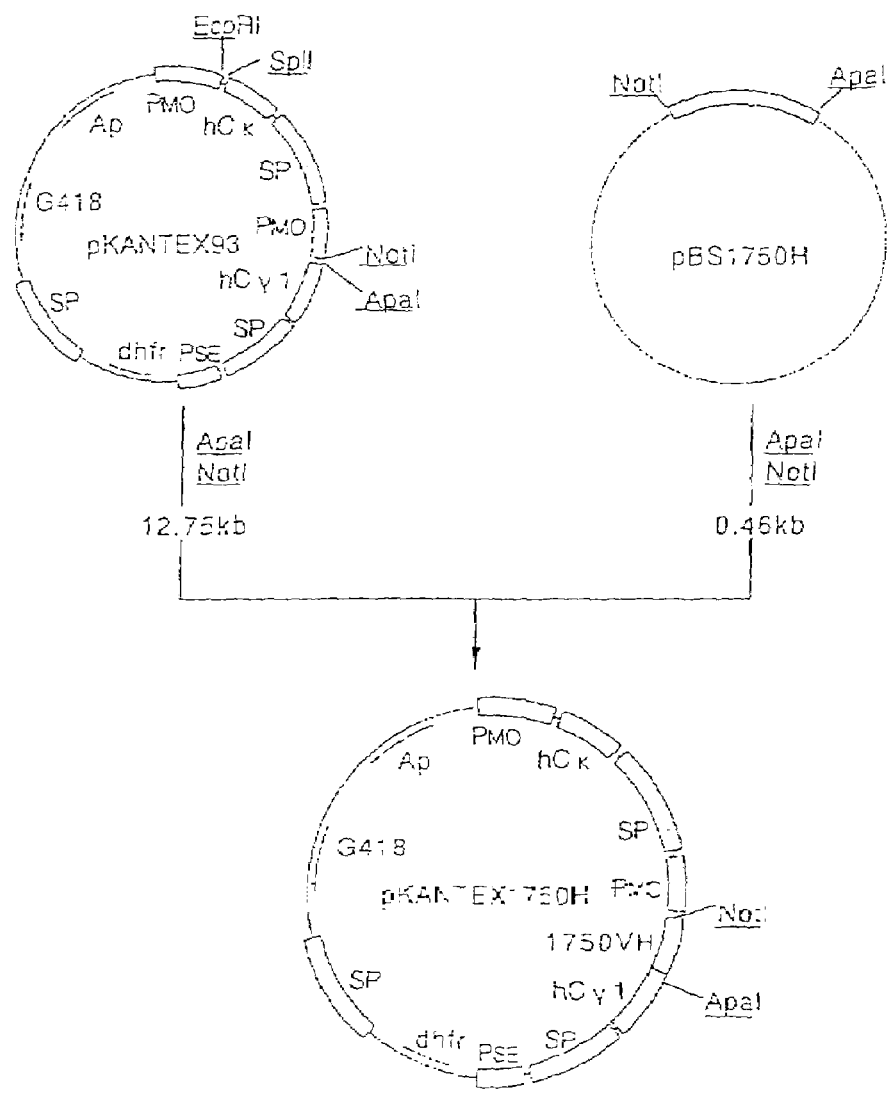
FIG. 21 is a graph showing construction steps of plasmid pKANTEX1750H.

A 0.1 μg portion of the ApaI-NotI fragment derived in the step 2-(1) of Example 2 from a tandem cassette vector pKANTEX93 for humanized antibody expression and 0.1 μg of the ApaI-NotI fragment derived from plasmid pBS1750H were added to 10 μl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain a plasmid pKANTEX1750H shown in FIG. 21.

Next, 3 μg of the just obtained plasmid pKANTEX1750H was added to 10 μl of a buffer solution comprising 50 mM Tris-HCl (pH 7.5), 100 mM sodium chloride, 10 mM magnesium chloride, 1 mM DTT and 100 μg/ml BSA, 10 units of a restriction enzyme EcoRI (manufactured by Takara Shuzo Co., Ltd.) and 10 units of a restriction enzyme SplI (manufactured by Takara Shuzo Co., Ltd.) were futher added thereto, and then the reaction was carried out at 37° C. for 1 hour. The reaction solution was fractionated by agarose gel electrophoresis to recover about 1 μg of an EcoRI-SplI fragment of about 13.20 kb. Next, 5 μg of the plasmid pBS1750L obtained in the foregoing was added to 10 μl of a buffer solution comprising 50 mM Tris-HCl (pH 7.5), 100 mM sodium chloride, 10 mM magnesium chloride, 1 mM DTT and 100 μg/ml BSA, 10 units of a restriction enzyme EcoRI (manufactured by Takara Shuzo Co., Ltd.) and 10 untis of a restriction enzyme SplI (manufactured by Takara Shuzo Co., Ltd.) were further added thereto, and then the reaction was carried out at 37° C. for 1 hour. The reaction solution was fractionated by agarose gel electrophoresis to recover about 0.5 μg of an EcoRI-SplI fragment of about 0.39 kb.

Figure 22:
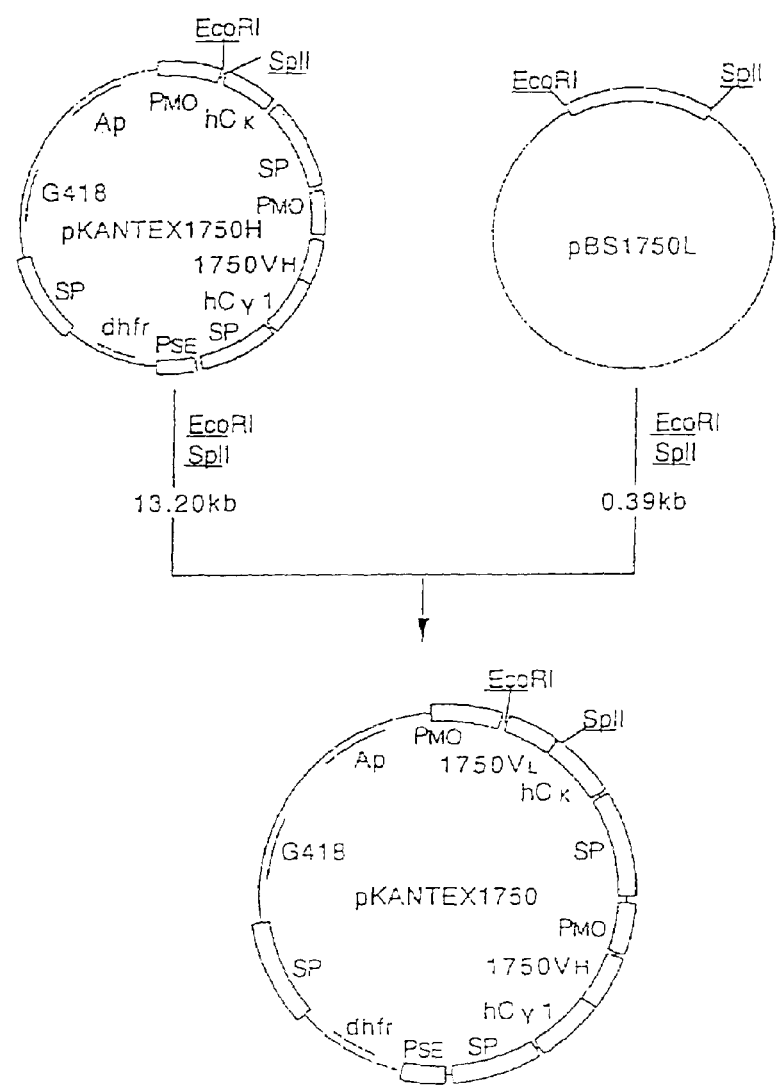
FIG. 22 is a graph showing construction steps of plasmid pKANTEX1750.

A 0.1 μg portion of the EcoRI-SplI fragment derived from plasmid pKANTEX1750H and 0.1 μg of the EcoRI-SplI fragment derived from plasmid pBS1750L, obtained by the just described procedures, were added to 10 μl in total volume of sterilized water and ligated using DNA Ligation Kit Ver. 2 (manufactured by Takara Shuzo Co., Ltd.) in accordance with the manual attached thereto. *Escherichia coli* DH5α (manufactured by TOYOBO CO., LTD.) was transformed with the thus prepared recombinant plasmid DNA solution to obtain plasmid pKANTEX1750 shown in FIG. 22.

(3) Expression of Anti-Human VEGF Receptor Flt-1 Human Chimeric Antibodies in Rat Myeloma YB2/0 Cells (ATCC CRL1581) Using pKANTEX1732 and pKANTEX1750

Introduction of anti-human VEGF receptor Flt-1 human chimeric antibody expression vectors pKANTEX1732 and pKANTEX1750 into YB2/0 cells was carried out by electroporation in accordance with the method of Miyagi et al. [*Cytotechnology*, 3: 133 (1990)].

A 5 μg portion of each of pKANTEX1732 and pKANTEX1750 obtained in the steps 2-(1) and (2) of Example 2 was introduced into $4\times10^6$ YB2/0 cells which were subsequently suspended in 40 ml of RPMI 1640-FCS(10) medium [RPMI 1640 medium (manufactured by Nissui Pharmaceutical) containing 10% fetal calf serum (FCS)] and dispensed in 200 μl portions into wells of a 96 well microtiter plate (manufactured by Sumilon). After 24 hours of culturing at 37° C. in a 5% $CO_2$ incubator, geneticin (hereinafter referred to as "G 418", manufactured by Gibco) was added to a final concentration of 0.5 mg/ml, and the culturing was continued for 1 to 2 weeks. When colonies of G 418-resistant transformants were formed and became confluent, the culture supernatant was recovered from each well, and the activity of anti-human VEGF receptor Flt-1 human chimeric antibody in the supernatant was measured by the following enzyme immunoassay.

Enzyme Immunoassay

Soluble human VEGF receptor Flt-1 7N was prepared in accordance with the method of Tanaka et al. [*Japanese Journal of Cancer Research*, 88: 867–876 (1997)]. The soluble human VEGF receptor Flt-1 7N diluted to 1 μg/ml with PBS was dispensed in 50 μl portions into wells of a 96 well plate for EIA (manufactured by Greiner) and allowed to stand overnight at 4° C. for its adsorption. After washing with PBS, 100 μl of PBS containing 1% BSA (hereinafter referred to as "1% BSA-PBS") was added to each well, and the remaining active groups was blocked by carrying out the reaction at room temperature for 1 hour. After discarding 1% BSA-PBS, the culture supernatant of each transformant was dispensed in 50 μl portions into the resulting wells to carry out the reaction at room temperature for 1 hour. After washing the plate with PBS containing 0.05% Tween 20 (hereinafter referred to as "0.05% Tween-PBS"), a peroxidase-labeled anti-human IgG antibody (manufactured by American Quarex) which had been diluted 3,000 times with 1% BSA-PBS was dispensed in 50 μl portions into the wells to carry out the reaction at room temperature for 1 hour, the resulting plate was washed with 0.5% Tween-PBS, and then an ABTS [ammonium 2,2-azinobis(3-ethylbenzothiazole-6-sulfonate)] substrate solution was dispensed in 50 μl portions into the wells to develop color and measure its absorbance at $OD_{415\ nm}$ using Emax (manufactured by Molecular Devices).

In order to increase productivity, each of the transformants which showed the anti-human VEGF receptor Flt-1 human chimeric antibody activity in the culture supernatant was suspended in RPMI 1640-FCS(10) medium supplemented with 0.5 mg/ml of G 418 and 50 nM of methotrexate (hereinafter referred to as "MTX", manufactured by Sigma) and cultured at 37° C. for 1 to 2 weeks in a 5% $CO_2$ incubator to induce transformants having 50 nM MTX resistance. When the transformants became confluent in the wells, the anti-human VEGF receptor Flt-1 human chimeric antibody activity in the culture supernatants was measured by the aforementioned enzyme immunoassay. Transformants in which the activity was found were cultured similarly by further increasing the MTX concentration to 100 nM and then to 200 nM to obtain transformants which can grow in RPMI 1640-FCS(10) medium containing 0.5 mg/ml of G 418 and 200 nM of MTX and are able to produce large amounts of anti-human VEGF receptor Flt-1 human chimeric antibodies. The thus obtained transformants were subjected to two times of cloning by limiting dilution to obtain final transformant cell strains capable of producing anti-human VEGF receptor Flt-1 human chimeric antibodies. KM2532 can be cited as an example of the transformant cell strain obtained by introducing the expression vector pKANTEX1732, namely a transformant which produces an anti-human VEGF receptor Flt-1 human chimeric antibody originated from the anti-human VEGF receptor Flt-1 mouse monoclonal antibody KM1732, and the anti-human VEGF receptor Flt-1 human chimeric antibody produced by this transformant was named KM2532. Also, KM2550 can be cited as an example of the transformant cell strain obtained by introducing the expression vector pKANTEX1750, namely a transformant which produces an anti-human VEGF receptor Flt-1 human chimeric antibody originated from the anti-human VEGF receptor Flt-1 mouse monoclonal antibody KM1750, and the anti-human VEGF receptor Flt-1 human chimeric antibody produced by this transformant was named KM2550. The productivity of anti-human VEGF receptor Flt-1 human chimeric antibodies by the thus cloned transformants was found to be about 5 $\mu g/10^6$ cells/24 hours.

(4) Purification of Anti-Human VEGF Receptor Flt-1 Human Chimeric Antibodies from Culture Supernatants Each of the anti-human VEGF receptor Flt-1 human chimeric antibody producing strains KM2532 and KM2550 obtained in 2-(3) of Example 2 was suspended in GIT medium (manufactured by Japan Pharmaceutical) supplemented with 0.5 mg/ml of G 418 and 200 nM of MTX, to a density of 1 to $2\times10^5$ cells/ml, and dispensed in 200 ml portions into a total of five 175 cm² flasks (manufactured by Greiner). When the cells became confluent after 5 to 7 days of culturing at 37° C. in a 5% $CO_2$ incubator, about 1.0 liter of each culture supernatant was recovered. A column was packed with about 1 ml of ProSep A (manufactured by Bioprocessing) and washed with 10 ml of 1 M glycine-0.15 M NaCl (pH 8.6) at a flow rate of 1 ml/minute. After the washing, 1,700 ml or 1,800 ml of the culture supernatant prepared in the above containing the anti-human VEGF receptor Flt-1 human chimeric antibody KM2532 or KM2550 was passed through the ProSep A column at a flow rate of 70 ml/hour. This was further washed with 10 ml of 1 M glycine-0.15 M NaCl (pH 8.6) at a flow rate of 1 ml/minute, again washed stepwise with 4 ml of 50 mM citrate buffer of pH 6, 5 and 4, and then 7 ml of 50 mM citrate buffer (pH 3.0) was passed through the column to elute the human chimeric antibody. As the results, 0.4 mg and 0.3 mg of the anti-human VEGF receptor Flt-1 human chimeric antibodies KM2532 and KM2550 were obtained.

Figure 23:
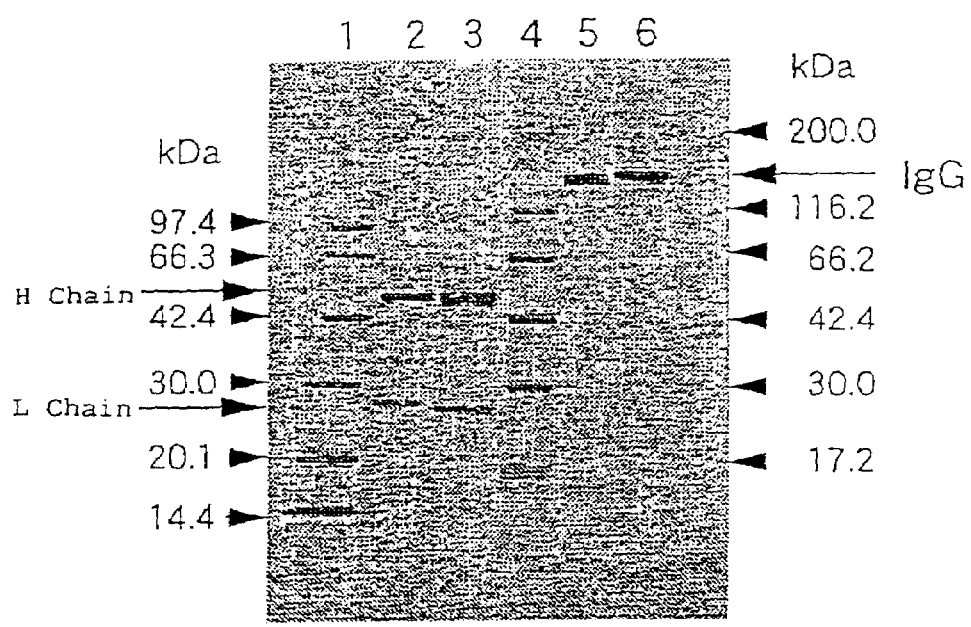
FIG. 23 is a graph showing SDS-PAGE (a 5 to 20% gradient gel was used) electrophoresis patterns of purified anti-human VEGF receptor Flt-1 human chimeric antibodies KM2532 and KM2550 (lane 1: low molecular weight marker, lane 2: KM2532 under reducing conditions, lane 3: KM2550 under reducing conditions, lane 4: high molecular weight marker, lane 5: KM2532 under non-reducing conditions, lane 6: KM2550 under non-reducing conditions).

The thus purified anti-human VEGF receptor Flt-1 human chimeric antibodies KM2532 and KM2550 were analyzed by SDS-PAGE in accordance with a known method [*Anticancer Research*, 12: 1121 (1992)]. A the gel, 5 to 20% gradient gel (manufactured by Atto Corp.) was used, a low molecular weight protein molecular marker "Daiichi" II and a high molecular weight protein molecular marker "Daiichi" III (both manufactured by Daiichi Pure Chemicals) were used as molecular markers, and 2.5 $\mu g$ as protein per lane of each of the anti-human VEGF receptor Flt-1 human chimeric antibodies KM2532 and KM2550 was electrophoresed under reducing and non-reducing conditions and stained with Coomassie Brilliant Blue. The results are shown in FIG. 23. The human chimeric antibodies KM2532 and KM2550 showed a band of IgG at a position corresponding to a molecular weight of about 150 kDa under the non-reducing condition, and a band of H chain at about 50 kDa and a band of L chain at about 25 kDa were found under the reducing condition. This result coincided with that the IgG type antibody is separated into two H chains and L chains under the reducing conditions caused by the cutting of intermolecular disulfide bond and present as a molecule of 150 kDa.

(5) Binding Activity of Anti-Human VEGF Receptor Flt-1 Human Chimeric Antibodies Upon Human VEGF Receptor Flt-1

Binding activity of the purified anti-human VEGF receptor Flt-1 human chimeric antibodies KM2532 and KM2550 upon human VEGF receptor Flt-1 was confirmed by the following procedure.

Soluble human VEGF receptor Flt-1 7N was prepared in accordance with the method of Tanaka et al. [*Japanese Journal of Cancer Research*, 88: 867–876 (1997)].

First, the binding activity was examined using an immunoassay method by fixing amount of the soluble human VEGF receptor Flt-1 7N to be adsorbed on a 96 well plate for EIA and varying concentration of the human chimeric antibody to be added. The soluble human VEGF receptor Flt-1 7N diluted to 1 $\mu g/ml$ with PBS was dispensed in 50 $\mu l$ portions into wells of a 96 well plate for EIA (manufactured by Greiner) and allowed to stand overnight at 4° C. for its adsorption. After washing the plate with PBS, 100 $\mu l$ of 1% BSA-PBS was added to each well, and the remaining active groups was blocked by carrying out the reaction at room temperature for 1 hour. After discarding 1% BSA-PBS, each of the purified anti-human VEGF receptor Flt-1 human chimeric antibodies KM2532 and KM2550 having a concentration of from 0.152 to 333 ng/ml was dispensed in 50 $\mu l$ portions into the resulting wells to carry out the reaction at room temperature for 1 hour. After washing the plate with 0.05% Tween-PBS, a peroxidase-labeled anti-human IgG antibody (manufactured by American Corlex) which had been diluted 3,000 times with 1% BSA-PBS was dispensed in 50 $\mu l$ portions into the wells to carry out the reaction at room temperature for 1 hour, the resulting plate was washed with 0.5% Tween-PBS, and then an ABTS [ammonium 2,2-azinobis(3-ethylbenzothiazole-6-sulfonate)] substrate solution was dispensed in 50 $\mu l$ portions into the wells to develop color and measure its absorbance at $OD_{415\ nm}$ using Emax (manufactured by Molecular Devices).

The results are shown in FIG. 24 (A). The anti-human VEGF receptor Flt-1 human chimeric antibodies KM2532 and KM2550 bound to the human VEGF receptor Flt-1 7N in an antibody concentration dependent fashion. In addition, the anti-human VEGF receptor Flt-1 human chimeric antibodies KM2532 and KM2550 showed almost the same binding activity.

Next, the binding activity of human chimeric antibodies was examined using an immunoassay method by varying amount of the soluble human Flt-1 7N to be adsorbed on a 96 well plate for EIA. The soluble human VEGF receptor Flt-1 7N diluted to a concentration of from 0.04 to 10 $\mu g/ml$ with PBS was dispensed in 50 $\mu l$ portions into wells of a 96 well plate for EIA (manufactured by Greiner) and allowed to stand overnight at 4° C. for its adsorption. After washing the plate with PBS, 100 $\mu l$ of 1% BSA-PBS was added to each well, and the remaining active groups was blocked by carrying out the reaction at room temperature for 1 hour. After discarding 1% BSA-PBS, each of the purified anti-human VEGF receptor Flt-1 human chimeric antibodies KM2532 and KM2550 having a concentration of 10 µg/ml was dispensed in 50 µl portions into the resulting wells to carry out the reaction at room temperature for 1 hour. After washing the plate with 0.05% Tween-PBS, a peroxidase-labeled anti-human IgG antibody (manufactured by American Corlex) which had been diluted 3,000 times with 1% BSA-PBS was dispensed in 50 µl portions into the wells to carry out the reaction at room temperature for 1 hour, the resulting plate was washed with 0.5% Tween-PBS, and then an ABTS [ammonium 2,2-azinobis(3-ethylbenzothiazole-6-sulfonate)] substrate solution was dispensed in 50 µl portions into the wells to develop color and measure its absorbance at $OD_{415\ nm}$ using Emax (manufactured by Molecular Devices).

The results are shown in FIG. 24 (B). Each of the anti-human VEGF receptor Flt-1 human chimeric antibodies KM2532 and KM2550 showed its binding activity dependently upon the concentration of the soluble human VEGF receptor Flt-1 7N adsorbed on the plate. In addition, the anti-human VEGF receptor Flt-1 human chimeric antibodies KM2532 and KM2550 showed almost the same binding activity.

Figure 25:
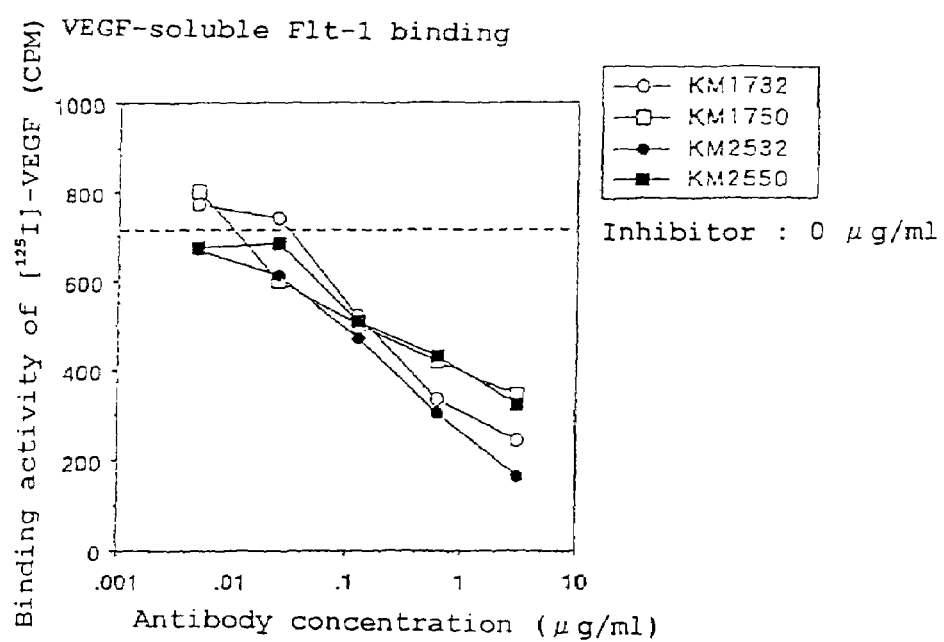
FIG. 25 is a graph showing the activity of purified anti-human VEGF receptor Flt-1 human chimeric antibodies KM2532 and KM2550 to inhibit binding between human VEGF and human VEGF receptor Flt-1. The symbols ○, □, ● and ■ shows the binding inhibition activities of KM1732, KM1750, KM2532 and KM2550, respectively.

Next, the activity of anti-human VEGF receptor Flt-1 human chimeric antibodies to inhibit binding of human VEGF with human VEGF receptor Flt-1 was examined in the following manner. Methanol was dispensed in 100 µl portions into wells of a 96 well multi-screen IP plate (manufactured by Millipore) to change PVDF membrane on the plate bottom into hydrophilic nature. After washing the plate with water, the soluble human VEGF receptor Flt-1 7N which had been diluted to 0.2 µg/ml with PBS was dispensed in 50 µl portions into the wells and allowed to stand overnight at 4° C. for its adsorption. After washing the plate with PBS, 50 µl of 1% BSA-PBS was added to each well, and the remaining active groups was blocked by carrying out the reaction at room temperature for 1 hour. After washing the plate with PBS, each of the purified anti-human VEGF receptor Flt-1 human chimeric antibodies KM2532 and KM2550 and purified anti-human VEGF receptor Flt-1 mouse monoclonal antibodies KM1732 and KM1750, which had been diluted with 1% BSA-PBS to a concentration of from 0.004 to 2 µg/ml, was dispensed in 50 µl portions into the resulting wells and then 3 ng/ml of $^{125}$I-labeled human VEGF (manufactured by Amersham) was dispensed in 50 µl portions into the wells to carry out the reaction at room temperature for 1.5 hours. After washing the plate with 0.05% Tween-PBS, the wells were dried at 50° C., Microscinti-0 (manufactured by Packard) was dispensed in 30 µl portions into the wells and then radioactivity of the $^{125}$I-labeled human VEGF bonded on each well was measured using Top Count (manufactured by Packard). The results are shown in FIG. 25. As shown in FIG. 25, each of the anti-human VEGF receptor Flt-1 human chimeric antibodies KM2532 and KM2550 inhibited binding of the human VEGF with the human VEGF receptor Flt-1 in an antibody concentration dependent fashion. In addition, the activity of the anti-human VEGF receptor Flt-1 human chimeric antibodies KM2532 and KM2550 to inhibit binding of the human VEGF with the human VEGF receptor Flt-1 was almost the same as that of the anti-human VEGF receptor Flt-1 mouse monoclonal antibodies M1732 and KM1750, thus showing that the human chimeric antibodies maintain the activity of mouse monoclonal antibodies.

(6) Analysis of Epitope which is Recognized by Anti-Human VEGF Receptor Flt-1 Human Chimeric Antibody (6-1) Preparation of Soluble Human VEGF Receptor KDR 7N and Soluble Human VEGF Receptor Chimeric Protein Flt-1 7N.K2

Soluble human VEGF receptor KDR 7N and soluble human VEGF receptor chimeric protein Flt-1 7N.K2 were produced in the following manner.

(6-2) Construction of Soluble Human VEGF Receptor KDR 7N Expression Vector

A vector was prepared in the following manner for the expression of 19 amino acids which constitute the signal peptide of human VEGF receptor KDR, a soluble human VEGF receptor KDR fragment (hereinafter referred to as "soluble human VEGF receptor KDR 7N") which corresponds to 738 amino acids counting from the N-terminal amino acid of its mature body and two amino acid residues derived from a linker.

The soluble human VEGF receptor KDR 7N consists of the one to seven immunoglobulin-like moiety counting from the N-terminal side of the extracellular region of soluble human VEGF receptor KDR.

A cDNA clone which encodes complete length cDNA of human VEGF receptor KDR, BCMGS-neo-KDR [A. Sawano et al., *Cell Growth & Differentiation*, 7: 213–221 (1996)], was digested with EcoRI, and a fragment of about 2.8 kb encoding the extracellular region and membrane-binding region of KDR was integrated into the EcoRI site of pUC18 to prepare pUC-KDR. The thus prepared pUC-KDR was digested with XhoI and treated with Klenow and then an XbaI linker (SEQ ID NO:57) was inserted to prepare pUC-KDR-Xb. An XbaI-BamHI fragment (2.3 kbp) of pUC-KDR-Xb was inserted into the XbaI-BamHI site of pBluescriptII KS(+) to prepare an SphI-BamHI fragment (5.2 kbp) into which were subsequently inserted synthetic linkers (SEQ ID NOS:58 and 59) containing SnaBI site to prepare pBS-KDR-Xb-S.

The thus obtained pBS-KDR-Xb-S was digested with SnaBI/BamHI, and synthetic linkers (SEQ ID NOS:60 and 61) containing terminal codon and NotI site were inserted to prepare pBS-KDR-Xb-S-N. An XbaI-NotI fragment (2.3 kb) of pBS-KDR-Xb-S-N was inserted into downstream 5' side XbaI and 3' side NotI site of the transcription initiation point of polyhedrin gene of baculovirus recombinant plasmid pVL1393 to obtain soluble human VEGF receptor KDR 7N expression vector pVL-KDR-7N.

(6-3) Construction of Soluble Human VEGF Receptor Chimeric Protein Flt-1 7N.K2 Expression Vector A vector was constructed in the following manner for the expression of a chimeric protein Flt-1.K2 in which an amino acid sequence of from the 100 position amino acid to the 204 position amino acid which corresponds to the second immunoglobulin-like moiety counting from the N-terminal side of the soluble human VEGF receptor Flt-1 7N that corresponds to 750 amino acids counting from the N-terminal containing the signal sequence of human VEGF receptor Flt-1 was replaced with an amino acid sequence of from the 95 position amino acid to the 199 position amino acid which corresponds to the second immunoglobulin-like moiety of the soluble human VEGF receptor KDR, via linkers of two amino acids (Gly-Ala and Gly-Thr).

An EcoRI/HindIII fragment (1.9 kb) of human Flt-1 cDNA [Shibuya et al., *Oncogene*, 5: 519 (1990)] was inserted into the EcoRI/HindIII site of a vector M13 mp19 to prepare pM13-flt. *Escherichia coli* XL1Blue was infected with the thus obtained pM13-flt and cultured, and ssDNA was prepared from the resulting culture supernatant in accordance with a manual supplied by Takara Shuzo. Using an oligonucleotide of 56 bases (SEQ ID NO:62) and a site-specific mutation introducing kit Mutan K (manufactured by Takara Shuzo Co., Ltd.), site-specific mutation was carried out using the thus obtained ssDNA as the template to prepare a plasmid pM13-flt'-D2N containing a Flt-1 mutant gene in which the region encoding the second immunoglobulin-like moiety of the extracellular region of Flt-1 was deleted. Next, using 10 ng of BCMGS-neo-KDR DNA [A. Sawano et al., *Cell Growth & Differentiation*, 7: 213 (1996)] as the template, PCR was carried out by adding 2.5 units of TaqDNA polymerase to 100 ml of a solution containing 10 pmol of each of primers having nucleotide sequences shown in SEQ ID NOS:63 and 64, TaqDNA polymerase buffer and 10 mM deoxynucleotide triphosphate. A serial reaction of 90 seconds at 95° C., 90 seconds at 50° C. and 90 seconds at 72° C. was repeated 30 times, and the thus amplified DNA fragment encoding the second immunoglobulin-like moiety counting from the N-terminal side of the extracellular region of KDR was recovered. This fragment was digested with NarI/KpnI to obtain an NarI/KpnI fragment of 340 bp. The thus obtained fragment and an SmaI/NarI fragment (0.5 kb) of pM13-flt'-D2N were inserted into the SmaI/KpnI site of pBluescriptII to prepare pBS-flt-1'-KDR2N. Thereafter, a BamH/KpnI fragment (0.8 kb) of pBS-flt-1'-KDR2N, a KpnI/MunI fragment (80 b) of pM13-flt'-D2N and an MunI/NotI fragment (1.5 kb) of pVL-flt-1 were inserted into the BamHII/NotI site of pVL1393 to obtain a plasmid PVL-fkf which carries the Flt-1 7N.K2 gene.

(6-4) Preparation of Recombinant Virus for the Expression of Soluble Human VEGF Receptor KDR 7N and Soluble Human VEGF Receptor chimeric Protein Flt-1 7N.K2 in Insect Cells In order to produce a protein in insect cells, it is necessary to prepare a recombinant virus into which the gene of interest is integrated, and such a preparation process comprises a step in which a cDNA called transfer vector which encodes the protein of interest is inserted into a special plasmid and a subsequent step in which a wild type virus and the transfer vector are co-transfected into insect cells to obtain the recombinant virus by homologous recombination. These steps were carried out in the following manner using BaculoGold Starter Kit manufactured by Fermingen (Product No. PM-21001K) in accordance with the manual attached thereto.

Recombinant baculovirus was prepared in the following manner by a lipofectin method [*Protein, Nucleic Acid and Enzyme*, 37: 2701 (1992)], by introducing filamentous baculovirus DNA (BaculoGold baculovirus DNA, manufactured by Fermingen) and transfer vector DNA into cells of an insect cell line Sf9 (manufactured by Fermingen) which had been cultured using TMN-FH insect medium (manufactured by Fermingen).

A 1 µg portion of the expression vector prepared in the step (6-2) and 20 ng of the filamentous baculovirus DNA were dissolved in 12 µl of distilled water, and a mixture consisting of 6 µl of lipofectin and 6 µl of distilled water was added to the resulting solution and allowed to stand at room temperature for 15 minutes. Separately from this, 1×10⁶ of Sf9 cells were suspended in 2 ml of Sf900-II medium (manufactured by Gibco) and put into a plastic Petri dish for cell culture having a diameter of 35 mm. Entire portion of the aforementioned mixture solution of plasmid DNA, filamentous baculovirus DNA and lipofectin was added to the dish, the cells were cultured at 27° C. for 3 days and then a 1 ml portion of the culture supernatant containing recombinant virus was collected. A 1 ml portion of fresh Sf900-II medium was added to the resulting Petri dish, and the cells were further cultured at 27° C. for 3 days to obtain 1.5 ml of the culture supernatant containing recombinant virus. Thereafter, the same procedure was repeated using the expression vector obtained in the step (6-3).

Next, in order to use it in protein expression, each of the thus obtained recombinant viruses was grown in the following manner.

A total of 2×10⁷ Sf9 cells were suspended in 10 ml of Sf900-II medium, put into a 175 cm² flask (manufactured by Greiner) and then allowed to stand at room temperature for 1 hour to adhere the cells to the flask. Thereafter, the supernatant was discarded and 15 ml of fresh TMN-FH insect medium and a 1 ml of portion of the aforementioned culture supernatant containing recombinant virus were added to the flask to carry out 3 days of culturing at 27° C. After the culturing, the supernatant was centrifuged at 1,500×g for 10 minutes to remove cells to obtain a recombinant virus solution to be used in protein expression.

The titer of virus in the thus obtained recombinant virus solution was calculated in accordance with the method described in BaculoGold Starter Kit Manual (manufactured by Farmigen).

A total of 6×10⁶ Sf9 cells were suspended in 4 ml of Sf900-II medium, put into a plastic Petri dish for cell culture having a diameter of 60 mm and then allowed to stand at room temperature for 1 hour to adhere the cells to the dish. Next, the supernatant was discarded, 400 µl of fresh Sf900-II medium and the aforementioned recombinant virus solution diluted 1,000 times with Sf900-II medium in advance were added to the dish and allowed to stand at room temperature for 1 hour, and then the medium was discarded and 5 ml of a medium containing 1% low melting point agarose (Agarplaque Agarose, manufactured by Farmigen) (a medium prepared by mixing 1 ml of sterilized 5% Agarplaque Agarose aqueous solution with 4 ml of TMN-FH insect medium and kept at 42° C.) was poured into the Petri dish. After 15 minutes of standing at room temperature, the Petri dish was sealed with a vinyl tape to prevent drying and put into a sealing type plastic container to carry out 6 days of culturing at 27° C. A 1 ml portion of PBS containing 0.01% Neutral Red was added to the Petri dish, and the culturing was continued for 1 day to count the number of formed plaques. It was found by the above procedure that each of the recombinant virus solutions contained about 1×10⁷ plaque forming units (hereinafter referred to as "PFU")/ml of viral particles.

(6-5) Expression of Soluble Human VEGF Receptor KDR 7N and Soluble Human VEGF Receptor Chimeric Protein Flt-1 7N.K2 in Insect Cells and their Purification The soluble human VEGF receptor KDR 7N and soluble human VEGF receptor chimeric protein Flt-1 7N.K2 shown in (6-1) to (6-4) were obtained in the following manner. A total of 4×10⁷ High Five cells were suspended in 30 ml of EX-CELL™ 400 medium (manufactured by JRH Bioscience) contained in a 175 cm² flask (manufactured by Greiner) and adhered to the flask by allowing them to stand at room temperature for 1 hour. A 1 ml portion of a solution containing about 1 to 3×10⁸ PFU/ml of the transfer vector-originated recombinant virus obtained in (6-3) and (6-4) was added to the flask to carry out infection at room temperature for 2 hours. The culture supernatant was discarded and replaced with 30 ml of fresh EX-CELL™ 400 medium to carry out 3 to 4 days of culturing at 27° C. After completion of the culturing, the culture supernatant was collected and centrifuged at 1,500×g for 10 minutes to recover the supernatant.

The soluble human VEGF receptor KDR 7N was purified in the following manner.

A column packed with 50 ml of DEAE-Sepharose CL-6B (manufactured by Pharmacia Biotech) and a column packed with 40 ml of Heparin Sepharose CL-6B (manufactured by Pharmacia Biotech) were connected in series, the former column on the inlet side and the latter on the outlet side, and washed with 300 ml of 20 mM sodium phosphate buffer (pH 8). After the washing, 400 to 800 ml of a culture solution containing soluble human VEGF receptor KDR was passed through the columns at a flow rate of from 50 to 100 ml/hour. The columns were again washed with 300 ml of 20 mM sodium phosphate buffer (pH 8) and then the adsorbed protein was eluted from the Heparin Sepharose CL-6B column by continuous density gradient using 400 ml of 0 to 1 M NaCl/20 mM sodium phosphate buffer. The eluate was fractionated in 7 ml portions, and 60 to 80 ml of fractions containing soluble human VEGF receptor KDR 7N were recovered by analyzing the protein contained in each fraction by SDS-PAGE. The thus recovered purification fractions were concentrated using CentriPrep 10 (manufactured by Amicon) to obtain 4.8 ml of a soluble human VEGF receptor KDR 7N solution (protein concentration and purity were 815 µg/ml and 70 to 80%, respectively).

The soluble human VEGF receptor chimeric protein Flt-1 7N.K2 was purified in the following manner.

A column was packed with about 20 ml of Heparin-Sepharose CL-6B gel (manufactured by Pharmacia Biotech AB) and washed with 100 ml of 20 mM Tris-HCl buffer (pH 7.5) at a flow rate of 0.5 ml/minute. After the washing, 900 ml of the culture solution containing soluble human VEGF receptor chimeric protein Flt-1 7N.K2 prepared in the foregoing was passed through the Heparin-Sepharose CL-6B column at a flow rate of 0.5 ml/minute. The column was washed again with 100 ml of 20 mM Tris-HCl buffer (pH 7.5) at a flow rate of 0.5 ml/minute, and then 200 ml of 20 mM Tris-HCl buffer (pH 7.5) containing NaCl having a density gradient of from 0 to 1.5 M was passed through the column to elute the protein adsorbed to Heparin-Sepharose, while the eluate was fractionated in 8 ml portions. By analyzing the protein contained in each fraction by SDS polyacrylamide gel electrophoresis (SDS-PAGE), 50 to 70 ml of fractions containing soluble human VEGF receptor chimeric protein Flt-1 7N.K2 were recovered and concentrated using CentriPrep 10 (manufactured by Amicon). After the concentration, human VEGF receptor chimeric protein Flt-1 7N.K2 was obtained as a 5.8 ml of solution (protein concentration, 588 µg/ml; purity, approximately 70%).

(6-6) Analysis of Epitope which is Recognized by Anti-Human VEGF Receptor Flt-1 Human Chimeric Antibody The epitope which is recognized by purified anti-human VEGF receptor Flt-1 human chimeric antibodies KM2532 and KM2550 was analyzed in the following manner.

Figure 35:
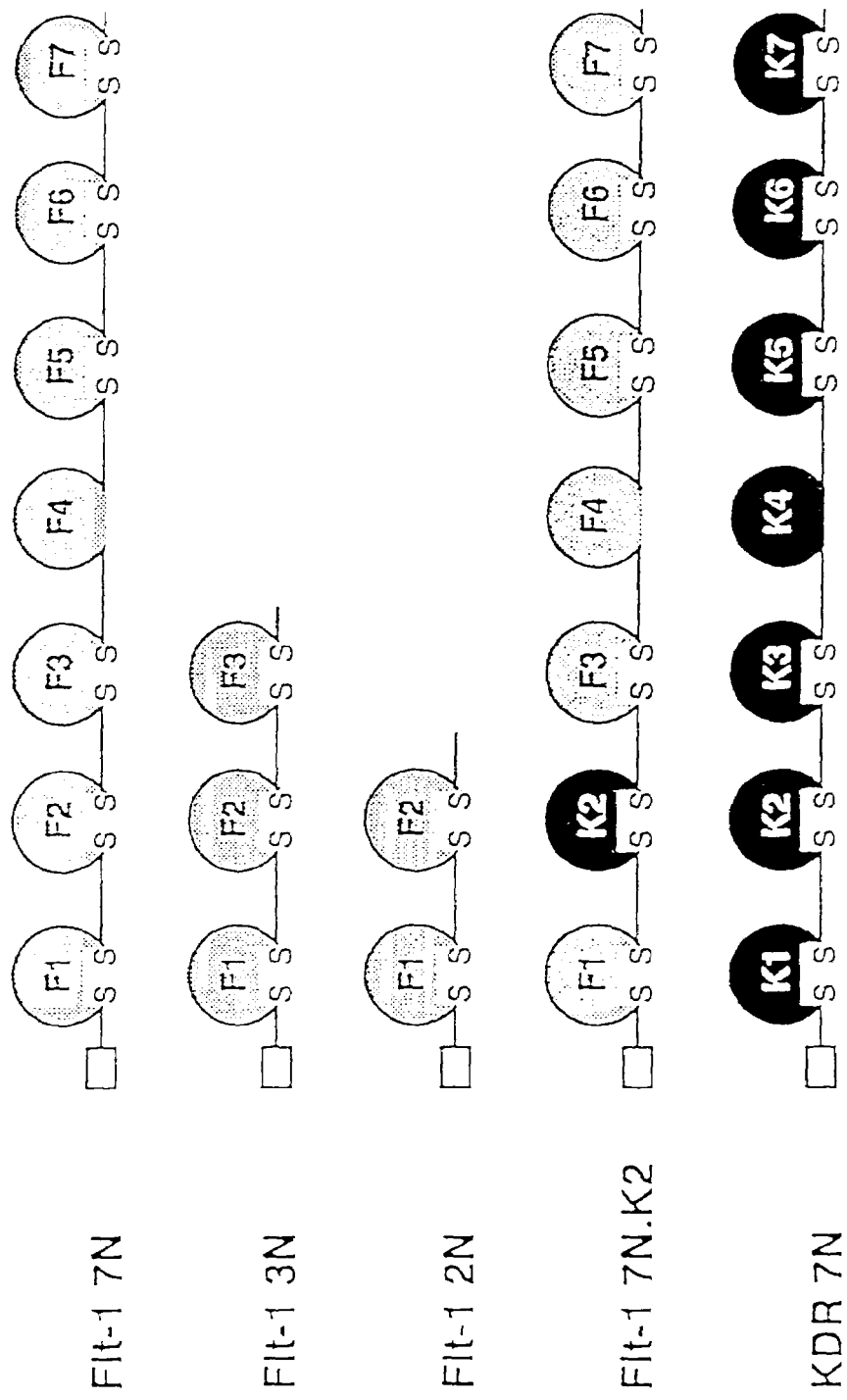
FIG. 35 is a schematic illustration of soluble human VEGF receptor derivatives.

Soluble human VEGF receptor Flt-1 7N (corresponds to a sequence from the N-terminal amino acid to the 750 position amino acid, including signal sequence), soluble human VEGF receptor Flt-1 3N (corresponds to a sequence from the N-terminal amino acid to the 338 position amino acid, including signal sequence) and soluble human VEGF receptor Flt-1 2N (corresponds to a sequence from the N-terminal amino acid to the 223 position amino acid, including signal sequence) were prepared in accordance with the method of Tanaka et al. [*Japanese Journal of Cancer Research*, 88: 867–876 (1997)]. Soluble human VEGF receptor KDR 7N (corresponds to a sequence from the N-terminal amino acid to the 738 position amino acid, does not include signal sequence) and soluble human VEGF receptor chimeric protein Flt-1 7N-K2 (100 to 204 position amino acids of human Flt-1 7N are replaced with 95 to 199 position amino acids of human KDR via links of two amino acids) were prepared in accordance with the method described in (6-5). Schematic illustration of each of the soluble human VEGF receptor derivatives used in the experiment is shown in FIG. 35.

First, the reactivity of anti-human VEGF receptor Flt-1 mouse monoclonal antibodies KM1732 and KM1750 and anti-human VEGF receptor Flt-1 human chimeric antibodies KM2532 and KM2550 was compared using an immunoassay method. Each of Flt-1 7N, Flt-1 3N, Flt-1 2N, Flt-1 7N.K2 and KDR 7N diluted to 4 µg/ml with PBS was dispensed in 50 µl portions into wells of a 96 well plate for EIA (manufactured by Greiner) and allowed to stand overnight at 4° C. for its adsorption. After washing the plate with PBS, 100 µl of 1% BSA-PBS was added to each well, and the remaining active groups was blocked by carrying out the reaction at room temperature for 1 hour. After discarding 1% BSA-PBS, each of the purified anti-human VEGF receptor Flt-1 mouse monoclonal antibodies KM1732 and KM1750 or purified anti-human VEGF receptor Flt-1 human chimeric antibodies KM2532 and KM2550, having a concentration of from 0.1 µg/ml, was dispensed in 50 µl portions into the resulting wells to carry out the reaction at room temperature for 1 hour. After washing the plate with 0.05% Tween-PBS, a peroxidase-labeled anti-mouse IgG antibody (manufactured by Dako) which had been diluted 400 times with 1% BSA-PBS, or a peroxidase-labeled anti-human IgG antibody (manufactured by American Qualex) which had been diluted 3,000 times, was dispensed in 50 µl portions into the wells to carry out the reaction at room temperature for 1 hour, the resulting plate was washed with 0.05% Tween-PBS, and then an ABTS [ammonium 2,2-azinobis(3-ethylbenzothiazole-6-sulfonate)] substrate solution was dispensed in 50 µl portions into the wells to develop color and measure its absorbance at $OD_{415\ nm}$ using Emax (manufactured by Molecular Devices).

The results are shown in FIG. 33. The anti-human VEGF receptor Flt-1 mouse monoclonal antibodies KM1732 and KM1750 and anti-human VEGF receptor Flt-1 human chimeric antibodies KM2532 and KM2550 bound to Flt-1 7N, Flt-1 3N and Flt-1 2N, but not to Flt-1 7N.K2 and KDR 7N. In consequence, it was confirmed that the epitope which is recognized by anti-human VEGF receptor Flt-1 mouse monoclonal antibodies KM1732 and KM1750 and anti-human VEGF receptor Flt-1 human chimeric antibodies KM2532 and KM2550 is contained in a region of from 100 to 204 positions of human Flt-1 counting from the N-terminal amino acid including a signal sequence.

Next, the binding activity was examined using an immunoassay method by fixing the amount of each of Flt-1 7N, Flt-1 3N, Flt-1 2N, Flt-1 7N.K2 and KDR 7N to be adsorbed on a 96 well plate for EIA and varying the concentration of human chimeric antibody to be added. Each of Flt-1 7N, Flt-1 3N, Flt-1 2N, Flt-1 7N.K2 and KDR 7N diluted to 4 µg/ml with PBS was dispensed in 50 µl portions into wells of a 96 well plate for EIA (manufactured by Greiner) and allowed to stand overnight at 4° C. for its adsorption. After washing the plate with PBS, 100 µl of 1% BSA-PBS was added to each well, and the remaining active groups was blocked by carrying out the reaction at room temperature for 1 hour. After discarding 1% BSA-PBS, each of the purified anti-human VEGF receptor Flt-1 human chimeric antibodies KM2532 and KM2550 having a concentration of from 0.0152 to 100 ng/ml was dispensed in 50 µl portions into the resulting wells to carry out the reaction at room temperature for 1 hour. After washing the plate with 0.05% Tween-PBS, a peroxidase-labeled anti-human IgG antibody (manufactured by American Qualex) which had been diluted 3,000 times with 1% BSA-PBS was dispensed in 50 µl portions into the wells to carry out the reaction at room temperature for 1 hour, the resulting plate was washed with 0.05% Tween-PBS, and then an ABTS [ammonium 2,2-azinobis (3-ethylbenzothiazole-6-sulfonate)] substrate solution was dispensed in 50 µl portions into the wells to develop color and measure its absorbance at $OD_{415\ nm}$ using Emax (manufactured by Molecular Devices).

Figure 34:
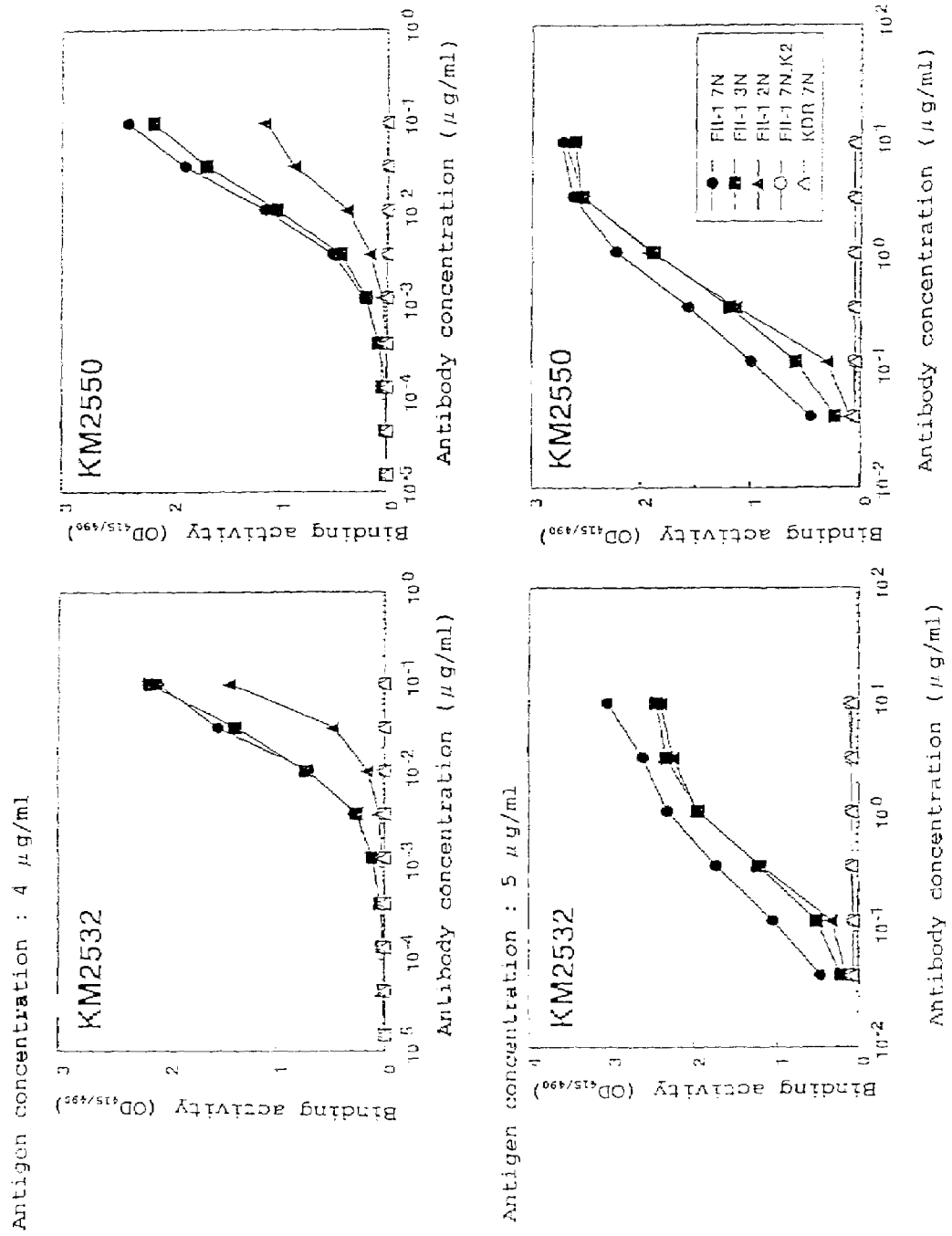
FIG. 34 is a graph showing results of the enzyme immunoassay evaluation of the binding reactivity of anti-human VEGF receptor Flt-1 human chimeric antibodies KM2532 and KM2550.

The results are shown in FIG. 34 (upper drawings). The anti-human VEGF receptor Flt-1 human chimeric antibodies KM2532 and KM2550 bound to Flt-1 7N, Flt-1 3N and Flt-1 2N in an antibody concentration dependent fashion, but not to Flt-1 7N.K2 and KDR 7N. In addition, the anti-human VEGF receptor Flt-1 human chimeric antibodies KM2532 and KM2550 showed almost the same binding activity.

Next, the binding activity of human chimeric antibodies was examined using an immunoassay method by varying the amount of each of Flt-1 7N, Flt-1 3N, Flt-1 2N, Flt-1 7N.K2 and KDR 7N to be adsorbed on a 96 well plate for EIA. Each of the soluble human VEGF receptors Flt-1 7N, Flt-1 3N, Flt-1 2N, Flt-1 7N.K2 and KDR 7N diluted to a concentration of from 0.041 to 10 µg/ml with PBS was dispensed in 50 µl portions into wells of a 96 well plate for EIA (manufactured by Greiner) and allowed to stand overnight at 4° C. for its adsorption. After washing the plate with PBS, 100 µl of 1% BSA-PBS was added to each well, and the remaining active groups was blocked by carrying out the reaction at room temperature for 1 hour. After discarding 1% BSA-PBS, each of the purified anti-human VEGF receptor Flt-1 human chimeric antibodies KM2532 and KM2550 having a concentration of 5 µg/ml was dispensed in 50 µl portions into the resulting wells to carry out the reaction at room temperature for 1 hour. After washing of the plate with 0.05% Tween-PBS, a peroxidase-labeled anti-human IgG antibody (manufactured by American Qualex) which had been diluted 3,000 times with 1% BSA-PBS was dispensed in 50 µl portions into the wells to carry out the reaction at room temperature for 1 hour, the resulting plate was washed with 0.05% Tween-PBS, and then an ABTS [ammonium 2,2-azinobis(3-ethylbenzothiazole-6-sulfonate)] substrate solution was dispensed in 50 µl portions into the wells to develop color and measure its absorbance at $OD_{415\ nm}$ using Emax (manufactured by Molecular Devices).

The results are shown in FIG. 34 (lower drawings). The anti-human VEGF receptor Flt-1 human chimeric antibodies KM2532 and KM2550 showed concentration dependent binding activity upon the human VEGF receptors Flt-1 7N, Flt-1 3N and Flt-1 2N, but did not react with Flt-1 7N.K2 and KDR 7N. In addition, the anti-human VEGF receptor Flt-1 human chimeric antibodies KM2532 and KM2550 showed almost the same binding activity.

3. Preparation of Anti-Human VEGF Receptor Flt-1 Human CDR Grafted Antibody

An anti-human VEGF receptor Flt-1 human CDR-grafted antibody having activities similar to the biological activities of anti-human VEGF receptor Flt-1 mouse monoclonal antibodies KM1732 and KM1750 and anti-human VEGF receptor Flt-1 human chimeric antibody KM2532 and KM2550 was prepared.

(1) Construction of cDNA Encoding VH of Anti-Human VEGF Receptor Flt-1 Human CDR-Grafted Antibody Based on Common Sequence of VH of Known Human Antibodies According to Kabat et al. (*Sequences of Proteins of Immunological Interest*), known human antibody VHs are classifiable into subgroups I to III [Human Sub Groups (HSG) I to III] based on the homology of amino acid sequences, and common sequences [Human Most Homologous Consensus Sequence (hereinafter referred to as "HMHCS")] have been identified for respective subgroups. An amino acid sequence of VH of an anti-human VEGF receptor Flt-1 human CDR-grafted antibody was designed based on HMHCS. For selecting HMHCS to serve as the base, the homology was examined between the amino acid sequence of FR of HMHCS of human antibody VH of each subgroup and amino acid sequences of FR of VH of anti-human VEGF receptor Flt-1 mouse monoclonal antibodies KM1732 and KH1750 (Table 3).

TABLE 3

Homology (%) between amino acid sequences of FR of HMHCS of human antibody VH of each subgroup and amino acid sequences of FR of VH of KM1732 and KM1750

|  | HSG I | HSG II | HSG III |
|---|---|---|---|
| KM1732 | 65.5 | 51.7 | 55.2 |
| KM1750 | 67.8 | 49.4 | 54.0 |

As a result, it was confirmed that KM1732 and KM1750 shows the highest homology with subgroup I. Thus, based on the HMHCS of subgroup I, an anti-human VEGF receptor Flt-1 human CDR-grafted antibody was designed, and the cDNA encoding the amino acid sequence was constructed by using the polymeraze chain reaction method (PCR) in the following manner.

The construction of cDNA encoding VH of an anti-human VEGF receptor Flt-1 human CDR-grafted antibody derived from the VH of anti-human VEGF mouse receptor Flt-1 mouse monoclonal antibody KM1732 is explained below. Six synthetic DNAs having a base sequence of SEQ ID NO:29 to 34 were synthesized (manufactured by Sawady Technology). The DNAs synthesized each was added, to have a final concentration of 0.1 µM, to 50 µl of 1×Ex Taq buffer (manufactured by Takara Shuzo Co., Ltd.) containing 200 µM dNTP, 0.5 µM M13 primer RV, 0.5 µM M13 primer M4 and 2.5 units of TaKaRa Ex Taq DNA polymerase (all manufactured by Takara Shuzo Co., Ltd.), the mixture was covered with 50 µl of mineral oil, DNA thermal cycler PJ480 (manufactured by Perkin Elmer) was loaded with the mixture, and 30 PCR cycles (at 94° C. for 2 minutes, at 55° C. for 2 minutes and at 72° C. for 2 minutes per cycle) were conducted. The reaction mixture was purified using QIAquick PCR Purification Kit (manufactured by Qiagen) according to the manual attached hereto, and the mixture was purified and eluted with 20 µl of sterilized water. Next, the obtained elution was added to 30 µl of a buffer solution comprising 10 mM Tris-HCl (pH 7.5), 10 mM magnesium chloride and 1 mM DTT, 20 units of a restriction enzyme ApaI (manufactured by Takara Shuzo Co., Ltd.) were further added thereto, and then the reaction was carried out at 37° C. for 1 hour. The reaction mixture was precipitated with ethanol, the precipitate was added to 10 µl of a buffer solution comprising 50 mM Tris-HCl (pH 7.5), 100 mM sodium chloride, 10 mM magnesium chloride, 1 mM DTT, 100 µg/ml BSA, and 0.01% Triton X-100, 10 units of restriction enzyme NotI (manufactured by Takara Shuzo Co., Ltd.) were further added thereto, and then the reaction was allowed to proceed at 37° C. for 1 hour. The reaction mixture was fractionated by agarose gel electrophoresis, and about 0.5 µg of an ApaI-NotI fragment about 0.44 kb was recovered.

Figure 26:
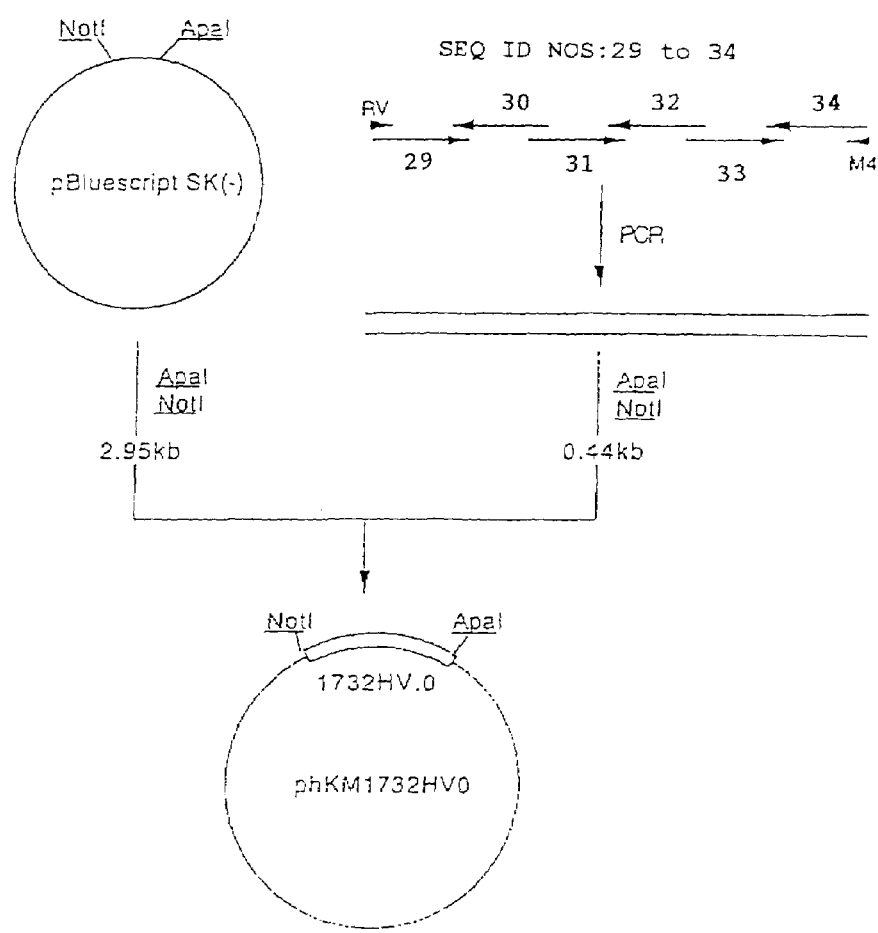
FIG. 26 is a graph showing construction steps of plasmid phKM1732HV0.
Figure 27:
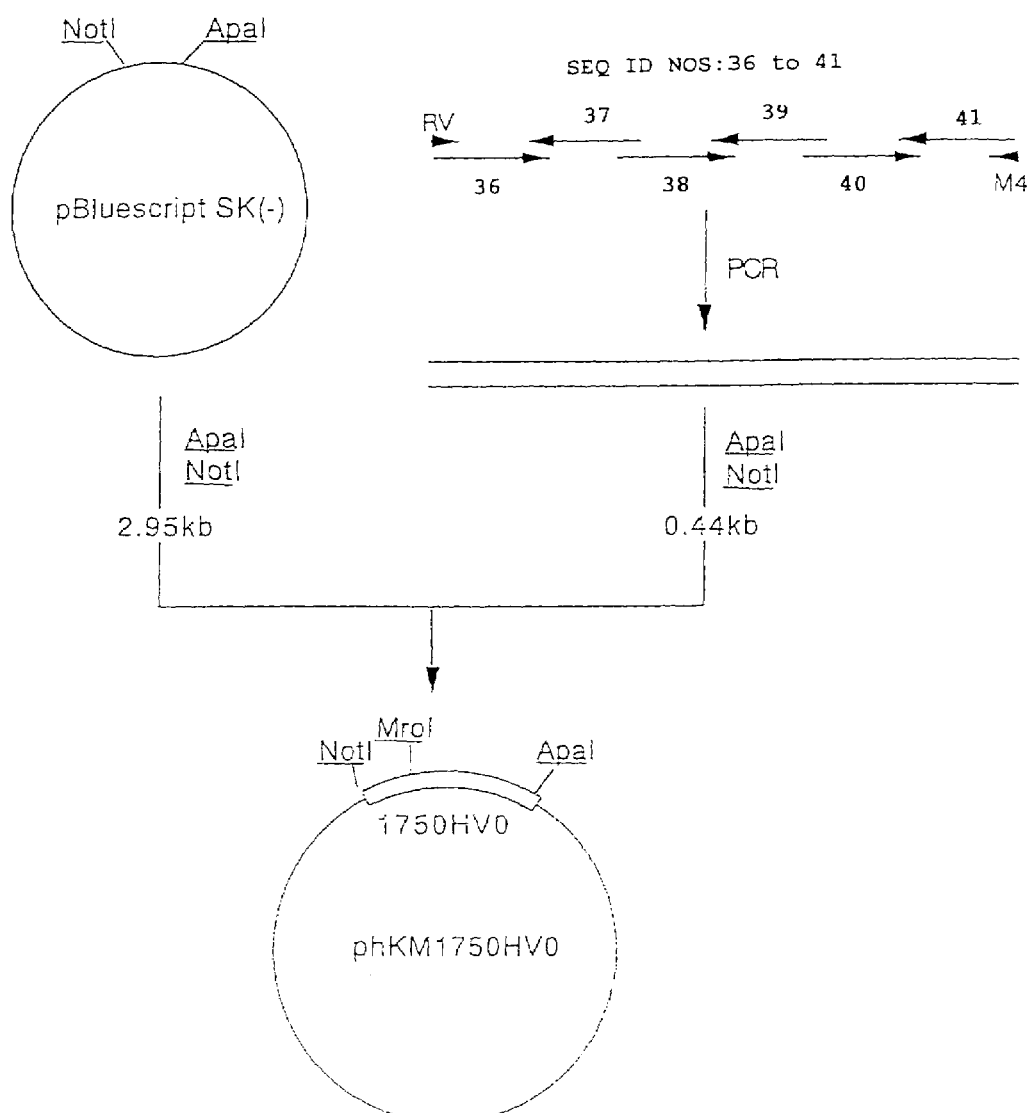
FIG. 27 is a graph showing construction steps of plasmid phKM1750HV0.

To 10 µl in total volume of sterilized water, 0.1 µg of the ApI-NotI fragment derived from plasmid pBluescript SK(−) obtained in 2(1) of Example 2, and 0.1 µg of the ApaI-NotI fragment which was the PCR amplified fragment obtained in the above were added, and the fragments were linked using DNA ligation Kit Ver. 2 (manufactured by Takara Shuzo Co., Ltd.) according to the manual attached hereto. *Escherichia coli* DH5α (manufactured by TOYOBO CO., LTD.) was transformed by using the thus-obtained recombinant plasmid DNA solution. Plasmid DNA was prepared from each of ten *E. coli* transformants. As a result that the nucleotide sequence was determined according to the method described in 1(4) of Example 2, plasmid phKM1732HV0 shown in FIG. 26 and containing cDNA encoding the amino acid sequence of interest was obtained. The nucleotide sequence and the amino acid sequence of the VH of the anti-human VEGF receptor Flt-1 human CDR-grafted antibody (hereinafter referred to as "1732HV0") contained in phKM1732HV0 are shown in SEQ ID NOS:35 and 90, respectively.

The construciton of cDNA encoding VH of an anti-human VEGF receptor Flt-1 human CDR-grafted antibody derived from the VH of the anti-human VEGF mouse receptor Flt-1 mouse monoclonal antibody KM1750 is explained below. The reactions were carried out in the same manner as described above using six synthetic DNAs having a base sequence of SEQ ID NO:36 to 41 were synthesized (manufactured by Sawady Technology) to obtain plasmid phKM1750HV0 containing cDNA encoding an amino acid sequence of interest shown in FIG. 13. The nucleotide sequence and the amino acid sequence of the VH of the anti-human VEGF receptor Flt-1 human CDR-grafted antibody (hereinafter referred to as "1750HV0") contained in phKM1750HV0 are shown in SEQ ID NOS:42 and 91, respectively.

(2) Construction of cDNA Encoding VL of Anti-Human VEGF Receptor Flt-1 Human CDR-Grafted Antibody Based on Common Sequence of VL of Known Human Antibodies According to Kabat et al. (*Sequences of Proteins of Immunological Interest*), known human antibody VLs are classifiable into subgroups I to IV (HSG I to IV) based on the homology of amino acid sequences, and HMHCS has been identified for respective subgroups. An amino acid sequence of VL of an anti-human VEGF receptor Flt-1 human CDR-grafted antibody was designed based on HMHCS. For selecting HMHCS to serve as the base, the homology was examined between the amino acid sequence of FR of HMHCS of human antibody VL of each subgroup and amino acid sequences of FR of VL of anti-human VEGF receptor Flt-1 mouse monoclonal antibodies KM1732 and KM1750 (Table 4).

TABLE 4

Homology (%) between amino acid sequences of FR of HMHCS of human antibody VH of each subgroup and the amino acid sequences of FR of VH of KM1732 and KM1750

|  | HSG I | HSG II | HSG III | HSG IV |
|---|---|---|---|---|
| KM1732 | 66.2 | 57.5 | 62.5 | 63.8 |
| KM1750 | 68.8 | 63.8 | 68.8 | 70.0 |

As a result, it was confirmed that KM1732 shows the highest homology with subgroup I and KM1750 shows almost the same high homology with subgroups I and IV, so that the amino acid sequence of the V-L of anti-human VEGF receptor Flt-1 human CDR-grafted antibody was designed based on the HMHCS of subgroup I in the case of KM1732 and the HMHCS of subgroups I and IV in the case of KM1750, and cDNA encoding the amino acid sequence was constructed by PCR in the following manner.

The construction of cDNA encoding VL of an anti-human VEGF receptor Flt-1 human CDR-grafted antibody derived from the VL of anti-human VEGF mouse receptor Flt-1 mouse monoclonal antibody KM1732 is explained below. Six synthetic DNAs having a base sequence of SEQ ID NO:43 to 48 were synthesized (manufactured by Sawady Technology). The DNAs synthesized each was added, to have a final concentration of 0.1 µM, to 50 µl of 1×Ex Taq buffer (manufactured by Takara Shuzo Co., Ltd.) containing 200 µM dNTP, 0.5 µM M13 primer RV, 0.5 µM M13 primer M4 and 2.5 units of TaKaRa Ex Taq DNA polymerase (all manufactured by Takara Shuzo Co., Ltd.), the mixture was covered with 50 µl of mineral oil, DNA thermal cycler PJ480 (manufactured by Perkin Elmer) was loaded with the mixture, and 30 PCR cycles (at 94° C. for 2 minutes, at 55° C. for 2 minutes and at 72° C. for 2 minutes per cycle) were conducted. The reaction mixture was purified using QIAquick PCR Purification Kit (manufactured by Qiagen) according to the manual attached hereto, and the mixture was purified and eluted with 20 µl of sterilized water. Next, the obtained elution was added to 30 µl of a buffer solution comprising 50 mM Tris-HCl (pH 7.5), 100 mM sodium chloride, 1 mM DTT, and 100 µg/ml BSA, 10 units of a restriction enzyme EcoRI (manufactured by Takara Shuzo Co., Ltd.), 10 units of a restriction enzyme SplL (manufactured by Takara Shuzo Co., Ltd.) were further added thereto, and then the reaction was carried out at 37° C. for 1 hour. The reaction mixture was fractionated by agarose gel electrophoresis, and about 0.5 µg of an EcoRI-SplI fragment about 0.39 kb was recovered.

Figure 28:
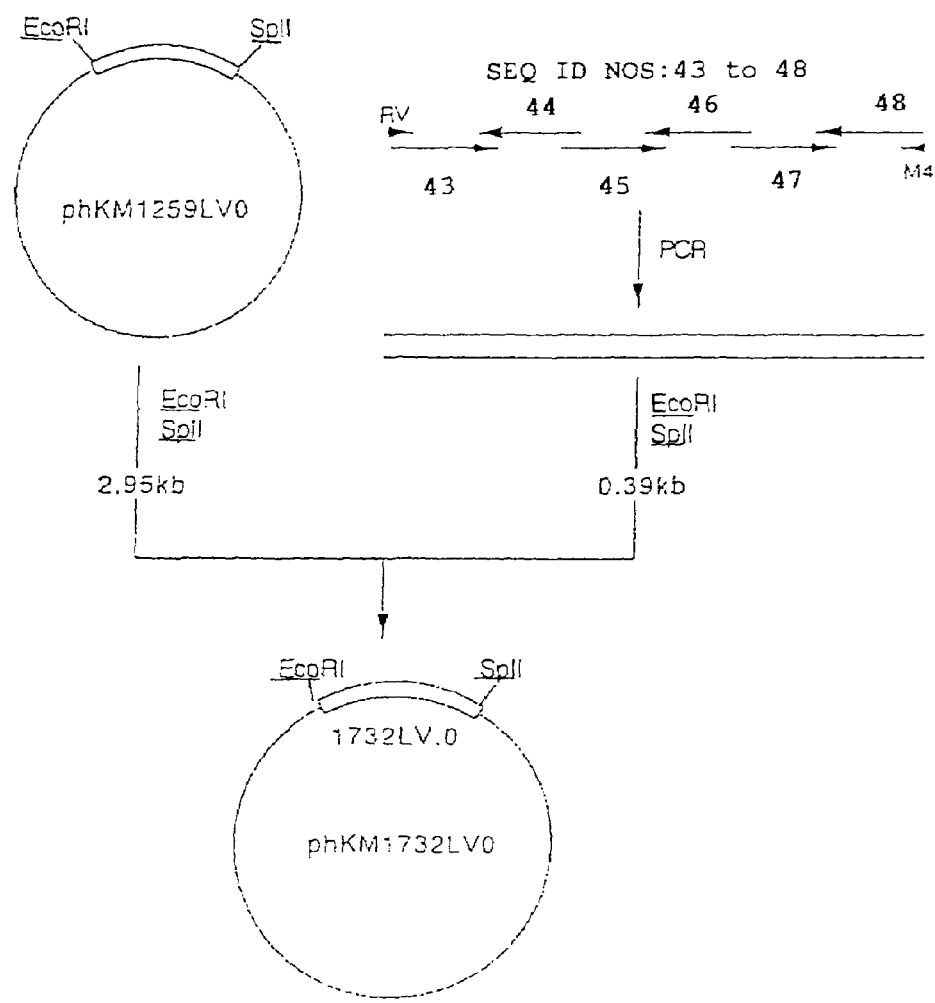
FIG. 28 is a graph showing construction steps of plasmid phKM1732LV0.

To 10 µl in total volume of sterilized water, 0.1 µg of the EcoRI-SplI fragment derived from plasmid phKM1259LV0 obtained in 2(1) of Example 2, and 0.1 µg of the EcoRI-SplI fragment which was the PCR amplified fragment obtained in the above were added, and the fragments were linked using DNA ligation Kit Ver. 2 (manufactured by Takara Shuzo Co., Ltd.) according to the manual attached hereto. *Escherichia coli* DH5α (manufactured by TOYOBO CO., LTD.) was transformed by using the thus-obtained recombinant plasmid DNA solution. Plasmid DNA was prepared from each of ten *E. coli* transformants. As a result that the nucleotide sequence was determined according to the method described in 1(4) of Example 2, plasmid phKM1732LV0 shown in FIG. 28 and containing cDNA encoding the amino acid sequence of interest was obtained. The nucleotide sequence and the amino acid sequence of the VL of the anti-human VEGF receptor Flt-1 human CDR-grafted antibody (hereinafter referred to as "11732LV0") contained in phKM1732LV0 are shown in SEQ ID NOS:49 and 92, respectively.

Figure 29:
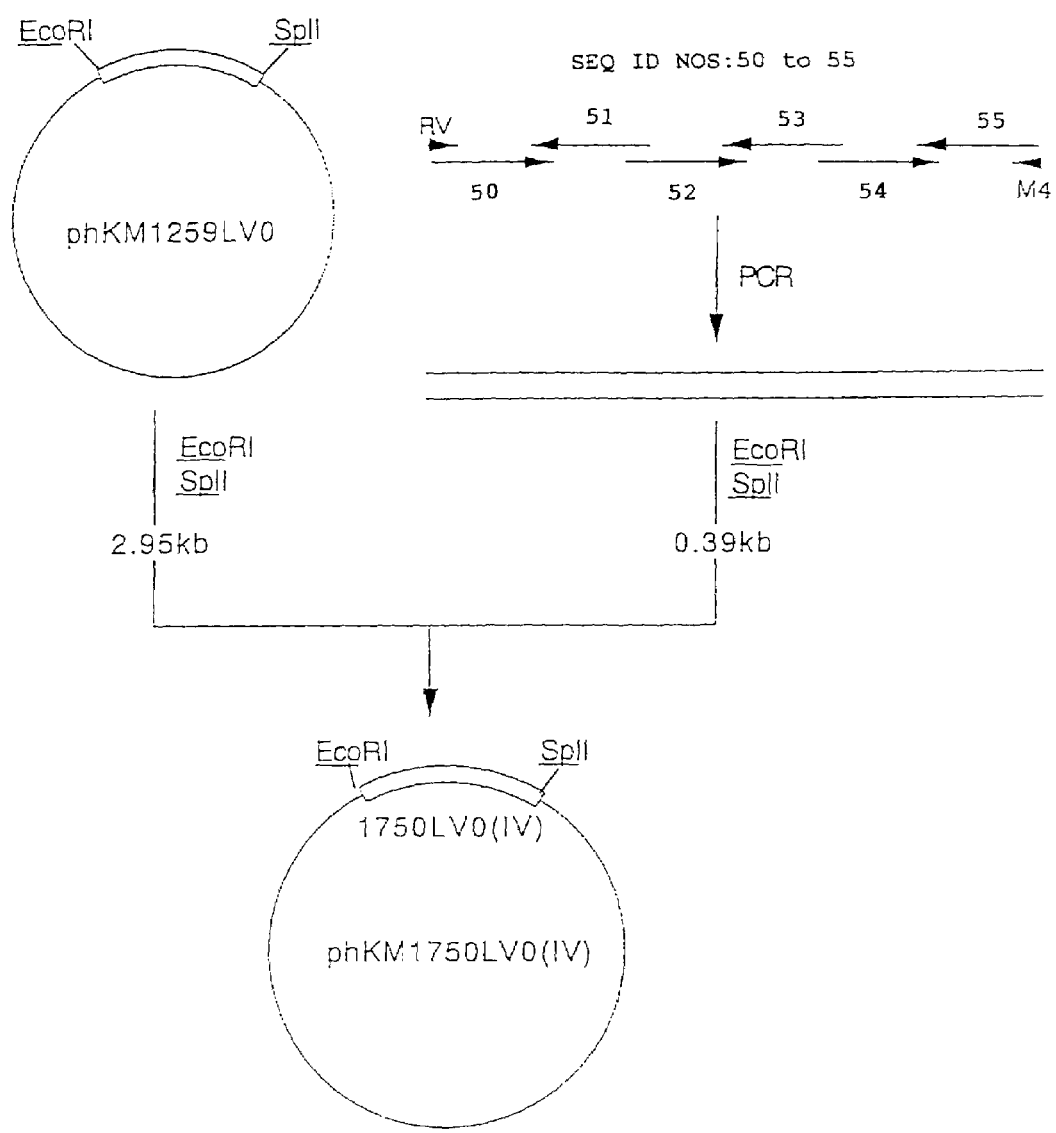
FIG. 29 is a graph showing construction steps of plasmid phKM1750LV0 (IV).
Figure 36:
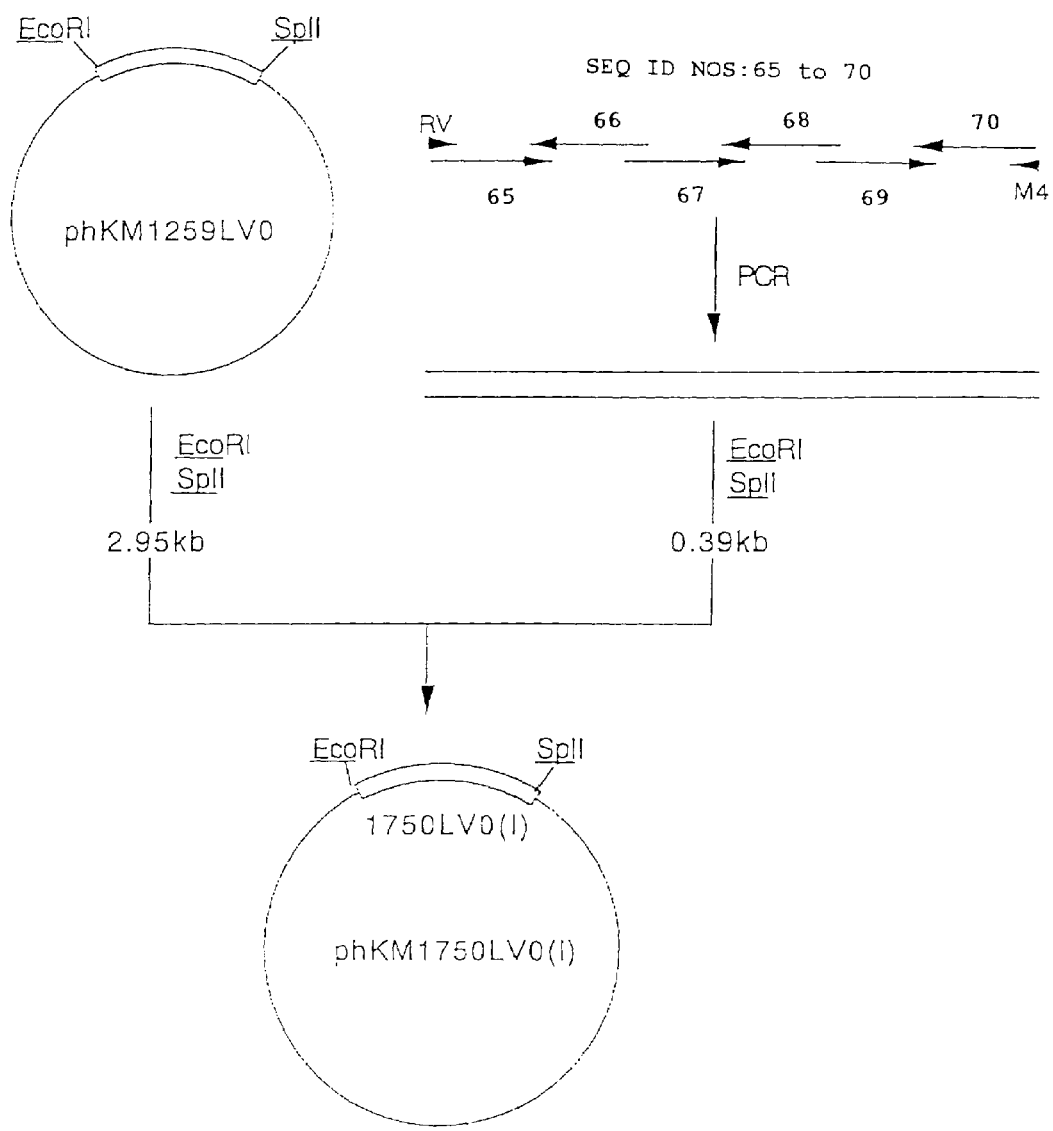
FIG. 36 is a graph showing construction steps of plasmid phKM1750LV0 (I).

When the HMHCS of human subgroup IV was used as the base in constructing cDNA encoding the VL of anti-human VEGF receptor Flt-1 human CDR-grafted antibody derived from the VL of anti-human VEGF receptor Flt-1 mouse monoclonal antibody KM1750, plasmid phKM1750LV0 (IV) containing cDNA encoding the amino acid sequence of interest shown in FIG. 29 was obtained by carrying out the reaction similar to the above using 6 synthetic DNA fragments (manufactured by Sawady Technology) having nucleotide sequences of SEQ ID NOS:50 to 55. Corresponding nucleotide sequence and amino acid sequence of the VL of anti-human VEGF receptor Flt-1 human CDR-grafted antibody contained in phKM1750LV0 (IV) [hereinafter referred to as "1750LV0 (IV)"] are shown in SEQ ID NOS:56 and 93, respectively. When the HMHCS of human subgroup I was used as the base, plasmid phKM1750LV0 (I) containing cDNA encoding the amino acid sequence of interest shown in FIG. 36 was obtained by carrying out the reaction similar to the above using 6 synthetic DNA fragments (manufactured by Sawady Technology) having nucleotide sequences of SEQ ID NOS:65 to 70. Corresponding nucleotide sequence and amino acid sequence of the VL of anti-human VEGF receptor Flt-1 human CDR-grafted antibody contained in phKM1750LV0 (I) [hereinafter referred to as "1750LV0 (I)"] are shown in SEQ ID NOS:71 and 94, respectively.

(3) Construction of Anti-Human VEGF Receptor Flt-1 Human CDR-Grafted Antibody Expression Vectors Based on HMHCS of V Regions of Known Human Antibodies Expression vectors of anti-human VEGF receptor Flt-1 human CDR-grafted antibody were constructed in the following manner using tandem cassette vector, pKANTEX93, for humanized antibody expression described in WO 97/10354 and plasmids phKM1732HV0, phKM1732LV0, phKM1750HV0, phKM1750LV0 (I) and phKM1750LV0 (IV) containing cDNA encoding the V region of anti-human VEGF receptor Flt-1 human CDR-grafted antibody obtained in 3(1) and (2) of Example 2.

The construction of an expression vector of anti-human VEGF receptor Flt-1 human CDR-grafted antibody derived from anti-human VEGF receptor Flt-1 mouse monoclonal antibody KM1732 is explained below.

To 10 µl of a buffer solution comprising 50 mM Tris-HCl (pH 7.5), 10 mM magnesium chloride and 1 mM DTT, 5 µg of plasmid phKM1732HV0 was added, 10 units of a restriction enzyme ApaI (manufactured by Takara Shuzo Co., Ltd.) were further added thereto, and then the reaction was carried out at 37° C. for 1 hour. The reaction mixture was precipitated with ethanol, the precipitate was added to 10 µl of a buffer solution comprising 50 mM Tris-HCl (pH 7.5), 100 mM sodium chloride, 10 mM magnesium chloride, 1 mM DTT, 100 µg/ml BSA, and 0.01% Triton X-100, 10 units of a restriction enzyme NotI (Takara Shuzo Co., Ltd.) were further added thereto, and then the reaction was carried out at 37° C. for 1 hour. The reaction mixture was fractionated by agarose gel electrophoresis, and about 0.5 µg of an ApaI-NotI fragment about 0.44 kb was recovered.

Figure 30:
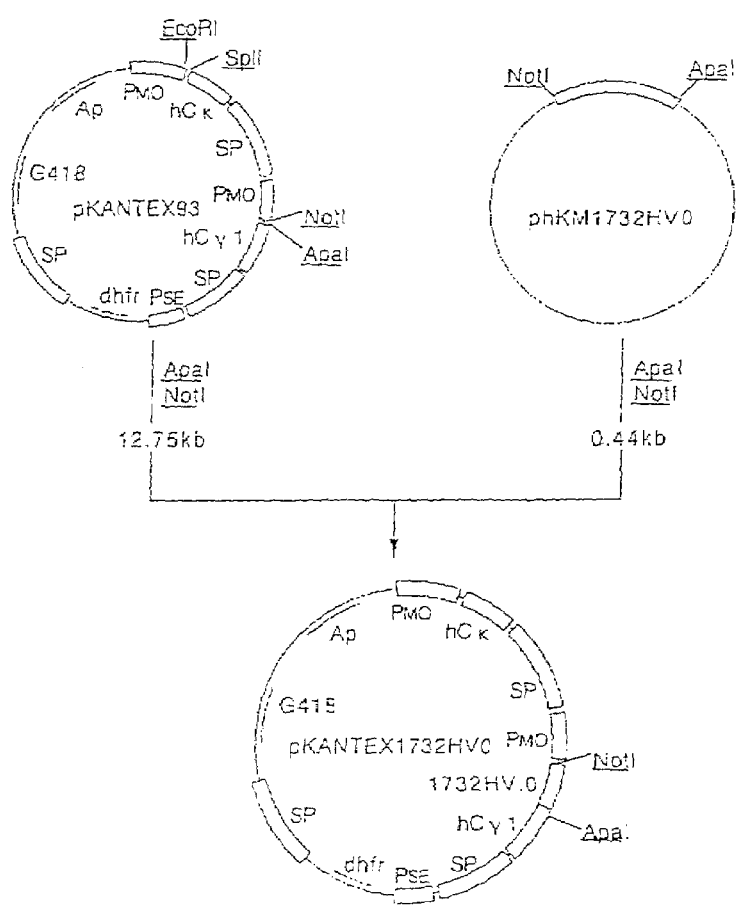
FIG. 30 is a graph showing construction steps of plasmid pKANTEX1732HV0.

To 10 µl in total volume of sterilized water, the ApaRI-NotI fragment obtained in Example 2(1) derived from tandem cassette vector for humanized antibody expression, pKANTEX93, and 0.1 µg of the ApaI-NotI fragment of phKM1732HV obtained in the above were added, and the fragments were linked using DNA ligation Kit Ver. 2 (manufactured by Takara Shuzo Co., Ltd.) according to the manual attached hereto. *Escherichia coli* DH5α (manufactured by TOYOBO CO., LTD.) was transformed by using the thus-obtained recombinant plasmid DNA solution to obtain plasmid pKANTEX1732HV0 shown in FIG. 30.

Next, 3 µg of the thus obtained plasmid pKANTEX1732HV0 was added to a buffer solution comprising 50 mM Tris-Hcl (pH 7.5), 100 mM sodium chloride, 10 mM magnesium chloride, 1 mM DTT and 100 µg/ml BSA, 10 units of a restriction enzyme EcoRI (manufactured by Takara Shuzo Co., Ltd.) and 10 units of a restriction enzyme SplI (manufactured by Takara Shuzo Co., Ltd.) were added thereto, and the reaction was carried out at 37° C. for 1 hour. The reaction mixture was fractionated by agarose gel electrophoresis, and about 1 µg of an EcoI-SplI fragment about 13.20 kb in size was recovered. Further, 5 µg of plasmid phKM1732LV0 was added to a buffer solution comprising 50 mM Tris-HCl (pH 7.5), 100 mM sodium chloride, 10 mM magnesium chloride, 1 mM DTT and 100 µg/ml BSA, 10 units of a restriction enzyme EcoRI (manufactured by Takara Shuzo Co., Ltd.) and 10 units of a restriction enzyme SplI (manufactured by Takara Shuzo Co., Ltd.) were added thereto, and the reaction was carried out at 37° C. for 1 hour. The reaction mixture was fractionated by agarose gel electrophoresis, and about 0.5 µg of an EcoI-SplI fragment about 0.39 kb in size was recovered.

Figure 31:
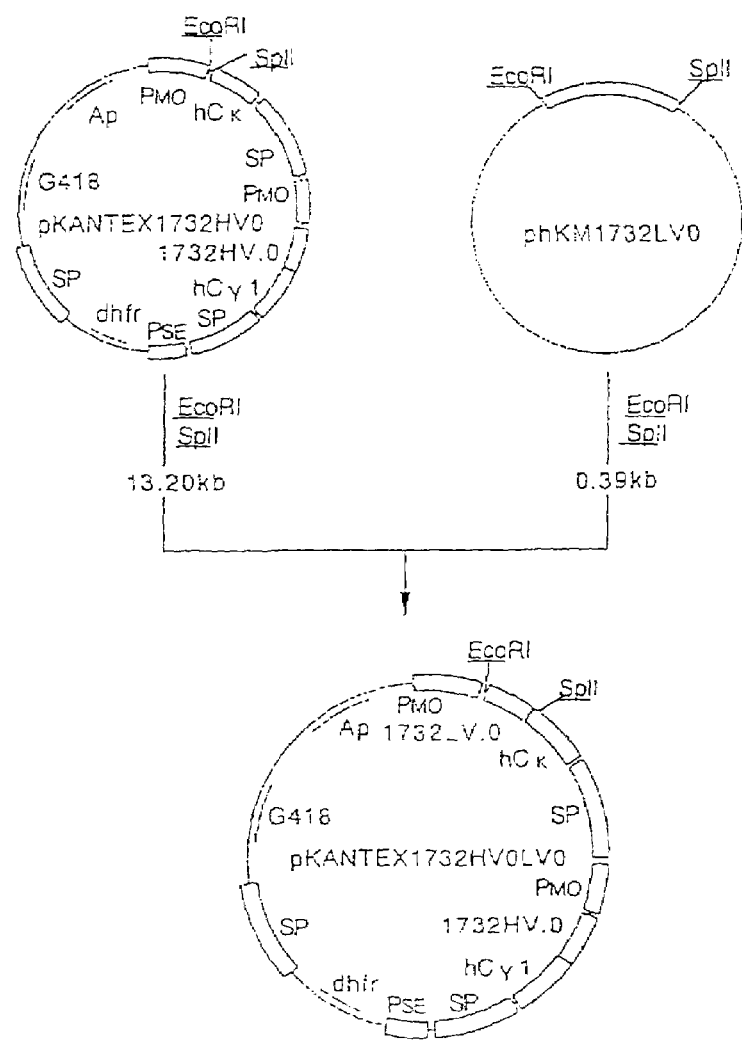
FIG. 31 is a graph showing construction steps of plasmid pKANTEX1732HV0LV0.

To 10 µl in total volume of sterilized water, 0.1 µg of the thus obtained EcoRI-SplI fragment derived from plasmid pKANTEX1732HV0 and 0.1 µg of the EcoI-SplI fragment derived from plasmid pKM1732LV0 were added, and the fragments were ligated using DNA ligation Kit Ver. 2 (manufactured by Takara Shuzo Co., Ltd.) according to the manual attached hereto. *Escherichia coli* DH5α (manufactured by TOYOBO CO., LTD.) was transformed by using the thus-obtained recombinant plasmid DNA solution to obtain an expression vector of anti-human VEGF receptor Flt-1 human CDR-grafted antibody, pKANTEX1732HV0LV0, shown in FIG. 31.

Figure 32:
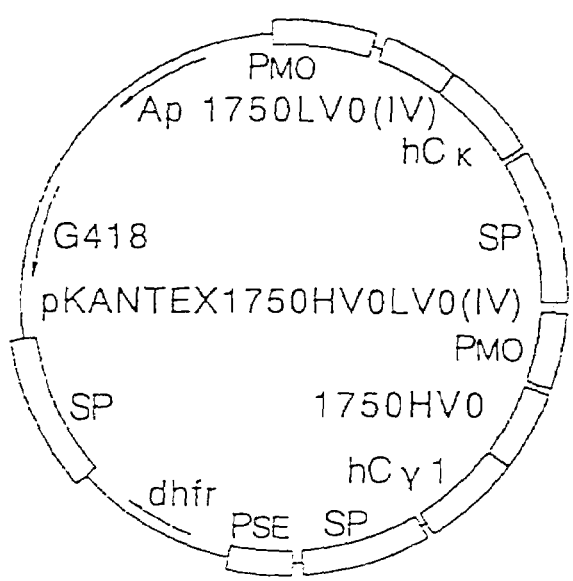
FIG. 32 is a graph showing construction steps of plasmid pKANTEX1750HV0LV0 (IV).
Figure 37:
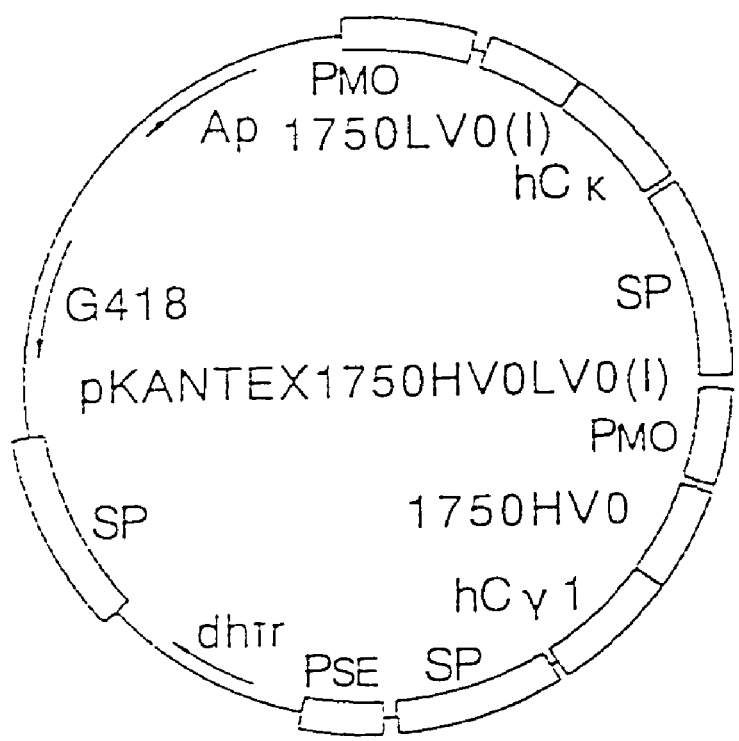
FIG. 37 is a graph showing construction steps of plasmid pKANTEX1750HV0LV0 (I).

Regarding the construction of expression vectors of anti-human VEGF receptor Flt-1 human CDR-grafted antibody originated from anti-human VEGF receptor Flt-1 mouse monoclonal antibody KM1750, the reaction similar to the above was carried out to obtain vectors for anti-human VEGF receptor Flt-1 human CDR-grafted antibody expression, pKANTEX1750HV0LV0 (IV) and pKANTEX1750HV0LV0 (I), shown in FIGS. 32 and 37, respectively.

4. Analysis of Amino Acid Sequence of FR of V Region of Anti-Human VEGF Receptor Flt-1 Human CDR-Grafted Antibody and Construction of Expression Vector for Modified Human CDR-Grafted Antibody in which Amino Acids of FR are Modified (1) Analysis of Amino Acid Sequence of FR of V Region of Anti-Human VEGF Receptor Flt-1 Human CDR-Grafted Antibody Among amino acid residues which are different between the amino acid sequence of the FR of the V region of each anti-human VEGF receptor Flt-1 human CDR-grafted antibody and the amino acid sequence of the FR of the V region of each anti-human VEGF receptor Flt-1 mouse monoclonal antibody, the positions of the amino acid residues which were considered to be important for binding to human VEGF receptor Flt-1 in the amino acid sequence of the FR of the V region of each anti-human VEGF receptor Flt-1 human CDR-grafted antibody were identified by constructing and comparing a computer three-dimensional structure model of each of the V region of anti-human VEGF receptor Flt-1 mouse monoclonal antibody KM1732 and KM1750 and that of each of the anti-human VEGF receptor Flt-1 human CDR-grafted antibodies prepared in 3 of Example 2. As a result, regarding the anti-human VEGF receptor Flt-1 human CDR- grafted antibody derived from anti-human VEGF receptor Flt-1 mouse monoclonal antibody KM1732, it was considered that the positions of 24-position alanine, 27-position tyrosine, 40-position alanine, 67-position arginine, 69-position threonine, 70-position isoleucine, 82-position glutamic acid and 93-position valine in the amino acid sequence of the VH of SEQ ID NO:90 and the positions of 39-position proline, 45-position leucine, 46-position leucine, 69-position asparatic acid, and 70-position phenylalanine in the amino acid sequence of VL of SEQ ID NO:92 are taking an important role in its binding to the human VEGF receptor Flt-1.

Regarding the anti-human VEGF receptor Flt-1 human CDR-grafted antibody derived from anti-human VEGF receptor Flt-1 mouse monoclonal antibody KM1750, it was considered that the positions of 3-position glutamine, 67-position arginine, 82-position glutamic acid, 84-position serine and 95-position tyrosine in the amino acid sequence of the VH of SEQ ID NO:91 and the positions of 17-position aspartic acid, 18-position arginine, 39-position proline, 59-position serine, 69-position aspartic acid and 70-position phenylalanine in the amino acid sequence of the VL of SEQ ID NO:93 are taking an important role in its binding to the human VEGF receptor Flt-1. These facts suggest that the activity of anti-human VEGF receptor Flt-1 human CDR-grafted antibody to bind to human VEGF receptor Flt-1 can be modified, for example, by modifying the just described positions of amino acid residues of anti-human VEGF receptor Flt-1 human CDR-grafted antibody into the amino acid residues of the corresponding positions of anti-human VEGF receptor Flt-1 mouse monoclonal antibody.

(2) Construction of cDNA Encoding VH of Modified Human CDR-Grafted Antibody in which Amino Acids of FR are Modified Regarding the H chain of anti-human VEGF receptor Flt-1 human CDR-grafted antibody derived from anti-human VEGF receptor Flt-1 mouse monoclonal antibody KM1750, the 3 residues (82-position glutamic acid, 84-position serine and 95-position tyrosine) among the above-described 5 amino acid residues considered to be taking an important role in its binding to the human VEGF receptor Flt-1 were considered to be particularly important, so that cDNA encoding an amino acid sequence which was converted into the corresponding residues (82-position glutamine, 84-position arginine and 95-position phenylalanine) found in KM1750 was constructed by PCR in the following manner.

Using 6 synthetic DNA fragments having the nucleotide sequences of SEQ ID NOS:72 to 77 (manufactured by Sawady Technology), an MroI-ApaI fragment of about 0.39 kb was recovered by PCR in accordance with the above-described method.

Figure 38:
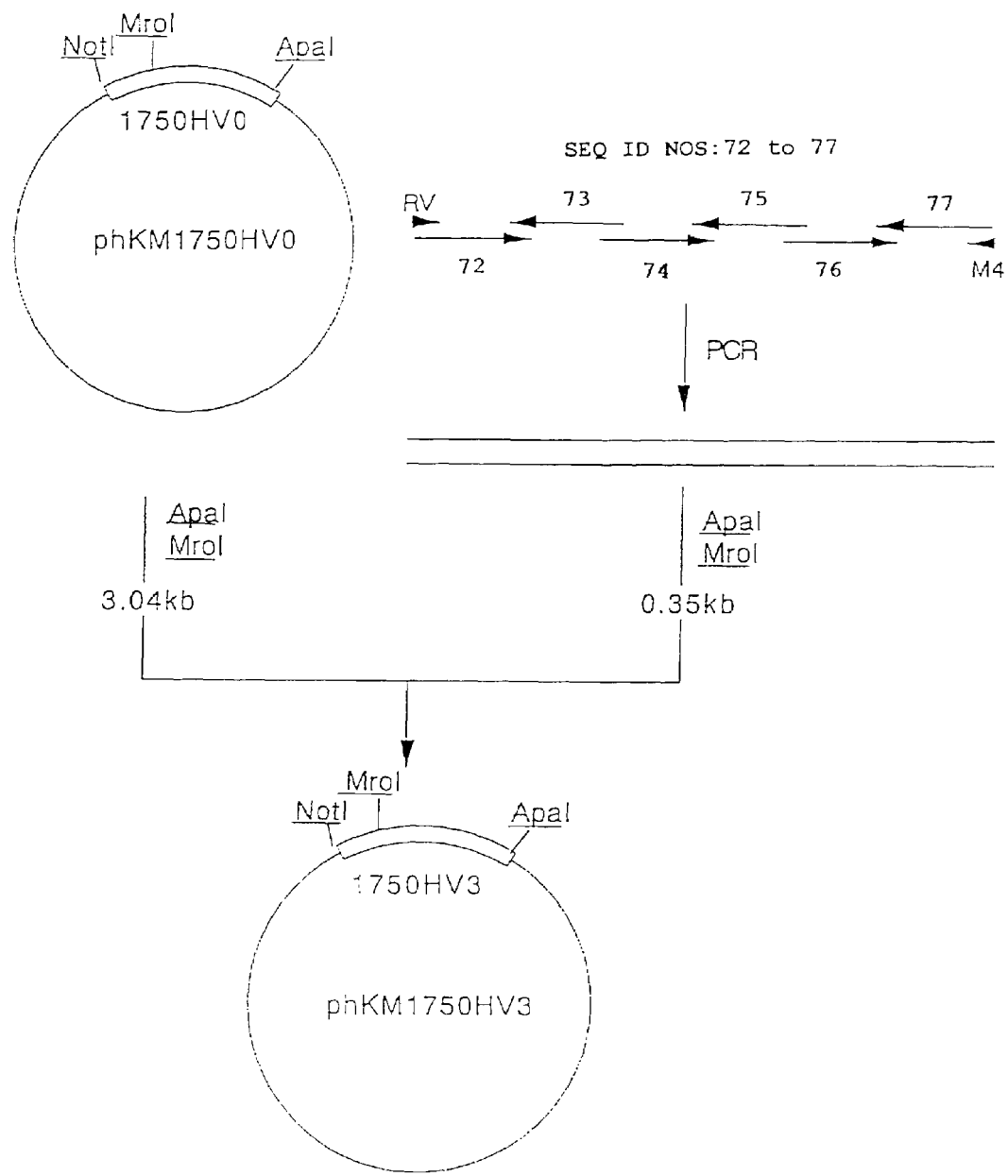
FIG. 38 is a graph showing construction steps of plasmid phKM1750HV3.

Plasmid phKM1750HV0 was treated with restriction enzymes ApaI and MroI to recover an ApaI-MroI fragment of about 3.04 kb which was subsequently connected with the PCR amplified fragment obtained in the above, and then *Escherichia coli* DH5α (manufactured by TOYOBO CO., LTD.) was transformed using the thus obtained recombinant plasmid DNA solution. Plasmid was prepared from each of ten *E. coli* transformants and its nucleotide sequence was determined in accordance with the method described in 1(4) of Example 2 to obtain plasmid phKM1750HV3 shown in FIG. 38 which contains cDNA encoding the amino acid sequence of interest.

Corresponding nucleotide sequence and amino acid sequence of the VH of anti-human VEGF receptor Flt-1 human CDR-grafted antibody contained in phKM1750HV3 (hereinafter referred to as "1750HV3") are shown in SEQ ID NOS:78 and 95, respectively.

(3) Construction of cDNA Encoding VL of Modified Human CDR-Grafted Antibody in which Amino Acids of FR are Modified Regarding L chain of anti-human VEGF receptor Flt-1 human CDR-grafted antibody derived from anti-human VEGF receptor Flt-1 mouse monoclonal antibody KM1750, the 4 residues (17-position aspartic acid, 18-position arginine, 69-position aspartic acid and 70-position phenylalanine) among the above-described 6 amino acid residues considered to be taking an important role in its binding to the human VEGF receptor Flt-1 were considered to be particularly important in KM1750LV0 (I), so that cDNA encoding an amino acid sequence which was converted into the corresponding residues (17-position glutamic acid, 18-position glutamic, 69-position phenylalanine and 70-position tyrosine) found in KM1750 was constructed by PCR in the following manner.

Figure 39:
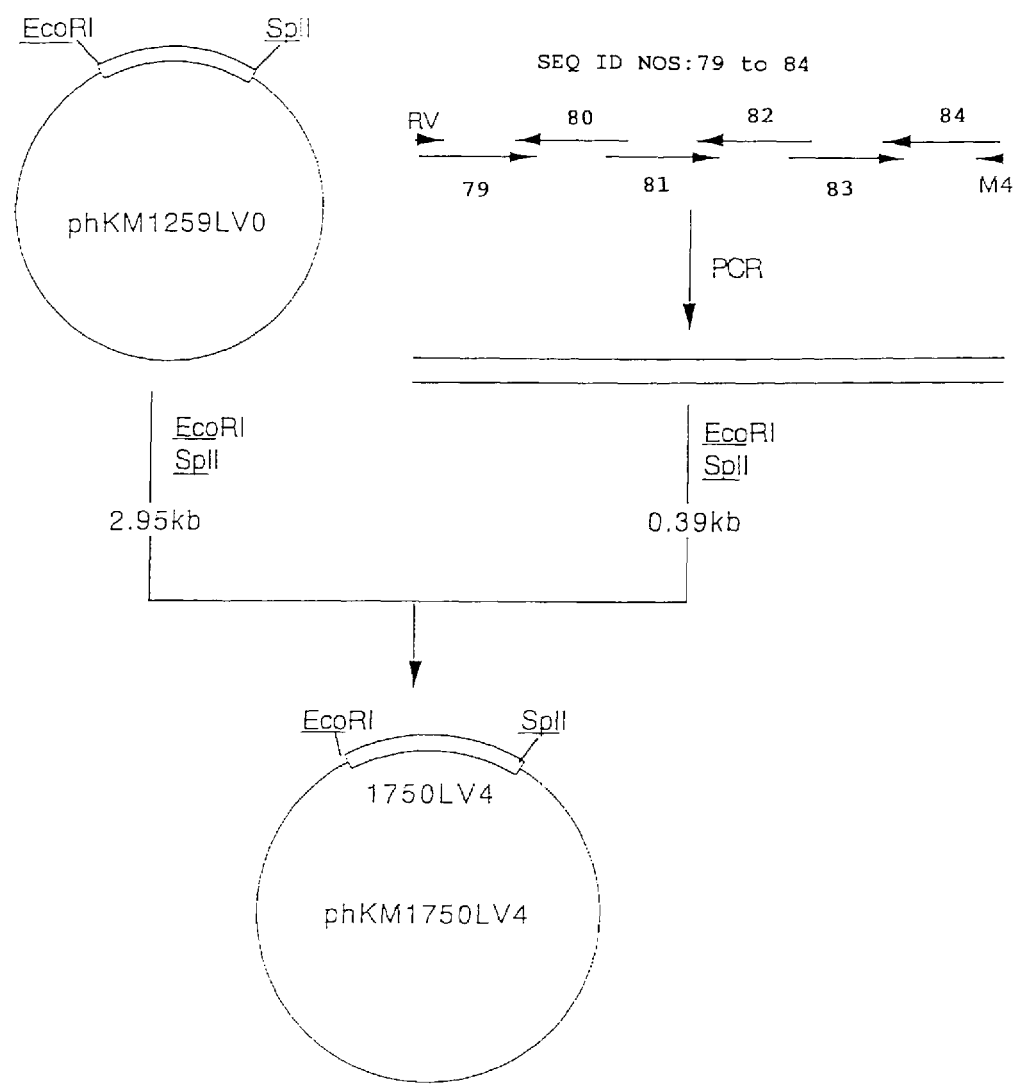
FIG. 39 is a graph showing construction steps of plasmid phKM1750LV4.
Figure 40:
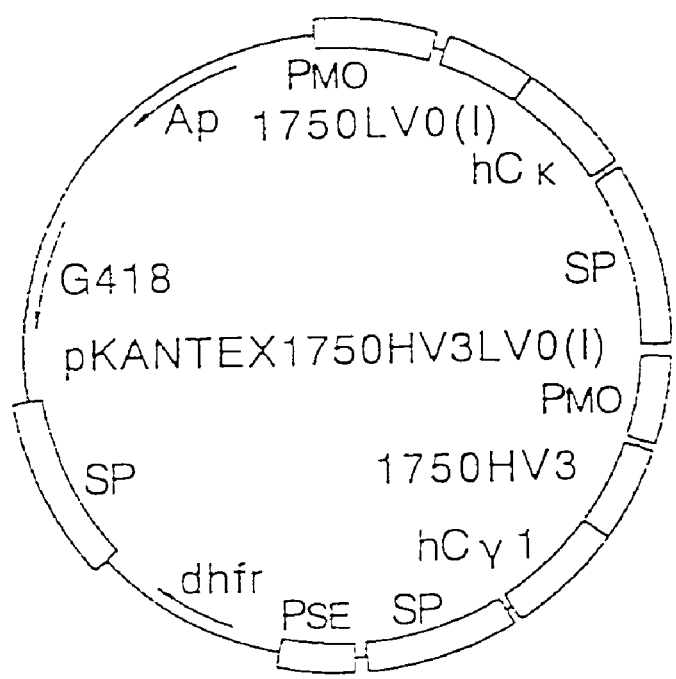
FIG. 40 is a graph showing construction steps of plasmid pKANTEX1750HV3LV0 (I).
Figure 41:
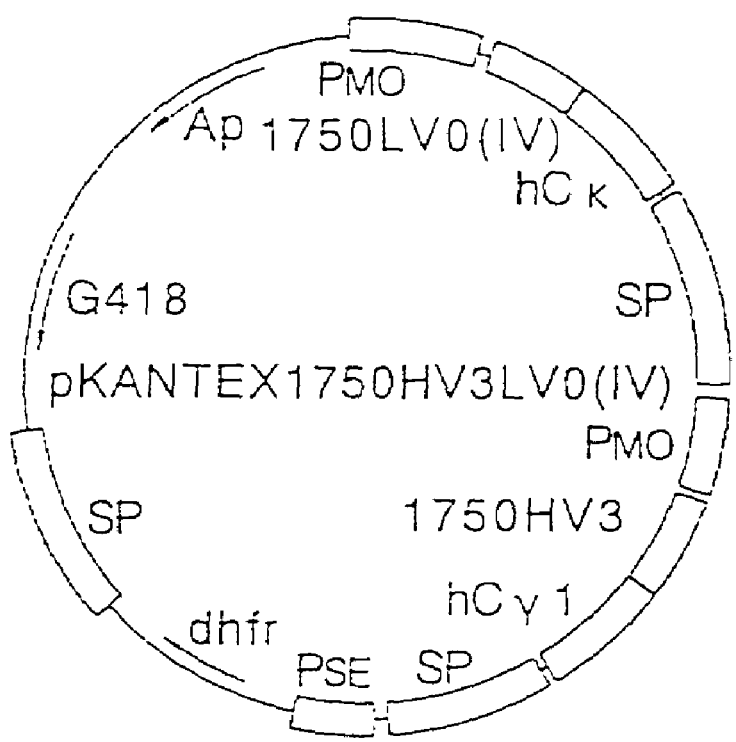
FIG. 41 is a graph showing construction steps of plasmid pKANTEX1750HV3LV0 (IV).
Figure 42:
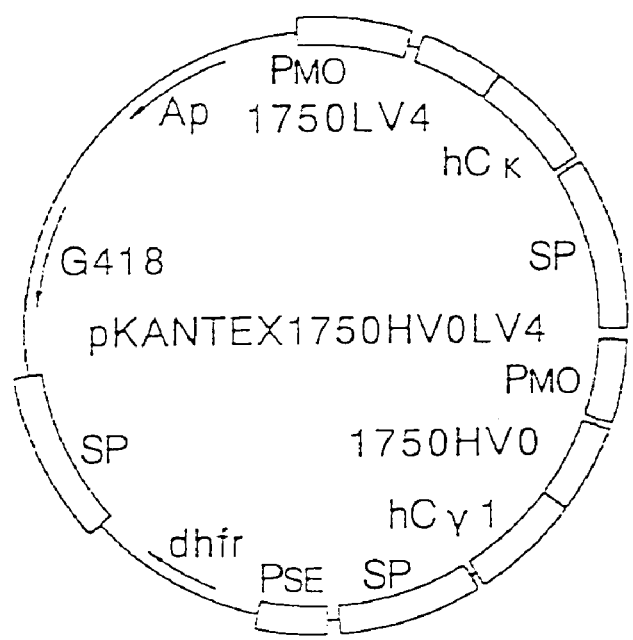
FIG. 42 is a graph showing construction steps of plasmid pKANTEX1750HV0LV4.
Figure 43:
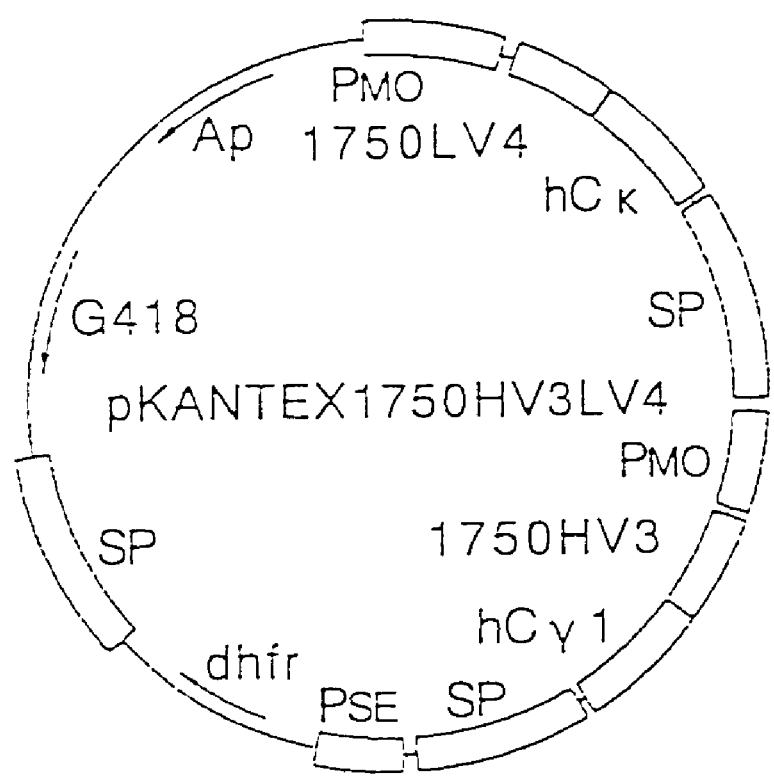
FIG. 43 is a graph showing construction steps of plasmid pKANTEX1750HV3LV4.

Using 6 synthetic DNA fragments having the nucleotide sequences of SEQ ID NOS:79 to 84 (manufactured by Sawady Technology), the same reaction was carried out to obtain the plasmid phKM1750LV4 shown in FIG. 39 which contains cDNA encoding the amino acid sequence of interest.

Corresponding nucleotide sequence and amino acid sequence of the VL of anti-human VEGF receptor Flt-1 human CDR-grafted antibody contained in phKM1750LV4 (hereinafter referred to as "1750LV4") are shown in SEQ ID NOS:85 and 96, respectively.

(4) Construction of Expression Vector for Modified Human CDR-Grafted Antibody in which Amino Acids of FR are Modified Using plasmids phKM1750HV3 and phKM1750LV4 obtained in 4(3) of Example 2 containing cDNA encoding the V region of anti-human VEGF receptor Flt-1 human CDR-grafted antibody and plasmids phKM1750HV0, phKM1750LV0 (I) and phKM1750LV0 (IV) obtained in 3(1) and (2) of Example 2, the reaction similar to that in 3(3) of Example 2 was carried out to obtain pKANTEX1750HV3LV0 (I), pKANTEX1750HV3LV0 (IV), pKANTEX1750HV0LV4, and pKANTEX1750HV3LV4 as expression vectors of modified anti-human VEGF receptor Flt-1 human CDR-grafted antibodies in which amino acids of FR were modified shown in FIGS. 40, 41, 42, and 43, respectively.

Amino acid sequences of KM1750 mouse H chain, KM1750HV0 and KM1750HV3 are shown in FIG. 48. Amino acid sequences of KM1750 mouse L chain, KM1750LV0 (I), KM1750LV0 (IV) and KM1750LV4 are shown in FIG. 49.

*Escherichia coli* DH5α/pHKM1750HV0 which harbors recombinant plasmid phKM1750HV0, *Escherichia coli* DH5α/pHKM1750HV3 which harbors recombinant plasmid phKM1750HV3, *Escherichia coli* XL1-Blue/phKM1750LV0 (I) which harbors recombinant plasmid phKM1750LV0 (I), *Escherichia coli* XL1-Blue/phKM1750LV0 (IV) which harbors recombinant plasmid phKM1750LV0 (IV), and *Escherichia coli* DH5α/phKM1750LV4 which harbors recombinant plasmid phKM1750LV4 have been deposited on May 12, 1999, in National Institute of Bioscience and Human Technology, Agency of Industrial Science and Technology, and have been assigned the designations as FERM BP-6719, FERM BP-6720, FERM BP-6716, FERM BP-6717, and FERM BP-6718, respectively.

5. Production and Activity Evaluation of Anti-Human VEGF Receptor Flt-1 Human CDR-Grafted Antibody (1) Expression of Anti-Human VEGF Receptor Flt-1 Human CDR-Grafted Antibody in Rat Myeloma YB2/0 Cells (ATCC CRL1581) Using pKANTEX1750HV0LV0 (I), pKANTEX1750HV0LV0 (IV), pKANTEX1750HV3LV0 (I), pKANTEX1750HV3LV0 (IV), pKANTEX1750HV0LV4 and pKANTEX1750HV3LV4

Introduction of anti-human VEGF receptor Flt-1 human CDR-grafted antibody expression vectors pKANTEX1750HV0LV0 (I), pKANTEX1750HV0LV0 (IV), pKANTEX1750HV3LV0 (I), pKANTEX1750HV3LV0 (IV), pKANTEX1750HV0LV4 and pKANTEX1750HV3LV4 into YB2/0 cells was carried out by the electroporation method [*Cytotechnology*, 3: 133 (1990)] according to 1(1) of Example 2.

A 5 μg portion of each of pKANTEX1750HV0LV0 (I), pKANTEX1750HV0LV0 (IV), pKANTEX1750HV3LV0 (I), pKANTEX1750HV3LV0 (IV), pKANTEX1750HV0LV4 and pKANTEX1750HV3LV4 obtained in 4(3) of Example 2 was introduced into $4 \times 10^6$ of YB2/0 cells, and the resulting cells were suspended in 40 ml of RPMI1640-FCS(10) medium [RPMI1640 medium (manufactured by Nissui Pharmaceutical) containing 10% fetal calf serum (FCS)] and dispensed in 200 μl portions into wells of a 96 well microtiter plate (manufactured by Sumilon). After 24 hours of culturing at 37° C. in a 5% $CO_2$ incubator, Geneticin (hereinafter referred to as "G 418"; manufactured by Gibco) was added to a concentration of 0.5 mg/ml, and the culturing was continued for 1 to 2 weeks. Culture supernatants were recovered from wells in which transformant colonies having G 418 resistance were formed and became confluent, and the activity of anti-human VEGF receptor Flt-1 human CDR-grafted antibody in each culture supernatant was measured by the enzyme immunoassay shown in 2(3) of Example 2.

Transformants which showed the activity of anti-human VEGF receptor Flt-1 human CDR-grafted antibody in their culture supernatants were subjected to cloning by carrying out limiting dilution twice to obtain transformant cell strains capable of producing anti-human VEGF receptor Flt-1 human CDR-grafted antibody. Examples of the transformants obtained by introducing the expression vectors pKANTEX1750HV0LV0 (I), pKANTEX1750HV0LV0 (IV), pKANTEX1750HV3LV0 (I), pKANTEX1750HV3LV0 (IV), pKANTEX1750HV0LV4 and pKANTEX1750HV3LV4, namely transformants capable of producing the anti-human VEGF receptor Flt-1 human CDR-grafted antibody originated from anti-human VEGF receptor Flt-1 monoclonal antibody KM1750, include KM8550, KM8551, KM8552, KM8553, KM8554 and KM8555, respectively, and the anti-human VEGF receptor Flt-1 human CDR-grafted antibodies produced by these transformants were named KM8550, KM8551, KM8552, KM8553, KM8554 and KM8555, respectively. Each of the thus obtained transformant cell clones showed an anti-human VEGF receptor Flt-1 human CDR-grafted antibody productivity of approximately from 0.1 to 1 μg/ml.

(2) Purification of Anti-Human VEGF Receptor Flt-1 Human CDR-Grafted Antibody from Culture Supernatant Each of the anti-human VEGF receptor Flt-1 human CDR-grafted antibody-producing cell lines KM8550, KM8551, KM8552, KM8553, KM8554 and KM8555 obtained in 5(1) of Example 2 was suspended in GIT medium (manufactured by Nippon Pharmaceutical) containing 0.5 mg/ml of G 418, to a cell density of 1 to $2 \times 10^5$ cells/ml, and the suspension was dispensed in 200 ml portions into a total of five 175 $cm^2$ flasks (manufactured by Greiner). When the cells became confluent after 5 to 7 days of culturing at 37° C. in a 5% $CO_2$ incubator, about 1.1 to 2.5 L of each culture supernatant was recovered. A column was packed with about 1 ml of ProSep A (manufactured by Bioprocessing) and washed with 10 ml of 1 M glycine-0.15 M NaCl (pH 8.6) at a flow rate of 1 ml/minute. After washing, 2.3 L, 2.5 L, 1.9 L, 2.4 L, 1.1 L or 2 L of the culture filtrate of anti-human VEGF receptor Flt-1 human CDR-grafted antibody-producing cell line KM8550, KM8551, KM8552, KM8553, KM8554 or KM8555, respectively, prepared in the above was passed through the ProSep A column at a flow rate of 70 ml/hour. After washing with 10 ml of 1 M glycine-0.15 M NaCl (pH 8.6) at a flow rate of 1 ml/minute, the column was further washed step by step with 4 ml each of 50 mM citrate buffer of pH 6, 5 and 4 in that order and then 7 ml of 50 mM citrate buffer (pH 3.0) was passed through the column to elute the human CDR-grafted antibody. As the results, anti-human VEGF receptor Flt-1 human CDR-grafted antibodies KM8550, KM8551, KM8552, KM8553, KM8554 and KM8555 were obtained in amounts of 1.1 mg, 1.8 mg, 1.6 mg, 2.2 mg, 1.3 mg and 1.6 mg, respectively.

Figure 44:
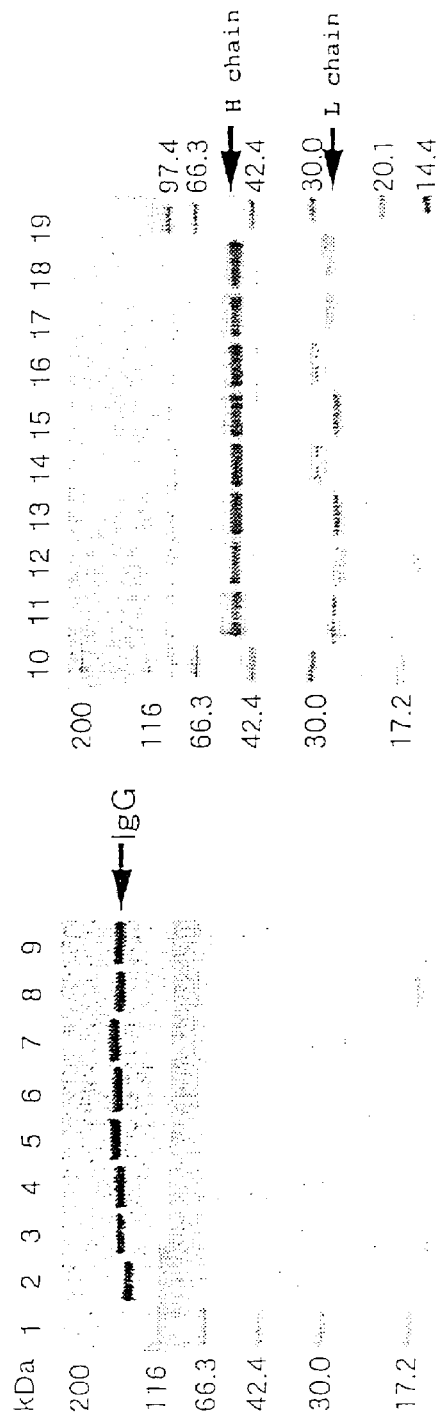
FIG. 44 is a graph showing SDS-PAGE (a 5 to 20% gradient gel was used) electrophoresis patterns of purified anti-human VEGF receptor Flt-1 human chimeric antibody KM2550 and human CDR-grafted antibodies KM8550, KM8551, KM8552, KM8553, KM8554 and KM8555. Lanes 1 to 9 show electrophoresis patterns under non-reducing conditions and lanes 10 to 19 shows electrophoresis patterns under reducing conditions.

The thus purified anti-human VEGF receptor Flt-1 human CDR-grafted antibodies KM8550, KM8551, KM8552, KM8553, KM8554 and KM8555 were analyzed by the SDS-PAGE method shown in 2(3) of Example 2. Each of the anti-human VEGF receptor Flt-1 human CDR-grafted antibodies KM8550, KM8551, KM8552, KM8553, KM8554 and KM8555, the anti-human VEGF receptor Flt-1 human chimeric antibody KM2550 shown in 2(4) of Example 2 and KM8969 (Japanese Published Unexamined Patent Application No. 257893/98) as a control human CDR-grafted antibody was applied to the electrophoresis in an amount of 2 μg protein per lane under reducing and non-reducing conditions, and then the gels were stained with Coomassie Brilliant Blue. The results are shown in FIG. 44. The human CDR-grafted antibodies KM8550, KM8551, KM8552, KM8553, KM8554 and KM8555 showed a band of IgG at a position of about 150 kDa under the non-reducing condition, and a band of H chain at a position of about 50 kDa and a band of L chain at about 25 kDa under the reducing condition. This result coincided with that the IgG type antibody is separated into two H chains and L chains under the reducing conditions caused by the cutting of intermolecular disulfide bond and present as a molecule of 150 kDa.

(3) Binding Activities of Anti-Human VEGF Receptor Flt-1 Human CDR-Grafted Antibodies Upon Human VEGF Receptor Flt-1

The activity of purified anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550 to bind to the human VEGF receptor Flt-1 was confirmed according to the method in 2(5) of Example 2.

Amount of Flt-1 7N to be coated on the plate was fixed to 2 μg/ml, and concentration of each of the purified antibodies was varied from 1.23 to 900 ng/ml (3-fold serial dilutions).

Figure 45:
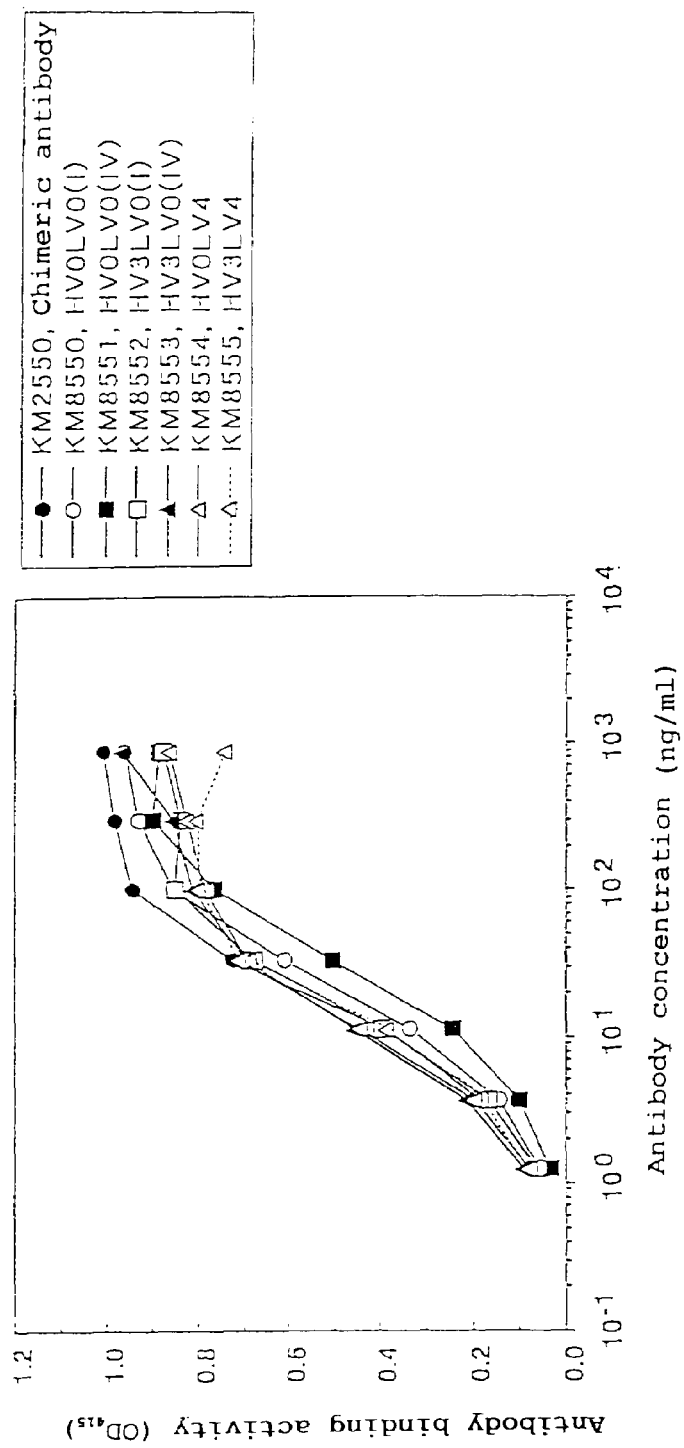
FIG. 45 is a graph showing the binding activity of purified anti-human VEGF receptor Flt-1 human chimeric antibody KM2550 and human CDR-grafted antibodies KM8550, KM8551, KM8552, KM8553, KM8554 and KM8555 upon soluble human VEGF receptor Flt-1 7N.

The results are shown in FIG. 45. The anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550 bound to the human VEGF receptor Flt-1 7N in an antibody concentration dependent fashion. In addition, the anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550 showed almost the same binding activity. In consequence, it was revealed that the six human CDR-grafted antibodies of the present invention keep the binding activity of human chimeric antibody KM2550.

Next, in order to examine binding specificity of anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550, their reactivity for five soluble human VEGF receptor derivative proteins Flt-1 7N, Flt-1 3N, Flt-1 2N (WO 98/22616), Flt-1 7N.K2 [2(6-5) of Example 2] and KDR 7N [2(6-5) of Example 2] was examined using an enzyme immunoassay. Concentration of each soluble human VEGF receptor derivative protein to be adsorbed on a 96 well plate for EIA was fixed to 10 μg/ml (3-fold dilution), and the antibody concentration was fixed to 5 μg/ml.

Figure 46:
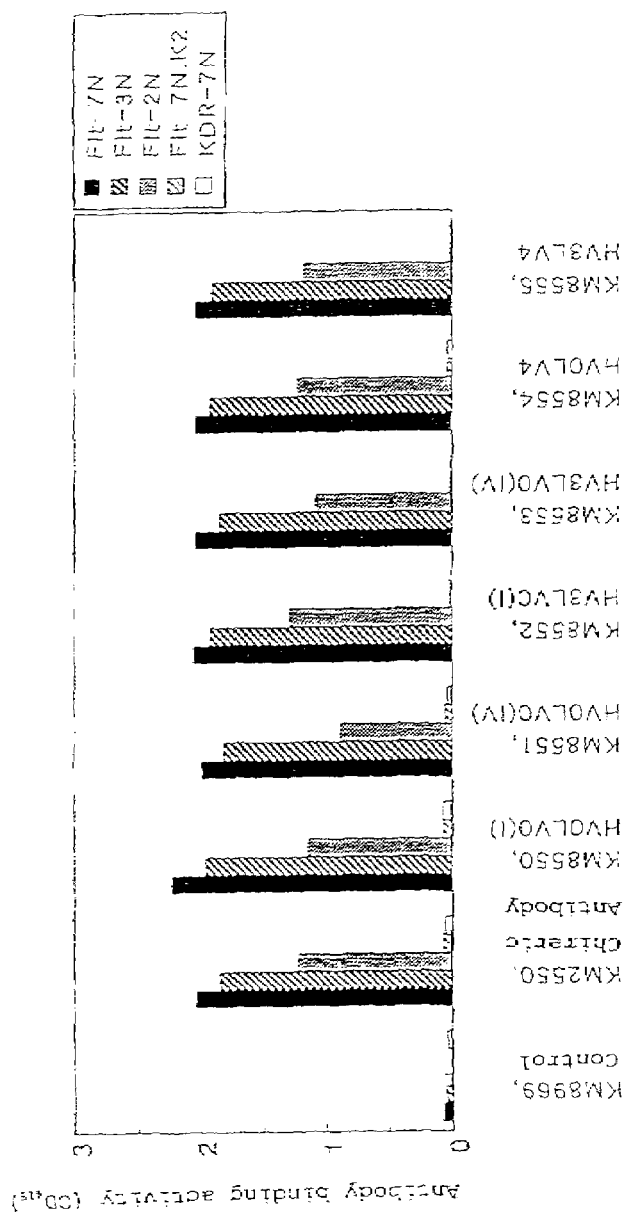
FIG. 46 is a graph showing the binding activity of purified anti-human VEGF receptor Flt-1 human chimeric antibody KM2550 and human CDR-grafted antibodies KM8550, KM8551, KM8552, KM8553, KM8554 and KM8555 upon soluble human VEGF receptor derivatives Flt-1 7N, Flt-1 3N, Flt-1 2N, Flt-1 7N.K2 and KDR-7N.

The results are shown in FIG. 46. The anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550 showed almost the same reaction specificity, reacting with Flt-1 7N, Flt-1 3N and Flt-1 2N and not reacting with Flt-1 7N.K2 and KDR 7N. The anti-$GM_2$ human CDR-grafted antibody KM8969 (Japanese Published Unexamined Patent Application No. 257893/98) used as a negative control antibody did not react with the soluble human VEGF receptor derivative proteins tested. In consequence, it was revealed that the six human CDR-grafted antibodies of the present invention keep the binding specificity of human chimeric antibody KM2550.

Figure 47:
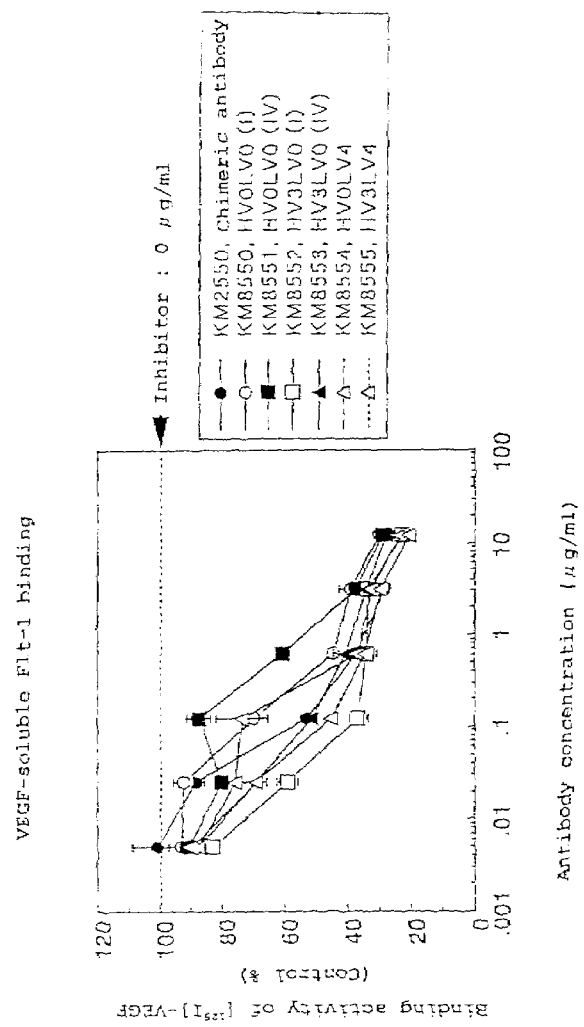
FIG. 47 is a graph showing the activity of purified anti-human VEGF receptor Flt-1 human chimeric antibody KM2550 and human CDR-grafted antibodies KM8550, KM8551, KM8552, KM8553, KM8554 and KM8555 to inhibit the binding between human VEGF and human VEGF receptor Flt-1.

Next, the activity of anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550 to inhibit binding between human VEGF and human VEGF receptor Flt-1 was examined in accordance with the method described in 2(5) of Example 2. Concentration of each antibody to be added was varied from 0.0048 to 15 μg/ml (5-fold dilutions). The results are shown in FIG. 47. As shown in FIG. 47, anti-human VEGF receptor Flt-1 human CDR-grafted antibodies KM8550, KM8551, KM8552, KM8553, KM8554 and KM8555 and anti-human VEGF receptor Flt-1 human chimeric antibody KM2550 inhibited the binding between human VEGF and human VEGF receptor Flt-1 in an antibody concentration dependent fashion. In consequence, it was revealed that the six human CDR-grafted antibodies of the present invention also keep the VEGF-Flt-1 binding inhibition activity of human chimeric antibody KM2550.

(4) VEGF-Dependent Cell-Migration Inhibition Test Using Anti-VEGF Receptor Flt-1 Monoclonal Antibody Effect of anti-VEGF receptor Flt-1 monoclonal antibody on the VEGF-dependent migration activity of human vascular endothelial cells, as an index of in vitro angiogenesis activity, was examined.

The cell migration test was carried out in accordance with the method of Sato et al. [*J. Cell Biology*, 107: 1199 (1988)]. HUVEC cultured in a 3.5 cm dish until they became confluent was scratched with a razor's edge and then washed with PBS. A 1.5 ml portion of a 5% FCS-containing M-199 medium was added thereto, and VEGF (final concentration: 10 ng/ml) and the anti-VEGF receptor Flt-1 monoclonal antibody KM1750 or KM1732 obtained in 5 of Example 1 (final concentration: 0, 1 or 10 μg/ml) were further added thereto, followed by culturing for 24 hours. After culturing, the number of cells migrated from the scratched position was measured.

As a result, cell migration ability of HUVEC increased by adding VEGF, but the migration was completely inhibited by adding the anti-VEGF receptor Flt-1 monoclonal antibody KM1750 or KM1732 (final concentration: 1 μg/ml). Thus, it was confirmed that Flt-1 is a main receptor relating to the migration of vascular endothelial cells.

Figure 50:
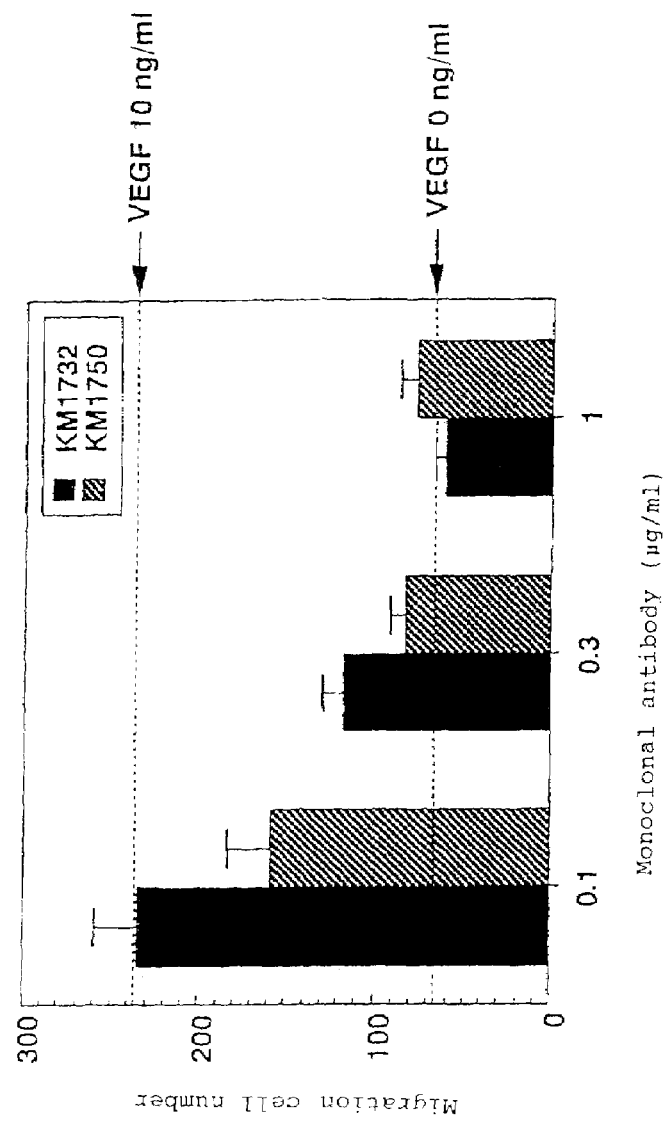
FIG. 50 is a graph showing results of the comparison of activities of anti-VEGF receptor Flt-1 monoclonal antibodies KM1750 and KM1732 to inhibit migration of vascular endothelial cells.

FIG. 50 shows results of the comparison of activities of anti-VEGF receptor Flt-1 monoclonal antibodies KM1750 and KM1732 to inhibit the migration of vascular endothelial cells. Both of the monoclonal antibodies showed the activity to inhibit the migration of vascular endothelial cells concentration-dependently at a monoclonal antibody concentration of 0.1 to 1 μg/ml.

Accordingly, it was found that migration of vascular endothelial cells induced by VEGF is completely inhibited by the anti-VEGF receptor Flt-1 monoclonal antibody.

While the invention has been described in detail and with reference to specific embodiments thereof, it will be apparent to one skilled in the art that various changes and modifications can be made therein without departing from the spirit and scope thereof.

This application is based on Japanese application No. Hei 8-311109 filed on Nov. 21, 1996, International application No. PCT/JP97/04259 filed on Nov. 21, 1997, Japanese application No. Hei. 10-13900 filed on May 20, 1998, and International application No. PCT/JP99/02661 filed on May 20, 1999, the entire contents of which are incorporated hereinto by reference.

What is claimed is:

1. A method for treating a disease in which the morbid state progresses by abnormal angiogenesis, comprising administering to a human or an animal in need of such treatment an effective amount of a recombinant monoclonal antibody selected from the group consisting of a human chimeric antibody and an antibody fragment, said recombinant monoclonal antibody specifically reacting with the human VEGF receptor Flt-1, wherein the recombinant monoclonal antibody binds to an epitope present in a region of the 1st to 338th positions from the N-terminal amino acid including a signal sequence of the human VEGF receptor Flt-1, said recombinant monoclonal antibody comprising an antibody H chain variable region (V region) and an antibody L chain V region of a monoclonal antibody, and H chain constant region (C region) and L chain C region of a human antibody, said H chain V region comprising an amino acid sequence of SEQ ID NO:88, and said L chain V region comprising an amino acid sequence of SEQ ID NO:89.

2. A method for treating a disease in which the morbid state progresses by abnormal angiogenesis, comprising administering to a human or an animal in need of such treatment an effective amount of a recombinant monoclonal antibody selected from the group consisting of a human chimeric antibody and an antibody fragment, said recombinant monoclonal antibody specifically reacting with the human VEGF receptor Flt-1, wherein the recombinant monoclonal antibody binds to an epitope present in a region of the 1st to 204th positions from the N-terminal amino acid including a signal sequence of the human VEGF receptor Flt-1, said recombinant monoclonal antibody comprising an antibody H chain variable region (V region) and an antibody L chain V region of a monoclonal antibody, and H chain constant region (C region) and L chain C region of a human antibody, said H chain V region comprising an amino acid sequence of SEQ ID NO:88, and said L chain V region comprising an amino acid sequence of SEQ ID NO:89.

3. A method for treating a disease in which the morbid state progresses by abnormal angiogenesis, comprising administering to a human or an animal in need of such treatment an effective amount of a recombinant monoclonal antibody selected from the group consisting of a human chimeric antibody and an antibody fragment, said recombinant monoclonal antibody specifically reacting with the human VEGF receptor Flt-1, said recombinant monoclonal antibody comprising an antibody H chain variable region (V region) and an antibody L chain V region of a monoclonal antibody, and H chain constant region (C region) and L chain C region of a human antibody, said H chain V region comprising an amino acid sequence of SEQ ID NO:88, and said L chain V region comprising an amino acid sequence of SEQ ID NO:89.

4. The method of claim 1 wherein said recombinant monoclonal antibody is a human chimeric antibody.

5. The method of claim 2 wherein said recombinant monoclonal antibody is a human chimeric antibody.

6. The method of claim 3 wherein said recombinant monoclonal antibody is a human chimeric antibody.

* * * * *

SEQUENCE LISTING

<160> NUMBER OF SEQ ID NOS: 111

<210> SEQ ID NO 1
<211> LENGTH: 23
<212> TYPE: DNA
<213> ORGANISM: Artificial Sequence -continued

```
<220> FEATURE:
<223> OTHER INFORMATION: Description of Artificial Sequence: Synthetic
      DNA

<400> SEQUENCE: 1
cgacaaacca atataatcta agc                                              23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ggccgcttag attatattgg tttgt                                            25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ggaatctaca tttgcatagc t                                                21

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ttatgcggcc gcttatccttt gaacagtgag gta                                  33

<210> SEQ ID NO 5
<211> LENGTH: 415
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 5 atg gaa tgg aac tgg gtc gtt ctc ttc ctc ctg tca tta act gca ggt        48
Met Glu Trp Asn Trp Val Val Leu Phe Leu Leu Ser Leu Thr Ala Gly
            -15                 -10                 -5 gtc tat gcc cag ggt cag atg cag cag tct gga gct gag ctg gtg aag        96
Val Tyr Ala Gln Gly Gln Met Gln Gln Ser Gly Ala Glu Leu Val Lys
         -1   1               5                  10 cct ggg gct tca gtg aag ctg tcc tgc aag cct tct ggc ttc acc ttc       144
Pro Gly Ala Ser Val Lys Leu Ser Cys Lys Pro Ser Gly Phe Thr Phe
     15                  20                  25
```

```
agt agt aac tat ata agt tgg ttg aag cag aag cct gga cag agt ctt    192
Ser Ser Asn Tyr Ile Ser Trp Leu Lys Gln Lys Pro Gly Gln Ser Leu
 30              35                  40                  45 gag tgg att gct tgg att tat gct gga act ggt gat gcc agc tat aat    240
Glu Trp Ile Ala Trp Ile Tyr Ala Gly Thr Gly Asp Ala Ser Tyr Asn
             50                  55                  60 cag aag ttc aca gcc aag gcc cac gtg act gta gac aca tcc tcc agc    288
Gln Lys Phe Thr Ala Lys Ala His Val Thr Val Asp Thr Ser Ser Ser
 65                  70                  75 aca gcc tac atg cag ttg agt agc ctg aca act gag gac tct gcc atc    336
Thr Ala Tyr Met Gln Leu Ser Ser Leu Thr Thr Glu Asp Ser Ala Ile
         80                  85                  90 tat tac tgt gca cga cac ggg ggg gac ggc tac tgg ttt gct tac tgg    384
Tyr Tyr Cys Ala Arg His Gly Gly Asp Gly Tyr Trp Phe Ala Tyr Trp
     95                 100                 105 ggc caa ggg act ctg gtc act gtc tct gca g                          415
Gly Gln Gly Thr Leu Val Thr Val Ser Ala
110             115

<210> SEQ ID NO 6
<211> LENGTH: 385
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(384)
<220> FEATURE:
<221> NAME/KEY: sig_peptide
<222> LOCATION: (1)..(66)
<220> FEATURE:
<221> NAME/KEY: mat_peptide
<222> LOCATION: (67)..(384)

<400> SEQUENCE: 6 atg gat ttt caa gtg cag att ttc agc ttc ctg cta atc agt gcc tca     48
Met Asp Phe Gln Val Gln Ile Phe Ser Phe Leu Leu Ile Ser Ala Ser
    -20                 -15                 -10 gtc ata ata tcc aga gga caa ctt gtt ctc acc cag tct cca gca atc     96
Val Ile Ile Ser Arg Gly Gln Leu Val Leu Thr Gln Ser Pro Ala Ile
     -5              -1   1               5                  10 atg tct gca tct caa ggg gag aag gtc acc atg acc tgc agt gcc agc    144
Met Ser Ala Ser Gln Gly Glu Lys Val Thr Met Thr Cys Ser Ala Ser
             15                  20                  25 tca agt gtc agt tac atg cac tgg tac cag cag aag tca ggc acc tcc    192
Ser Ser Val Ser Tyr Met His Trp Tyr Gln Gln Lys Ser Gly Thr Ser
         30                  35                  40 ccc aaa aga tgg att tat gac aca tcc aaa ctg cct tct ggt gtc cct    240
Pro Lys Arg Trp Ile Tyr Asp Thr Ser Lys Leu Pro Ser Gly Val Pro
     45                  50                  55 gct cgc ttc agt ggc agt ggg tct ggg acc tct tac tct ctc aca atc    288
Ala Arg Phe Ser Gly Ser Gly Ser Gly Thr Ser Tyr Ser Leu Thr Ile
 60                  65                  70 agc agc atg gag gct gaa gat gct gcc act tat tat tgc cag cag tgg    336
Ser Ser Met Glu Ala Glu Asp Ala Ala Thr Tyr Tyr Cys Gln Gln Trp
 75                  80                  85                  90 agt agt aac cca ccc acg ttc ggt gct ggg acc aag ctg gaa ctg aaa c  385
Ser Ser Asn Pro Pro Thr Phe Gly Ala Gly Thr Lys Leu Glu Leu Lys
             95                 100                 105

<210> SEQ ID NO 7
<211> LENGTH: 409
```

```
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(408)
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 7 atg gga ttc agc agg atc ttt ctc ttc ctc ctg tca gtg act aca ggt      48
Met Gly Phe Ser Arg Ile Phe Leu Phe Leu Leu Ser Val Thr Thr Gly
        -15                 -10                  -5 gtc cac tcc cag gct ttt cta cag cag tct ggg gct gag ctg gtg agg      96
Val His Ser Gln Ala Phe Leu Gln Gln Ser Gly Ala Glu Leu Val Arg
     -1   1                5                  10 cct ggg gcc tca gtg aag atg tcc tgc aag gct tct ggc tac aca ttt     144
Pro Gly Ala Ser Val Lys Met Ser Cys Lys Ala Ser Gly Tyr Thr Phe
 15                  20                  25 atc aat tac aat atg cac tgg gta aag cag aca cct aga cag ggc ctg     192
Ile Asn Tyr Asn Met His Trp Val Lys Gln Thr Pro Arg Gln Gly Leu
 30                  35                  40                  45 gaa tgg att gga gct att ttt cca gga aat ggt ttt act tcc tac aat     240
Glu Trp Ile Gly Ala Ile Phe Pro Gly Asn Gly Phe Thr Ser Tyr Asn
                 50                  55                  60 cag aag ttc aag ggc aag gcc aca ctg act gta gac aaa tcc tcc agc     288
Gln Lys Phe Lys Gly Lys Ala Thr Leu Thr Val Asp Lys Ser Ser Ser
             65                  70                  75 aca gtc tac atg cag ctc cgc agc ctg aca tct gaa gac tct gcg gtc     336
Thr Val Tyr Met Gln Leu Arg Ser Leu Thr Ser Glu Asp Ser Ala Val
         80                  85                  90 tat ttc tgt gca aga gat ggt gac tat tac ttt gac tac tgg ggc caa     384
Tyr Phe Cys Ala Arg Asp Gly Asp Tyr Tyr Phe Asp Tyr Trp Gly Gln
     95                 100                 105 ggc acc act ctc aca gtc tcc tca g                                   409
Gly Thr Thr Leu Thr Val Ser Ser
110                 115

<210> SEQ ID NO 8
<211> LENGTH: 379
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(378)
<220> FEATURE:
<221> NAME/KEY: sig_peptide
<222> LOCATION: (1)..(66)
<220> FEATURE:
<221> NAME/KEY: mat_peptide
<222> LOCATION: (67)..(378)

<400> SEQUENCE: 8 atg gat ttt cag gtg cag att ttc agc ttc ctg cta atc agt gcc tca      48
Met Asp Phe Gln Val Gln Ile Phe Ser Phe Leu Leu Ile Ser Ala Ser
        -20                 -15                 -10 gtc ata atg tcc aga gga caa att gtt ctc acc cag tcg cca gca atc      96
Val Ile Met Ser Arg Gly Gln Ile Val Leu Thr Gln Ser Pro Ala Ile
```

-continued

```
      -5              -1  1                5                       10
atg  tct  gca  tct  cta  ggg  gag  gag  atc  acc  cta  acc  tgc  agt  gcc  agc        144
Met  Ser  Ala  Ser  Leu  Gly  Glu  Glu  Ile  Thr  Leu  Thr  Cys  Ser  Ala  Ser
                         15                      20                      25 tcg  agt  gta  agt  tac  atg  cac  tgg  tac  cag  cag  aag  tca  ggc  act  tct        192
Ser  Ser  Val  Ser  Tyr  Met  His  Trp  Tyr  Gln  Gln  Lys  Ser  Gly  Thr  Ser
               30                      35                      40 ccc  aaa  ctc  ttg  att  tat  aga  aca  tcc  aac  ctg  gct  tct  gga  gtc  cct        240
Pro  Lys  Leu  Leu  Ile  Tyr  Arg  Thr  Ser  Asn  Leu  Ala  Ser  Gly  Val  Pro
          45                      50                      55 ttt  cgc  ttc  agt  ggc  agt  ggg  tct  ggg  acc  ttt  tat  tct  ctc  aca  atc        288
Phe  Arg  Phe  Ser  Gly  Ser  Gly  Ser  Gly  Thr  Phe  Tyr  Ser  Leu  Thr  Ile
     60                      65                      70 agc  agt  gtg  gag  gct  gaa  gat  gct  gcc  gat  tat  tac  tgc  cat  cag  tgg        336
Ser  Ser  Val  Glu  Ala  Glu  Asp  Ala  Ala  Asp  Tyr  Tyr  Cys  His  Gln  Trp
75                      80                      85                      90 agt  atg  tac  acg  ttc  gga  ggg  ggg  acc  aag  ctg  gaa  ata  aaa  c               379
Ser  Met  Tyr  Thr  Phe  Gly  Gly  Gly  Thr  Lys  Leu  Glu  Ile  Lys
                    95                     100
```

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Asn Tyr Ile Ser
 1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Ile Tyr Ala Gly Thr Gly Asp Ala Ser Tyr Asn Gln Lys Phe Thr
 1               5                  10                  15

Ala

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Gly Gly Asp Gly Tyr Trp Phe Ala Tyr
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Ser Ala Ser Ser Ser Val Ser Tyr Met His
 1               5                  10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Thr Ser Lys Leu Pro Ser
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Trp Ser Ser Asn Pro Pro Thr
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Tyr Asn Met His
 1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ile Phe Pro Gly Asn Gly Phe Thr Ser Tyr Asn Gln Lys Phe Lys
 1               5                  10                  15
Gly

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Gly Asp Tyr Tyr Phe Asp Tyr
 1               5

<210> SEQ ID NO 18
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ala Ser Ser Ser Val Ser Tyr Met His
 1               5                  10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Thr Ser Asn Leu Ala Ser
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His Gln Trp Ser Met Tyr Thr
 1               5

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gccaagggac tctggtcact gtctctgcag cctccaccaa gggcc              45

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
cttggtggag gctgcagaga cagtgaccag agtcccttgg c                  41

<210> SEQ ID NO 23
<211> LENGTH: 69
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
cttattattg ccagcagtgg agtagtaacc cacccacgtt cggtgctggg accaagctgg   60
```

```
aactgaaac                                                                 69

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gtacgtttca gttccagctt ggtcccagca ccgaacgtgg gtgggttact actccactgc         60
tggcaataat aagt                                                           74

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
tcagcctcca ccaagggcc                                                      19

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
cttggtggag g                                                              11

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
cgttcggagg ggggaccaag ctggaaataa aac                                      33

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
gtacgtttta tttccagctt ggtccccct ccgaa                                     35

<210> SEQ ID NO 29
<211> LENGTH: 94
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
```

```
caggaaacag ctatgacgcg gccgccacca tggaatggaa ctgggtcgtt ctcttcctcc      60
tgtcattaac tgcaggtgtc tatgcccagg tgca                                 94

<210> SEQ ID NO 30
<211> LENGTH: 95
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
gtgtatccag aagccttgca ggagaccttc actgaggcgc caggcttctt cacctcagcc      60
ccagactgca ccagctgcac ctgggcatag acacc                                95

<210> SEQ ID NO 31
<211> LENGTH: 94
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
tgcaaggctt ctggatacac cttcagcagt aactatataa gttgggtgcg acaggcccct      60
ggacaagggc ttgagtggat gggatggatt tatg                                 94

<210> SEQ ID NO 32
<211> LENGTH: 101
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
aggctgtgct cgtggatgtg tcgacggtaa tggtgactct ggctgtgaac ttctgattat      60
agctggcatc accagttcca gcataaatcc atcccatcca c                         101

<210> SEQ ID NO 33
<211> LENGTH: 100
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
cacatccacg agcacagcct acatggagct gagcagcctg agatctgagg acacggccgt      60
gtattactgt gcgagacacg gggggacgg ctactggttt                            100

<210> SEQ ID NO 34
<211> LENGTH: 93
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
gttttcccag tcacgacggg cccttggtgg aggctgagga cacggtgacc agggttccct      60
ggccccagta agcaaaccag tagccgtccc ccc                                  93
```

<210> SEQ ID NO 35
<211> LENGTH: 415
<212> TYPE: DNA
<213> ORGANISM: Artificial Sequence
<220> FEATURE:
<223> OTHER INFORMATION: Description of Artificial Sequence: Synthetic DNA
<220> FEATURE:
<221> NAME/KEY: CDS
<222> LOCATION: (1)..(414)
<220> FEATURE:
<221> NAME/KEY: sig_peptide
<222> LOCATION: (1)..(57)
<220> FEATURE:
<221> NAME/KEY: mat_peptide
<222> LOCATION: (58)..(414)

<400> SEQUENCE: 35

```
atg gaa tgg aac tgg gtc gtt ctc ttc ctc ctg tca tta act gca ggt      48
Met Glu Trp Asn Trp Val Val Leu Phe Leu Leu Ser Leu Thr Ala Gly
            -15                 -10                 -5 gtc tat gcc cag gtg cag ctg gtg cag tct ggg gct gag gtg aag aag      96
Val Tyr Ala Gln Val Gln Leu Val Gln Ser Gly Ala Glu Val Lys Lys
        -1   1               5                  10 cct ggc gcc tca gtg aag gtc tcc tgc aag gct tct gga tac acc ttc     144
Pro Gly Ala Ser Val Lys Val Ser Cys Lys Ala Ser Gly Tyr Thr Phe
 15                  20                  25 agc agt aac tat ata agt tgg gtg cga cag gcc cct gga caa ggg ctt     192
Ser Ser Asn Tyr Ile Ser Trp Val Arg Gln Ala Pro Gly Gln Gly Leu
 30                  35                  40                  45 gag tgg atg gga tgg att tat gct gga act ggt gat gcc agc tat aat     240
Glu Trp Met Gly Trp Ile Tyr Ala Gly Thr Gly Asp Ala Ser Tyr Asn
                 50                  55                  60 cag aag ttc aca gcc aga gtc acc att acc gtc gac aca tcc acg agc     288
Gln Lys Phe Thr Ala Arg Val Thr Ile Thr Val Asp Thr Ser Thr Ser
             65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
         80                  85                  90 tat tac tgt gcg aga cac ggg ggg gac ggc tac tgg ttt gct tac tgg     384
Tyr Tyr Cys Ala Arg His Gly Gly Asp Gly Tyr Trp Phe Ala Tyr Trp
 95                 100                 105 ggc cag gga acc ctg gtc acc gtc tcc tca g                           415
Gly Gln Gly Thr Leu Val Thr Val Ser Ser
110                 115
```

<210> SEQ ID NO 36
<211> LENGTH: 96
<212> TYPE: DNA
<213> ORGANISM: Artificial Sequence
<220> FEATURE:
<223> OTHER INFORMATION: Description of Artificial Sequence: Synthetic DNA

<400> SEQUENCE: 36
caggaaacag ctatgacgcg gccgccacca tgggattcag caggatcttt ctcttcctcc    60
tgtcagtgac tacaggtgtc cactcccagg tgcagc                              96

<210> SEQ ID NO 37
<211> LENGTH: 94
<212> TYPE: DNA
<213> ORGANISM: Artificial Sequence
<220> FEATURE:
<223> OTHER INFORMATION: Description of Artificial Sequence: Synthetic

```
                           DNA

<400> SEQUENCE: 37
ggtgtatcca gaagccttgc aggagacctt cactgaggcc ccaggcttct tcacctcagc      60
tccggactgc accagctgca cctgggagtg gaca                                  94

<210> SEQ ID NO 38
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
gcaaggcttc tggatacacc ttcattaatt acaatatgca ctgggtgcga caggcccctg      60
gacaagggct tgagtggatg ggagctattt                                       90

<210> SEQ ID NO 39
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
tgtgctcgtg gacttgtcga cggtaatggt gactctgccc ttgaacttct gattgtagga      60
agtaaaacca tttcctggaa aaatagctcc                                       90

<210> SEQ ID NO 40
<211> LENGTH: 95
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
tcgacaagtc cacgagcaca gcctacatgg agctgagcag cctgagatct gaggacacgg      60
ccgtgtatta ctgtgcgaga gatggtgact attac                                 95

<210> SEQ ID NO 41
<211> LENGTH: 96
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
gttttcccag tcacgacggg cccttggtgg aggctgagga gacggtgacc agggttccct      60
ggccccagta gtcaaagtaa tagtcaccat ctctcg                                96

<210> SEQ ID NO 42
<211> LENGTH: 409
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(408)
```

```
-continued

<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 42 atg gga ttc agc agg atc ttt ctc ttc ctc ctg tca gtg act aca ggt      48
Met Gly Phe Ser Arg Ile Phe Leu Phe Leu Leu Ser Val Thr Thr Gly
                -15                 -10                  -5 gtc cac tcc cag gtg cag ctg gtg cag tcc gga gct gag gtg aag aag      96
Val His Ser Gln Val Gln Leu Val Gln Ser Gly Ala Glu Val Lys Lys
         -1   1               5                  10 cct ggg gcc tca gtg aag gtc tcc tgc aag gct tct gga tac acc ttc     144
Pro Gly Ala Ser Val Lys Val Ser Cys Lys Ala Ser Gly Tyr Thr Phe
 15                  20                  25 att aat tac aat atg cac tgg gtg cga cag gcc cct gga caa ggg ctt     192
Ile Asn Tyr Asn Met His Trp Val Arg Gln Ala Pro Gly Gln Gly Leu
 30                  35                  40                  45 gag tgg atg gga gct att ttt cca gga aat ggt ttt act tcc tac aat     240
Glu Trp Met Gly Ala Ile Phe Pro Gly Asn Gly Phe Thr Ser Tyr Asn
                 50                  55                  60 cag aag ttc aag ggc aga gtc acc att acc gtc gac aag tcc acg agc     288
Gln Lys Phe Lys Gly Arg Val Thr Ile Thr Val Asp Lys Ser Thr Ser
                 65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
             80                  85                  90 tat tac tgt gcg aga gat ggt gac tat tac ttt gac tac tgg ggc cag     384
Tyr Tyr Cys Ala Arg Asp Gly Asp Tyr Tyr Phe Asp Tyr Trp Gly Gln
         95                 100                 105 gga acc ctg gtc acc gtc tcc tca g                                   409
Gly Thr Leu Val Thr Val Ser Ser
110             115

<210> SEQ ID NO 43
<211> LENGTH: 87
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
caggaaacag ctatgacgaa ttccaccatg gattttcaag tgcagatttt cagcttcctg     60
ctaatcagtg cctcagtcat aatatcc                                         87

<210> SEQ ID NO 44
<211> LENGTH: 93
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
aagtgatggt gactctgtct cctacagatg cagacaggga ggatggagac tgggtcatct     60
ggatatctcc tctggatatt atgactgagg cac                                  93

<210> SEQ ID NO 45
<211> LENGTH: 85
<212> TYPE: DNA
```

<210> SEQ ID NO 45
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
agacagagtc accatcactt gtagtgctag ctcaagtgtc agttacatgc actggtatca    60
gcagaaacca gggaaagccc ctaag                                          85

<210> SEQ ID NO 46
<211> LENGTH: 84
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
atccactgcc gctgaacctt gatgggaccc cagaaggcag tttggatgtg tcatagatca    60
gaagcttagg ggctttccct ggtt                                           84

<210> SEQ ID NO 47
<211> LENGTH: 94
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
aaggttcagc ggcagtggat ctgggacaga tttcactctc accatcagca gcctgcagcc    60
tgaagatttt gcaacttatt actgtcagca gtgg                                94

<210> SEQ ID NO 48
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
gttttcccag tcacgaccgt acgtttgatc tctaccttgg tcccttggcc gaacgtgggt    60
gggttactac tccactgctg acagtaataa g                                   91

<210> SEQ ID NO 49
<211> LENGTH: 385
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(384)
<220> FEATURE:
<221> NAME/KEY: sig_peptide
<222> LOCATION: (1)..(66)
<220> FEATURE:
<221> NAME/KEY: mat_peptide
<222> LOCATION: (67)..(384)

<400> SEQUENCE: 49 atg gat ttt caa gtg cag att ttc agc ttc ctg cta atc agt gcc tca    48
Met Asp Phe Gln Val Gln Ile Phe Ser Phe Leu Leu Ile Ser Ala Ser
    -20             -15                 -10

```
gtc ata ata tcc aga gga gat atc cag atg acc cag tct cca tcc tcc      96
Val Ile Ile Ser Arg Gly Asp Ile Gln Met Thr Gln Ser Pro Ser Ser
    -5              -1  1               5                      10 ctg tct gca tct gta gga gac aga gtc acc atc act tgt agt gct agc     144
Leu Ser Ala Ser Val Gly Asp Arg Val Thr Ile Thr Cys Ser Ala Ser
                15                  20                  25 tca agt gtc agt tac atg cac tgg tat cag cag aaa cca ggg aaa gcc     192
Ser Ser Val Ser Tyr Met His Trp Tyr Gln Gln Lys Pro Gly Lys Ala
            30                  35                  40 cct aag ctt ctg atc tat gac aca tcc aaa ctg cct tct ggg gtc cca     240
Pro Lys Leu Leu Ile Tyr Asp Thr Ser Lys Leu Pro Ser Gly Val Pro
        45                  50                  55 tca agg ttc agc ggc agt gga tct ggg aca gat ttc act ctc acc atc     288
Ser Arg Phe Ser Gly Ser Gly Ser Gly Thr Asp Phe Thr Leu Thr Ile
    60                  65                  70 agc agc ctg cag cct gaa gat ttt gca act tat tac tgt cag cag tgg     336
Ser Ser Leu Gln Pro Glu Asp Phe Ala Thr Tyr Tyr Cys Gln Gln Trp
75                  80                  85                  90 agt agt aac cca ccc acg ttc ggc caa ggg acc aag gta gag atc aaa c   385
Ser Ser Asn Pro Pro Thr Phe Gly Gln Gly Thr Lys Val Glu Ile Lys
                95                  100                 105

<210> SEQ ID NO 50
<211> LENGTH: 84
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
caggaaacag ctatgacgaa ttccaccatg gattttcagg tgcagatttt cagcttcctg     60
ctaatcagtg cctcagtcat aatg                                           84

<210> SEQ ID NO 51
<211> LENGTH: 96
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
agttgatggt ggccctctcg cccagagaca cagccaggga gtctggagac tgggtcatca     60
cgatgtctcc tctggacatt atgactgagg cactga                              96

<210> SEQ ID NO 52
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
cgagagggcc accatcaact gcagtgccag ctcgagtgta agttacatgc actggtacca     60
gcagaaacca ggacagcctc ctaag                                          85

<210> SEQ ID NO 53
<211> LENGTH: 87
<212> TYPE: DNA
<213> ORGANISM: Artificial Sequence
```

<220> FEATURE:
<223> OTHER INFORMATION: Description of Artificial Sequence: Synthetic DNA

<400> SEQUENCE: 53

```
cagacccgct gccactgaat cggtcaggga ccccagaagc caggttggat gttctgtaaa    60
tgagcagctt aggaggctgt cctggtt                                        87
```

<210> SEQ ID NO 54
<211> LENGTH: 86
<212> TYPE: DNA
<213> ORGANISM: Artificial Sequence
<220> FEATURE:
<223> OTHER INFORMATION: Description of Artificial Sequence: Synthetic DNA

<400> SEQUENCE: 54

```
attcagtggc agcgggtctg ggacagattt cactctcacc atcagcagcc tgcaggctga    60
agacgtcgca gtttattact gtcatc                                         86
```

<210> SEQ ID NO 55
<211> LENGTH: 90
<212> TYPE: DNA
<213> ORGANISM: Artificial Sequence
<220> FEATURE:
<223> OTHER INFORMATION: Description of Artificial Sequence: Synthetic DNA

<400> SEQUENCE: 55

```
gttttcccag tcacgaccgt acgtttgatc tccaccttgg tcccttggcc gaacgtgtac    60
atactccact gatgacagta ataaactgcg                                     90
```

<210> SEQ ID NO 56
<211> LENGTH: 379
<212> TYPE: DNA
<213> ORGANISM: Artificial Sequence
<220> FEATURE:
<223> OTHER INFORMATION: Description of Artificial Sequence: Synthetic DNA
<220> FEATURE:
<221> NAME/KEY: CDS
<222> LOCATION: (1)..(378)
<220> FEATURE:
<221> NAME/KEY: sig_peptide
<222> LOCATION: (1)..(66)
<220> FEATURE:
<221> NAME/KEY: mat_peptide
<222> LOCATION: (67)..(378)

<400> SEQUENCE: 56

```
atg gat ttt cag gtg cag att ttc agc ttc ctg cta atc agt gcc tca    48
Met Asp Phe Gln Val Gln Ile Phe Ser Phe Leu Leu Ile Ser Ala Ser
    -20                 -15                 -10 gtc ata atg tcc aga gga gac atc gtg atg acc cag tct cca gac tcc    96
Val Ile Met Ser Arg Gly Asp Ile Val Met Thr Gln Ser Pro Asp Ser
 -5              -1   1               5                       10 ctg gct gtg tct ctg ggc gag agg gcc acc atc aac tgc agt gcc agc   144
Leu Ala Val Ser Leu Gly Glu Arg Ala Thr Ile Asn Cys Ser Ala Ser
                15                  20                  25 tcg agt gta agt tac atg cac tgg tac cag cag aaa cca gga cag cct   192
Ser Ser Val Ser Tyr Met His Trp Tyr Gln Gln Lys Pro Gly Gln Pro
            30                  35                  40 cct aag ctg ctc att tac aga aca tcc aac ctg gct tct ggg gtc cct   240
Pro Lys Leu Leu Ile Tyr Arg Thr Ser Asn Leu Ala Ser Gly Val Pro
        45                  50                  55
```

```
gac cga ttc agt ggc agc ggg tct ggg aca gat ttc act ctc acc atc     288
Asp Arg Phe Ser Gly Ser Gly Ser Gly Thr Asp Phe Thr Leu Thr Ile
    60                  65                  70 agc agc ctg cag gct gaa gac gtc gca gtt tat tac tgt cat cag tgg     336
Ser Ser Leu Gln Ala Glu Asp Val Ala Val Tyr Tyr Cys His Gln Trp
75                  80                  85                  90 agt atg tac acg ttc ggc caa ggg acc aag gtg gag atc aaa c           379
Ser Met Tyr Thr Phe Gly Gln Gly Thr Lys Val Glu Ile Lys
                95                  100

<210> SEQ ID NO 57
<211> LENGTH: 8
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57 ctctagag                                                              8

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
cagtgttctt ggctgtgcaa aaagtggagg cattttttcat aatagaaggt gcctacgtag   60

<210> SEQ ID NO 59
<211> LENGTH: 67
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
gatcctacgt aggcaccttc tattatgaaa aatgcctcca cttttgcaca gccaagaaca    60
ctgcatg                                                              67

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
gtataatgag cggccgcg                                                  18

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
gatccgcggc cgctcattat ac                                             22
```

<210> SEQ ID NO 62
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
gaaggaaaca gaaggcgcca tctatatatt tattcgaggt accaatacaa tcatag        56

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
aaactgactt ggccggcgcc atttatgtct                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
cataaatcct ataggtacca acgacaacta                                    30

<210> SEQ ID NO 65
<211> LENGTH: 87
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
caggaaacag ctatgacgaa ttccaccatg gattttcaag tgcagatttt cagcttcctg   60
ctaatcagtg cctcagtcat aatatcc                                       87

<210> SEQ ID NO 66
<211> LENGTH: 93
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
aagtgatggt gactctgtct cctacagatg cagacaggga ggatggagac tgggtcatct   60
ggatatctcc tctggatatt atgactgagg cac                                93

<210> SEQ ID NO 67
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA -continued

<400> SEQUENCE: 67
agacagagtc accatcactt gtagtgccag ctcgagtgta agttacatgc actggtatca    60
gcagaaacca gggaaagccc ctaag    85

<210> SEQ ID NO 68
<211> LENGTH: 84
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
atccactgcc gctgaacctt gatgggaccc cagaagccag gttggatgtt ctatagatca    60
gaagcttagg ggctttccct ggtt    84

<210> SEQ ID NO 69
<211> LENGTH: 94
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
aaggttcagc ggcagtggat ctgggacaga tttcactctc accatcagca gcctgcagcc    60
tgaagatttt gcaacttatt actgtcatca gtgg    94

<210> SEQ ID NO 70
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
gttttcccag tcacgaccgt acgtttgatc tctaccttgg tcccttggcc gaacgtgtac    60
atactccact gatgacagta ataag    85

<210> SEQ ID NO 71
<211> LENGTH: 379
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(378)
<220> FEATURE:
<221> NAME/KEY: sig_peptide
<222> LOCATION: (1)..(66)
<220> FEATURE:
<221> NAME/KEY: mat_peptide
<222> LOCATION: (67)..(378)

<400> SEQUENCE: 71

```
atg gat ttt caa gtg cag att ttc agc ttc ctg cta atc agt gcc tca      48
Met Asp Phe Gln Val Gln Ile Phe Ser Phe Leu Leu Ile Ser Ala Ser
        -20                 -15                 -10 gtc ata ata tcc aga gga gat atc cag atg acc cag tct cca tcc tcc      96
Val Ile Ile Ser Arg Gly Asp Ile Gln Met Thr Gln Ser Pro Ser Ser
    -5              -1   1               5                  10
```

```
ctg tct gca tct gta gga gac aga gtc acc atc act tgt agt gcc agc    144
Leu Ser Ala Ser Val Gly Asp Arg Val Thr Ile Thr Cys Ser Ala Ser
             15                  20                  25 tcg agt gta agt tac atg cac tgg tat cag cag aaa cca ggg aaa gcc    192
Ser Ser Val Ser Tyr Met His Trp Tyr Gln Gln Lys Pro Gly Lys Ala
         30                  35                  40 cct aag ctt ctg atc tat aga aca tcc aac ctg gct tct ggg gtc cca    240
Pro Lys Leu Leu Ile Tyr Arg Thr Ser Asn Leu Ala Ser Gly Val Pro
     45                  50                  55 tca agg ttc agc ggc agt gga tct ggg aca gat ttc act ctc acc atc    288
Ser Arg Phe Ser Gly Ser Gly Ser Gly Thr Asp Phe Thr Leu Thr Ile
 60                  65                  70 agc agc ctg cag cct gaa gat ttt gca act tat tac tgt cat cag tgg    336
Ser Ser Leu Gln Pro Glu Asp Phe Ala Thr Tyr Tyr Cys His Gln Trp
 75                  80                  85                  90 agt atg tac acg ttc ggc caa ggg acc aag gta gag atc aaa c          379
Ser Met Tyr Thr Phe Gly Gln Gly Thr Lys Val Glu Ile Lys
                 95                 100

<210> SEQ ID NO 72
<211> LENGTH: 80
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
caggaaacag ctatgactcc ggagctgagg tgaagaagcc tggggcctca gtgaaggtct    60
cctgcaaggc ttctggatac                                               80

<210> SEQ ID NO 73
<211> LENGTH: 80
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
ccactcaagc ccttgtccag gggcctgtcg cacccagtgc atattgtaat taatgaaggt    60
gtatccagaa gccttgcagg                                               80

<210> SEQ ID NO 74
<211> LENGTH: 81
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
ctggacaagg gcttgagtgg atgggagcta tttttccagg aaatggtttt acttcctaca    60
atcagaagtt caagggcaga g                                             81

<210> SEQ ID NO 75
<211> LENGTH: 79
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
```

-continued tctcaggctg cgcagctgca tgtaggctgt gctcgtggac ttgtcgacgg taatggtgac    60
tctgcccttg aacttctga    79

<210> SEQ ID NO 76
<211> LENGTH: 83
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
tgcagctgcg cagcctgaga tctgaggaca cggccgtgta tttctgtgcg agagatggtg    60
actattactt tgactactgg ggc    83

<210> SEQ ID NO 77
<211> LENGTH: 81
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
gttttcccag tcacgacggg cccttggtgg aggctgagga dacggtgacc agggttccct    60
ggccccagta gtcaaagtaa t    81

<210> SEQ ID NO 78
<211> LENGTH: 409
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(408)
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 78

```
atg gga ttc agc agg atc ttt ctc ttc ctc ctg tca gtg act aca ggt     48
Met Gly Phe Ser Arg Ile Phe Leu Phe Leu Leu Ser Val Thr Thr Gly
            -15                 -10                 -5 gtc cac tcc cag gtg cag ctg gtg cag tcc gga gct gag gtg aag aag     96
Val His Ser Gln Val Gln Leu Val Gln Ser Gly Ala Glu Val Lys Lys
         -1   1               5                  10 cct ggg gcc tca gtg aag gtc tcc tgc aag gct tct gga tac acc ttc    144
Pro Gly Ala Ser Val Lys Val Ser Cys Lys Ala Ser Gly Tyr Thr Phe
         15                  20                  25 att aat tac aat atg cac tgg gtg cga cag gcc cct gga caa ggg ctt    192
Ile Asn Tyr Asn Met His Trp Val Arg Gln Ala Pro Gly Gln Gly Leu
 30                  35                  40                  45 gag tgg atg gga gct att ttt cca gga aat ggt ttt act tcc tac aat    240
Glu Trp Met Gly Ala Ile Phe Pro Gly Asn Gly Phe Thr Ser Tyr Asn
                 50                  55                  60 cag aag ttc aag ggc aga gtc acc att acc gtc gac aag tcc acg agc    288
Gln Lys Phe Lys Gly Arg Val Thr Ile Thr Val Asp Lys Ser Thr Ser
             65                  70                  75
```

-continued

| aca | gcc | tac | atg | cag | ctg | cgc | agc | ctg | aga | tct | gag | gac | acg | gcc | gtg | 336 |
| Thr | Ala | Tyr | Met | Gln | Leu | Arg | Ser | Leu | Arg | Ser | Glu | Asp | Thr | Ala | Val | |
| | | | 80 | | | | | 85 | | | | | 90 | | | |

| tat | ttc | tgt | gcg | aga | gat | ggt | gac | tat | tac | ttt | gac | tac | tgg | ggc | cag | 384 |
| Tyr | Phe | Cys | Ala | Arg | Asp | Gly | Asp | Tyr | Tyr | Phe | Asp | Tyr | Trp | Gly | Gln | |
| | 95 | | | | | 100 | | | | | 105 | | | | | |

| gga | acc | ctg | gtc | acc | gtc | tcc | tca | g | | | | | | | | 409 |
| Gly | Thr | Leu | Val | Thr | Val | Ser | Ser | | | | | | | | | |
| 110 | | | | | 115 | | | | | | | | | | | |

<210> SEQ ID NO 79
<211> LENGTH: 87
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 79
caggaaacag ctatgacgaa ttccaccatg gattttcaag tgcagatttt cagcttcctg      60
ctaatcagtg cctcagtcat aatatcc                                          87

<210> SEQ ID NO 80
<211> LENGTH: 93
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 80
aagtgatggt gacctcctct cctacagatg cagacaggga ggatggagac tgggtcatct      60
ggatatctcc tctggatatt atgactgagg cac                                   93

<210> SEQ ID NO 81
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 81
agaggaggtc accatcactt gtagtgccag ctcgagtgta agttacatgc actggtatca      60
gcagaaacca gggaaagccc ctaag                                            85

<210> SEQ ID NO 82
<211> LENGTH: 84
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 82
atccactgcc gctgaacctt gatgggaccc cagaagccag gttggatgtt ctatagatca      60
gaagcttagg ggctttccct ggtt                                             84

<210> SEQ ID NO 83
<211> LENGTH: 94
<212> TYPE: DNA
<213> ORGANISM: Artificial Sequence
<220> FEATURE:
<223> OTHER INFORMATION: Description of Artificial Sequence: Synthetic -continued

```
         DNA

<400> SEQUENCE: 83
aaggttcagc ggcagtggat ctgggacatt ttatactctc accatcagca gcctgcagcc      60
tgaagatttt gcaacttatt actgtcatca gtgg                                  94

<210> SEQ ID NO 84
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
gttttcccag tcacgaccgt acgtttgatc tctaccttgg tcccttggcc gaacgtgtac      60
atactccact gatgacagta ataag                                            85

<210> SEQ ID NO 85
<211> LENGTH: 379
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(378)
<220> FEATURE:
<221> NAME/KEY: sig_peptide
<222> LOCATION: (1)..(66)
<220> FEATURE:
<221> NAME/KEY: mat_peptide
<222> LOCATION: (67)..(378)

<400> SEQUENCE: 85 atg gat ttt caa gtg cag att ttc agc ttc ctg cta atc agt gcc tca         48
Met Asp Phe Gln Val Gln Ile Phe Ser Phe Leu Leu Ile Ser Ala Ser
        -20                 -15                 -10 gtc ata ata tcc aga gga gat atc cag atg acc cag tct cca tcc tcc         96
Val Ile Ile Ser Arg Gly Asp Ile Gln Met Thr Gln Ser Pro Ser Ser
 -5              -1   1               5                      10 ctg tct gca tct gta gga gag gag gtc acc atc act tgt agt gcc agc        144
Leu Ser Ala Ser Val Gly Glu Glu Val Thr Ile Thr Cys Ser Ala Ser
                 15                  20                  25 tcg agt gta agt tac atg cac tgg tat cag cag aaa cca ggg aaa gcc        192
Ser Ser Val Ser Tyr Met His Trp Tyr Gln Gln Lys Pro Gly Lys Ala
             30                  35                  40 cct aag ctt ctg atc tat aga aca tcc aac ctg gct tct ggg gtc cca        240
Pro Lys Leu Leu Ile Tyr Arg Thr Ser Asn Leu Ala Ser Gly Val Pro
         45                  50                  55 tca agg ttc agc ggc agt gga tct ggg aca ttt tat act ctc acc atc        288
Ser Arg Phe Ser Gly Ser Gly Ser Gly Thr Phe Tyr Thr Leu Thr Ile
     60                  65                  70 agc agc ctg cag cct gaa gat ttt gca act tat tac tgt cat cag tgg        336
Ser Ser Leu Gln Pro Glu Asp Phe Ala Thr Tyr Tyr Cys His Gln Trp
 75                  80                  85                  90 agt atg tac acg ttc ggc caa ggg acc aag gta gag atc aaa c              379
Ser Met Tyr Thr Phe Gly Gln Gly Thr Lys Val Glu Ile Lys
                 95                 100

<210> SEQ ID NO 86
<211> LENGTH: 138
<212> TYPE: PRT
```

<213> ORGANISM: Artificial Sequence
<220> FEATURE:
<223> OTHER INFORMATION: Description of Artificial Sequence: Synthetic
      protein

<400> SEQUENCE: 86

Met Glu Trp Asn Trp Val Val Leu Phe Leu Leu Ser Leu Thr Ala Gly
                -15                 -10                  -5

Val Tyr Ala Gln Gly Gln Met Gln Gln Ser Gly Ala Glu Leu Val Lys
            -1   1               5                  10

Pro Gly Ala Ser Val Lys Leu Ser Cys Lys Pro Ser Gly Phe Thr Phe
         15                  20                  25

Ser Ser Asn Tyr Ile Ser Trp Leu Lys Gln Lys Pro Gly Gln Ser Leu
 30                  35                  40                  45

Glu Trp Ile Ala Trp Ile Tyr Ala Gly Thr Gly Asp Ala Ser Tyr Asn
                 50                  55                  60

Gln Lys Phe Thr Ala Lys Ala His Val Thr Val Asp Thr Ser Ser Ser
             65                  70                  75

Thr Ala Tyr Met Gln Leu Ser Ser Leu Thr Thr Glu Asp Ser Ala Ile
         80                  85                  90

Tyr Tyr Cys Ala Arg His Gly Gly Asp Gly Tyr Trp Phe Ala Tyr Trp
     95                 100                 105

Gly Gln Gly Thr Leu Val Thr Val Ser Ala
110                 115

<210> SEQ ID NO 87
<211> LENGTH: 128
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 87

Met Asp Phe Gln Val Gln Ile Phe Ser Phe Leu Leu Ile Ser Ala Ser
                -20                 -15                 -10

Val Ile Ile Ser Arg Gly Gln Leu Val Leu Thr Gln Ser Pro Ala Ile
 -5              -1   1               5                  10

Met Ser Ala Ser Gln Gly Glu Lys Val Thr Met Thr Cys Ser Ala Ser
             15                  20                  25

Ser Ser Val Ser Tyr Met His Trp Tyr Gln Gln Lys Ser Gly Thr Ser
         30                  35                  40

Pro Lys Arg Trp Ile Tyr Asp Thr Ser Lys Leu Pro Ser Gly Val Pro
     45                  50                  55

Ala Arg Phe Ser Gly Ser Gly Ser Gly Thr Ser Tyr Ser Leu Thr Ile
 60                  65                  70

Ser Ser Met Glu Ala Glu Asp Ala Ala Thr Tyr Tyr Cys Gln Gln Trp
 75                  80                  85                  90

Ser Ser Asn Pro Pro Thr Phe Gly Ala Gly Thr Lys Leu Glu Leu Lys
                 95                 100                 105

<210> SEQ ID NO 88
<211> LENGTH: 136
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 88

Met Gly Phe Ser Arg Ile Phe Leu Phe Leu Leu Ser Val Thr Thr Gly
            -15                 -10                 -5

Val His Ser Gln Ala Phe Leu Gln Gln Ser Gly Ala Glu Leu Val Arg
         -1   1               5                  10

Pro Gly Ala Ser Val Lys Met Ser Cys Lys Ala Ser Gly Tyr Thr Phe
        15              20                  25

Ile Asn Tyr Asn Met His Trp Val Lys Gln Thr Pro Arg Gln Gly Leu
30                  35                  40                  45

Glu Trp Ile Gly Ala Ile Phe Pro Gly Asn Gly Phe Thr Ser Tyr Asn
                50                  55                  60

Gln Lys Phe Lys Gly Lys Ala Thr Leu Thr Val Asp Lys Ser Ser Ser
            65                  70                  75

Thr Val Tyr Met Gln Leu Arg Ser Leu Thr Ser Glu Asp Ser Ala Val
            80                  85                  90

Tyr Phe Cys Ala Arg Asp Gly Asp Tyr Tyr Phe Asp Tyr Trp Gly Gln
        95                  100                 105

Gly Thr Thr Leu Thr Val Ser Ser
110                 115

<210> SEQ ID NO 89
<211> LENGTH: 126
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 89

Met Asp Phe Gln Val Gln Ile Phe Ser Phe Leu Leu Ile Ser Ala Ser
        -20                 -15                 -10

Val Ile Met Ser Arg Gly Gln Ile Val Leu Thr Gln Ser Pro Ala Ile
    -5              -1   1               5                  10

Met Ser Ala Ser Leu Gly Glu Glu Ile Thr Leu Thr Cys Ser Ala Ser
                15                  20                  25

Ser Ser Val Ser Tyr Met His Trp Tyr Gln Gln Lys Ser Gly Thr Ser
            30                  35                  40

Pro Lys Leu Leu Ile Tyr Arg Thr Ser Asn Leu Ala Ser Gly Val Pro
            45                  50                  55

Phe Arg Phe Ser Gly Ser Gly Ser Gly Thr Phe Tyr Ser Leu Thr Ile
        60                  65                  70

Ser Ser Val Glu Ala Glu Asp Ala Ala Asp Tyr Tyr Cys His Gln Trp
75                  80                  85                  90

Ser Met Tyr Thr Phe Gly Gly Gly Thr Lys Leu Glu Ile Lys
                95                  100

<210> SEQ ID NO 90
<211> LENGTH: 138
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 90

Met Glu Trp Asn Trp Val Val Leu Phe Leu Leu Ser Leu Thr Ala Gly
            -15                 -10                 -5

Val Tyr Ala Gln Val Gln Leu Val Gln Ser Gly Ala Glu Val Lys Lys
         -1   1               5                  10

```
Pro Gly Ala Ser Val Lys Val Ser Cys Lys Ala Ser Gly Tyr Thr Phe
    15                  20                  25

Ser Ser Asn Tyr Ile Ser Trp Val Arg Gln Ala Pro Gly Gln Gly Leu
        30                  35                  40              45

Glu Trp Met Gly Trp Ile Tyr Ala Gly Thr Gly Asp Ala Ser Tyr Asn
                50                  55                  60

Gln Lys Phe Thr Ala Arg Val Thr Ile Thr Val Asp Thr Ser Thr Ser
            65                  70                  75

Thr Ala Tyr Met Glu Leu Ser Ser Leu Arg Ser Glu Asp Thr Ala Val
        80                  85                  90

Tyr Tyr Cys Ala Arg His Gly Gly Asp Gly Tyr Trp Phe Ala Tyr Trp
    95                  100                 105

Gly Gln Gly Thr Leu Val Thr Val Ser Ser
110                 115
```

<210> SEQ ID NO 91
<211> LENGTH: 136
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 91

```
Met Gly Phe Ser Arg Ile Phe Leu Phe Leu Leu Ser Val Thr Thr Gly
            -15                 -10                  -5

Val His Ser Gln Val Gln Leu Val Gln Ser Gly Ala Glu Val Lys Lys
        -1   1               5                   10

Pro Gly Ala Ser Val Lys Val Ser Cys Lys Ala Ser Gly Tyr Thr Phe
    15                  20                  25

Ile Asn Tyr Asn Met His Trp Val Arg Gln Ala Pro Gly Gln Gly Leu
        30                  35                  40              45

Glu Trp Met Gly Ala Ile Phe Pro Gly Asn Gly Phe Thr Ser Tyr Asn
                50                  55                  60

Gln Lys Phe Lys Gly Arg Val Thr Ile Thr Val Asp Lys Ser Thr Ser
            65                  70                  75

Thr Ala Tyr Met Glu Leu Ser Ser Leu Arg Ser Glu Asp Thr Ala Val
        80                  85                  90

Tyr Tyr Cys Ala Arg Asp Gly Asp Tyr Tyr Phe Asp Tyr Trp Gly Gln
    95                  100                 105

Gly Thr Leu Val Thr Val Ser Ser
110                 115
```

<210> SEQ ID NO 92
<211> LENGTH: 128
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 92

```
Met Asp Phe Gln Val Gln Ile Phe Ser Phe Leu Leu Ile Ser Ala Ser
        -20                 -15                 -10

Val Ile Ile Ser Arg Gly Asp Ile Gln Met Thr Gln Ser Pro Ser Ser
    -5                  -1   1               5                   10

Leu Ser Ala Ser Val Gly Asp Arg Val Thr Ile Thr Cys Ser Ala Ser
            15                  20                  25
```

```
Ser Ser Val Ser Tyr Met His Trp Tyr Gln Gln Lys Pro Gly Lys Ala
            30                  35                  40

Pro Lys Leu Leu Ile Tyr Asp Thr Ser Lys Leu Pro Ser Gly Val Pro
            45                  50                  55

Ser Arg Phe Ser Gly Ser Gly Ser Gly Thr Asp Phe Thr Leu Thr Ile
            60                  65                  70

Ser Ser Leu Gln Pro Glu Asp Phe Ala Thr Tyr Tyr Cys Gln Gln Trp
        75                  80                  85                  90

Ser Ser Asn Pro Pro Thr Phe Gly Gln Gly Thr Lys Val Glu Ile Lys
                95                  100                 105
```

<210> SEQ ID NO 93
<211> LENGTH: 126
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 93

```
Met Asp Phe Gln Val Gln Ile Phe Ser Phe Leu Leu Ile Ser Ala Ser
        -20                 -15                 -10

Val Ile Met Ser Arg Gly Asp Ile Val Met Thr Gln Ser Pro Asp Ser
        -5                  -1  1               5                   10

Leu Ala Val Ser Leu Gly Glu Arg Ala Thr Ile Asn Cys Ser Ala Ser
                15                  20                  25

Ser Ser Val Ser Tyr Met His Trp Tyr Gln Gln Lys Pro Gly Gln Pro
            30                  35                  40

Pro Lys Leu Leu Ile Tyr Arg Thr Ser Asn Leu Ala Ser Gly Val Pro
            45                  50                  55

Asp Arg Phe Ser Gly Ser Gly Ser Gly Thr Asp Phe Thr Leu Thr Ile
            60                  65                  70

Ser Ser Leu Gln Ala Glu Asp Val Ala Val Tyr Tyr Cys His Gln Trp
        75                  80                  85                  90

Ser Met Tyr Thr Phe Gly Gln Gly Thr Lys Val Glu Ile Lys
                95                  100
```

<210> SEQ ID NO 94
<211> LENGTH: 126
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 94

```
Met Asp Phe Gln Val Gln Ile Phe Ser Phe Leu Leu Ile Ser Ala Ser
        -20                 -15                 -10

Val Ile Ile Ser Arg Gly Asp Ile Gln Met Thr Gln Ser Pro Ser Ser
        -5                  -1  1               5                   10

Leu Ser Ala Ser Val Gly Asp Arg Val Thr Ile Thr Cys Ser Ala Ser
                15                  20                  25

Ser Ser Val Ser Tyr Met His Trp Tyr Gln Gln Lys Pro Gly Lys Ala
            30                  35                  40

Pro Lys Leu Leu Ile Tyr Arg Thr Ser Asn Leu Ala Ser Gly Val Pro
            45                  50                  55

Ser Arg Phe Ser Gly Ser Gly Ser Gly Thr Asp Phe Thr Leu Thr Ile
            60                  65                  70
```

```
Ser Ser Leu Gln Pro Glu Asp Phe Ala Thr Tyr Tyr Cys His Gln Trp
 75                  80                  85                  90

Ser Met Tyr Thr Phe Gly Gln Gly Thr Lys Val Glu Ile Lys
                 95                 100
```

<210> SEQ ID NO 95
<211> LENGTH: 136
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 95

```
Met Gly Phe Ser Arg Ile Phe Leu Phe Leu Ser Val Thr Thr Gly
            -15                 -10                  -5

Val His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
     15                  20                  25

Ile Asn Tyr Asn Met His Trp Val Arg Gln Ala Pro Gly Gln Gly Leu
 30                  35                  40                  45

Glu Trp Met Gly Ala Ile Phe Pro Gly Asn Gly Phe Thr Ser Tyr Asn
                 50                  55                  60

Gln Lys Phe Lys Gly Arg Val Thr Ile Thr Val Asp Lys Ser Thr Ser
             65                  70                  75

Thr Ala Tyr Met Gln Leu Arg Ser Leu Arg Ser Glu Asp Thr Ala Val
         80                  85                  90

Tyr Phe Cys Ala Arg Asp Gly Asp Tyr Tyr Asp Tyr Trp Gly Gln
     95                 100                 105

Gly Thr Leu Val Thr Val Ser Ser
110                 115
```

<210> SEQ ID NO 96
<211> LENGTH: 126
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 96

```
Met Asp Phe Gln Val Gln Ile Phe Ser Phe Leu Leu Ile Ser Ala Ser
        -20                 -15                 -10

Val Ile Ile Ser Arg Gly Asp Ile Gln Met Thr Gln Ser Pro Ser Ser
     -5              -1   1               5                  10

Leu Ser Ala Ser Val Gly Glu Glu Val Thr Ile Thr Cys Ser Ala Ser
                 15                  20                  25

Ser Ser Val Ser Tyr Met His Trp Tyr Gln Gln Lys Pro Gly Lys Ala
             30                  35                  40

Pro Lys Leu Leu Ile Tyr Arg Thr Ser Asn Leu Ala Ser Gly Val Pro
         45                  50                  55

Ser Arg Phe Ser Gly Ser Gly Ser Gly Thr Phe Tyr Thr Leu Thr Ile
     60                  65                  70

Ser Ser Leu Gln Pro Glu Asp Phe Ala Thr Tyr Tyr Cys His Gln Trp
 75                  80                  85                  90

Ser Met Tyr Thr Phe Gly Gln Gly Thr Lys Val Glu Ile Lys
                 95                 100
```

```
<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 97

Gln Gly Gln Met Gln Gln Ser Gly Ala Glu Leu Val Lys Pro Gly Ala
 1               5                  10                  15

Ser Val Lys Leu Ser Cys Lys Pro Ser Gly Phe Thr Phe Ser Ser Asn
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Asp Ala Ser Tyr Asn Gln Lys Phe
    50                  55                  60

Thr Ala Lys Ala His Val Thr Val Asp Thr Ser Ser Ser Thr Ala Tyr
65                  70                  75                  80

Met Gln Leu Ser Ser Leu Thr Thr Glu Asp Ser Ala Ile Tyr Tyr Cys
                85                  90                  95

Ala Arg His Gly Gly Asp Gly Tyr Trp Phe Ala Tyr Trp Gly Gln Gly
            100                 105                 110

Thr Leu Val Thr Val Ser Ala
        115

<210> SEQ ID NO 98
<211> LENGTH: 106
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 98

Gln Leu Val Leu Thr Gln Ser Pro Ala Ile Met Ser Ala Ser Gln Gly
 1               5                  10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Pro Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105

<210> SEQ ID NO 99
<211> LENGTH: 117
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 99
```

-continued

```
Gln Ala Phe Leu Gln Gln Ser Gly Ala Glu Leu Val Arg Pro Gly Ala
  1               5                  10                 15

Ser Val Lys Met Ser Cys Lys Ala Ser Gly Tyr Thr Phe Ile Asn Tyr
             20                  25                  30

Asn Met His Trp Val Lys Gln Thr Pro Arg Gln Gly Leu Glu Trp Ile
         35                  40                  45

Gly Ala Ile Phe Pro Gly Asn Gly Phe Thr Ser Tyr Asn Gln Lys Phe
     50                  55                  60

Lys Gly Lys Ala Thr Leu Thr Val Asp Lys Ser Ser Thr Val Tyr
 65                  70                  75                  80

Met Gln Leu Arg Ser Leu Thr Ser Glu Asp Ser Ala Val Tyr Phe Cys
                 85                  90                  95

Ala Arg Asp Gly Asp Tyr Tyr Phe Asp Tyr Trp Gly Gln Gly Thr Thr
                100                 105                 110

Leu Thr Val Ser Ser
            115
```

<210> SEQ ID NO 100
<211> LENGTH: 104
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 100

```
Gln Ile Val Leu Thr Gln Ser Pro Ala Ile Met Ser Ala Ser Leu Gly
  1               5                  10                 15

Glu Glu Ile Thr Leu Thr Cys Ser Ala Ser Ser Ser Val Ser Tyr Met
             20                  25                  30

His Trp Tyr Gln Gln Lys Ser Gly Thr Ser Pro Lys Leu Leu Ile Tyr
         35                  40                  45

Arg Thr Ser Asn Leu Ala Ser Gly Val Pro Phe Arg Phe Ser Gly Ser
     50                  55                  60

Gly Ser Gly Thr Phe Tyr Ser Leu Thr Ile Ser Ser Val Glu Ala Glu
 65                  70                  75                  80

Asp Ala Ala Asp Tyr Tyr Cys His Gln Trp Ser Met Tyr Thr Phe Gly
                 85                  90                  95

Gly Gly Thr Lys Leu Glu Ile Lys
                100
```

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 101

```
Gln Val Gln Leu Val Gln Ser Gly Ala Glu Val Lys Lys Pro Gly Ala
  1               5                  10                 15

Ser Val Lys Val Ser Cys Lys Ala Ser Gly Tyr Thr Phe Ser Ser Asn
             20                  25                  30

Tyr Ile Ser Trp Val Arg Gln Ala Pro Gly Gln Gly Leu Glu Trp Met
         35                  40                  45

Gly Trp Ile Tyr Ala Gly Thr Gly Asp Ala Ser Tyr Asn Gln Lys Phe
     50                  55                  60
```

```
Thr Ala Arg Val Thr Ile Thr Val Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Gly Gly Asp Gly Tyr Trp Phe Ala Tyr Trp Gly Gln Gly
            100                 105                 110

Thr Leu Val Thr Val Ser Ser
            115
```

<210> SEQ ID NO 102
<211> LENGTH: 117
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 102

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Ile Asn Tyr
                 20                  25                  30

Asn Met His Trp Val Arg Gln Ala Pro Gly Gln Gly Leu Glu Trp Met
             35                  40                  45

Gly Ala Ile Phe Pro Gly Asn Gly Phe Thr Ser Tyr Asn Gln Lys Phe
         50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Asp Tyr Tyr Phe Asp Tyr Trp Gly Gln Gly Thr Leu
            100                 105                 110

Val Thr Val Ser Ser
            115
```

<210> SEQ ID NO 103
<211> LENGTH: 106
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 103

```
Asp Ile Gln Met Thr Gln Ser Pro Ser Ser Leu Ser Ala Ser Val Gly
  1               5                  10                  15

Asp Arg Val Thr Ile Thr Cys Ser Ala Ser Ser Ser Val Ser Tyr Met
                 20                  25                  30

His Trp Tyr Gln Gln Lys Pro Gly Lys Ala Pro Lys Leu Leu Ile Tyr
             35                  40                  45

Asp Thr Ser Lys Leu Pro Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Asn Pro Pro Thr
                 85                  90                  95

Phe Gly Gln Gly Thr Lys Val Glu Ile Lys
            100                 105
```

```
<210> SEQ ID NO 104
<211> LENGTH: 104
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 104

Asp Ile Val Met Thr Gln Ser Pro Asp Ser Leu Ala Val Ser Leu Gly
 1               5                  10                  15

Glu Arg Ala Thr Ile Asn Cys Ser Ala Ser Ser Ser Val Ser Tyr Met
            20                  25                  30

His Trp Tyr Gln Gln Lys Pro Gly Gln Pro Pro Lys Leu Leu Ile Tyr
        35                  40                  45

Arg Thr Ser Asn Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys His Gln Trp Ser Met Tyr Thr Phe Gly
                85                  90                  95

Gln Gly Thr Lys Val Glu Ile Lys
            100

<210> SEQ ID NO 105
<211> LENGTH: 104
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 105

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Met Tyr Thr Phe Gly
                85                  90                  95

Gln Gly Thr Lys Val Glu Ile Lys
            100

<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 106

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ile Asn Tyr
```

```
                    20                  25                  30
Asn Met His Trp Val Arg Gln Ala Pro Gly Gln Gly Leu Glu Trp Met
        35                  40                  45

Gly Ala Ile Phe Pro Gly Asn Gly Phe Thr Ser Tyr Asn Gln Lys Phe
    50                  55                  60

Lys Gly Arg Val Thr Ile Thr Val Asp Lys Ser Thr Ser Thr Ala Tyr
65                  70                  75                  80

Met Gln Leu Arg Ser Leu Arg Ser Glu Asp Thr Ala Val Tyr Phe Cys
                85                  90                  95

Ala Arg Asp Gly Asp Tyr Tyr Phe Asp Tyr Trp Gly Gln Gly Thr Leu
            100                 105                 110

Val Thr Val Ser Ser
        115

<210> SEQ ID NO 107
<211> LENGTH: 104
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 107

Asp Ile Gln Met Thr Gln Ser Pro Ser Ser Leu Ser Ala Ser Val Gly
1               5                   10                  15

Glu Glu Val Thr Ile Thr Cys Ser Ala Ser Ser Ser Val Ser Tyr Met
                20                  25                  30

His Trp Tyr Gln Gln Lys Pro Gly Lys Ala Pro Lys Leu Leu Ile Tyr
            35                  40                  45

Arg Thr Ser Asn Leu Ala Ser Gly Val Pro Ser Arg Phe Ser Gly Ser
        50                  55                  60

Gly Ser Gly Thr Phe Tyr Thr Leu Thr Ile Ser Ser Leu Gln Pro Glu
65                  70                  75                  80

Asp Phe Ala Thr Tyr Tyr Cys His Gln Trp Ser Met Tyr Thr Phe Gly
                85                  90                  95

Gln Gly Thr Lys Val Glu Ile Lys
            100

<210> SEQ ID NO 108
<211> LENGTH: 105
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 108

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
                20                  25                  30

His Trp Tyr Gln Gln Lys Ser Gly Thr Ser Pro Lys Leu Leu Ile Tyr
            35                  40                  45

Arg Thr Ser Asn Leu Ala Ser Gly Val Pro Phe Arg Phe Ser Gly Ser
        50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Met Tyr Thr Phe Gly
```

```
                    85                  90                  95

Gly Gly Thr Lys Leu Glu Ile Lys Arg
            100                 105

<210> SEQ ID NO 109
<211> LENGTH: 105
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 109

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
            35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Met Tyr Thr Phe Gly
                85                  90                  95

Gln Gly Thr Lys Val Glu Ile Lys Arg
            100                 105

<210> SEQ ID NO 110
<211> LENGTH: 105
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 110

Asp Ile Gln Met Thr Gln Ser Pro Ser Ser Leu Ser Ala Ser Val Gly
 1               5                  10                  15

Glu Glu Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
            35                  40                  45

Arg Thr Ser Asn Leu Ala Ser Gly Val Pro Ser Arg Phe Ser Gly Ser
    50                  55                  60

Gly Ser Gly Thr Phe Tyr Thr Leu Thr Ile Ser Ser Leu Gln Pro Glu
65                  70                  75                  80

Asp Phe Ala Thr Tyr Tyr Cys His Gln Trp Ser Met Tyr Thr Phe Gly
                85                  90                  95

Gln Gly Thr Lys Val Glu Ile Lys Arg
            100                 105

<210> SEQ ID NO 111
<211> LENGTH: 105
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 111
```

-continued

```
Asp Ile Val Met Thr Gln Ser Pro Asp Ser Leu Ala Val Ser Leu Gly
 1               5                  10                 15
Glu Arg Ala Thr Ile Asn Cys Ser Ala Ser Ser Ser Val Ser Tyr Met
                20                  25                 30
His Trp Tyr Gln Gln Lys Pro Gly Gln Pro Pro Lys Leu Leu Ile Tyr
            35                  40              45
Arg Thr Ser Asn Leu Ala Ser Gly Val Pro Asp Arg Phe Ser Gly Ser
         50                  55              60
Gly Ser Gly Thr Asp Phe Thr Leu Thr Ile Ser Ser Leu Gln Ala Glu
 65              70                  75                 80
Asp Val Ala Val Tyr Tyr Cys His Gln Trp Ser Met Tyr Thr Phe Gly
                 85                 90                 95
Gln Gly Thr Lys Val Glu Ile Lys Arg
             100             105
```